United States Patent
Liu et al.

(10) Patent No.: US 10,966,970 B2
(45) Date of Patent: Apr. 6, 2021

(54) FUSED TRICYCLIC COMPOUNDS AND USES THEREOF IN MEDICINE

(71) Applicants: SUNSHINE LAKE PHARMA CO., LTD., Guangdong (CN); NORTH & SOUTH BROTHER PHARMACY INVESTMENT COMPANY LIMITED, Hong Kong (CN)

(72) Inventors: Xinchang Liu, Dongguan (CN); Qingyun Ren, Dongguan (CN); Jianzhou Huang, Dongguan (CN); Zhimin Xiong, Dongguan (CN); Jinfeng Xiong, Dongguan (CN); You Li, Dongguan (CN); Yang Liu, Dongguan (CN); Zhifu Zou, Dongguan (CN); Guanghua Yan, Dongguan (CN); Siegfried Goldmann, Wuppertal (DE); Yingjun Zhang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

(21) Appl. No.: 16/611,778

(22) PCT Filed: Jun. 2, 2018

(86) PCT No.: PCT/CN2018/089699
§ 371 (c)(1),
(2) Date: Nov. 7, 2019

(87) PCT Pub. No.: WO2018/219356
PCT Pub. Date: Dec. 6, 2018

(65) Prior Publication Data
US 2020/0113879 A1    Apr. 16, 2020

(30) Foreign Application Priority Data

Jun. 1, 2017  (CN) .......................... 201710403592.5
Nov. 22, 2017  (CN) .......................... 201711170576.2

(51) Int. Cl.

| | |
|---|---|
| A61K 31/444 | (2006.01) |
| A61P 31/20 | (2006.01) |
| A61K 31/4375 | (2006.01) |
| A61K 31/496 | (2006.01) |
| A61K 31/4985 | (2006.01) |
| A61K 31/506 | (2006.01) |
| A61K 31/5377 | (2006.01) |
| A61K 31/685 | (2006.01) |
| A61K 45/06 | (2006.01) |
| C07D 455/06 | (2006.01) |

(Continued)

(52) U.S. Cl.
CPC ........ *A61K 31/444* (2013.01); *A61K 31/4375* (2013.01); *A61K 31/496* (2013.01); *A61K 31/4985* (2013.01); *A61K 31/506* (2013.01); *A61K 31/5377* (2013.01); *A61K 31/685* (2013.01); *A61K 45/06* (2013.01); *A61P 31/20* (2018.01); *C07D 455/06* (2013.01); *C07D 519/00* (2013.01); *C07F 9/6561* (2013.01)

(58) Field of Classification Search
CPC ... A61P 31/20; A61K 31/4375; A61K 31/496; A61K 31/4985; A61K 31/506; A61K 31/5377; A61K 31/685; A61K 45/06; C07D 455/06; C07D 519/00; C07F 9/6561
See application file for complete search history.

(56) References Cited

U.S. PATENT DOCUMENTS

| | | |
|---|---|---|
| 9,458,153 B2 | 10/2016 | Han et al. |
| 9,637,485 B2 | 5/2017 | Han et al. |

(Continued)

FOREIGN PATENT DOCUMENTS

| | | |
|---|---|---|
| AL | 2017/216685 A1 | 12/2017 |
| CN | 105899508 A | 8/2016 |

(Continued)

OTHER PUBLICATIONS

Han; J. Med. Chem. 2018, 61, 23, 10619-10634. (Year: 2018).*

(Continued)

*Primary Examiner* — Daniel R Carcanague
(74) *Attorney, Agent, or Firm* — Oliff PLC

(57) ABSTRACT

A fused tricyclic compound and use thereof as a medicament, in particular as a medicament for the treatment and/or prevention of hepatitis B. Specifically, a compound having Formula (I) or a stereoisomer, a tautomer, an N-oxide, a solvate, a metabolite, a pharmaceutically acceptable salt or a prodrug thereof, wherein each variate is as defined in specification. The compound also includes a Formula (I) or a stereoisomer, a tautomer, an N-oxide, a solvate, a metabolite, a pharmaceutically acceptable salt or a prodrug thereof as a medicament, especially as a medicament for the treatment and/or prevention of hepatitis B.

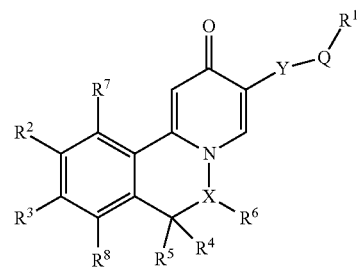

25 Claims, No Drawings

(51) Int. Cl.
    *C07D 519/00*    (2006.01)
    *C07F 9/6561*    (2006.01)

(56) References Cited

U.S. PATENT DOCUMENTS

| | | | |
|---|---|---|---|
| 9,845,325 | B2 | 12/2017 | Fu et al. |
| 9,920,049 | B2 | 3/2018 | Yang et al. |
| 10,053,461 | B2 | 8/2018 | Han et al. |
| 10,093,671 | B2 | 10/2018 | Han et al. |
| 10,150,740 | B2 | 12/2018 | Cheng et al. |
| 10,239,872 | B2 | 3/2019 | Chen et al. |
| 10,301,312 | B2 | 5/2019 | Fu et al. |
| 10,336,751 | B2 | 7/2019 | Cheng et al. |
| 10,442,804 | B2 | 10/2019 | Aktoudianakis et al. |
| 2015/0210682 | A1* | 7/2015 | Han .................. A61P 31/20 514/233.2 |
| 2016/0122344 | A1* | 5/2016 | Han .................. C07D 471/04 514/233.2 |
| 2017/0240548 | A1* | 8/2017 | Fu .................... C07D 491/14 |
| 2017/0342068 | A1* | 11/2017 | Aktoudianakis ........ A61P 31/20 |
| 2018/0170925 | A1* | 6/2018 | Chen .................. C07D 471/04 |
| 2018/0251460 | A1* | 9/2018 | Aktoudianakis ..... C07D 491/22 |
| 2019/0194768 | A1* | 6/2019 | Han .................. C12N 15/1137 |
| 2019/0224188 | A1* | 7/2019 | Panarese ................ A61P 31/20 |
| 2019/0314347 | A1* | 10/2019 | Bailey .................. A61K 9/0031 |
| 2019/0381014 | A1* | 12/2019 | Chen .................. A61K 31/5365 |
| 2019/0389855 | A1* | 12/2019 | Peng .................... A61P 1/16 |

FOREIGN PATENT DOCUMENTS

| | | | | |
|---|---|---|---|---|
| CN | 106459032 | A | 2/2017 | |
| CN | 106810548 | * | 6/2017 | |
| CN | 106928215 | * | 7/2017 | |
| CN | 106928245 | * | 7/2017 | |
| CN | 108530449 | A | 9/2018 | |
| CN | 108727378 | A | 11/2018 | |
| CN | 108976223 | * | 12/2018 | |
| CN | 110950860 | * | 4/2020 | |
| WO | WO-2015173164 | A1 * | 11/2015 | ........... C07D 455/06 |
| WO | 2016/071215 | A1 | 5/2016 | |
| WO | WO-2016071215 | A1 * | 5/2016 | ........... C07D 471/04 |
| WO | 2016/128335 | A1 | 8/2016 | |
| WO | 2017016921 | A1 | 2/2017 | |
| WO | WO-2017016960 | A1 * | 2/2017 | ........... C07C 231/02 |
| WO | WO-2017017043 | A1 * | 2/2017 | ........... C07D 471/04 |
| WO | WO2017114812 | * | 7/2017 | |
| WO | 2017/216686 | A1 | 12/2017 | |
| WO | WO2017211791 | * | 12/2017 | |
| WO | WO-2018019297 | A1 * | 2/2018 | ........... C07D 471/04 |
| WO | 2018/047109 | A1 | 3/2018 | |
| WO | 2018/073753 | A1 | 4/2018 | |
| WO | WO-2018130152 | A1 * | 7/2018 | ........... C07D 455/06 |
| WO | WO-2018154466 | A1 * | 8/2018 | ........... C07D 471/04 |
| WO | 2018/161960 | A1 | 9/2018 | |
| WO | 2018/214875 | A1 | 11/2018 | |
| WO | WO-2019100735 | A1 * | 5/2019 | ........... C07D 471/04 |
| WO | WO-2019129681 | A1 * | 7/2019 | ............. A61P 31/20 |
| WO | WO2020043080 | * | 3/2020 | |
| WO | WO2020051375 | * | 3/2020 | |

OTHER PUBLICATIONS

Mueller; Journal of Hepatology 2018, 68, 412-420. (Year: 2018).*
Rajbhandari; Clin Transl Gastroenterol. 2016, 7, e190. (Year: 2016).*
White, Chapter 1, Encyclopedia of Drug Metabolism and Interactions, 2012, Wiley, pp. 1-40. (Year: 2012).*
Xu; Tetrahedron Letters 2014, 55, 7194-7197. (Year: 2014).*
Zhang; Current Pharmaceutical Design, 2009, 15, 2220-2235. (Year: 2009).*
Chemical Abstracts Registry Database, record for RN 79-31-2, "2-Methylpropanoic acid", entered into database on Nov. 16, 1984. (Year: 1984).*
Chemical Abstracts Registry Database, record for RN 98-89-5, "Cyclohexanecarboxylic acid", entered into database on Nov. 16, 1984. (Year: 1984).*
Sep. 5, 2018 Search Report issued in International Patent Application No. PCT/CN2018/089699.
Sep. 5, 2018 Written Opinion of the International Searching Authority issued in International Patent Application No. PCT/CN2018/089699.

* cited by examiner

FUSED TRICYCLIC COMPOUNDS AND USES THEREOF IN MEDICINE

CROSS-REFERENCE TO RELATED APPLICATIONS

This application claims priorities and benefits of Chinese Patent Application No. 201710403592.5, filed with State Intellectual Property Office on Jun. 1, 2017; and Chinese Patent Application No. 201711170576.2, filed with State Intellectual Property Office on Nov. 22, 2017, both of which are hereby incorporated by reference in their entireties.

FIELD

The present invention relates to a fused tricyclic compound and use thereof as a medicament, in particular as a medicament for the treatment and prevention of hepatitis B. The present invention also relates to compositions containing these fused tricyclic compounds and other antiviral agents, and their use for the treatment and prevention of Hepatitis B (HBV) infection.

BACKGROUND

The hepatitis B virus belongs to the family of hepadnaviridae. It can cause acute and/or persistent or progressive chronic diseases. Many other clinical manifestations in the pathological morphology can also be caused by HBV' in particular chronic hepatitis, cirrhosis and hepatocellular carcinoma. According to estimates by the World Health Organization, 2 billion people in the world have been infected with HBV, and about 350 million people are chronically infected. About 1 million people die each year because of liver failure, cirrhosis and primary hepatocellular carcinoma (hepatocellular carcinoma, HCC) which result form HBV infection.

Currently, the treatment of chronic hepatitis B (CHB) is mainly based on antiviral therapy. Interferon alpha (IFN-alpha), pegylated IFN-alpha and five nucleoside (acid) analogs (lamivudine, adefovir dipivoxil, entecavir, telbivudine, and tenofovir) have been approved by Food and Drug Administration (FDA) for clinical treatment. Interferon is the earliest FDA-approved anti-HBV drug. It mainly through direct antiviral effect and induction of the body s immune response to achieve the effect of removing the virus, but because of its low response rate, having a variety of side effects, high price and restrictions of the treatment object, etc, its application is subject to many restrictions. The common point of nucleoside (acid) analogues in anti-HBV action is specifically acting viral DNA polymerase, which has a strong effect of inhibiting viral replication, and the patient s tolerance to drugs is better than interferon. However, with the widespread long-term use of nucleoside (acid) drugs, mutations in DNA polymerase can be induced to form drug resistance, and leads to the emergence of drug-resistant strains, thus it makes the treatment is far less than that of ideal.

Therefore, there is still a need in the clinic for new compounds that can effectively be used as antiviral drugs, especially these compounds as drugs for treating and/or preventing hepatitis B.

SUMMARY

The present invention relates to a novel fused tricyclic compound and its use in the preparation of a medicament for the treatment and prevention of HBV infections. The inventor found that the novel fused tricyclic compound of present invention has good pharmacokinetic properties, good solubility, low toxicity, good liver microsome stability, and good inhibitory activity against HBsAg production or secretion and HBV DNA replication, and other advantages, it has a good application prospects in anti-HBV virus action. In particular, the compounds of the present invention and pharmaceutically acceptable compositions thereof, are effective in inhibiting HBV infection.

In one aspect, the invention relates to a compound having Formula (I) or a stereoisomer, a tautomer, an N-oxide, a solvate, a metabolite, a pharmaceutically acceptable salt or a prodrug thereof, wherein,

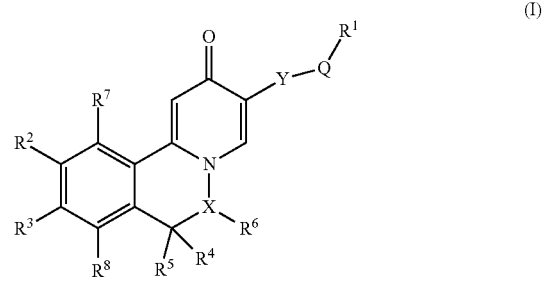

X is N or —$CR^{6a}$—;
Y is a single bond, —$CH_2$— or —C(=O)—;
Q is a single bond, —O— or —N($R^9$)—;
$R^1$ is H, deuterium, F, Cl, Br, I, OH, —COOH, 5- to 6-membered heterocyclyl, 5- to 6-membered heteroaryl, $C_{1-6}$ alkyl, $C_{2-6}$ alkenyl, $C_{2-6}$ alkynyl, $C_{3-7}$ cycloalkyl, $R^{12}$—S(=O)$_2$—, $R^{12}$—(CR$^e$R$^f$)$_n$— or R$^a$R$^b$N—, wherein each of the 5- to 6-membered heterocyclyl, 5- to 6-membered heteroaryl, $C_{1-6}$ alkyl, $C_{2-6}$ alkenyl, $C_{2-6}$ alkynyl and $C_{3-7}$ cycloalkyl is independently unsubstituted or substituted with 1, 2, 3 or 4 $R^v$;
$R^9$ is H, deuterium, $C_{1-6}$ alkyl or $C_{1-6}$ haloalkyl; or, $R^9$ and $R^1$, together with the nitrogen atom to which they are attached, form a 3- to 12-membered heterocyclyl, wherein each of the $C_{1-6}$ alkyl, $C_{1-6}$ haloalkyl and 3- to 12-membered heterocyclyl is independently unsubstituted or substituted with 1, 2, 3 or 4 substituents selected from —COOH, =O, tetrazolyl or $C_{1-6}$ alkyl-O—C(=O)—;
each of $R^4$ and $R^5$ is independently H, deuterium, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl or 3- to 12-membered heterocyclyl, wherein each of the $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl and 3- to 12-membered heterocyclyl is independently unsubstituted or substituted with 1, 2, 3 or 4 $R^y$;
$R^6$ is H, deuterium, $C_{1-6}$ alkyl, $C_{2-6}$ alkenyl, $C_{3-7}$ cycloalkyl, 3- to 12-membered heterocyclyl, $C_{6-10}$ aryl, 5- to 10-membered heteroaryl or $R^{17}$—C(=O)—O—(CR$^e$R$^f$)$_q$—, wherein each of the $C_{1-6}$ alkyl, $C_{2-6}$ alkenyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^z$;
$R^{6a}$ is H, deuterium, F, Cl, Br, CN, OH, $C_{1-6}$ alkyl, $C_{2-6}$ alkenyl, $C_{3-7}$ cycloalkyl, 3- to 12-membered heterocyclyl, $C_{6-10}$ aryl, 5- to 10-membered heteroaryl or $R^{17}$—C(=O)—O—(CR$^e$R$^f$)$_q$—, wherein each of the $C_{1-6}$ alkyl, $C_{2-6}$ alkenyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^z$;

$R^2$ is deuterium, Br, cyano, methyl, ethyl, $C_{3-12}$ alkyl, cyclopropyl, $C_{4-7}$ cycloalkyl, 3- to 12-membered heterocyclyl, $C_{6-10}$ aryl, 5- to 10-membered heteroaryl, $R^{13}$—$(CR^eR^f)_t$—, $R^{13a}$—$(CR^eR^f)_f$—O—, $R^{13}$—C(=O)—$(CR^eR^f)_m$—, $R^{13}$—C(=O)—N($R^g$)—$(CR^eR^f)_m$—, $R^{18}$—N($R^g$)—C(=O)—O—, $R^{19}$—N($R^n$)—C(=O)—N($R^n$)—, $R^{13}$—O—C(=O)—$(CR^eR^f)_m$—, $R^{13}$—O—C(=O)—N($R^g$)—$(CR^eR^f)_m$—, $R^c$—C(=O)—$(CR^eR^f)_m$—O—C(=O)—,

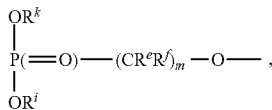

$R^{14}$—S(=O)$_2$—$(CR^eR^f)_m$—, $R^{14}$—S(=O)$_2$—N($R^g$)—$(CR^eR^f)_m$—, $R^{14}$—S(=O)$_2$—N($R^g$)—C(=O)—, $R^aR^bN$—, $R^cC$(=O)—, $R^aR^bNC$(=O)—, $R^dOC$(=O)— or $R^{10a}O$—, wherein each of the methyl, ethyl and cyclopropyl is independently substituted with 1, 2, 3 or 4 $R^w$, and wherein each of the $C_{3-12}$ alkyl, $C_{4-7}$ cycloalkyl, 3- to 12-membered heterocyclyl, $C_{6-10}$ aryl and 5- to 10-membered heteroaryl is independently unsubstituted or substituted with 1, 2, 3 or 4 $R^w$;

each of $R^3$, $R^7$ and $R^8$ is independently H, deuterium, F, Cl, Br, hydroxy, cyano, $C_{1-12}$ alkyl, $C_{3-7}$ cycloalkyl, 3- to 12-membered heterocyclyl, $C_{6-10}$ aryl, 5- to 10-membered heteroaryl, $R^{13}$—$(CR^eR^f)_m$—, $R^{13}$—$(CR^eR^f)_m$—, $R^{13}$—C(O)—$(CR^eR^f)_m$—, $R^{13}$—C(=O)—N($R^g$)—$(CR^eR^f)_m$—, $R^{13}$—O—C(=O)—$(CR^eR^f)_m$—, $R^{13}$—O—C(=O)—N($R^g$)—$(CR^eR^f)_m$—, $R^c$—C(=O)—$(CR^eR^f)_m$—O—C(=O)—,

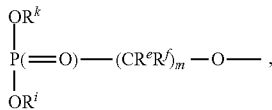

$R^{14}$—S(=O)$_2$—$(CR^eR^f)_m$—, $R^{14}$—S(=O)$_2$—N($R^g$)—$(CR^eR^f)_m$—, $R^{14}$—S(=O)$_2$—N($R^g$)—C(=O)—, $R^aR^bN$—, $R^cC$(=O)—, $R^aR^bNC$(=O)—, $R^dOC$(=O)— or $R^{10}O$—, wherein each of the $C_{1-12}$ alkyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^w$;

$R^{10}$ is H, deuterium, $C_{1-12}$ alkyl, $C_{2-12}$ alkynyl, $C_{3-7}$ cycloalkyl, 3- to 12-membered heterocyclyl, $C_{6-10}$ aryl, 5- to 10-membered heteroaryl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the $C_{1-12}$ alkyl, $C_{2-12}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^x$;

$R^{10a}$ is deuterium, methyl, ethyl, $C_{3-12}$ alkyl, $C_{2-12}$ alkynyl, $C_{3-7}$ cycloalkyl, 3- to 12-membered heterocyclyl, $C_{6-10}$ aryl, 5- to 10-membered heteroaryl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)N($R^g$)—$(CR^eR^f)_g$—, $R^{16}$—S(=O)$_2$—$(CR^eR^f)_g$— or $R^{16}$—S (=O)$_2$—N($R^g$)—$(CR^eR^f)_g$—, wherein each of the methyl and ethyl is independently substituted with 1, 2, 3 or 4 substituents selected from F, Cl, Br, CN, OH, =O, —COOH, amino, $C_{2-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alkynyl, $C_{3-6}$ cycloalkyl, 5- to 6-membered heteroaryl, 5- to 6-membered heterocyclyl, $C_{1-6}$ alkoxy-$C_{1-6}$-alkyl or $C_{1-6}$ alkylamino-$C_{1-6}$-alkyl, and wherein each of the $C_{3-12}$ alkyl, $C_{2-12}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^x$;

or $R^{10a}$ is methyl or ethyl, meanwhile $R^3$ is thienyl, furyl, pyrrolyl, triazolyl, imidazolyl, tetrazolyl, isothiazolyl, oxazolyl, thiazolyl, isoxazolyl, thiadiazolyl, oxadiazolyl or 6-membered heteroaryl, and wherein each of the thienyl, furyl, pyrrolyl, triazolyl, imidazolyl, tetrazolyl, isothiazolyl, oxazolyl, thiazolyl, isoxazolyl, thiadiazolyl, oxadiazolyl and 6-membered heteroaryl is independently unsubstituted or substituted with 1, 2, 3, or 4 substituents selected from F, Cl, Br, CN, OH, amino, $C_{1-6}$ alkyl, $C_{1-6}$ haloalkyl, $C_{1-6}$ alkoxy, $C_{1-6}$ alkoxy-$C_{1-3}$-alkyl or $C_{1-6}$ alkylamino;

each $R^{12}$ and $R^{17}$ is independently $C_{3-7}$ cycloalkyl, $C_{6-10}$ aryl, $C_{1-6}$ alkoxy, amino or $C_{1-6}$ alkylamino, wherein each of the $C_{3-7}$ cycloalkyl, $C_{6-10}$ aryl, $C_{1-6}$ alkoxy, amino and $C_{1-6}$ alkylamino is independently unsubstituted or substituted with 1, 2, 3 or 4 $R^j$;

each $R^{13}$, $R^{14}$, $R^{15}$, $R^{16}$, $R^{18}$ and $R^{19}$ is independently $C_{1-12}$ alkyl, $C_{1-12}$ alkoxy, $C_{3-7}$ cycloalkyl, 5- to 10-membered heteroaryl, 3- to 12-membered heterocyclyl or $C_{6-10}$ aryl, wherein each of the $C_{1-12}$ alkyl, $C_{1-12}$ alkoxy, $C_{3-7}$ cycloalkyl, 5- to 10-membered heteroaryl, 3- to 12-membered heterocyclyl and $C_{6-10}$ aryl is independently unsubstituted or substituted with 1, 2, 3 or 4 $R^h$;

$R^{13a}$ is methyl, $C_{2-12}$ alkyl, $C_{1-12}$ alkoxy, $C_{3-7}$ cycloalkyl, 5- to 10-membered heteroaryl, 3- to 12-membered heterocyclyl or $C_{6-10}$ aryl, wherein each of the methyl and $C_{6-10}$ aryl is independently substituted with 1, 2, 3 or 4 $R^h$, and wherein $C_{2-12}$ alkyl, $C_{1-12}$ alkoxy, $C_{3-7}$ cycloalkyl, 5- to 10-membered heteroaryl and 3- to 12-membered heterocyclyl is independently unsubstituted or substituted with 1, 2, 3 or 4 $R^h$;

each $R^a$, $R^b$, $R^c$, $R^d$, $R^e$, $R^f$, $R^g$, $R^k$, $R^i$, $R^m$ and $R^n$ is independently H, deuterium, OH, $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, 3- to 12-membered heterocyclyl or 5- to 10-membered heteroaryl, wherein each of the $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, 3- to 12-membered heterocyclyl and 5- to 10-membered heteroaryl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

or, $R^a$ and $R^b$, together with the nitrogen atom to which they are attached, form a 3- to 8-membered heterocyclyl or 5- to 8-membered heteroaryl, wherein each of the 3- to 8-membered heterocyclyl and 5- to 8-membered heteroaryl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

or, $R^m$ and $R^n$, together with the nitrogen atom to which they are attached, form a 3- to 8-membered heterocyclyl, wherein 3- to 8-membered heterocyclyl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

each $R^v$, $R^w$, $R^x$, $R^y$, $R^z$, $R^j$ and $R^h$ is independently F, Cl, Br, CN, OH, —COOH, amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl or 5- to 10-membered heteroaryl, wherein each of the amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 substituents independently selected from F, Cl, Br, CN, OH, =O, —COOH, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alkynyl, $C_{6-10}$ aryl, $C_{3-6}$ cycloalkyl, 5- to 6-membered heteroaryl, 5- to 6-membered heterocyclyl, $C_{1-6}$ alkoxy-$C_{1-6}$-alkyl or $C_{1-6}$ alkylamino-$C_{1-6}$-alkyl;

each n and q is independently 0, 1, 2, 3, 4, 5 or 6;
each t and f is independently 1, 2, 3, 4, 5 or 6; and
each m and g is independently 0, 1, 2, 3, 4, 5, 6, 7, 8, 9 or 10.

In some embodiments, $R^1$ is H, deuterium, F, Cl, Br, I, OH, —COOH, 5-membered heterocyclyl, 5-membered heteroaryl, $C_{1-4}$ alkyl, $C_{2-4}$ alkenyl, $C_{2-4}$ alkynyl, $C_{3-6}$ cycloalkyl, $R^{12}$—S(=O)$_2$—, $R^{12}$—(CR$^e$R$^f$)$_n$— or R$^a$R$^b$N—, wherein each of the 5-membered heterocyclyl, 5-membered heteroaryl, $C_{1-4}$ alkyl, $C_{2-4}$ alkenyl, $C_{2-4}$ alkynyl and $C_{3-6}$ cycloalkyl is independently unsubstituted or substituted with 1, 2, 3 or 4 R$^v$;

$R^9$ is H, deuterium, $C_{1-4}$ alkyl or $C_{1-4}$ haloalkyl; or, $R^9$ and $R^1$, together with the nitrogen atom to which they are attached, form a 5- to 6-membered heterocyclyl, wherein each of the $C_{1-4}$ alkyl, $C_{1-4}$ haloalkyl and 5- to 6-membered heterocyclyl is independently unsubstituted or substituted with 1, 2, 3 or 4 substituents selected from —COOH, =O, tetrazolyl or $C_{1-6}$ alkyl-O—C(=O)—; and each $R^{12}$, n, R$^e$, R$^f$, R$^a$, R$^b$ and R$^v$ is as defined herein.

In other embodiments, $R^1$ is H, deuterium, F, Cl, Br, I, OH, —COOH, thiazolyl, tetrazolyl, methyl, ethyl, n-propyl, isopropyl, vinyl, propenyl, ethynyl, propynyl, cyclopropyl, cyclobutyl, cyclopentyl, $R^{12}$—S(=O)$_2$—, $R^{12}$—(CR$^e$R$^f$)$_n$— or R$^a$R$^b$N—, wherein each of the thiazolyl, methyl, ethyl, n-propyl, isopropyl, vinyl, propenyl, ethynyl, propynyl, cyclopropyl, cyclobutyl and cyclopentyl is independently unsubstituted or substituted with 1, 2, 3 or 4 R$^v$;

$R^9$ is H, deuterium, methyl, ethyl, n-propyl, isopropyl or $C_{1-3}$ haloalkyl; or, $R^9$ and $R^1$, together with the nitrogen atom to which they are attached, form pyrrolidinyl, piperazinyl, piperidyl or morpholinyl, wherein each of the methyl, ethyl, n-propyl, isopropyl, $C_{1-3}$ haloalkyl, pyrrolidinyl, piperazinyl, piperidyl and morpholinyl is independently unsubstituted or substituted with 1, 2, 3 or 4 substituents selected from —COOH, =O, tetrazolyl or $C_{1-6}$ alkyl-O—C(=O)—; and each $R^{12}$, n, R$^e$, R$^f$, R$^a$, R$^b$ and R$^v$ is as defined herein.

In some embodiments, $R^2$ is deuterium, Br, cyano, methyl, ethyl, $C_{3-6}$ alkyl, cyclopropyl, $C_{4-6}$ cycloalkyl, 5- to 6-membered heterocyclyl, phenyl, naphthyl, 5- to 6-membered heteroaryl, $R^{13}$—(CR$^e$R$^f$)$_t$—, $R^{13a}$—(CR$^e$R$^f$)$_f$—O—, $R^{13}$—C(=O)—(CR$^e$R$^f$)$_m$—, $R^{13}$—C(=O)—N(R$^g$)—(CR$^e$R$^f$)$_m$—, $R^{18}$—N(R$^g$)—C(=O)—O—, $R^{19}$—N(R$^m$)—C(=O)—N(R$^n$)—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)$_m$—O—C(=O)—,

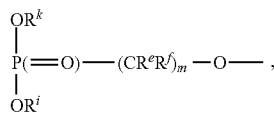

$R^{14}$—S(=O)$_2$—(CR$^e$R$^f$)$_m$—, $R^{14}$—S(=O)$_2$—N(R$^g$)—(CR$^e$R$^f$)$_m$—, $R^{14}$—S(=O)$_2$—N(R$^g$)—C(=O)—, R$^a$R$^b$N—, R$^c$C(=O)—, R$^a$R$^b$NC(=O)—, R$^d$OC(=O)— or R$^{10a}$O—, wherein each of the methyl, ethyl and cyclopropyl is independently substituted with 1, 2, 3 or 4 R$^w$, and wherein each of the $C_{3-6}$ alkyl, $C_{4-6}$ cycloalkyl, 5- to 6-membered heterocyclyl, phenyl, naphthyl and 5- to 6-membered heteroaryl is independently unsubstituted or substituted with 1, 2, 3 or 4 R$^w$; and each $R^{13a}$, $R^{10a}$, t, f, m, $R^{13}$, $R^{14}$, $R^{18}$, $R^{19}$, R$^a$, R$^b$, R$^c$, R$^d$, R$^e$, R$^f$, R$^g$, R$^m$, R$^n$, R$^k$, R$^i$ and R$^w$ is as defined herein.

In other embodiments, $R^2$ is deuterium, Br, cyano, methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{13}$—(CR$^e$R$^f$)$_t$—, $R^{13a}$—(CR$^e$R$^f$)$_f$—O—, $R^{13}$—C(=O)—(CR$^e$R$^f$)$_m$—, $R^{13}$—C(=O)—N(R$^g$)—(CR$^e$R$^f$)$_m$—, $R^{18}$—N(R$^g$)—C(=O)—O—, $R^{19}$—N(R$^m$)—C(=O)—N(R$^n$)—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)$_m$—O—C(=O)—,

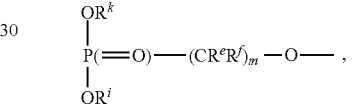

$R^{14}$—S(=O)$_2$—(CR$^e$R$^f$)$_m$—, $R^{14}$—S(=O)$_2$—N(R$^g$)—C(=O)—, $R^{14}$—S(=O)$_2$—N(R$^9$)—(CR$^e$R$^f$)$_m$—, R$^a$R$^b$N—, R$^c$C(=O)—, R$^a$R$^b$NC(=O)—, R$^d$OC(=O)— or R$^{10a}$O—, wherein each of the methyl, ethyl and cyclopropyl is independently substituted with 1, 2, 3 or 4 R$^w$, and wherein each of the n-propyl, isopropyl, n-butyl, isobutyl, n-pentyl, n-hexyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 R$^w$; and each $R^{13a}$, $R^{10a}$, t, f, m, $R^{13}$, $R^{14}$, $R^{18}$, $R^{19}$, R$^a$, R$^b$, R$^c$, R$^d$, R$^e$, R$^f$, R$^g$, R$^m$, R$^n$, R$^k$, R$^i$ and R$^w$ is as defined herein.

In some embodiments, each of $R^3$, $R^7$ and $R^8$ is independently H, deuterium, F, Cl, Br, hydroxy, cyano, $C_{1-6}$ alkyl, $C_{3-6}$ cycloalkyl, 5- to 6-membered heterocyclyl, phenyl, naphthyl, 5- to 6-membered heteroaryl, $R^{13}$—(CR$^e$R$^f$)$_m$—, $R^{13}$—(CR$^e$R$^f$)$_m$—O—, $R^{13}$—C(=O)—(CR$^e$R$^f$)$_m$—, $R^{13}$—C(=O)—N(R$^g$)—(CR$^e$R$^f$)$_m$—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)—O—C(=O)—,

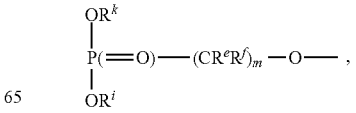

$R^{14}$—S(=O)$_2$—(CR$^e$R$^f$)$_m$—, $R^{14}$—S(=O)$_2$—N(R$^g$)—(CR$^e$R$^f$)$_m$—, $R^{14}$—S(=O)$_2$—N(R$^g$)—C(=O)—, $R^aR^bN$—, $R^cC$(=O)—, $R^aR^bNC$(=O)—, $R^dOC$(=O)— or $R^{10}O$—, and wherein each of the $C_{1-6}$ alkyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^w$;

$R^{10}$ is H, deuterium, $C_{1-6}$ alkyl, $C_{2-6}$ alkynyl, $C_{3-6}$ cycloalkyl, 5- to 6-membered heterocyclyl, phenyl, naphthyl, 5- to 6-membered heteroaryl, $R^{15}$—(CR$^e$R$^f$)$_g$—, $R^{15}$—O—(CR$^e$R$^f$)$_g$—, $R^{15}$—C(=O)—(CR$^e$R$^f$)$_g$—, $R^{15}$—O—C(=O)—(CR$^e$R$^f$)$_g$—, $R^{15}$—O—C(=O)—N(R$^g$)—(CR$^e$R$^f$)$_g$—, $R^{16}$—S(=O)$_2$—(CR$^e$R$^f$)$_g$— or $R^{16}$—S(=O)$_2$—N(R$^g$)—(CR$^e$R$^f$)$_g$—, wherein each of the $C_{1-6}$ alkyl, $C_{2-6}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^x$;

$R^{10a}$ is deuterium, methyl, ethyl, $C_{3-6}$ alkyl, $C_{2-6}$ alkynyl, $C_{3-6}$ cycloalkyl, 5- to 6-membered heterocyclyl, phenyl, naphthyl, 5- to 6-membered heteroaryl, $R^{15}$—(CR$^e$R$^f$)$_g$—, $R^{15}$—O—(CR$^e$R$^f$)$_g$—, $R^{15}$—C(=O)—(CR$^e$R$^f$)$_g$—, $R^{15}$—O—C(=O)—(CR$^e$R$^f$)$_g$—, $R^{15}$—O—C(=O)—N(R$^g$)—(CR$^e$R$^f$)$_g$—, $R^{16}$—S(=O)$_2$—(CR$^e$R$^f$)$_g$— or $R^{16}$—S(=O)$_2$—N(R$^g$)—(CR$^e$R$^f$)$_g$—, wherein each of the methyl and ethyl is independently substituted with 1, 2, 3 or 4 substituents selected from F, Cl, Br, CN, OH, =O, —COOH, amino, $C_{2-4}$ alkyl, $C_{1-4}$ haloalkyl, $C_{1-4}$ alkoxy, $C_{1-4}$ alkylthio, $C_{1-4}$ haloalkoxy, $C_{1-6}$ alkylamino, $C_{2-4}$ alkenyl, $C_{2-4}$ alkynyl, $C_{3-6}$ cycloalkyl, 5- to 6-membered heteroaryl, 5- to 6-membered heterocyclyl, $C_{1-4}$ alkoxy-$C_{1-4}$-alkyl or $C_{1-4}$ alkylamino-$C_{1-4}$-alkyl, and wherein each of the $C_{3-6}$ alkyl, $C_{2-6}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^x$;

or $R^{10a}$ is methyl or ethyl, meanwhile $R^3$ is thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl or pyrimidinyl, and wherein each of the thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl and pyrimidinyl is independently unsubstituted or substituted with 1, 2, 3, or 4 substituents selected from F, Cl, Br, CN, OH, amino, $C_{1-4}$ alkyl, $C_{1-4}$ haloalkyl, $C_{1-4}$ alkoxy, $C_{1-4}$ alkoxy-$C_{1-2}$-alkyl or $C_{1-4}$ alkylamino; and each m, g, $R^{13}$, $R^{14}$, $R^{15}$, $R^{16}$, $R^a$, $R^b$, $R^c$, $R^d$, $R^e$, $R^f$, $R^g$, $R^x$, $R^k$, $R^i$ and $R^w$ is as defined herein.

In some embodiments, each of $R^3$, $R^7$ and $R^8$ is independently H, deuterium, F, Cl, Br, hydroxy, cyano, methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{13}$—(CR$^e$R$^f$)$_m$—, $R^{13}$—(CR$^e$R$^f$)$_m$—O—, $R^{13}$—C(=O)—(CR$^e$R$^f$)$_m$—, $R^{13}$—C(=O)—N(R$^g$)—(CR$^e$R$^f$)$_m$—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)$_m$—O—C(=O)—,

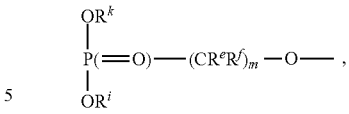

$R^{14}$—S(=O)$_2$—(CR$^e$R$^f$)$_m$—, $R^{14}$—S(=O)$_2$—N(R$^g$)—(CR$^e$R$^f$)$_m$—, $R^{14}$—S(=O)$_2$—N(R$^g$)—C(=O)—, $R^aR^bN$—, $R^cC$(=O)—, $R^aR^bNC$(=O)—, $R^dOC$(=O)— or $R^{10}O$—, and wherein each of the methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^w$;

$R^{10}$ is H, deuterium, methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{15}$—(CR$^e$R$^f$)$_g$—, $R^{15}$—O—(CR$^e$R$^f$)$_g$—, $R^{15}$—C(=O)—(CR$^e$R$^f$)$_g$—, $R^{15}$—O—C(=O)—(CR$^e$R$^f$)$_g$—, $R^{15}$—O—C(=O)—N(R$^g$)—(CR$^e$R$^f$)$_g$—, $R^{16}$—S(=O)$_2$—(CR$^e$R$^f$)$_g$— or $R^{16}$—S(=O)$_2$—N(R$^g$)—(CR$^e$R$^f$)$_g$—, wherein each of the methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^x$;

$R^{10a}$ is deuterium, methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{15}$—(CR$^e$R$^f$)$_g$—, $R^{15}$—O—(CR$^e$R$^f$)$_g$—, $R^{15}$—C(=O)—(CR$^e$R$^f$)$_g$—, $R^{15}$—O—C(=O)—(CR$^e$R$^f$)$_g$—, $R^{15}$—O—C(=O)—N(R$^g$)—(CR$^e$R$^f$)$_g$—, $R^{16}$—S(=O)$_2$—(CR$^e$R$^f$)$_g$— or $R^{16}$—S(=O)$_2$—N(R$^g$)—(CR$^e$R$^f$)$_g$—, wherein each of the methyl and ethyl is independently substituted with 1, 2, 3 or 4 substituents selected from F, Cl, Br, CN, OH, =O, —COOH, amino, $C_{2-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, $C_{3-6}$ cycloalkyl, 5- to 6-membered heterocyclyl, 5- to 6-membered heterocyclyl, $C_{1-4}$ alkoxy-$C_{1-3}$-alkyl or $C_{1-4}$ alkylamino-$C_{1-3}$-alkyl, wherein each of the n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^x$;

or $R^{10a}$ is methyl or ethyl, meanwhile $R^3$ is thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl or pyrimidinyl, and wherein each of the thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl and pyrimidinyl is independently unsubstituted or substituted with 1, 2, 3, or 4 substituents selected from F, Cl, Br, CN, OH, amino, $C_{1-3}$ alkyl, $C_{1-3}$ haloalkyl, $C_{1-3}$ alkoxy, $C_{1-3}$ alkoxymethyl or $C_{1-3}$ alkylamino; and each m, g, $R^{13}$, $R^{14}$, $R^{15}$, $R^{16}$, $R^a$, $R^b$, $R^c$, $R^d$, $R^e$, $R^f$, $R^g$, $R^x$, $R^k$, $R^i$ and $R^w$ is as defined herein.

In some embodiments, each of $R^4$ and $R^5$ is independently H, deuterium, $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl or 5- to 6-membered heterocyclyl, and wherein each of the $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl and 5- to 6-membered heterocyclyl is independently unsubstituted or substituted with 1, 2, 3 or 4 $R^y$;

$R^6$ is H, deuterium, $C_{1-4}$ alkyl, $C_{2-4}$ alkenyl, $C_{3-6}$ cycloalkyl, 5- to 6-membered heterocyclyl, phenyl, naphthyl, 5- to 10-membered heteroaryl or $R^{17}-C(=O)-O-(CR^eR^f)_q-$, wherein each of the $C_{1-4}$ alkyl, $C_{2-4}$ alkenyl, $C_{3-6}$ cycloalkyl, 5- to 6-membered heterocyclyl, phenyl, naphthyl and 5- to 10-membered heteroaryl is independently unsubstituted or substituted with 1, 2, 3 or 4 $R^z$;

$R^{6a}$ is H, deuterium, F, Cl, Br, CN, OH, $C_{1-4}$ alkyl, $C_{2-4}$ alkenyl, $C_{3-6}$ cycloalkyl, 5- to 6-membered heterocyclyl, phenyl, naphthyl, 5- to 10-membered heteroaryl or $R^{17}-C(=O)-O-(CR^eR^f)_q-$, wherein each of the $C_{1-4}$ alkyl, $C_{2-4}$ alkenyl, $C_{3-6}$ cycloalkyl, 5- to 6-membered heterocyclyl, phenyl, naphthyl and 5- to 10-membered heteroaryl is independently unsubstituted or substituted with 1, 2, 3 or 4 $R^z$; and each q, $R^{17}$, $R^e$, $R^f$, $R^z$ and $R^y$ is as defined herein.

In other embodiments, each of $R^4$ and $R^5$ is independently H, deuterium, $C_{1-3}$ alkyl, $C_{1-3}$ alkylamino, $C_{1-3}$ alkoxy, $C_{2-4}$ alkynyl, $C_{2-4}$ alkenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl or piperazinyl, wherein each of the $C_{1-3}$ alkyl, $C_{1-3}$ alkylamino, $C_{1-3}$ alkoxy, $C_{2-4}$ alkynyl, $C_{2-4}$ alkenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl and piperazinyl is independently unsubstituted or substituted with 1, 2, 3, or 4 $R^y$;

$R^6$ is H, deuterium, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl, naphthyl, or $R^{17}-C(=O)-O-(CR^eR^f)_q-$, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl and naphthyl is independently unsubstituted or substituted with 1, 2, 3, or 4 $R^z$;

$R^{6a}$ is H, deuterium, F, Cl, Br, CN, OH, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl, naphthyl, or $R^{17}-C(=O)-O-(CR^eR^f)_q-$, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl and naphthyl is independently unsubstituted or substituted with 1, 2, 3, or 4 $R^z$; and each q, $R^{17}$, $R^e$, $R^f$, $R^z$ and $R^y$ is as defined herein.

In some embodiments, each $R^{12}$ and $R^{17}$ is independently $C_{3-6}$ cycloalkyl, phenyl, naphthyl, $C_{1-4}$ alkoxy, amino or $C_{1-4}$ alkylamino, wherein each of the $C_{3-6}$ cycloalkyl, phenyl, naphthyl, $C_{1-4}$ alkoxy, amino and $C_{1-4}$ alkylamino is independently unsubstituted or substituted with 1, 2, 3 or 4 $R^j$;

each $R^{13}$, $R^{14}$, $R^{15}$, $R^{16}$, $R^{18}$ and $R^{19}$ is independently $C_{1-6}$ alkyl, $C_{1-6}$ alkoxy, $C_{3-6}$ cycloalkyl, 5- to 6-membered heteroaryl, 5- to 6-membered heterocyclyl, phenyl or naphthyl, wherein each of the $C_{1-6}$ alkyl, $C_{1-6}$ alkoxy, $C_{3-6}$ cycloalkyl, 5- to 6-membered heteroaryl, 5- to 6-membered heterocyclyl, phenyl and naphthyl is independently unsubstituted or substituted with 1, 2, 3 or 4 $R^h$;

$R^{13a}$ is methyl, $C_{2-6}$ alkyl, $C_{1-6}$ alkoxy, $C_{3-6}$ cycloalkyl, 5- to 6-membered heteroaryl, 5- to 6-membered heterocyclyl, phenyl or naphthyl, wherein each of the methyl, phenyl and naphthyl is independently substituted with 1, 2, 3 or 4 $R^h$, and wherein each of the $C_{2-6}$ alkyl, $C_{1-6}$ alkoxy, $C_{3-6}$ cycloalkyl, 5- to 6-membered heteroaryl and 5- to 6-membered heterocyclyl is independently unsubstituted or substituted with 1, 2, 3 or 4 $R^h$; and each $R^j$ and $R^h$ is as defined herein.

In other embodiments, each $R^{12}$ and $R^{17}$ is independently cyclopropyl, cyclobutyl, cyclopentyl, cyclohexyl, phenyl, naphthyl, methoxy, ethoxy, propoxy, isopropoxy, n-butoxy, amino, N-methylamino, N-ethylamino, N,N-dimethylamino or N,N-diethylamino, wherein each of the cyclopropyl, cyclobutyl, cyclopentyl, cyclohexyl, phenyl, naphthyl, methoxy, ethoxy, propoxy, isopropoxy, n-butoxy, amino, N-methylamino, N-ethylamino, N,N-dimethylamino and N,N-diethylamino is independently unsubstituted or substituted with 1, 2, 3, or 4 $R^j$;

each $R^{13}$, $R^{14}$, $R^{15}$, $R^{16}$, $R^{18}$ and $R^{19}$ is independently methyl, ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the methyl, ethyl, n-propyl, isopropyl, n-butyl, isobutyl, tert-butyl, methoxy, ethoxy, propoxy, isopropyl, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3, or 4 $R^h$;

$R^{13a}$ is methyl, ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the methyl, phenyl and naphthyl is independently substituted with 1, 2, 3 or 4 $R^h$, and wherein each of the ethyl, n-propyl, isopropyl, n-butyl, isobutyl, tert-butyl, methoxy, ethoxy, propoxy, isopropyl, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted with 1, 2, 3, or 4 $R^h$; and each $R^j$ and $R^h$ is as defined herein.

In some embodiments, each $R^a$, $R^b$, $R^c$, $R^d$, $R^e$, $R^f$, $R^g$, $R^k$, $R^i$, $R^m$ and $R^n$ is independently H, deuterium, OH, $C_{1-4}$ haloalkyl, $C_{1-6}$ alkyl, $C_{1-4}$ alkoxy, $C_{2-4}$ alkenyl, $C_{2-4}$ alkynyl, $C_{3-6}$ cycloalkyl, phenyl, naphthyl, 5- to 6-membered heterocyclyl or 5- to 6-membered heteroaryl, wherein each of the $C_{1-4}$ haloalkyl, $C_{1-6}$ alkyl, $C_{1-4}$ alkoxy, $C_{2-4}$ alkenyl, $C_{2-4}$ alkynyl, $C_{3-6}$ cycloalkyl, phenyl, naphthyl, 5- to 6-membered heterocyclyl and 5- to 6-membered heteroaryl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^a$ and $R^b$, together with the nitrogen atom to which they are attached, form a 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^m$ and $R^n$, together with the nitrogen atom to which they are attached, form a 3- to 6-membered heterocyclyl, wherein 3- to 6-membered heterocyclyl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino.

In other embodiments, each $R^a$, $R^b$, $R^c$, $R^d$, $R^e$, $R^f$, $R^g$, $R^k$, $R^i$, $R^m$ and $R^n$ is independently H, deuterium, OH, $C_{1-3}$ haloalkyl, methyl, ethyl, n-propyl, isopropyl, n-butyl, isobutyl, tert-butyl, n-pentyl, 3-pentyl, methoxy, ethoxy, propoxy, isopropoxy, n-butoxy, ethenyl, propenyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the $C_{1-3}$ haloalkyl, methyl, ethyl, n-propyl, isopropyl, n-butyl, isobutyl, tert-butyl, methoxy, ethoxy, propoxy, isopropoxy, n-butoxy, ethenyl, propenyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3, or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^a$ and $R^b$, together with the nitrogen atom to which they are attached, form pyrrolidinyl, pyrazolidinyl, imidazolidinyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, pyrazinyl, pyridazinyl or pyrimidinyl, wherein each of the pyrrolidinyl, pyrazolidinyl, imidazolidinyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, pyrazinyl, pyridazinyl and pyrimidinyl is independently unsubstituted or substituted with 1, 2, 3, or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^m$ and $R^n$, together with the nitrogen atom to which they are attached, form a 4- to 6-membered heterocyclyl, wherein 4- to 6-membered heterocyclyl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino.

In some embodiments, each $R^v$, $R^w$, $R^x$, $R^y$, $R^z$, $R^j$ and $R^h$ is independently F, Cl, Br, CN, OH, —COOH, amino, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylamino, $C_{2-4}$ alkenyl, $C_{2-4}$ alkynyl, $C_{3-6}$ cycloalkyl, 5- to 6-membered heterocyclyl, phenyl, naphthyl or 5- to 6-membered heteroaryl, wherein each of the amino, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylamino, $C_{2-4}$ alkenyl, $C_{2-4}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 substituents independently selected from F, Cl, Br, CN, OH, =O, —COOH, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, phenyl, naphthyl, $C_{3-6}$ cycloalkyl, 5- to 6-membered heteroaryl, 5- to 6-membered heterocyclyl, $C_{1-4}$ alkoxy-$C_{1-4}$-alkyl or $C_{1-4}$ alkylamino-$C_{1-4}$-alkyl.

In other embodiments, each $R^v$, $R^w$, $R^x$, $R^y$, $R^z$, $R^j$ and $R^h$ is independently F, Cl, Br, CN, OH, —COOH, amino, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl or naphthyl, wherein each of the cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 substituents independently selected from F, Cl, Br, CN, OH, =O, —COOH, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $C_{1-3}$ alkoxy-$C_{1-3}$-alkyl and $C_{1-3}$ alkylamino-$C_{1-3}$-alkyl.

In still other embodiments, each $R^v$, $R^w$, $R^x$, $R^y$, $R^z$, $R^j$ and $R^h$ is independently F, Cl, Br, CN, OH, —COOH, amino, methyl, ethyl, n-propyl, isopropyl, n-butyl, i-butyl, t-butyl, $C_{1-4}$ haloalkyl, $C_{1-4}$ alkoxy, $C_{1-4}$ haloalkoxy, $C_{1-4}$ alkylthio, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl or naphthyl, wherein each of the cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 substituents independently selected from F, Cl, Br, CN, OH, =O, —COOH, amino, methyl, ethyl, n-propyl, isopropyl, n-butyl, i-butyl, t-butyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $C_{1-3}$ alkoxy-$C_{1-3}$-alkyl and $C_{1-3}$ alkylamino-$C_{1-3}$-alkyl.

In another aspect, provided herein is a pharmaceutical composition comprising the compound of the invention; optionally, wherein the pharmaceutical composition further comprises a pharmaceutically acceptable excipient, or a combination of the excipients.

In some embodiments, the pharmaceutical composition disclosed herein further comprises other anti-HBV drug.

In some embodiments, the pharmaceutical composition disclosed herein, wherein the other anti-HBV drug is a HBV polymerase inhibitor, an immunomodulator or an interferon.

In some embodiments, the pharmaceutical composition disclosed herein, wherein the other anti-HBV agent is lamivudine, telbivudine, tenofovir, entecavir, adefovir dipivoxil, alfaferone, alloferon, celmoleukin, clevudine, emtricitabine, famciclovir, interferon, hepatect C P, intefen, interferon-1b, interferon, interferon-2a, interferon $\beta$-1a, interferon-2, interleukin-2, mivotilate, nitazoxanide, peginterferon alfa-2a, ribavirin, roferon-A, sizofiran, euforavac, ampligen, phosphazid, heplisav, interferon-2b, levamisole or propagermanium.

In another aspect, provided herein is use of the compound or the pharmaceutical composition of the invention in the manufacture of a medicament for preventing, treating or lessening a disorder or disease caused by a virus infection in a patient.

In some embodiments, the use disclosed herein, wherein the virus disease is hepatitis B infection or a disease caused by hepatitis B infection.

In other embodiments, the use disclosed herein, wherein the disease caused by hepatitis B infection is cirrhosis or hepatocellular carcinogenesis.

In another aspect, provided herein is use of the compound of the invention in the manufacture of a medicament for preventing, managing or treating a HBV disorder or disease in a patient, or lessening the severity of the HBV disorder or disease in a patient.

In another aspect, provided herein is use of the pharmaceutical composition comprising the compound of the invention in the manufacture of a medicament for preventing, managing or treating a HBV disorder or disease in a patient, or lessening the severity of the HBV disorder or disease in a patient.

In another aspect, provided herein is use of the compound or the pharmaceutical composition of the invention in the manufacture a medicament for inhibiting the production or secretion of HBsAg, and/or for inhibiting the production of HBV DNA.

In another aspect, provided herein is the compound or the pharmaceutical composition of the invention for use in preventing, treating or lessening a disorder or disease caused by a virus infection in a patient.

In some embodiments, the compound or the pharmaceutical composition disclosed herein, wherein the virus disease is hepatitis B infection or a disease caused by hepatitis B infection.

In other embodiments, the compound or the pharmaceutical composition disclosed herein, wherein the disease caused by hepatitis B infection is cirrhosis or hepatocellular carcinogenesis.

In another aspect, provided herein is the compound or the pharmaceutical composition of the invention for use in inhibiting the production or secretion of HBsAg, and/or in inhibiting the production of HBV DNA in a patient.

In another aspect, provided herein is a method of preventing, treating or lessening a disorder or disease caused by a virus infection in a patient comprising administering to the patient a therapeutically effective amount of the compound or the pharmaceutical composition of the invention.

In some embodiments, the method disclosed herein, wherein the virus disease is hepatitis B infection or a disease caused by hepatitis B infection.

In other embodiments, the method disclosed herein, wherein the disease caused by hepatitis B infection is cirrhosis or hepatocellular carcinogenesis.

In another aspect, provided herein is a method of preventing, treating or lessening a HBV disorder or disease in a patient comprising administering to the patient a therapeutically effective amount of the compound of the invention.

In another aspect, provided herein is a method of preventing, treating or lessening a HBV disorder or disease in a patient comprising administering to the patient a therapeutically effective amount of the pharmaceutical composition comprising the compound of the invention.

In another aspect, provided herein is a method of inhibiting the production or secretion of HBsAg, and/or inhibiting the production of HBV DNA in a patient, comprising administering to the patient a therapeutically effective amount of the compound or the pharmaceutical composition of the invention.

In another aspect, provided herein is a method of inhibiting HBV infection, comprising contacting a cell with an amount of the compound or composition of the invention that is effective to inhibit HBV. In other embodiments, the method further comprises contacting the cell with an anti-HBV agent.

In another aspect, provided herein is a method of treating HBV disorder or disease in a patient, comprising administering to the patient an effective therapeutic amount of the compound or composition of the invention. In other embodiments, the method further comprises administration of other HBV therapy.

In another aspect, provided herein is a method of inhibiting HBV infection in a patient, comprising administering to the patient an effective therapeutic amount of the compound or composition of the invention. In other embodiments, the method further comprises administration of other HBV therapy.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application prevails.

As used herein, the following definitions shall be applied unless otherwise indicated. For purposes disclosed herein, the chemical elements are identified in accordance with the Periodic Table of the Elements, CAS version, and the Handbook of Chemistry and Physics, 75 thE d. 1994. Additionally, general principles of organic chemistry are described in Sorrell et al., 'Organic Chemistry_, University Science Books, Sausalito: 1999, and 'March˜s Advanced Organic Chemistry_, by Michael B. Smith and Jerry March, John Wiley & Sons, New York: 2007, all of which are incorporated herein by reference in their entireties.

As described herein, compounds disclosed herein may optionally be substituted with one or more substituents, such as are illustrated generally below, or as exemplified by particular classes, subclasses, and species of the invention. In general, the term 'substituted_ refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substitutents may be, but are not limited to F, Cl, Br, CN, OH, —COOH, amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl or 5- to 10-membered heteroarylo, and the like.

At various places in the present specification, substituents of compounds disclosed herein are disclosed in groups or in ranges. It is specifically intended that the invention include each and every individual subcombination of the members of such groups and ranges. For example, the term '$C_1$-$C_6$ alkyl_ or '$C_{1-6}$ alkyl_ is specifically intended to individually disclose methyl, ethyl, $C_3$ alkyl, $C_4$ alkyl, $C_5$ alkyl and $C_6$ alkyl.

Furthermore, what need to be explained is that the phrase 'eachǔ is independently_, 'eachǔ andǔ is independently_ and 'each ofǔ andǔ is independently_, unless otherwise stated, should be used exchangeably and broadly understood. The specific options expressed by the same symbol are independent of each other in different groups; or the specific options expressed by the same symbol are independent of each other in same groups.

The term 'alkyl_ or 'alkyl group_ refers to a saturated linear or branched-chain monovalent hydrocarbon radical of 1 to 20 carbon atoms, wherein the alkyl radical may be optionally and independently substituted with one or more substituents described herein. In some embodiments, the alkyl group contains 1-12 carbon atoms. In other embodiments, the alkyl group contains 1-8 carbon atoms. In other embodiments, the alkyl group contains 1-6 carbon atoms. In other embodiments, the alkyl group contains 2-6 carbon atoms. In still other embodiments, the alkyl group contains 1-4 carbon atoms. In yet other embodiments, the alkyl group contains 2-4 carbon atoms and in still yet other embodiments, the alkyl group contains 1-3 carbon atoms. Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), 2-methylpropyl or isobutyl (i-Bu, —$CH_2CH(CH_3)_2$), 1-methylpropyl or sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)$ CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3, 3-dimethyl-2-butyl (—CH(CH$_3$)C(CH$_3$)$_3$), n-heptyl and n-octyl, etc. The term 'alkyl_ or the prefix 'alk-_ is inclusive of both straight chain and branched saturated carbon chain. The term 'halogenated aliphatic_ as used herein refers to an aliphatic group that is substituted with one or more of the same or different halogen atoms, wherein the aliphatic or alkyl group are as defined herein, and the halogen atom is fluorine, chlorine, bromine or iodine, and such examples include, but are not limited to, trifluoromethyl, trifluoroethyl, and the like.

The terms 'haloalkyl_, 'haloalkenyl_ or 'haloalkoxy_ refer to alkyl, alkenyl or alkoxy, as the case may be, substituted with one or more halogen atoms. In some embodiments, the haloalkyl group contains 1-12 carbon atoms. In other embodiments, the haloalkyl group contains 1-10 carbon atoms. In other embodiments, the haloalkyl group contains 1-8 carbon atoms. In still other embodiments, the haloalkyl group contains 1-6 carbon atoms. In yet other embodiments, the haloalkyl group contains 1-4 carbon atoms; and in still yet other embodiments, the haloalkyl group contains 1-3 carbon atoms. Such examples include, but are not limited to, trifluoromethyl, trifluoroethyl, trifluoromethoxy, 2-fluorovinyl, etc. Wherein each of the haloalkyl, haloalkenyl and haloalkoxy may be independently unsubstituted or substituted with one or more substituents described herein.

The terms 'carboxy_ or 'carboxyl_, whether used alone or with other terms, such as 'carboxyalkyl_, refer to —CO$_2$H or —COOH.

The term 'carbonyl_, whether used alone or with other terms, such as 'aminocarbonyl_, 'acyloxy_, denotes —(C=O)—.

The term 'alkylamino_ refers to 'N-alkylamino_ and 'N,N-dialkylamino_ wherein amino groups are independently substituted with one alkyl radical or two alkyl radicals, respectively. In some embodiments, the alkylamino radical is 'lower alkylamino_ radical having one or two $C_{1-12}$ alkyl groups attached to a nitrogen atom. In some embodiments, the alkylamino radical refers to $C_{1-6}$ lower alkylamino group. In some embodiments, the alkylamino radical refers to $C_{1-4}$ lower alkylamino group. The suitable alkylamino group include monoalkylamino or dialkylamino, such examples include, but are not limited to N-methylamino, N-ethylamino, N,N-dimethylamino, N,N-diethylamino, N-propylamino, N,N-dipropylamino, and the like, wherein the alkylamino group may be independently unsubstituted or substituted with one or more substituents described herein.

The term 'alkylene_ refers to a saturated divalent hydrocarbon group derived from a straight or branched chain saturated hydrocarbon by the removal of two hydrogen atoms. Unless otherwise specified, the alkylene group contains 1-12 carbon atoms. In other embodiments, the alkylene group contains 1-6 carbon atoms. In other embodiments, the alkylene group contains 1-4 carbon atoms. In still other embodiments, the alkylene group contains 1-3 carbon atoms.

In yet other embodiments, the alkylene group contains 1-2 carbon atoms. Examples of such group include, methylene (—CH$_2$—), ethylene (—CH$_2$CH$_2$—), propylene (—CH$_2$CH$_2$CH$_2$—), isopropylene (—CH(CH$_3$)CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), heptylene (—CH$_2$CH$_2$CH$_2$CH$_2$CH$_2$CH$_2$CH$_2$—), octylene (—CH$_2$CH$_2$CH$_2$CH$_2$CH$_2$CH$_2$CH$_2$CH$_2$—), and the like. Wherein the alkylene group may independently be unsubstituted or substituted by one or more substituents described herein.

The term 'alkenyl_ refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, $sp^2$ double bond, wherein the alkenyl radical may be independently unsubstituted or substituted with one or more substituents described herein, and includes radicals having 'cis_ and 'trans_ orientations, or alternatively, 'E_ and 'Z_ orientations. Specific examples of the alkenyl group include, but are not limited to, vinyl (—CH=CH$_2$), allyl (—CH$_2$CH=CH$_2$), and the like. Wherein the alkenyl group may independently be unsubstituted or substituted by one or more substituents described herein.

The term 'alkynyl_ refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical may be independently unsubstituted or substituted with one or more substituents described herein. Specific examples of the alkynyl group include, but are not limited to, ethynyl (—C CH), propargyl (—CH$_2$C CH), 1-propinyl (—C C—CH$_3$), butyl-1-yne (—CH$_2$CH$_2$C CH), butyl-2-yne (—CH$_2$C CCH$_3$), butyl-3-yne (—C CCH$_2$CH$_3$), and the like. The alkynyl group may independently be unsubstituted or substituted by one or more substituents described herein.

The term 'alkoxy_ refers to an alkyl group, as previously defined, attached to the parent molecular moiety via an oxygen atom. Unless otherwise specified, the alkoxy group contains 1-20 carbon atoms. In other embodiments, the alkoxy group contains 1-12 carbon atoms. In other embodiments, the alkoxy group contains 1-8 carbon atoms. In still other embodiments, the alkoxy group contains 1-6 carbon atoms. In yet other embodiments, the alkoxy group contains 1-4 carbon atoms; and in still yet other embodiments, the alkoxy group contains 1-3 carbon atoms.

Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like. Wherein the alkoxy group is independently unsubstituted or substituted with one or more substitutents disclosed herein.

The term 'carbocycle_, 'carbocyclyl_, 'carbocyclic_ or 'carbocyclic ring_ used interchangeably herein refers to a non-aromatic carbocyclic ring system having 3 to 14 ring carbon atoms, which is saturated or contains one or more units of unsaturation. In some embodiments, the number of carbon atom is 3 to 12; in other embodiments, the number of carbon atom is 3 to 10; in other embodiments, the number of carbon atom is 3 to 8; in other embodiments, the number of carbon atom is 3 to 6; in other embodiments, the number of carbon atom is 5 to 6; in other embodiments, the number of carbon atom is 5 to 8; in other embodiments, the number of carbon atom is 6 to 8. The 'carbocyclyl_ includes a monocyclic, bicyclic, or polycyclic fused ring, spiro ring or bridged ring system, and a polycyclic ring system containing one carbocyclic ring fused with one or more non-aromatic carbocyclic ring or heterocyclic ring, or one or more aromatic ring, or a combination thereof, wherein the linked group or point exists on carbocyclic ring. The bicyclic carbocyclyl groups includes bridged bicyclic carbocyclyl, fused bicyclic carbocyclyl and spiro bicyclic carbocyclyl group, and fused bicyclic system contains two rings which share two adjacent ring atoms. Bridged bicyclic group contains two rings which share three or four adjacent ring atoms. Spiro bicyclic system contains two rings which share one ring atom. Some non-limiting examples of the cycloaliphatic group include cycloalkyl, cycloalkenyl and cycloalkynyl. Further examples of carbocyclyl groups include cyclopropyl, cyclobutyl, cyclopentyl, 1-cyclopent-l-enyl, l-cyclopent-2-enyl, l-cyclopent-3-enyl, cyclohexyl, 1-cyclohex-l-enyl, l-cyclohex-2-enyl, l-cyclohex-3-enyl, cyclohexadienyl, cycloheptyl, cyclooctyl, cyclononyl, cyclodecyl, cycloundecyl, cyclododecyl, and the like. Bridged bicyclic carbocyclyl group includes, but are not limited to, bicyclo[2.2.2]octyl, bicyclo[2.2.1]heptyl, bicyclo[3.3.1]nonyl, bicyclo[3.2.3]nonyl, and the like.

The term 'cycloalkyl_ refers to a saturated ring having 3 to 12 ring carbon atoms as a monocyclic, bicyclic, or tricyclic ring system, which has one or more attachments attaching to the rest of the molecule. In some embodiments, the cycloalkyl group contains 3 to 10 ring carbon atoms. In other embodiments, the cycloalkyl group contains 3 to 8 ring carbon atoms. In other embodiments, the cycloalkyl group contains 3 to 7 ring carbon atoms. In other embodiments, the cycloalkyl group contains 5 to 8 ring carbon atoms. In still other embodiments, the cycloalkyl group contains 3 to 6 ring carbon atoms. In yet other embodiments, the cycloalkyl group contains 5 to 6 ring carbon atoms. Examples of cycloalkyl group include, but are not limited to, cyclopropyl, cyclobutyl, cyclopentyl, cyclohexyl, and the like. The cycloalkyl radical is independently unsubstituted or substituted with one or more substituents described herein.

The term 'heterocycle_, 'heterocyclyl_, or 'heterocyclic ring_ as used interchangeably herein refers to a saturated or partially unsaturated non-aromatic monocyclic, bicyclic or tricyclic ring containing 3-12 ring atoms of which at least one ring atom is selected from nitrogen, sulfur and oxygen, and of which may has one ore more attachments attached to the rest of the molecule. The term 'heterocyclyl_ includes a monocyclic, bicyclic, or polycyclic fused, spiro, bridged heterocyclic ring system, and a polycyclic ring system containing one heterocyclic ring fused with one or more non-aromatic carbocyclic ring or heterocyclic ring, or one or more aromatic ring, or a combination thereof, wherein the linked group or attachment exists on heterocyclic ring. Biheterocyclyl radical includes bridged biheterocyclyl, fused biheterocyclyl and spiro biheterocyclyl. Unless otherwise specified, the heterocyclyl group may be carbon or nitrogen linked, and a —CH$_2$— group can be optionally replaced by a —C(=O)— group. In which, the sulfur can be optionally oxygenized to S-oxide. and the nitrogen can be optionally oxygenized to N-oxide. In some embodiments, the heterocyclyl group is a 3- to 12-membered ring system; in other embodiments, the heterocyclyl group is a 3- to 8-membered ring system; in other embodiments, the heterocyclyl group is a 3- to 6-membered ring system; in other embodiments, the heterocyclyl group is a 5- to 7-membered ring system; in other embodiments, the heterocyclyl group is a 5- to 8-membered ring system; in other embodiments, the heterocyclyl group is a 6- to 8-membered ring system; in other embodiments, the heterocyclyl group is a 5- to 6-membered ring system; in other embodiments, the heterocyclyl group is a 3-membered ring system; in other embodiments, the heterocyclyl group is a 4-membered ring system; in other embodiments, the heterocyclyl group is a 5-membered ring system; in other embodiments, the heterocyclyl group is a 6-membered ring system; in other embodiments, the heterocyclyl group is a 7-membered ring system; in other embodiments, the heterocyclyl group is a 8-membered ring system.

Examples of heterocyclyl group include, but are not limited to, heterocyclyl group may be a carbon radical or heteroatom radical. The heterocyclyl group also includes a group in which the heterocyclyl group is fused with a saturated or partially unsaturated ring or a heterocyclic ring. Examples of heterocyclyl group include, but are not limited to, pyrrolidinyl, tetrahydrofuranyl, dihydrofuranyl, tetrahydrothiophenyl, tetrahydropyranyl, dihydropyranyl, tetrahydrothiopyranyl, piperidyl, morpholinyl, thiomorpholinyl, thioxanyl, piperazinyl, homopiperazinyl, azetidinyl, oxetanyl, thietanyl, homopiperidyl, glycidyl, azacycloheptyl, oxacycloheptyl, thiacycloheptyl, oxazepinyl, diazepinyl, thiazepinyl, 2-pyrrolinyl, 3-pyrrolinyl, dihydroindolyl, 2H-pyranyl, 4H-pyranyl, dioxanyl, 1,3-dioxolanyl, pyrazolinyl, dithianyl, dithiolanyl, dihydrothiophenyl, pyrazolidinyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolylquinolizinyl and N-pyridyl urea. Examples of heterocyclyl group also include, 1,1-dioxythiomorpholinyl; wherein examples of ring carbon atom is replaced with oxo (=O) group include, but are not limited to, pyrimidinyl-dione, 1,2,4-thiadiazol-5(4H)-yl-one, 1,2,4-oxadiazol-5(4H)-yl-one, 1H-1,2,4-triazol-5 (4H)-yl-one, and the like; examples of the ring carbon atom is replaced with a =S group include, but are not limited to, 1,2,4-oxadiazol-5(4H)-yl-thione, 1,3,4-oxadiazol-2(3H)-yl-thione and so on. The heterocyclyl group may be optionally substituted with one or more substituents disclosed herein.

The terms 'heterocyclylalkylene_ and 'heterocyclylalkyl_ are used interchangeably herein to refer that an alkyl group is substituted with 1, 2, 3, or 4 heterocyclyl groups, wherein the heterocyclyl group, alkyl and alkylene group are as defined herein. Some non-limiting examples of such group include pyrrol-2-ylmethyl, morpholin-4-yl methyl, etc.

The term 'heterocyclylalkoxy_ refers that an alkoxy group is substituted with 1, 2, 3, or 4 heterocyclyl groups, wherein the heterocyclyl group and alkoxy group are as defined herein. Some non-limiting examples of such group include pyrrol-2-ylmethoxy, piperid-2-ylethoxy, etc.

The term 'heterocyclylalkylamino_ refers to an alkylamino group substituted with heterocyclyl group, wherein the nitrogen atom attaches to the rest of the molecule; and wherein the heterocyclyl and alkylamino are as defined herein. Examples of such groups include, but are not limited to, piperazin-2-ylethylamino, morpholin-4-ylpropoxy, morpholin-4-yl ethylamino, and the like.

The term 'heteroatom_ refers to one or more of oxygen (O), sulfur (S), nitrogen (N), phosphorus (P) and silicon (Si), including any oxidized form of nitrogen (N), sulfur (S), or phosphorus (P); primary, secondary, tertiary or quaternary ammonium salts; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term 'halogen_ or 'halogen atom_ refers to fluorine (F), chlorine (Cl), bromine (Br), or iodine (I).

The term 'unsaturated_ refers to a moiety having one or more units of unsaturation.

The term 'aryl_ used alone or as a great part of 'arylalkyl_, 'arylalkoxy_, or 'aryloxyalkyl_ refers to monocyclic, bicyclic and tricyclic carbocyclic ring systems having a total of 6 to 14 ring carbon atoms, or 6 to 12 ring carbon atoms, or 6 to 10 ring carbon atoms, wherein at least one ring in the system is aromatic, wherein each ring in the system contains 3 to 7 ring carbon atoms and that has a single point or multipoint of attachment to the rest of the molecule. The term 'aryl_ may be used interchangeably with the term 'aryl ring_ or 'aromatic ring_. Some non-limiting examples of the aryl group include phenyl, naphthyl and anthracene. The aryl group may be optionally unsubstituted or substituted with one or more substituents disclosed herein.

The term 'heteroaryl_ used alone or as a great part of 'heteroarylalkyl_ or 'heteroarylalkoxy_, refers to monocyclic, bicyclic or tricyclic ring system having a total of five to sixteen ring members, wherein at least one ring in the system is aromatic, and in which at least one ring member is selected from heteroatom, and wherein each ring in the system contains 5 to 7 ring members and that has a single point or multipoint of attachment to the rest of the molecule. The term 'hetreroaryl_ and 'heteroaromatic ring_ or 'heteroaromatic compound_ can be used interchangeably herein. In one embodiment, the heteroaryl group is a 5- to 14-membered heteroaryl comprising 1, 2, 3 or 4 heteroatoms independently selected from O, S and N. In another embodiment, the heteroaryl group is a 5- to 12-membered heteroaryl comprising 1, 2, 3 or 4 heteroatoms independently selected from O, S and N. In another embodiment, the heteroaryl group is a 5- to 10-membered heteroaryl comprising 1, 2, 3 or 4 heteroatoms independently selected from O, S and N. In another embodiment, the heteroaryl group is a 5- to 8-membered heteroaryl comprising 1, 2, 3 or 4 heteroatoms independently selected from O, S and N. In another embodiment, the heteroaryl group is a 5- to 7-membered heteroaryl comprising 1, 2, 3 or 4 heteroatoms independently selected from O, S and N. In another embodiment, the heteroaryl group is a 5- to 6-membered heteroaryl comprising 1, 2, 3 or 4 heteroatoms independently selected from O, S and N. In another embodiment, the heteroaryl group is a 5-membered heteroaryl comprising 1, 2, 3 or 4 heteroatoms independently selected from O, S and N. In another embodiment, the heteroaryl group is a 6-membered heteroaryl comprising 1, 2, 3 or 4 heteroatoms independently selected from O, S and N.

In the embodiments, some non-limiting examples of heteroaryl rings include the following monocyclic ring: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl, 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiodiazolyl, 1,3,4-thiodiazolyl, 1,2,5-thiodiazolyl, pyrazinyl, 1,3,5-triazinyl, and the following non-limiting bicycles or tricycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxathiinyl, dibenzoimidazolyl, dibenzofuranyl, or dibenzothiophenyl, etc. The heteroaryl group is optionally substituted with one or more substituents disclosed herein.

The term 'heteroarylalkyl_ refers to an alkyl group substituted with one or more heteroaryl groups, wherein the alkyl group and heteroaryl group are as defined herein. Some non-limiting examples of the heteroarylalkyl group include (pyrid-2-yl)ethyl, (thiazol-2-yl)methyl, (imidazol-2-yl) ethyl, (pyrimidin-2-yl)propyl, and the like.

The term 'sulfonyl_, whether used alone or in combination with other terms such as 'alkylsulfonyl _, respectively denotes the divalent group —$SO_2$—. The term 'alkylsulfonyl _ refers to an alkyl-substituted sulfonyl group forming an alkylsulfonyl group (e.g., —$SO_2CH_3$).

The term 'alkylthio_ refers to a linear or branched $C_{1-12}$ alkyl chain binding to a bivalent sulphur atom, wherein the alkyl group is as defined herein. In some embodiments, the alkylthio group is a lower $C_{1-6}$ alkylthio. In other embodiments, the alkylthio group is a lower $C_{1-6}$ alkylthio. Some non-limiting examples of such groups include methylthio ($CH_3S$—), ethylthio, and the like.

The term 'aralkyl_ or 'arylalkyl_ refers to an alkyl group substituted with one or more aryl radicals, wherein the aryl and the alkyl group are as defined herein. In some embodiments, the aralkyl group refers to a 'lower aralkyl_ group having aryl radical(s) attached to a $C_{1-6}$ alkyl radical. In some embodiments, the 'aralkyl_ group or 'arylalkyl_ group is a 'phenylalkylene_ having $C_{1-3}$ alkyl radical. Some non-limiting examples of such group include benzyl, diphenylmethyl, phenylethyl, and the like. The aralkyl group may be optionally unsubstituted or substituted with one or more substituents disclosed herein.

The term 'haloalkyl-substituted aryl_ includes aryl groups that may be substituted with one or more of the same or different haloalkyl groups, wherein the haloalkyl and aryl groups are as described herein. Such examples include, but are not limited to, 2-trifluoromethylphenyl, 3,5-bis(trifluoromethyl)phenyl, 3-trifluoromethyl phenyl, 4-trifluoromethyl phenyl, 2,6-bis(trifluoromethyl)phenyl and the like.

The term 'halo-substituted aryl_ includes aryl groups that may be substituted with one or more of the same or different halogen atoms, wherein the halogen atom and aryl groups are as described herein. Such examples include, but are not limited to, fluorophenyl, difluorophenyl, trifluorophenyl, chlorophenyl, dichlorophenyl, trichlorophenyl, bromophenyl, tribromophenyl, dibromophenyl, fluorochlorophenyl, fluorobromophenyl, chlorobromophenyl, and the like.

The term 'cycloalkylalkyl_ refers to an alkyl group substituted with one or more cycloalkyl groups, wherein the cycloalkyl and alkyl groups are as defined herein. Some non-limiting examples of such group include cyclohexylmethyl, cyclopropylethyl and cyclopropylpropyl, etc. The cycloalkyl group may be independently unsubstituted or substituted with one or more substituents disclosed herein.

Furthermore, unless otherwise stated, the phrase 'eachŭ is independently_ is used interchangeably with the phrase 'each (of)ŭ andŭ is independently_. It should be understood broadly that the specific options expressed by the same symbol are independently of each other in different radicals; or the specific options expressed by the same symbol are independently of each other in same radicals. Such as Formula (p1) and Formula (p2), specific options of two m are independent of each other, specific options of two $R^{13}$ are independent of each other, specific option of each $R^e$ is independent of each other, specific option of each $R^f$ is independent of each other.

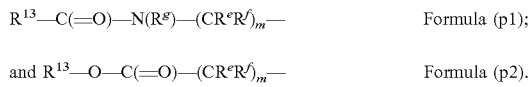

$R^{13}$—C(=O)—N($R^g$)—(C$R^e R^f$)$_m$—  Formula (p1);

and $R^{13}$—O—C(=O)—(C$R^e R^f$)$_m$—  Formula (p2).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational)) mixtures of the present compounds are within the scope disclosed herein.

An 'N-oxide_ refers to one or more than one nitrogen atoms oxidised to form an N-oxide or N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term 'prodrug_ refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyl oxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A 'metabolite_ is a product produced through metabolism in the body of a specified compound or salt thereof. The metabolites of a compound may be identified using routine techniques known in the art and their activities may be determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker, Ed., McGraw-Hill Dictionary of Chemical Terms (1984) McGraw-Hill Book Company, NewYork; and Eliel, E. and Wilen, S., 'Stereocherrmistry of Organic Compounds_, John Wiley&Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term 'racemic mixture_ or 'racemate_ refers to an equimolar mixture of two enantiomeric species, devoid of optical activity.

The term 'tautomer_ or 'tautomeric form_ refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A 'pharmaceutically acceptable salts_ refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66: 1-19, 1-19, 1977. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. If the compound disclosed herein is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$ aryl-$C_{1-4}$-alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate or aryl sulfonate.

The term 'solvate_ refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term 'hydrate_ refers to the complex where the solvent molecule is water.

The term 'protecting group_ or 'Pg_ refers to a substituent that is commonly employed to block or protect a particular functionality while reacting with other functional groups on the compound. For example, an 'amino-protecting group_ is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenyl methylenoxy-carbonyl (Fmoc). Similarly, a 'hydroxy-protecting group_ refers to a substituent of a hydroxy group that blocks or protects the hydroxy functionality. Suitable protecting groups include acetyl and silyl. A 'carboxy-protecting group_ refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxy-methyl, 2-(p-toluenesulfonyl)ethyl, 2-(p-nitrophenyl sulfonyl)-ethyl, 2-(diphenylphosphino) ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

The compounds of the present invention and pharmaceutically acceptable compositions thereof are effective in inhibiting HBV infection.

In one aspect, the invention relates to a compound having Formula (I) or a stereoisomer, a tautomer, an N-oxide, a solvate, a metabolite, a pharmaceutically acceptable salt or a prodrug thereof, wherein,

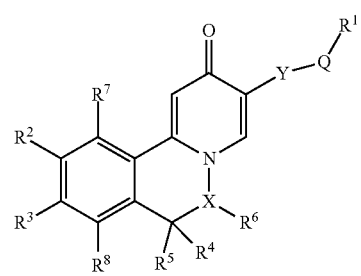

X is N or —$CR^{6a}$—;
Y is a single bond, —$CH_2$— or —C(═O)—;
Q is a single bond, —O— or —N($R^9$)—;
$R^1$ is H, deuterium, F, Cl, Br, I, OH, —COOH, 5- to 6-membered heterocyclyl, 5- to 6-membered heteroaryl, $C_{1-6}$ alkyl, $C_{2-6}$ alkenyl, $C_{2-6}$ alkynyl, $C_{3-7}$ cycloalkyl, $R^{12}$—S(═O)$_2$—, $R^{12}$—(CR$^e$R$^f$)$_n$— or $R^aR^bN$—, wherein each of the 5- to 6-membered heterocyclyl, 5- to 6-membered heteroaryl, $C_{1-6}$ alkyl, $C_{2-6}$ alkenyl, $C_{2-6}$ alkynyl and $C_{3-7}$ cycloalkyl is independently unsubstituted or substituted with 1, 2, 3 or 4 $R^v$;

$R^9$ is H, deuterium, $C_{1-6}$ alkyl or $C_{1-6}$ haloalkyl; or, $R^9$ and $R^1$, together with the nitrogen atom to which they are attached, form a 3- to 12-membered heterocyclyl, wherein each of the $C_{1-6}$ alkyl, $C_{1-6}$ haloalkyl and 3- to 12-membered heterocyclyl is independently unsubstituted or substituted with 1, 2, 3 or 4 substituents selected from —COOH, ═O, tetrazolyl or $C_{1-6}$ alkyl-O—C(═O)—;

each of $R^4$ and $R^5$ is independently H, deuterium, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl or 3- to 12-membered heterocyclyl, wherein each of the $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl and 3- to 12-membered heterocyclyl is independently unsubstituted or substituted with 1, 2, 3 or 4 $R^y$;

$R^6$ is H, deuterium, $C_{1-6}$ alkyl, $C_{2-6}$ alkenyl, $C_{3-7}$ cycloalkyl, 3- to 12-membered heterocyclyl, $C_{6-10}$ aryl, 5- to 10-membered heteroaryl or $R^{17}$—C(═O)—O—(CR$^e$R$^f$)$_q$—, wherein each of the $C_{1-6}$ alkyl, $C_{2-6}$ alkenyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^z$;

$R^{6a}$ is H, deuterium, F, Cl, Br, CN, OH, $C_{1-6}$ alkyl, $C_{2-6}$ alkenyl, $C_{3-7}$ cycloalkyl, 3- to 12-membered heterocyclyl, $C_{6-10}$ aryl, 5- to 10-membered heteroaryl or $R^{17}$—C(═O)—O—(CR$^e$R$^f$)$_q$—, wherein each of the $C_{1-6}$ alkyl, $C_{2-6}$ alkenyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^z$;

$R^2$ is deuterium, Br, cyano, methyl, ethyl, $C_{3-12}$ alkyl, cyclopropyl, $C_{4-7}$ cycloalkyl, 3- to 12-membered heterocyclyl, $C_{6-10}$ aryl, 5- to 10-membered heteroaryl, $R^{13}$—(CR$^e$R$^f$)$_t$—, $R^{13a}$—(CR$^e$R$^f$)$_f$—O—, $R^{13}$—C(═O)—(CR$^e$R$^f$)$_m$—, $R^{13}$—C(═O)—N(R$^g$)—(CR$^e$R$^f$)$_m$—, $R^{18}$—N(R$^g$)—C(═O)—O—, $R^{19}$—N(R$^m$)—C(═O)—N(R$^n$)—, $R^{13}$—O—C(═O)—(CR$^e$R$^f$)$_m$—, $R^{13}$—O—C(═O)—N(R$^g$)—(CR$^e$R$^f$)$_m$—, $R^c$—C(═O)—(CR$^e$R$^f$)$_m$—O—C(═O)—,

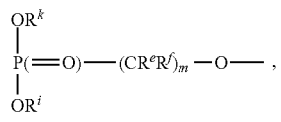

$R^{14}-S(=O)_2-(CR^eR^f)_m-$, $R^{14}-S(=O)_2-N(R^g)-(CR^eR^f)_m-$, $R^{14}-S(=O)_2-N(R^g)-C(=O)-$, $R^aR^bN-$, $R^cC(=O)-$, $R^aR^bNC(=O)-$, $R^dOC(=O)-$ or $R^{10a}O-$, wherein each of the methyl, ethyl and cyclopropyl is independently substituted with 1, 2, 3 or 4 $R^w$, and wherein each of the $C_{3-12}$ alkyl, $C_{4-7}$ cycloalkyl, 3- to 12-membered heterocyclyl, $C_{6-10}$ aryl and 5- to 10-membered heteroaryl is independently unsubstituted or substituted with 1, 2, 3 or 4 $R^w$;

each of $R^3$, $R^7$ and $R^8$ is independently H, deuterium, F, Cl, Br, hydroxy, cyano, $C_{1-12}$ alkyl, $C_{3-7}$ cycloalkyl, 3- to 12-membered heterocyclyl, $C_{6-10}$ aryl, 5- to 10-membered heteroaryl, $R^{13}-(CR^eR^f)_m-$, $R^{13}-(CR^eR^f)_m-O-$, $R^{13}-C(=O)-(CR^eR^f)_m-$, $R^{13}-C(=O)-N(R^g)-(CR^eR^f)_m-$, $R^{13}-O-C(=O)-(CR^eR^f)_m-$, $R^{13}-O-C(=O)-N(R^g)-(CR^eR^f)_m-$, $R^c-C(=O)-(CR^eR^f)_m-O-C(=O)-$,

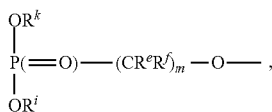

$R^{14}-S(=O)_2-(CR^eR^f)_m-$, $R^{14}-S(=O)_2-N(R^g)-(CR^eR^f)_m-$, $R^{14}-S(=O)_2-N(R^g)-C(=O)-$, $R^aR^bN-$, $R^cC(=O)-$, $R^aR^bNC(=O)-$, $R^dOC(=O)-$ or $R^{10}O-$, wherein each of the $C_{1-12}$ alkyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^w$;

$R^{10}$ is H, deuterium, $C_{1-12}$ alkyl, $C_{2-12}$ alkynyl, $C_{3-7}$ cycloalkyl, 3- to 12-membered heterocyclyl, $C_{6-10}$ aryl, 5- to 10-membered heteroaryl, $R^{15}-(CR^eR^f)_g-$, $R^{15}-O-(CR^eR^f)_g-$, $R^{15}-C(=O)-(CR^eR^f)_g-$, $R^{15}-O-C(=O)-(CR^eR^f)_g-$, $R^{15}-O-C(=O)-N(R^g)-(CR^eR^f)_g-$, $R^{16}-S(=O)_2-(CR^eR^f)_g-$ or $R^{16}-S(=O)_2-N(R^g)-(CR^eR^f)_g-$, wherein each of the $C_{1-12}$ alkyl, $C_{2-12}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^x$;

$R^{10a}$ is deuterium, methyl, ethyl, $C_{3-12}$ alkyl, $C_{2-12}$ alkynyl, $C_{3-7}$ cycloalkyl, 3- to 12-membered heterocyclyl, $C_{6-10}$ aryl, 5- to 10-membered heteroaryl, $R^{15}-(CR^eR^f)_g-$, $R^{15}-O-(CR^eR^f)_g-$, $R^{15}-C(=O)-(CR^eR^f)_g-$, $R^{15}-O-C(=O)-(CR^eR^f)_g-$, $R^{15}-O-C(=O)-N(R^g)-(CR^eR^f)_g-$, $R^{16}-S(=O)_2-(CR^eR^f)_g-$ or $R^{16}-S(=O)_2-N(R^g)-(CR^eR^f)_g-$, wherein each of the methyl and ethyl is independently substituted with 1, 2, 3 or 4 substituents selected from F, Cl, Br, CN, OH, =O, —COOH, amino, $C_{2-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alkynyl, $C_{3-6}$ cycloalkyl, 5- to 6-membered heteroaryl, 5- to 6-membered heterocyclyl, $C_{1-6}$ alkoxy-$C_{1-6}$-alkyl or $C_{1-6}$ alkylamino-$C_{1-6}$-alkyl, and wherein each of the $C_{3-12}$ alkyl, $C_{2-12}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^x$;

or $R^{10a}$ is methyl or ethyl, meanwhile $R^3$ is thienyl, furyl, pyrrolyl, triazolyl, imidazolyl, tetrazolyl, isothiazolyl, oxazolyl, thiazolyl, isoxazolyl, thiadiazolyl, oxadiazolyl or 6-membered heteroaryl, and wherein each of the thienyl, furyl, pyrrolyl, triazolyl, imidazolyl, tetrazolyl, isothiazolyl, oxazolyl, thiazolyl, isoxazolyl, thiadiazolyl, oxadiazolyl and 6-membered heteroaryl is independently unsubstituted or substituted with 1, 2, 3, or 4 substituents selected from F, Cl, Br, CN, OH, amino, $C_{1-6}$ alkyl, $C_{1-6}$ haloalkyl, $C_{1-6}$ alkoxy, $C_{1-6}$ alkoxy-$C_{1-3}$-alkyl or $C_{1-6}$ alkylamino;

each $R^{12}$ and $R^{17}$ is independently $C_{3-7}$ cycloalkyl, $C_{6-10}$ aryl, $C_{1-6}$ alkoxy, amino or $C_{1-6}$ alkylamino, wherein each of the $C_{3-7}$ cycloalkyl, $C_{6-10}$ aryl, $C_{1-6}$ alkoxy, amino and $C_{1-6}$ alkylamino is independently unsubstituted or substituted with 1, 2, 3 or 4 $R^j$;

each $R^{13}$, $R^{14}$, $R^{15}$, $R^{16}$, $R^{18}$ and $R^{19}$ is independently $C_{1-12}$ alkyl, $C_{1-12}$ alkoxy, $C_{3-7}$ cycloalkyl, 5- to 10-membered heteroaryl, 3- to 12-membered heterocyclyl or $C_{6-10}$ aryl, wherein each of the $C_{1-12}$ alkyl, $C_{1-12}$ alkoxy, $C_{3-7}$ cycloalkyl, 5- to 10-membered heteroaryl, 3- to 12-membered heterocyclyl and $C_{6-10}$ aryl is independently unsubstituted or substituted with 1, 2, 3 or 4 $R^h$;

$R^{13a}$ is methyl, $C_{2-12}$ alkyl, $C_{1-12}$ alkoxy, $C_{3-7}$ cycloalkyl, 5- to 10-membered heteroaryl, 3- to 12-membered heterocyclyl or $C_{6-10}$ aryl, wherein each of the methyl and $C_{6-10}$ aryl is independently substituted with 1, 2, 3 or 4 $R^h$, and wherein $C_{2-12}$ alkyl, $C_{1-12}$ alkoxy, $C_{3-7}$ cycloalkyl, 5- to 10-membered heteroaryl and 3- to 12-membered heterocyclyl is independently unsubstituted or substituted with 1, 2, 3 or 4 $R^h$;

each $R^a$, $R^b$, $R^c$, $R^d$, $R^e$, $R^f$, $R^g$, $R^k$, $R^i$, $R^m$ and $R^n$ is independently H, deuterium, OH, $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, 3- to 12-membered heterocyclyl or 5- to 10-membered heteroaryl, wherein each of the $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, 3- to 12-membered heterocyclyl and 5- to 10-membered heteroaryl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

or, $R^a$ and $R^b$, together with the nitrogen atom to which they are attached, form a 3- to 8-membered heterocyclyl or 5- to 8-membered heteroaryl, wherein each of the 3- to 8-membered heterocyclyl and 5- to 8-membered heteroaryl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

or, $R^m$ and $R^n$, together with the nitrogen atom to which they are attached, form a 3- to 8-membered heterocyclyl, wherein 3- to 8-membered heterocyclyl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

each $R^v$, $R^w$, $R^x$, $R^y$, $R^z$, $R^j$ and $R^h$ is independently F, Cl, Br, CN, OH, —COOH, amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl or 5- to 10-membered heteroaryl, wherein each of the amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 substituents independently selected from F, Cl, Br, CN, OH, =O, —COOH, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alkynyl, $C_{6-10}$ aryl, $C_{3-6}$ cycloalkyl, 5- to 6-membered heteroaryl, 5- to 6-membered heterocyclyl, $C_{1-6}$ alkoxy-$C_{1-6}$-alkyl or $C_{1-6}$ alkylamino-$C_{1-6}$-alkyl;

each n and q is independently 0, 1, 2, 3, 4, 5 or 6;

each t and f is independently 1, 2, 3, 4, 5 or 6; and each m and g is independently 0, 1, 2, 3, 4, 5, 6, 7, 8, 9 or 10.

In some embodiments, $R^1$ is H, deuterium, F, Cl, Br, I, OH, —COOH, 5-membered heterocyclyl, 5-membered heteroaryl, $C_{1-4}$ alkyl, $C_{2-4}$ alkenyl, $C_{2-4}$ alkynyl, $C_{3-6}$ cycloalkyl, $R^{12}$—S(=O)$_2$—, $R^{12}$—(CR$^e$R$^f$)$_n$— or $R^aR^bN$—, wherein each of the 5-membered heterocyclyl, 5-membered heteroaryl, $C_{1-4}$ alkyl, $C_{2-4}$ alkenyl, $C_{2-4}$ alkynyl and $C_{3-6}$ cycloalkyl is independently unsubstituted or substituted with 1, 2, 3 or 4 $R^v$;

$R^9$ is H, deuterium, $C_{1-4}$ alkyl or $C_{1-4}$ haloalkyl; or, $R^9$ and $R^1$, together with the nitrogen atom to which they are attached, form a 5- to 6-membered heterocyclyl, wherein each of the $C_{1-4}$ alkyl, $C_{1-4}$ haloalkyl and 5- to 6-membered heterocyclyl is independently unsubstituted or substituted with 1, 2, 3 or 4 substituents selected from —COOH, =O, tetrazolyl or $C_{1-6}$ alkyl-O—C(=O)—; and each $R^{12}$, n, $R^e$, $R^f$, $R^a$, $R^b$ and $R^v$ is as defined herein.

In other embodiments, $R^1$ is H, deuterium, F, Cl, Br, I, OH, —COOH, thiazolyl, tetrazolyl, methyl, ethyl, n-propyl, isopropyl, vinyl, propenyl, ethynyl, propynyl, cyclopropyl, cyclobutyl, cyclopentyl, $R^{12}$—S(=O)$_2$—, $R^{12}$—(CR$^e$R$^f$)$_n$— or $R^aR^bN$—, wherein each of the thiazolyl, methyl, ethyl, n-propyl, isopropyl, vinyl, propenyl, ethynyl, propynyl, cyclopropyl, cyclobutyl and cyclopentyl is independently unsubstituted or substituted with 1, 2, 3 or 4 $R^v$;

$R^9$ is H, deuterium, methyl, ethyl, n-propyl, isopropyl or $C_{1-3}$ haloalkyl; or, $R^9$ and $R^1$, together with the nitrogen atom to which they are attached, form pyrrolidinyl, piperazinyl, piperidyl or morpholinyl, wherein each of the methyl, ethyl, n-propyl, isopropyl, $C_{1-3}$ haloalkyl, pyrrolidinyl, piperazinyl, piperidyl and morpholinyl is independently unsubstituted or substituted with 1, 2, 3 or 4 substituents selected from —COOH, =O, tetrazolyl or $C_{1-6}$ alkyl-O—C(=O)—; and each $R^{12}$, n, $R^e$, $R^f$, $R^a$, $R^b$ and $R^v$ is as defined herein.

In some embodiments, $R^2$ is deuterium, Br, cyano, methyl, ethyl, $C_{3-6}$ alkyl, cyclopropyl, $C_{4-6}$ cycloalkyl, 5- to 6-membered heterocyclyl, phenyl, naphthyl, 5- to 6-membered heteroaryl, $R^{13}$—(CR$^e$R$^f$)$_t$—, $R^{13a}$—(CR$^e$R$^f$)$_f$—O—, $R^{13}$—C(=O)—(CR$^e$R$^f$)$_m$—, $R^{13}$—C(=O)—N(R$^g$)—(CR$^e$R$^f$)$_m$—, $R^{18}$—N(R$^g$)—C(=O)—O—, $R^{19}$—N(R$^m$)—C(=O)—N(R$^n$)—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)$_m$—O—C(=O)—,

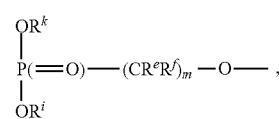

$R^{14}$—S(=O)$_2$—(CR$^e$R$^f$)$_m$—, $R^{14}$—S(=O)$_2$—N(R$^g$)—C(=O)—, $R^{14}$—S(=O)$_2$—N(R$^g$)—(CR$^e$R$^f$)$_m$—, $R^aR^bN$—, $R^cC(=O)$—, $R^aR^bNC(=O)$—, $R^dOC(=O)$— or $R^{10a}O$—, wherein each of the methyl, ethyl and cyclopropyl is independently substituted with 1, 2, 3 or 4 $R^w$, and wherein each of the $C_{3-6}$ alkyl, $C_{4-6}$ cycloalkyl, 5- to 6-membered heterocyclyl, phenyl, naphthyl and 5- to 6-membered heteroaryl is independently unsubstituted or substituted with 1, 2, 3 or 4 $R^w$; and each $R^{13a}$, $R^{10a}$, t, f, m, $R^{13}$, $R^{14}$, $R^{18}$, $R^{19}$, $R^a$, $R^b$, $R^c$, $R^d$, $R^e$, $R^f$, $R^g$, $R^m$, $R^n$, $R^k$, $R^i$ and $R^w$ is as defined herein.

In other embodiments, $R^2$ is deuterium, Br, cyano, methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{13}$—(CR$^e$R$^f$)$_t$—, $R^{13a}$—(CR$^e$R$^f$)$_f$—O—, $R^{13}$—C(CR$^e$R$^f$)$_m$—, $R^{13}$—C(=O)—N(R$^g$)—(CR$^e$R$^f$)$_m$—, $R^{18}$—N(R$^g$)—C(=O)—O—, $R^{19}$—N(R$^m$)—C(=O)—N(R$^n$)—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)$_m$—O—C(=O)—,

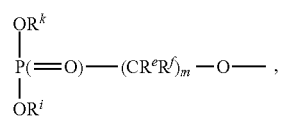

$R^{14}$—S(=O)$_2$—(CR$^e$R$^f$)$_m$—, $R^{14}$—S(=O)$_2$—N(R$^g$)—C(=O)—, $R^{14}$—S(=O)$_2$—N(R$^g$)—(CR$^e$R$^f$)$_m$—, $R^aR^bN$—, $R^cC(=O)$—, $R^aR^bNC(=O)$—, $R^dOC(=O)$— or $R^{10a}O$—, wherein each of the methyl, ethyl and cyclopropyl is independently substituted with 1, 2, 3 or 4 $R^w$, and wherein each of the n-propyl, isopropyl, n-butyl, isobutyl, n-pentyl, n-hexyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^w$; and each $R^{13a}$, $R^{10a}$, t, f, m, $R^{13}$, $R^{14}$, $R^{18}$, $R^{19}$, $R^a$, $R^b$, $R^c$, $R^d$, $R^e$, $R^f$, $R^g$, $R^m$, $R^n$, $R^k$, $R^i$ and $R^w$ is as defined herein.

In some embodiments, each of $R^3$, $R^7$ and $R^8$ is independently H, deuterium, F, Cl, Br, hydroxy, cyano, $C_{1-6}$ alkyl, $C_{3-6}$ cycloalkyl, 5- to 6-membered heterocyclyl, phenyl, naphthyl, 5- to 6-membered heteroaryl, $R^{13}$—(CR$^e$R$^f$)$_m$—, $R^{13}$—(CR$^e$R$^f$)$_m$—O—, $R^{13}$—C(=O)—(CR$^e$R$^f$)$_m$—, $R^{13}$—C(=O)—N(R$^g$)—(CR$^e$R$^f$)$_m$—, $R^{13}$—O—C(=O)—(CR$^e$R$^f$)$_m$—, $R^{13}$—O—C(=O)—N(R$^g$)—(CR$^e$R$^f$)$_m$—, $R^c$—C(=O)—(CR$^e$R$^f$)$_m$—O—C(=O)—,

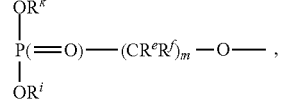

$R^{14}$—S(=O)$_2$—(CR$^e$R$^f$)$_m$—, $R^{14}$—S(=O)$_2$—N(R$^g$)—C(=O)—, $R^{14}$—S(=O)$_2$—N(R$^g$)—(CR$^e$R$^f$)$_m$—, $R^aR^bN$—, $R^cC(=O)$—, $R^aR^bNC(=O)$—, $R^dOC(=O)$— or $R^{10}O$—, and wherein each of the $C_{1-6}$ alkyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^w$;

$R^{10}$ is H, deuterium, $C_{1-6}$ alkyl, $C_{2-6}$ alkynyl, $C_{3-6}$ cycloalkyl, 5- to 6-membered heterocyclyl, phenyl, naphthyl, 5- to 6-membered heteroaryl, $R^{15}$—(CR$^e$R$^f$)$_g$—, $R^{15}$—O—(CR$^e$R$^f$)$_g$—, $R^{15}$—C(=O)—(CR$^e$R$^f$)$_g$—, $R^{15}$—O—C(=O)—(CR$^e$R$^f$)$_g$—, $R^{15}$—O—C(=O)—N(R$^g$)—(CR$^e$R$^f$)$_g$—, $R^{16}$—S(=O)$_2$—(CR$^e$R$^f$)$_g$— or $R^{16}$—S(=O)$_2$—N(R$^g$)—(CR$^e$R$^f$)$_g$—, wherein each of the $C_{1-6}$ alkyl, $C_{2-6}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^x$;

$R^{10a}$ is deuterium, methyl, ethyl, $C_{3-6}$ alkyl, $C_{2-6}$ alkynyl, $C_{3-6}$ cycloalkyl, 5- to 6-membered heterocyclyl, phenyl, naphthyl, 5- to 6-membered heteroaryl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the methyl and ethyl is independently substituted with 1, 2, 3 or 4 substituents selected from F, Cl, Br, CN, OH, =O, —COOH, amino, $C_{2-4}$ alkyl, $C_{1-4}$ haloalkyl, $C_{1-4}$ alkoxy, $C_{1-4}$ alkylthio, $C_{1-4}$ haloalkoxy, $C_{1-6}$ alkylamino, $C_{2-4}$ alkenyl, $C_{2-4}$ alkynyl, $C_{3-6}$ cycloalkyl, 5- to 6-membered heteroaryl, 5- to 6-membered heterocyclyl, $C_{1-4}$ alkoxy-$C_{1-4}$-alkyl or $C_{1-4}$ alkylamino-$C_{1-4}$-alkyl, and wherein each of the $C_{3-6}$ alkyl, $C_{2-6}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^x$;

or $R^{10a}$ is methyl or ethyl, meanwhile $R^3$ is thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl or pyrimidinyl, and wherein each of the thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl and pyrimidinyl is independently unsubstituted or substituted with 1, 2, 3, or 4 substituents selected from F, Cl, Br, CN, OH, amino, $C_{1-4}$ alkyl, $C_{1-4}$ haloalkyl, $C_{1-4}$ alkoxy, $C_{1-4}$ alkoxy-$C_{1-2}$-alkyl or $C_{1-4}$ alkylamino; and each m, g, $R^{13}$, $R^{14}$, $R^{15}$, $R^{16}$, $R^a$, $R^b$, $R^c$, $R^d$, $R^e$, $R^f$, $R^g$, R, $R^k$, $R^i$ and $R^w$ is as defined herein.

In some embodiments, each of $R^3$, $R^7$ and $R^8$ is independently H, deuterium, F, Cl, Br, hydroxy, cyano, methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{13}$—$(CR^eR^f)_m$—, $R^{13}$—$(CR^eR^f)_m$—O—, $R^{13}$—C(=O)—$(CR^eR^f)_m$—, $R^{13}$—C(=O)—N($R^g$)—$(CR^eR^f)_m$—, $R^{13}$—O—C(=O)—$(CR^eR^f)_m$—, $R^{13}$—O—C(=O)—N($R^g$)—$(CR^eR^f)_m$—, $R^c$—C(=O)—$(CR^eR^f)_m$—O—C(=O)—,

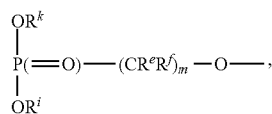

$R^{14}$—S(=O)$_2$—$(CR^eR^f)_m$—, $R^{14}$—S(=O)$_2$—N($R^g$)—$(CR^eR^f)_m$—, $R^{14}$—S(=O)$_2$—N($R^g$)—C(=O)—, $R^aR^bN$—, $R^cC(=O)$—, $R^aR^bNC(=O)$—, $R^dOC(=O)$— or $R^{10}O$—, and wherein each of the methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^w$;

$R^{10}$ is H, deuterium, methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^x$;

$R^{10a}$ is deuterium, methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the methyl and ethyl is independently substituted with 1, 2, 3 or 4 substituents selected from F, Cl, Br, CN, OH, =O, —COOH, amino, $C_{2-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, $C_{3-6}$ cycloalkyl, 5- to 6-membered heteroaryl, 5- to 6-membered heterocyclyl, $C_{1-4}$ alkoxy-$C_{1-3}$-alkyl or $C_{1-4}$ alkylamino-$C_{1-3}$-alkyl, wherein each of the n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^x$;

or $R^{10a}$ is methyl or ethyl, meanwhile $R^3$ is thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl or pyrimidinyl, and wherein each of the thienyl, furyl, pyrrolyl, triazolyl, imidazolyl, tetrazolyl, isothiazolyl, oxazolyl, thiazolyl, isoxazolyl, thiadiazolyl, oxadiazolyl, pyridyl, 1,3,5-triazinyl, pyrazinyl, pyridazinyl and pyrimidinyl is independently unsubstituted or substituted with 1, 2, 3, or 4 substituents selected from F, Cl, Br, CN, OH, amino, $C_{1-3}$ alkyl, $C_{1-3}$ haloalkyl, $C_{1-3}$ alkoxy, $C_{1-3}$ alkoxymethyl or $C_{1-3}$ alkylamino; and each m, g, $R^{13}$, $R^{14}$, $R^{15}$, $R^{16}$, $R^a$, $R^b$, $R^c$, $R^d$, $R^e$, $R^f$, $R^g$, $R^x$, $R^k$, $R^i$ and $R^w$ is as defined herein.

In some embodiments, each of $R^4$ and $R^5$ is independently H, deuterium, $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl or 5- to 6-membered heterocyclyl, and wherein each of the $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl and 5- to 6-membered heterocyclyl is independently unsubstituted or substituted with 1, 2, 3 or 4 $R^y$;

$R^6$ is H, deuterium, $C_{1-4}$ alkyl, $C_{2-4}$ alkenyl, $C_{3-6}$ cycloalkyl, 5- to 6-membered heterocyclyl, phenyl, naphthyl, 5- to 10-membered heteroaryl or $R^{17}$—C(=O)—O—(CR$^e$R$^f$)$_q$—, wherein each of the $C_{1-4}$ alkyl, $C_{2-4}$ alkenyl, $C_{3-6}$ cycloalkyl, 5- to 6-membered heterocyclyl, phenyl, naphthyl and 5- to 10-membered heteroaryl is independently unsubstituted or substituted with 1, 2, 3 or 4 $R^z$;

$R^{6a}$ is H, deuterium, F, Cl, Br, CN, OH, $C_{1-4}$ alkyl, $C_{2-4}$ alkenyl, $C_{3-6}$ cycloalkyl, 5- to 6-membered heterocyclyl, phenyl, naphthyl, 5- to 10-membered heteroaryl or $R^{17}$—C(=O)—O—(CR$^e$R$^f$)$_q$—, wherein each of the $C_{1-4}$ alkyl, $C_{2-4}$ alkenyl, $C_{3-6}$ cycloalkyl, 5- to 6-membered heterocyclyl, phenyl, naphthyl and 5- to 10-membered heteroaryl is independently unsubstituted or substituted with 1, 2, 3 or 4 $R^z$; and each q, $R^{17}$, $R^e$, $R^f$, $R^z$ and $R^y$ is as defined herein.

In other embodiments, each of $R^4$ and $R^5$ is independently H, deuterium, $C_{1-3}$ alkyl, $C_{1-3}$ alkylamino, $C_{1-3}$ alkoxy, $C_{2-4}$ alkynyl, $C_{2-4}$ alkenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl or piperazinyl, wherein each of the $C_{1-3}$ alkyl, $C_{1-3}$ alkylamino, $C_{1-3}$ alkoxy, $C_{2-4}$ alkynyl, $C_{2-4}$ alkenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl and piperazinyl is independently unsubstituted or substituted with 1, 2, 3, or 4 $R^v$;

$R^6$ is H, deuterium, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl, naphthyl, or $R^{17}$—C(=O)—O—(CR$^e$R$^f$)$_q$—, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl and naphthyl is independently unsubstituted or substituted with 1, 2, 3, or 4 $R^z$;

$R^{6a}$ is H, deuterium, F, Cl, Br, CN, OH, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl, naphthyl, or $R^{17}$—C(=O)—O—(CR$^e$R$^f$)$_q$—, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl and naphthyl is independently unsubstituted or substituted with 1, 2, 3, or 4 $R^z$; and each q, $R^{17}$, $R^e$, $R^f$, $R^z$ and $R^y$ is as defined herein.

In some embodiments, each $R^{12}$ and $R^{17}$ is independently $C_{3-6}$ cycloalkyl, phenyl, naphthyl, $C_{1-4}$ alkoxy, amino or $C_{1-4}$ alkylamino, wherein each of the $C_{3-6}$ cycloalkyl, phenyl, naphthyl, $C_{1-4}$ alkoxy, amino and $C_{1-4}$ alkylamino is independently unsubstituted or substituted with 1, 2, 3 or 4 $R^j$;

each $R^{13}$, $R^{14}$, $R^{15}$, $R^{16}$, $R^{18}$ and $R^{19}$ is independently $C_{1-6}$ alkyl, $C_{1-6}$ alkoxy, $C_{3-6}$ cycloalkyl, 5- to 6-membered heteroaryl, 5- to 6-membered heterocyclyl, phenyl or naphthyl, wherein each of the $C_{1-6}$ alkyl, $C_{1-6}$ alkoxy, $C_{3-6}$ cycloalkyl, 5- to 6-membered heteroaryl, 5- to 6-membered heterocyclyl, phenyl and naphthyl is independently unsubstituted or substituted with 1, 2, 3 or 4 $R^h$;

$R^{13a}$ is methyl, $C_{2-6}$ alkyl, $C_{1-6}$ alkoxy, $C_{3-6}$ cycloalkyl, 5- to 6-membered heteroaryl, 5- to 6-membered heterocyclyl, phenyl or naphthyl, wherein each of the methyl, phenyl or naphthyl is independently substituted with 1, 2, 3 or 4 $R^h$, wherein each of the $C_{2-6}$ alkyl, $C_{1-6}$ alkoxy, $C_{3-6}$ cycloalkyl, 5- to 6-membered heteroaryl and 5- to 6-membered heterocyclyl is independently unsubstituted or substituted with 1, 2, 3 or 4 $R^h$; and each $R^j$ and $R^h$ is as defined herein.

In other embodiments, each $R^{12}$ and $R^{17}$ is independently cyclopropyl, cyclobutyl, cyclopentyl, cyclohexyl, phenyl, naphthyl, methoxy, ethoxy, propoxy, isopropoxy, n-butoxy, amino, N-methylamino, N-ethylamino, N,N-dimethylamino or N,N-diethylamino, wherein each of the cyclopropyl, cyclobutyl, cyclopentyl, cyclohexyl, phenyl, naphthyl, methoxy, ethoxy, propoxy, isopropoxy, n-butoxy, amino, N-methylamino, N-ethylamino, N,N-dimethylamino and N,N-diethylamino is independently unsubstituted or substituted with 1, 2, 3, or 4 $R^j$;

each $R^{13}$, $R^{14}$, $R^{15}$, $R^{16}$, $R^{18}$ and $R^{19}$ is independently methyl, ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the methyl, ethyl, n-propyl, isopropyl, n-butyl, isobutyl, tert-butyl, methoxy, ethoxy, propoxy, isopropyl, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3, or 4 $R^h$;

$R^{13a}$ is methyl, ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the methyl, phenyl and naphthyl is independently substituted with 1, 2, 3 or 4 $R^h$, and wherein each of the ethyl, n-propyl, isopropyl, n-butyl, isobutyl, tert-butyl, methoxy, ethoxy, propoxy, isopropyl, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted with 1, 2, 3, or 4 $R^h$; and each $R^j$ and $R^h$ is as defined herein.

In some embodiments, each $R^a$, $R^b$, $R^c$, $R^d$, $R^e$, $R^f$, $R^g$, $R^k$, $R^i$, $R^m$ and $R^n$ is independently H, deuterium, OH, $C_{1-4}$ haloalkyl, $C_{1-6}$ alkyl, $C_{1-4}$ alkoxy, $C_{2-4}$ alkenyl, $C_{2-4}$ alkynyl, $C_{3-6}$ cycloalkyl, phenyl, naphthyl, 5- to 6-membered heterocyclyl or 5- to 6-membered heteroaryl, wherein each of the $C_{1-4}$ haloalkyl, $C_{1-6}$ alkyl, $C_{1-4}$ alkoxy, $C_{2-4}$ alkenyl, $C_{2-4}$ alkynyl, $C_{3-6}$ cycloalkyl, phenyl, naphthyl, 5- to 6-membered heterocyclyl and 5- to 6-membered heteroaryl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^a$ and $R^b$, together with the nitrogen atom to which they are attached, form a 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^m$ and $R^n$, together with the nitrogen atom to which they are attached, form a 3- to 6-membered heterocyclyl, wherein 3- to 6-membered heterocyclyl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino.

In other embodiments, each $R^a$, $R^b$, $R^c$, $R^d$, $R^e$, $R^f$, $R^g$, $R^k$, $R^i$, $R^m$ and $R^n$ is independently H, deuterium, OH, $C_{1-3}$ haloalkyl, methyl, ethyl, n-propyl, isopropyl, n-butyl, isobutyl, tert-butyl, n-pentyl, 3-pentyl, methoxy, ethoxy, propoxy, isopropoxy, n-butoxy, ethenyl, propenyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the $C_{1-3}$ haloalkyl, methyl, ethyl, n-propyl, isopropyl, n-butyl, isobutyl, tert-butyl, methoxy, ethoxy, propoxy, isopropoxy, n-butoxy, ethenyl, propenyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3, or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^a$ and $R^b$, together with the nitrogen atom to which they are attached, form pyrrolidinyl, pyrazolidinyl, imidazolidinyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, pyrazinyl, pyridazinyl or pyrimidinyl, wherein each of the pyrrolidinyl, pyrazolidinyl, imidazolidinyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, pyrazinyl, pyridazinyl and pyrimidinyl is independently unsubstituted or substituted with 1, 2, 3, or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;

or, $R^m$ and $R^n$, together with the nitrogen atom to which they are attached, form a 4- to 6-membered heterocyclyl, wherein 4- to 6-membered heterocyclyl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino.

In some embodiments, each $R^v$, $R^w$, $R^x$, $R^y$, $R^z$, $R^j$ and $R^h$ is independently F, Cl, Br, CN, OH, —COOH, amino, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylamino, $C_{2-4}$ alkenyl, $C_{2-4}$ alkynyl, $C_{3-6}$ cycloalkyl, 5- to 6-membered heterocyclyl, phenyl, naphthyl or 5- to 6-membered heteroaryl, wherein each of the amino, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylamino, $C_{2-4}$ alkenyl, $C_{2-4}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 substituents independently selected from F, Cl, Br, CN, OH, =O, —COOH, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, phenyl, naphthyl, $C_{3-6}$ cycloalkyl, 5- to 6-membered heteroaryl, 5- to 6-membered heterocyclyl, $C_{1-4}$ alkoxy-$C_{1-4}$-alkyl or $C_{1-4}$ alkylamino-$C_{1-4}$-alkyl.

In other embodiments, each $R^v$, $R^w$, $R^x$, $R^y$, $R^z$, $R^j$ and $R^h$ is independently F, Cl, Br, CN, OH, —COOH, amino, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl or naphthyl, wherein each of the cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 substituents independently selected from F, Cl, Br, CN, OH, =O, —COOH, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $C_{1-3}$ alkoxy-$C_{1-3}$-alkyl and $C_{1-3}$ alkylamino-$C_{1-3}$-alkyl.

In still other embodiments, each $R^v$, $R^w$, $R^x$, $R^y$, $R^z$, $R^j$ and $R^h$ is independently F, Cl, Br, CN, OH, —COOH, amino, methyl, ethyl, n-propyl, isopropyl, n-butyl, i-butyl, t-butyl, $C_{1-4}$ haloalkyl, $C_{1-4}$ alkoxy, $C_{1-4}$ haloalkoxy, $C_{1-4}$ alkylthio, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl or naphthyl, wherein each of the cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 substituents independently selected from F, Cl, Br, CN, OH, =O, —COOH, amino, methyl, ethyl, n-propyl, isopropyl, n-butyl, i-butyl, t-butyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $C_{1-3}$ alkoxy-$C_{1-3}$-alkyl and $C_{1-3}$ alkylamino-$C_{1-3}$-alkyl.

In other embodiments, the invention relates to a compound having one of the following structures, or a stereoisomer, a tautomer, an N-oxide, a solvate, a metabolite, a pharmaceutically acceptable salt or a prodrug thereof, but is not limited to:

(1)

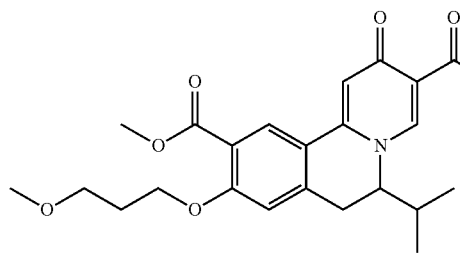

(2)

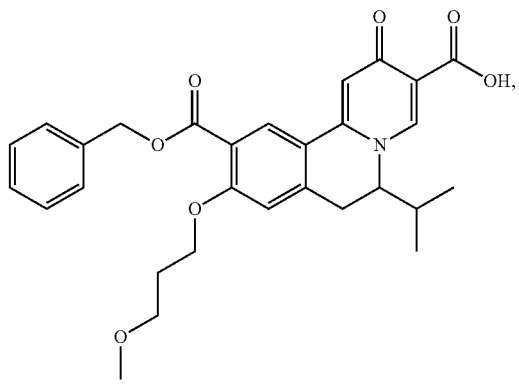

(3)

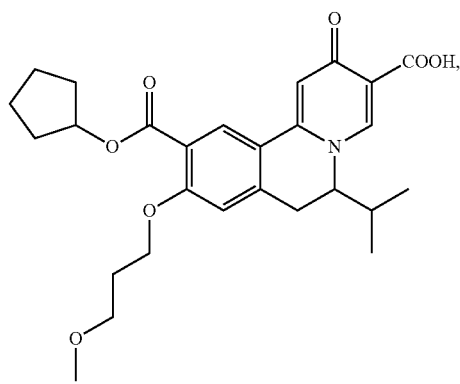

(4)

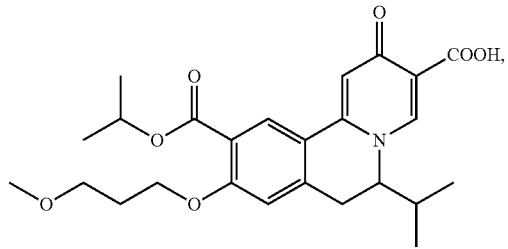

(5)

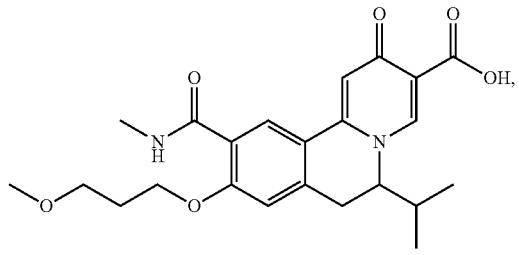

(6)

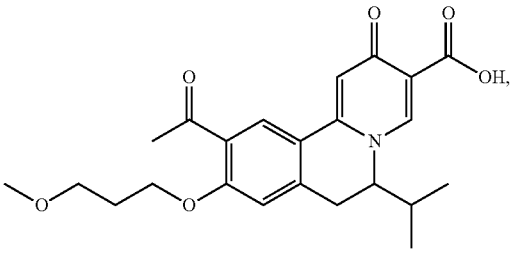

-continued
(7)
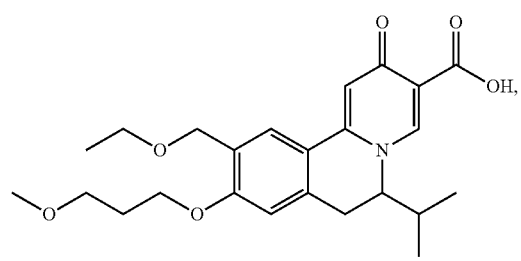
(8)
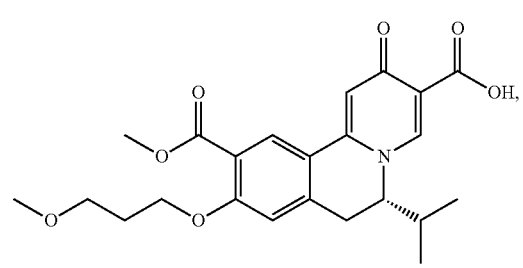
(9)
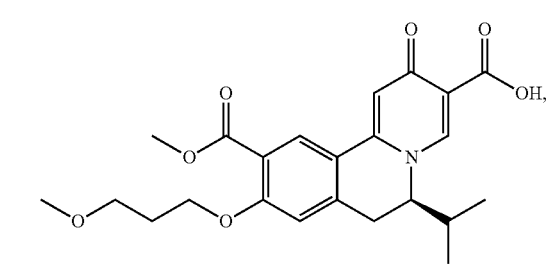
(10)
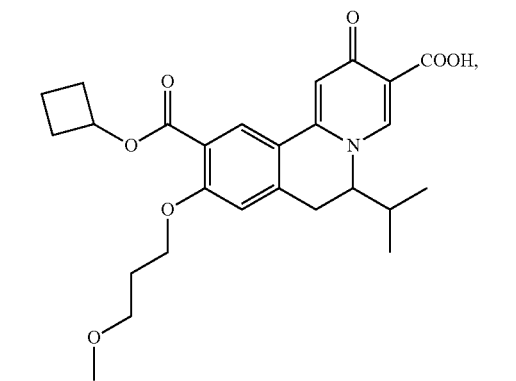
(11)
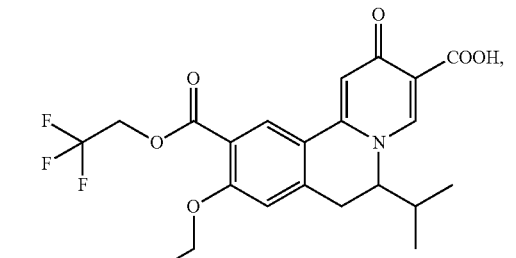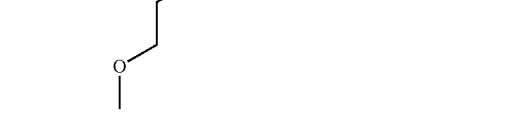
-continued
(12)
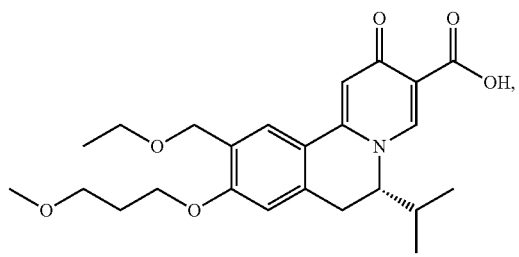
(13)
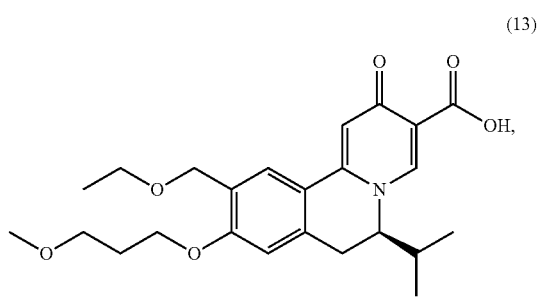
(14)
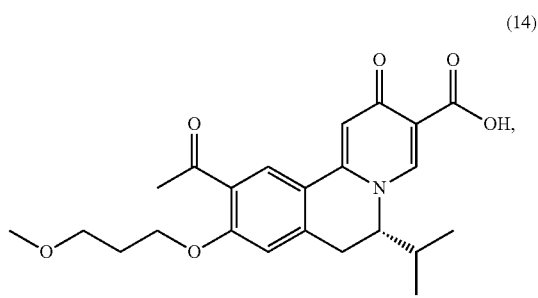
(15)
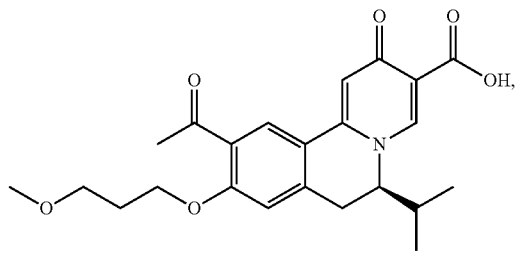
(16)
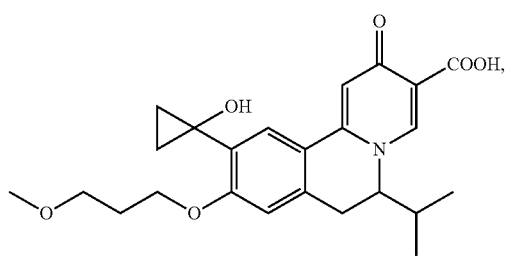

(17) 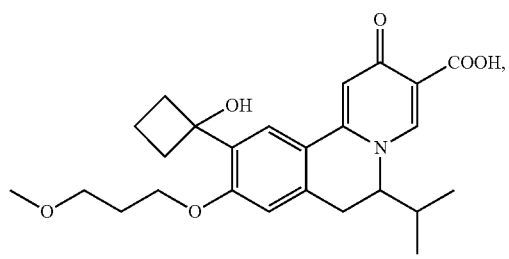
(18) 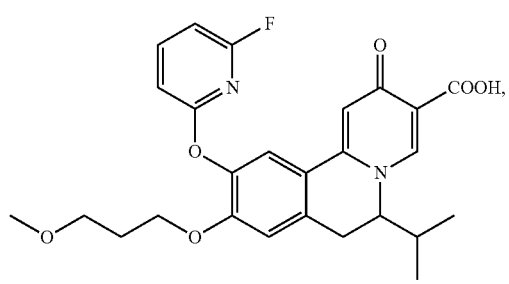
(19) 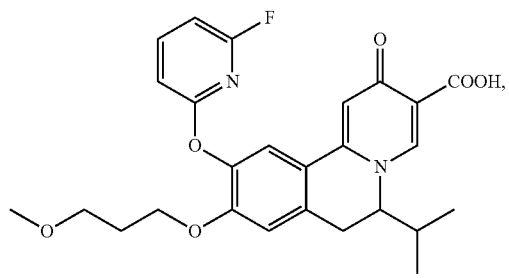
(20) 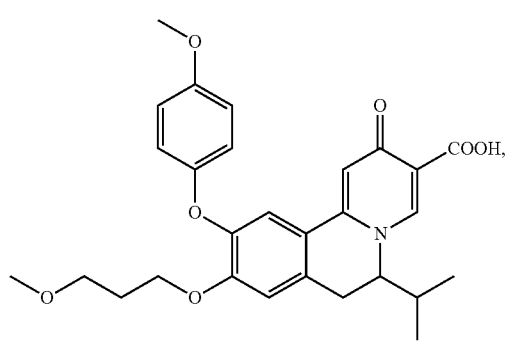
(21) 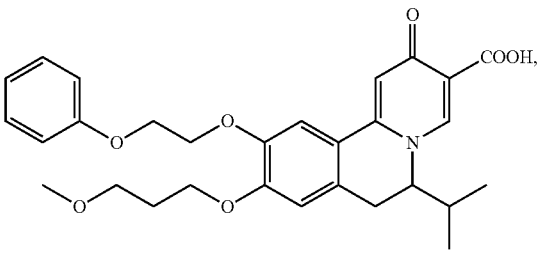
(22) 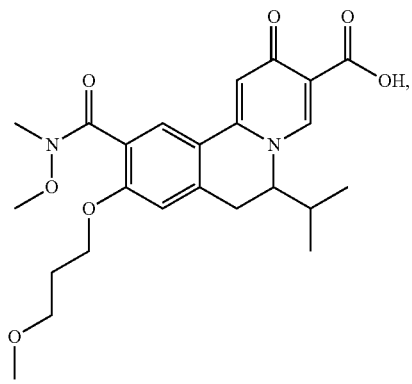
(23) 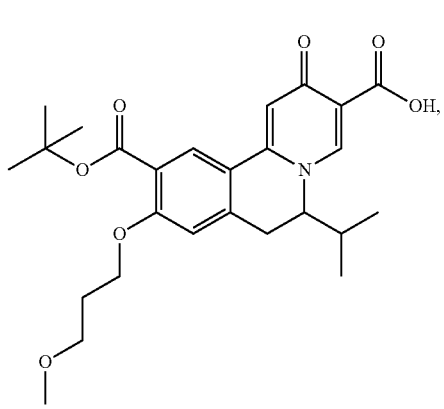
(24) 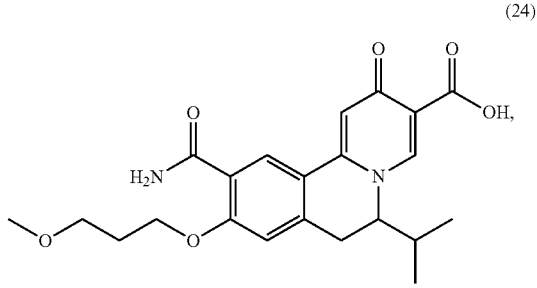
(25) 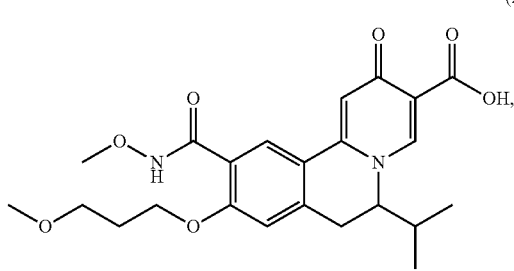
(26) 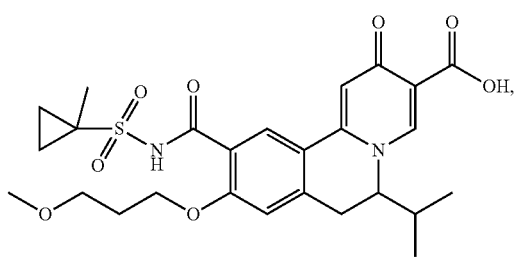

(27) 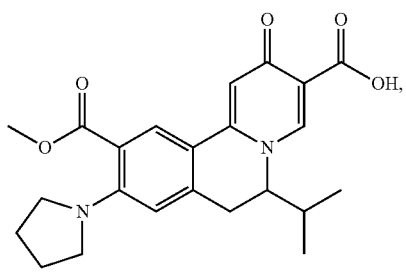
(28) 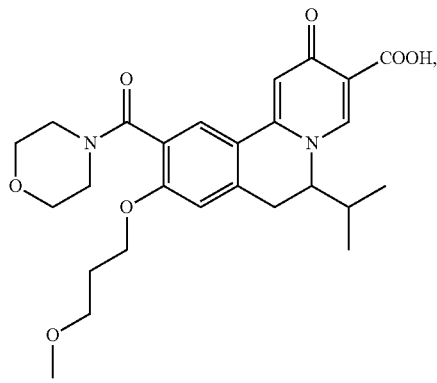
(29)
(30)
(31) 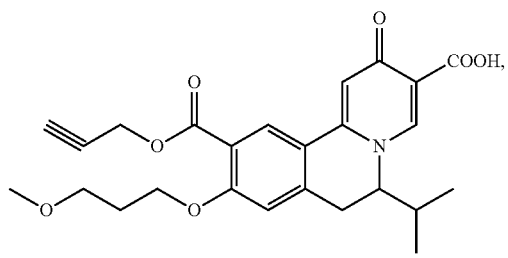
(32)
(33) 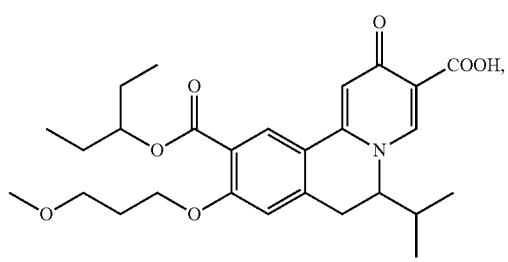
(34) 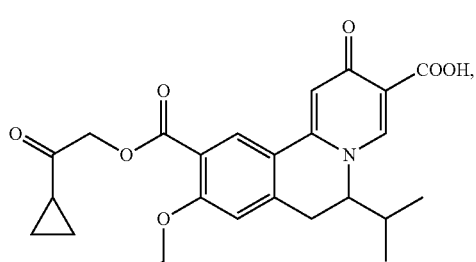
(35) 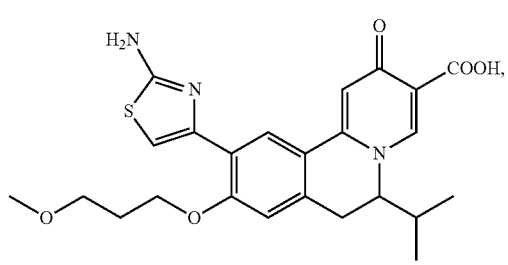

-continued
(36)
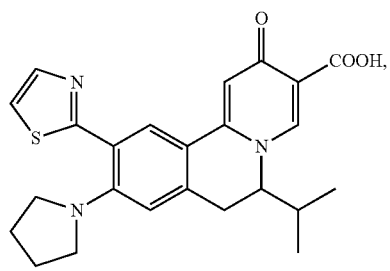
(37)
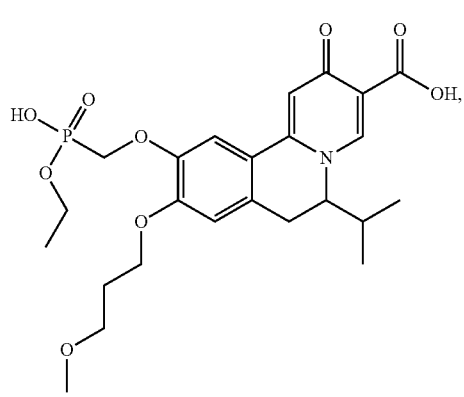
(38)
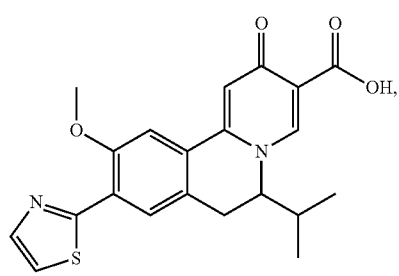
(39)
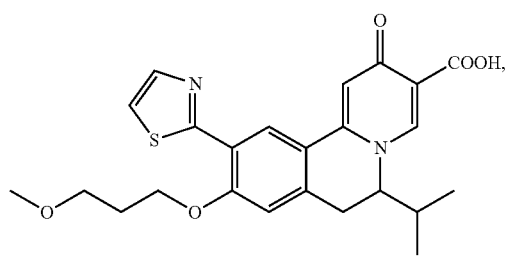
(40)
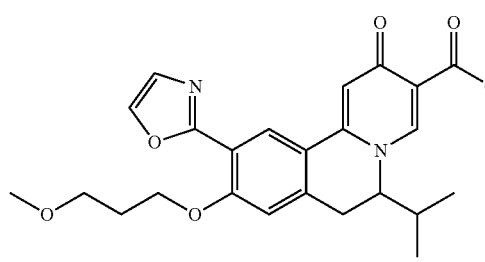
-continued
(41)
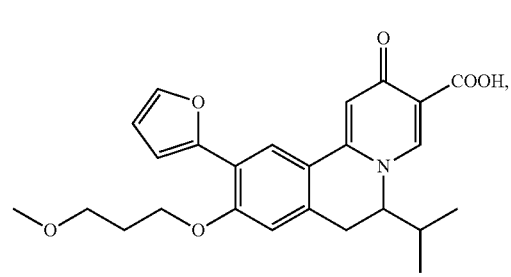
(42)
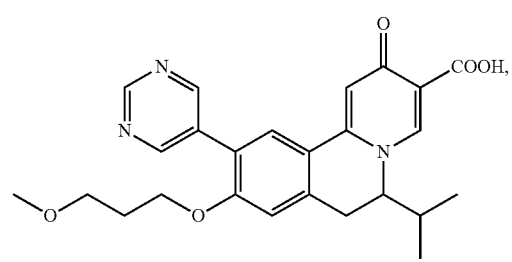
(43)
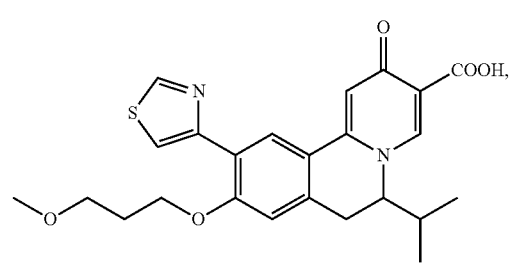
(44)
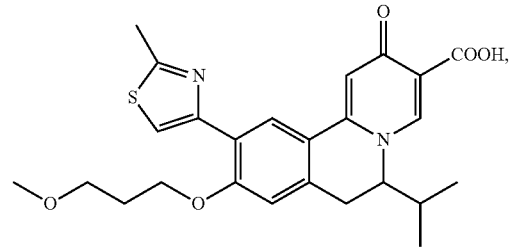
(45)
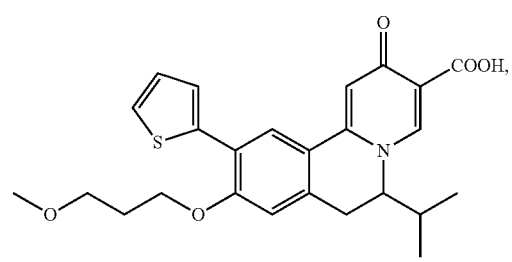

(46)
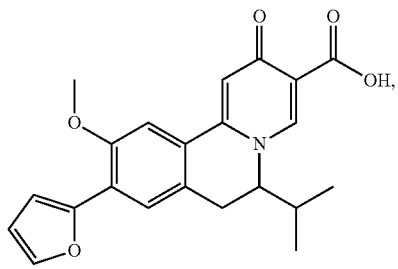
(47)
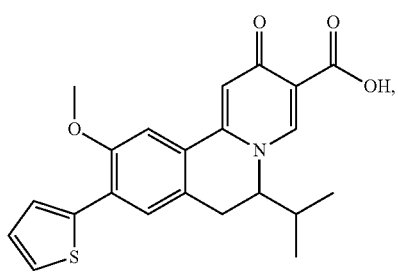
(48)
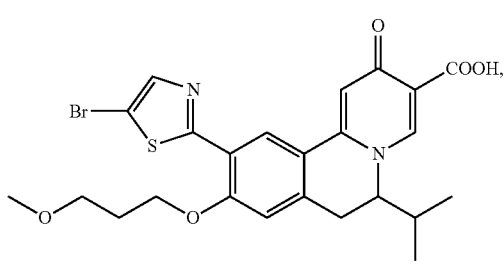
(49)
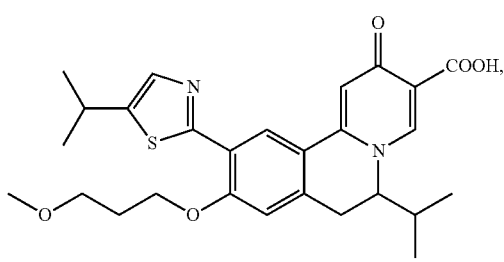
(50)
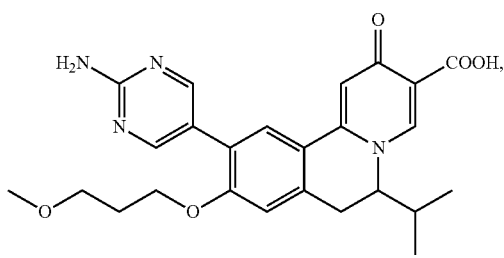
(51)
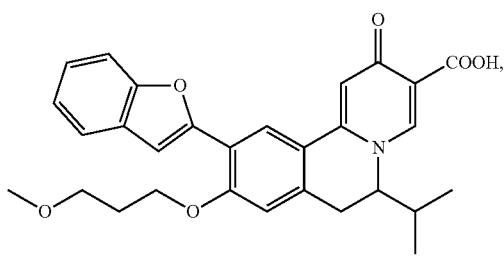
(52)
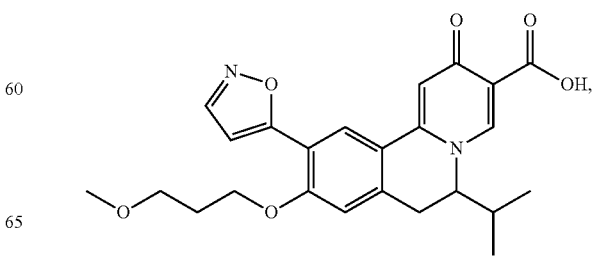
(53)
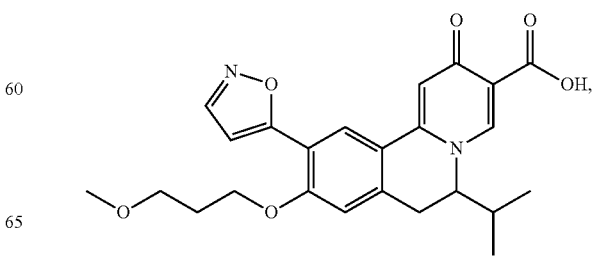
(54)
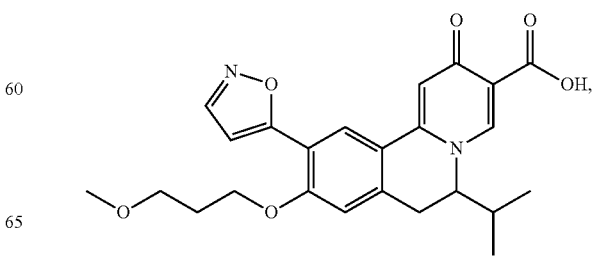
(55)
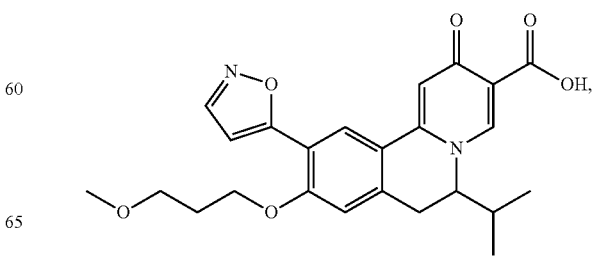

(56)
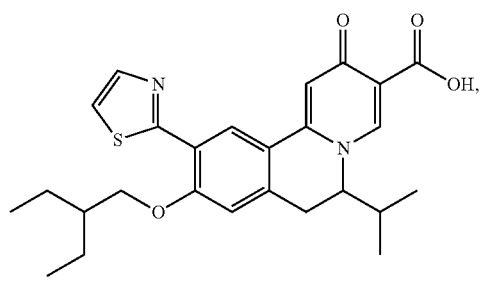
(57)
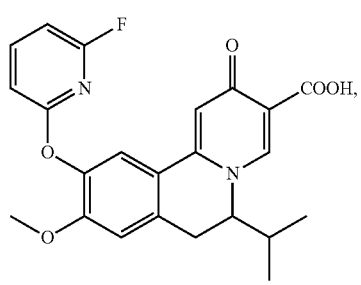
(58)
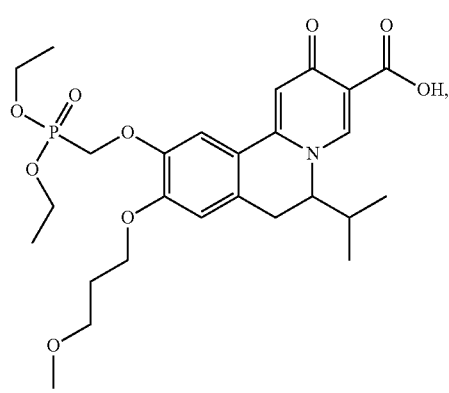
(59)
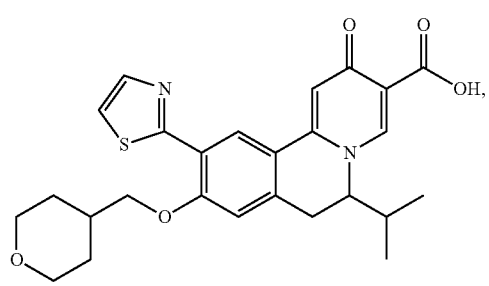
(60)
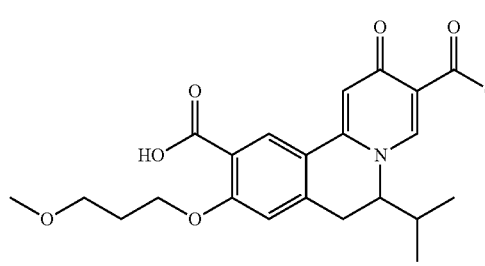
(61)
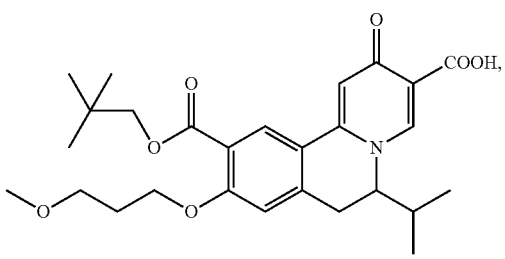
(62)
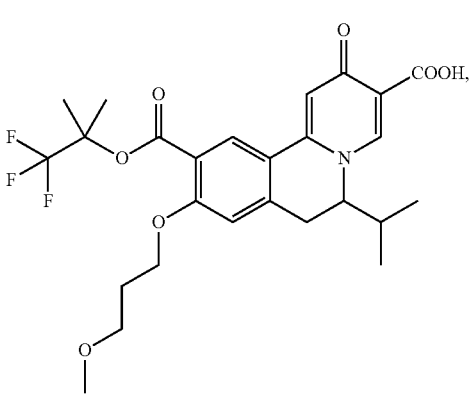
(63)
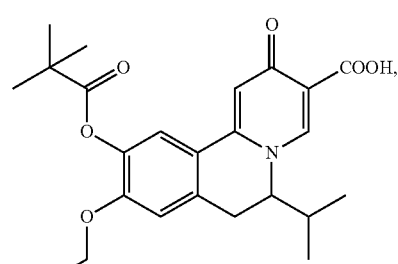
(64)
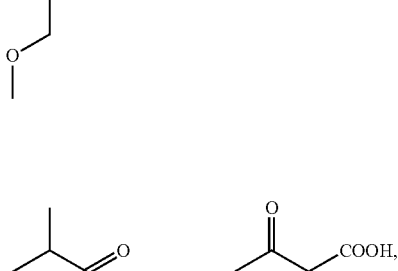
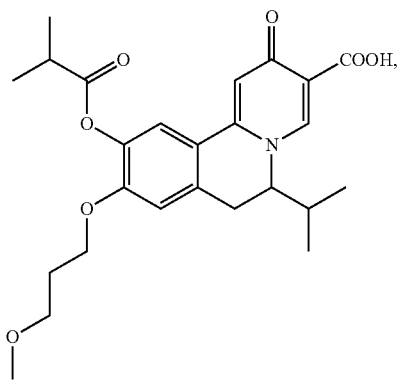

51
(65)
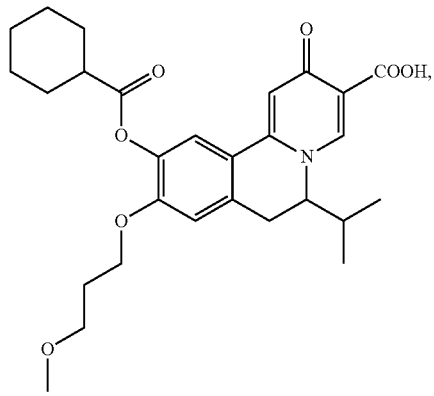
(66)
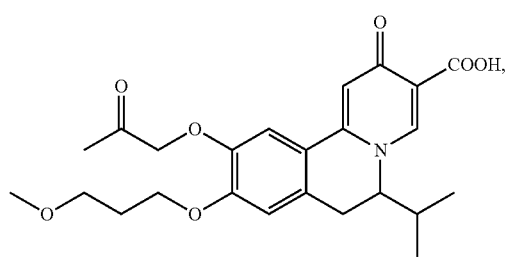
(67)
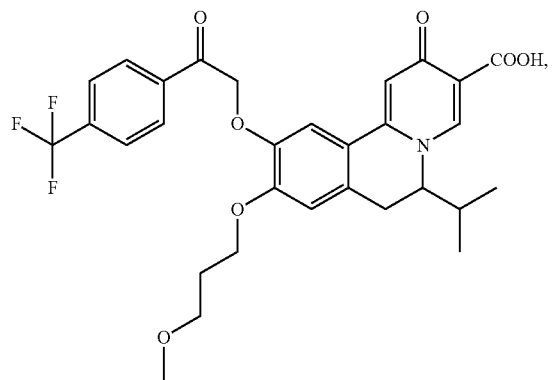
(68)
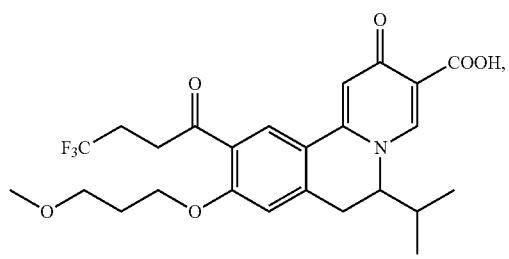
(69)
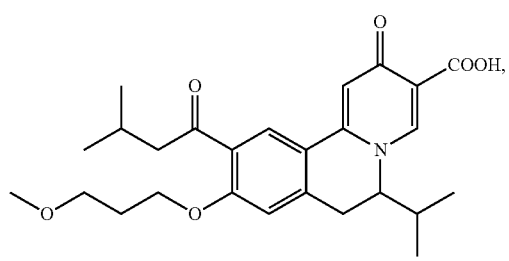
52
(70)
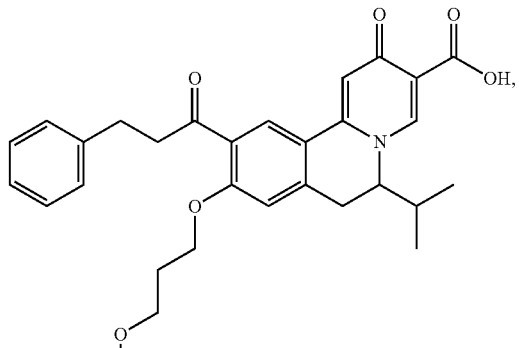
(71)
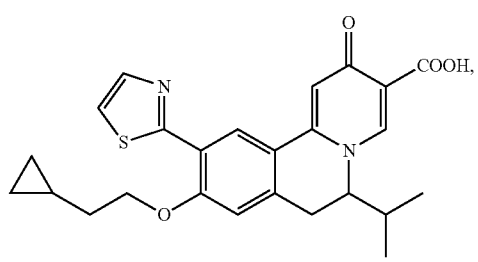
(72)
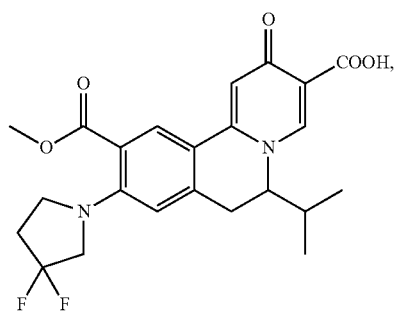
(73)
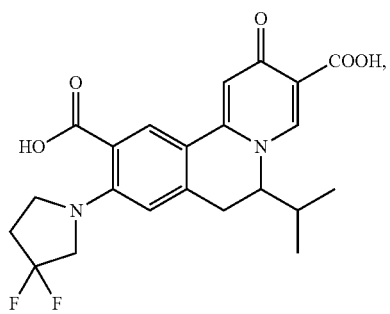
(74)
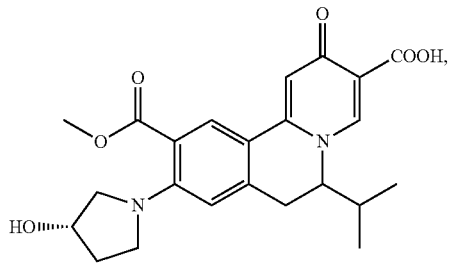

(75) 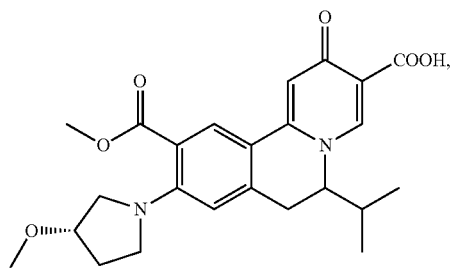
(76) 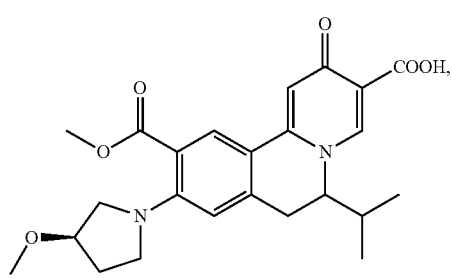
(77) 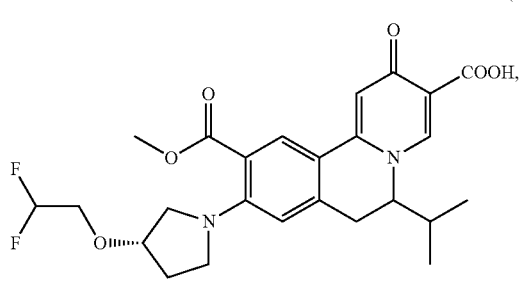
(78) 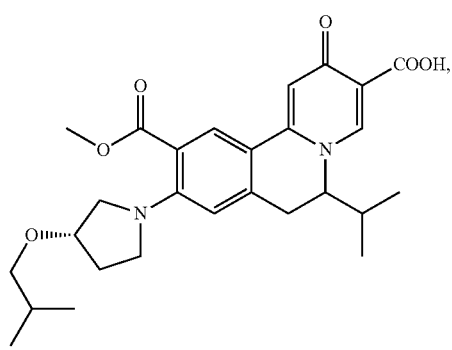
(79) 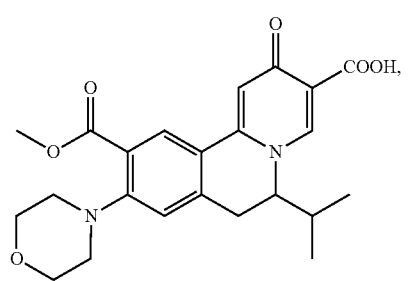
(80) 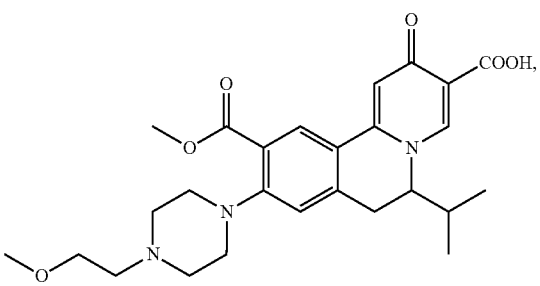
(81) 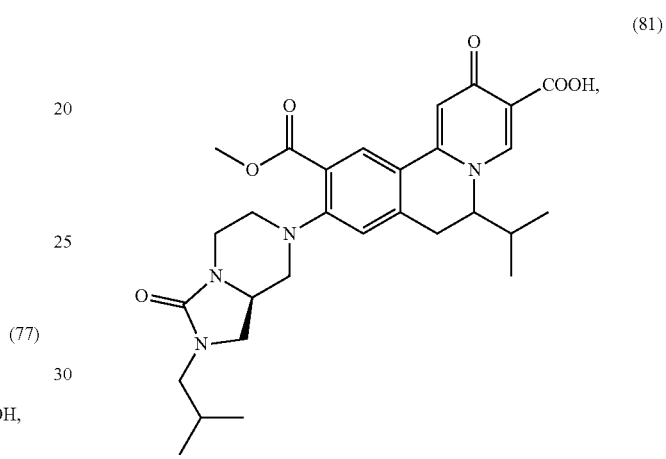
(82) 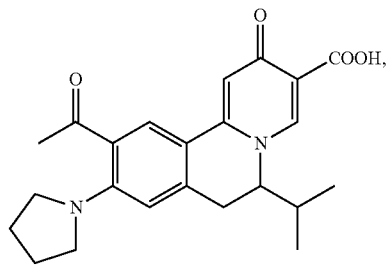
(83) 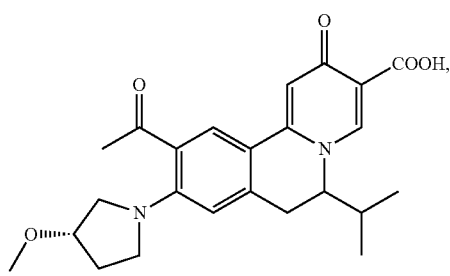
(84) 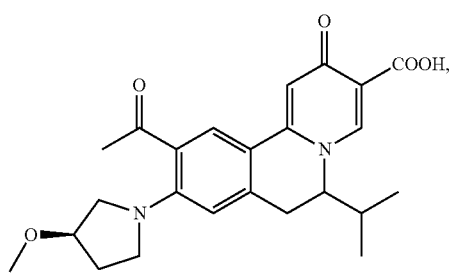

-continued
(85)
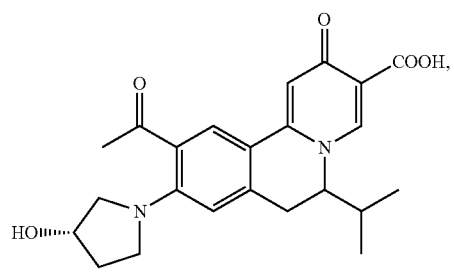
(86)
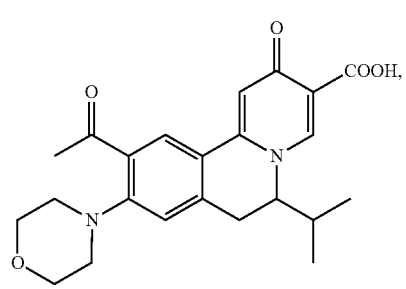
(87)
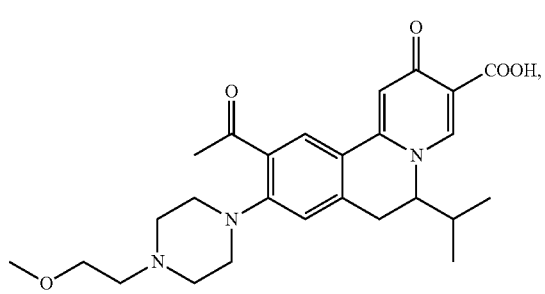
(88)
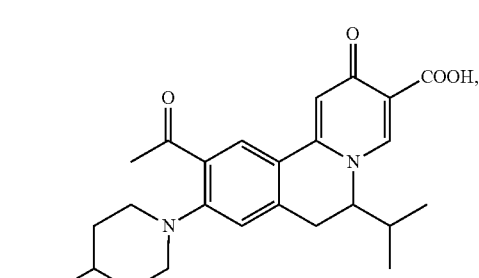
(89)
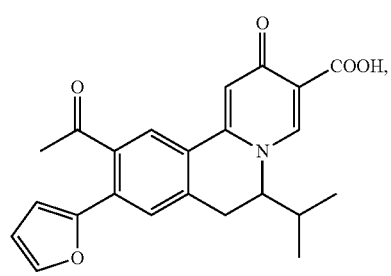
-continued
(90)
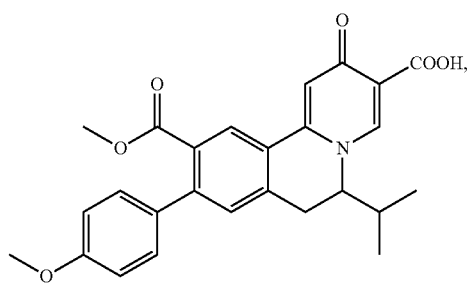
(91)
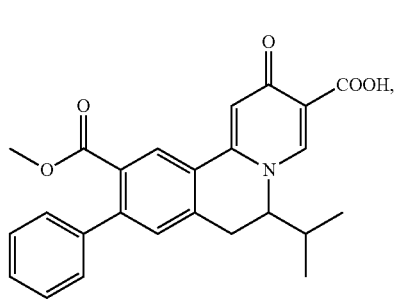
(92)
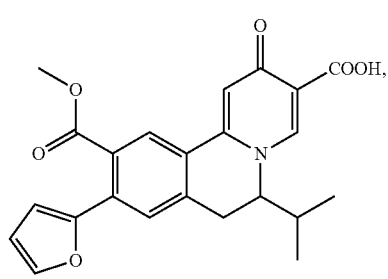
(93)
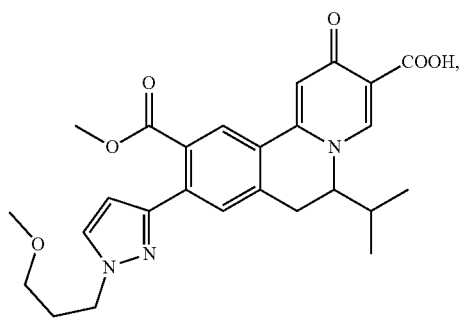
(94)
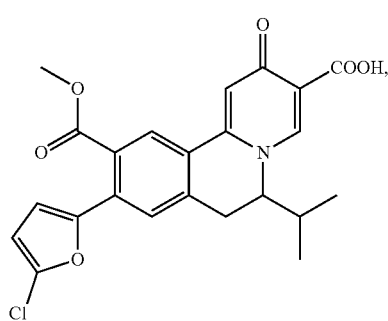

(95)
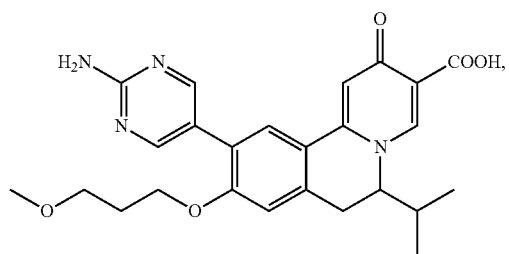
(96)
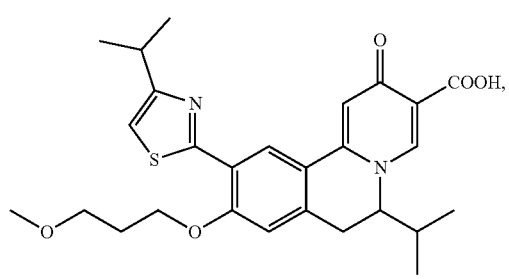
(97)
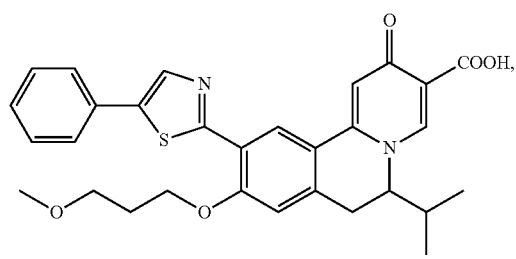
(98)
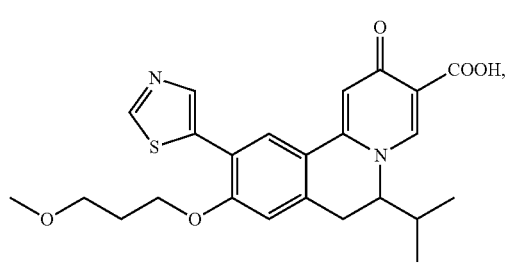
(99)
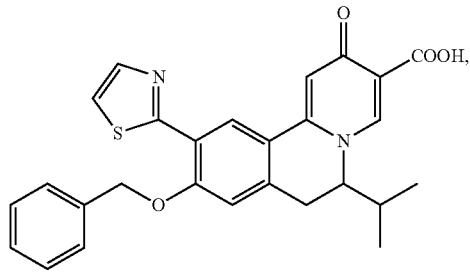
(100)
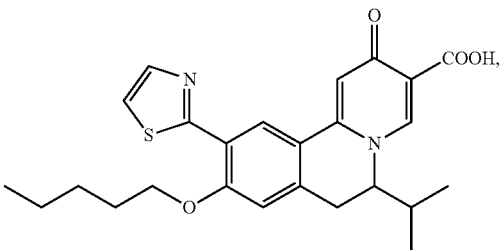
(101)
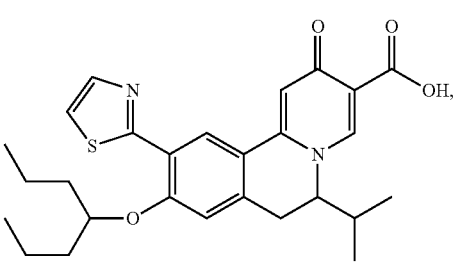
(102)
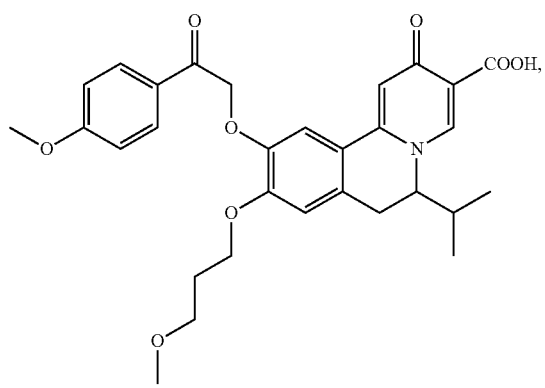
(103)
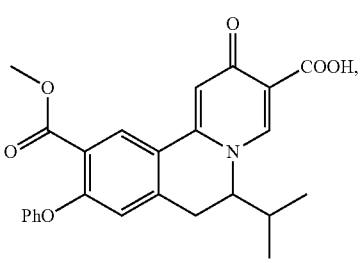
(104)
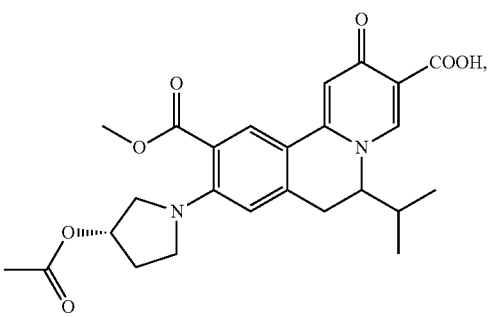

(105)
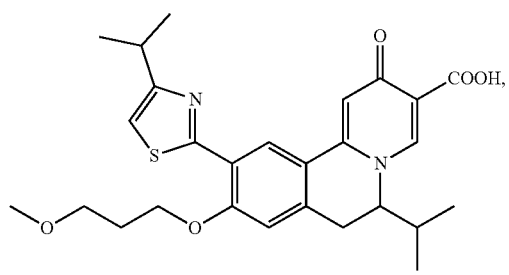
(106)
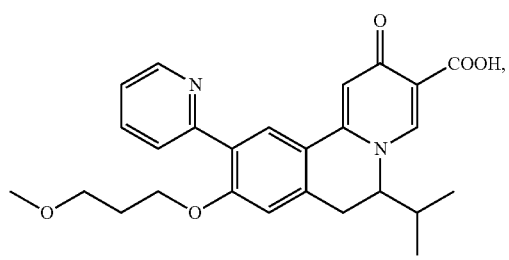
(107)
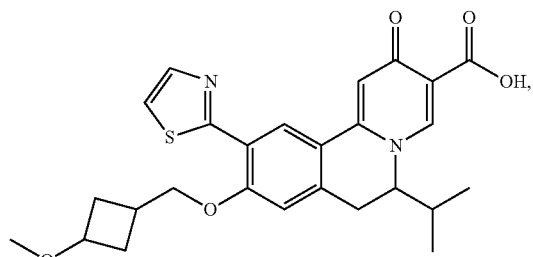
(108)
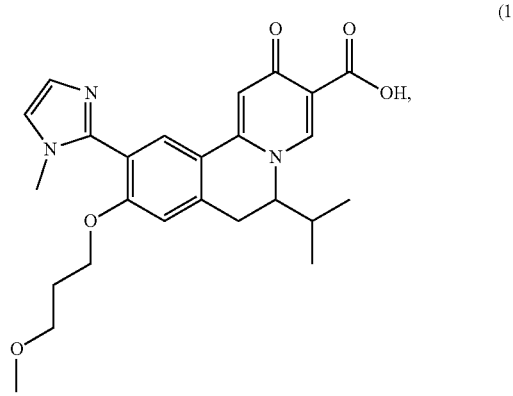
(109)
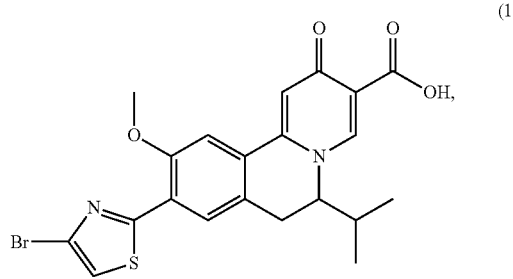
(110)
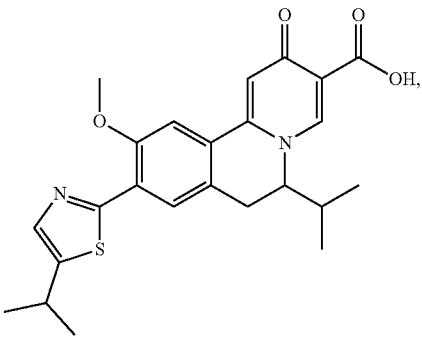
(111)
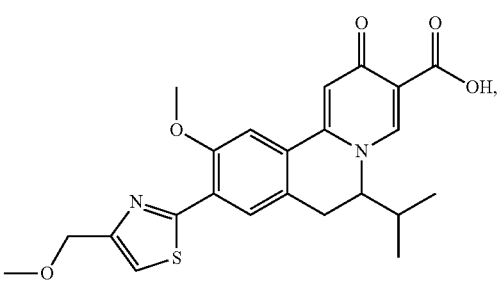
(112)
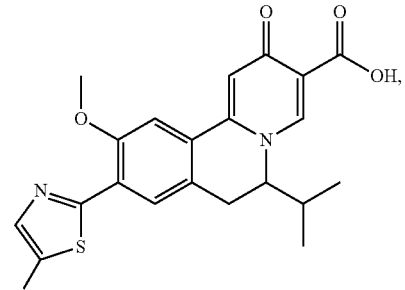
(113)
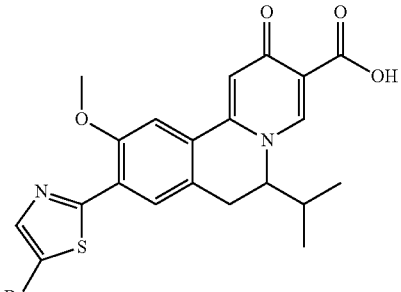
or
(114)
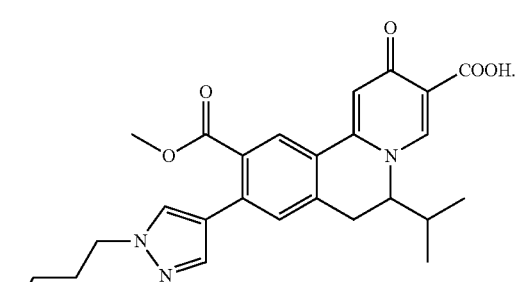

Unless otherwise specified, all stereoisomers, tautomers, N-oxides, solvates, metabolites, pharmaceutically acceptable salts or prodrugs of the compound having formula (I) are within the scope of the present invention.

In another aspect, provided herein is a pharmaceutical composition comprising the compound of the invention; optionally, wherein the pharmaceutical composition further comprises a pharmaceutically acceptable excipient, or a combination of the excipients.

In some embodiments, the pharmaceutical composition disclosed herein further comprises other anti-HBV drug.

In some embodiments, the pharmaceutical composition disclosed herein, wherein the other anti-HBV drug is a HBV polymerase inhibitor, an immunomodulator or an interferon.

In some embodiments, the pharmaceutical composition disclosed herein, wherein the other anti-HBV agent is lamivudine, telbivudine, tenofovir, entecavir, adefovir dipivoxil, alfaferone, alloferon, celmoleukin, clevudine, emtricitabine, famciclovir, interferon, hepatect C P, intefen, interferon-1b, interferon, interferon-2a, interferon $f$-1a, interferon-2, interleukin-2, mivotilate, nitazoxanide, peginterferon alfa-2a, ribavirin, roferon-A, sizofiran, euforavac, ampligen, phosphazid, heplisav, interferon-2b, levamisole or propagermanium.

In another aspect, provided herein is use of the compound or the pharmaceutical composition of the invention in the manufacture of a medicament for preventing, treating or lessening a disorder or disease caused by a virus infection in a patient.

In some embodiments, the use disclosed herein, wherein the virus disease is hepatitis B infection or a disease caused by hepatitis B infection.

In other embodiments, the use disclosed herein, wherein the disease caused by hepatitis B infection is cirrhosis or hepatocellular carcinogenesis.

In another aspect, provided herein is use of the compound of the invention in the manufacture of a medicament for preventing, managing or treating a HBV disorder or disease in a patient, or lessening the severity of the HBV disorder or disease in a patient.

In another aspect, provided herein is use of the pharmaceutical composition comprising the compound of the invention in the manufacture of a medicament for preventing, managing or treating a HBV disorder or disease in a patient, or lessening the severity of the HBV disorder or disease in a patient.

In another aspect, provided herein is use of the compound or the pharmaceutical composition of the invention in the manufacture a medicament for inhibiting the production or secretion of HBsAg, and/or for inhibiting the production of HBV DNA.

In another aspect, provided herein is the compound or the pharmaceutical composition of the invention for use in preventing, treating or lessening a disorder or disease caused by a virus infection in a patient.

In another aspect, provided herein is a method of preventing, treating or lessening a HBV disorder or disease in a patient comprising administering to the patient a therapeutically effective amount of the compound of the invention.

In another aspect, provided herein is a method of preventing, treating or lessening a HBV disorder or disease in a patient comprising administering to the patient a therapeutically effective amount of the pharmaceutical composition comprising the compound of the invention.

In another aspect, provided herein is a method of inhibiting HBV infection, comprising contacting a cell with an amount of the compound or composition of the invention that is effective to inhibit HBV. In other embodiments, the method further comprises contacting the cell with an anti-HBV agent.

In another aspect, provided herein is a method of treating HBV disorder or disease in a patient, comprising administering to the patient an effective amount of the compound or composition of the invention. In other embodiments, the method further comprises administration of HBV therapy.

In another aspect, provided herein is a method of inhibiting HBV infection in a patient, comprising administering to the patient an effective therapeutic amount of the compound or composition of the invention. In other embodiments, the method further comprises administration of other HBV therapy.

In other aspect, provided herein is a method of preparing, separating or purifying the compound of Formula (I).

The present invention also comprises uses of the compound and pharmaceutically acceptable salts thereof in the manufacture of a medicine for effectively treating HBV infections including those described in the invention. In other aspect, provided herein is use of the compound of the invention in the manufacture of a medicament for effective inhibition of HBV infection. The compound disclosed herein also can be used in the manufacture of a medicine for lessening, preventing, managing or treating diseases mediated by hepatitis B. The present invention provides a pharmaceutical composition comprising a therapeutically effective amount of a compound of Formula (I) required for the combination of the compound represented by formula (I) and at least one pharmaceutically acceptable excipient.

The present invention also provides a method of effectively treating HBV infections, or sensitive to these diseases in a patient comprising administering to the patient a therapeutically effective amount of the compound of Formula (I).

Unless otherwise stated, all stereoisomers, tautomers, N-oxides, solvates, metabolites, pharmaceutically acceptable salts or prodrugs of the compounds disclosed herein are within the scope of the invention.

In certain embodiments, the salt is a pharmaceutically acceptable salt. The phrase 'pharmaceutically acceptable_ refers to that the substance or composition must be compatible chemically and/or toxicologically, with the other ingredients comprising a formulation, and/or the mammal being treated therewith.

The salts of the compounds also include salts that may be useful for preparing and/or purifying the intermediates of compounds represented by Formula (I), compounds represented by Formula (I), and/or enantiomers of compounds represented by Formula (I), which are not necessarily pharmaceutically acceptable salts.

The term as used herein, 'pharmaceutically acceptable_ means a substance is acceptable for pharmaceutical applications from the standpoint of toxicology and does not adversely interact with active ingredients.

The salts of the compounds also include salts that may be useful for preparing and/or purifying the intermediates of compounds represented by Formula (I), and/or separated enantiomers of compounds represented by Formula (I), which are not necessarily pharmaceutically acceptable salts.

If the compound of the invention is basic, the desired salt can be prepared by any suitable method provided in the literature, for example, using an inorganic acid such as hydrochloric acid, hydrobromic acid, sulfuric acid, nitric acid, phosphoric acid, and the like; or using an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound of the present invention is acidic, the desired salt can be prepared by an appropriate method. Inorganic bases, such as the lithium salt, sodium salt, potassium salt, calcium salt, magnesium salt, aluminum salt, iron salts, ferrous salts, manganese salts, manganous salts, copper salts, zinc salts and ammonium salts of the compound represented by formula (I) are obtained; inorganic bases, such as the compounds represented by the formula (I) and methylamine, dimethylamine, trimethylamine, ethylamine, diethylamine, triethylamine, tromethamine, diethylaminoethanol, isopropylamine, 2-ethylaminoethanol, pyridine, picoline, ethanolamine, diethanolamine, ammonium, dimethylethanolamine, tetramethylammonium, tetraethylammonium, triethanolamine, piperidine, piperazine, morpholine, imidazole salts, lysine, arginine, L-arginine, histidine, N-methylglucamine, dimethylglucosamine, ethylglucosamine, dicyclohexyl amine, 1,6-hexamethylenediamine, ethylenediamine, glucosamine, sarcosine, serinol, aminopropylene glycol, 1-aminobutan-2,3,4-triol, L-lysine, ornithine and the like.

Composition of the Compound of the Invention, Preparations, Administration, and Uses of Compound and Composition The invention features pharmaceutical compositions that include a compound of Formula (I) or a compound listed in Examples, or a stereoisomer, a tautomer, an N-oxide, a solvate, a metabolite, a pharmaceutically acceptable salt or a prodrug thereof, and a pharmaceutically acceptable excipient. Chronic viral diseases caused by HBV may cause serious pathological changes. Chronic hepatitis B virus infection can lead to cirrhosis and/or hepatocellular carcinogenesis in many cases. The compounds in the composition of the present invention can effectively inhibit hepatitis B virus. Diseases caused by viruses are especially acute and chronic persistent HBV viral infections.

Areas of indication which may be mentioned for the compounds of the invention are, for example: the treatment of acute and chronic viral infections which may lead to infectious hepatitis, for example infections with hepatitis B viruses. The compounds of the invention are particularly suitable for the treatment of chronic hepatitis B infections and the treatment of acute and chronic hepatitis B viral infections.

The present invention includes pharmaceutical preparations which, besides nontoxic, inert pharmaceutically suitable excipients, comprise one or more compounds having Formula (I) or a composition of the invention.

The pharmaceutical preparations mentioned above may also comprise other active pharmaceutical ingredients apart from the compounds having Formula (I).

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically compositions disclosed herein comprise any one of the compound having Formula (I), and further comprise a pharmaceutically acceptable excipient, which, as used herein, includes any and all solvents, diluents, solid excipients, diluent, adhesives, disintegrant or other liquid vehicle, dispersion, flavoring agents or suspension aids, surface active agents, isotonic agents, thickening or emulsifying agents, preservatives, solid binders, lubricants and the like, as suited to the particular dosage form desired. As the following described: In Remington: The Science and Practice of Pharmacy, 21st edition, 2005, ed. D. B. Troy, Lippincott Williams& Wilkins, Philadelphia, and Encyclopedia of Pharmaceutical Technology, eds. J. Swarbrick and J. C. Boylan, 1988-1999, Marcel Dekker, New York, both of which are herein incorporated by reference in their entireties, discloses various excipients used in formulating pharmaceutically acceptable compositions and known techniques for the preparation thereof. Except insofar as any conventional adjuvant incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable adjuvants include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The pharmaceutical composition of the compound disclosed herein may be administered in any of the following routes: orally, inhaled by spray, locally, rectally, nasally, vaginally, parenterally such as subcutaneous, intravenous, intramuscular, intraperitoneal, intrapulmonary, intrathecal, intraventricular, intrasternal, or intracranial injection or infusion, or administered with the aid of an explanted reservoir. Administration routes by orally, intramuscular, intraperitoneal or intravenous injection are preferred.

The compound and pharmaceutically composition thereof of the invention may be administered in a unit dosage form. The dosage form may be in a liquid form, or a solid form. The liquid form includes true solutions, colloids, particulates, suspensions. Other dosage forms include tablets, capsules, dropping pills, aerosols, pills, powders, solutions, suspensions, emulsions, granules, suppositories, freeze-dried powder injection, clathrates, implants, patches, liniments, and the like.

Oral tablets and capsules may comprise excipients, e.g., binders, such as syrup, arabic gum, sorbitol, tragacanth or polyvinylpyrrolidone; fillers, such as lactose, sucrose, corn starch, calcium phosphate, sorbitol, glycine; lubricants such as magnesium stearate, talc, polyethylene glycol, silica; disintegrating agents, such as potato starch, or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other suitable medium is added before use. This liquid preparation may comprise conventional additives, e.g., suspending agents such sorbitol, cellulose methyl ether, glucose syrup, gel, hydroxyethyl cellulose, carboxymethyl cellulose, aluminum stearate gel, hydrogenated edible greases; emulsifying agents such as lecithin, sorbitan monoleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppositories may comprise a conventional suppository base, such as cocoa butter or other glyceride.

For parenteral administration, the liquid dosage form is usually made from the compound and a sterilized excipient. Water is the preferred excipient. According to the difference of selected excipient and drug concentration, the compound can be either dissolved in the excipient or made into a supernatant solution. When being made into a solution for injection, the compound is firstly dissolved in water, and then filtered and sterilized before being packaged into an sealed bottle or an ampoule.

For application topically to the skin, the compound disclosed herein may be made into a suitable form of ointments, lotions or creams, wherein the active ingredient is suspended or dissolved in one or more excipient(s). Wherein excipients used for an ointment preparation include, but are not limited to: mineral oil, liquid vaseline, white vaseline, propylene glycol, polyoxyethylene, polyoxypropylene, emulsified wax and water; excipients used for a lotion and a cream include, but are not limited to: mineral oil, sorbitan monostearate, Tween 60, cetyl ester wax, hexadecylene aromatic alcohol, 2-octyl dodecanol, benzyl alcohol and water.

In general, it has proved to be advantageous in either human medicine or veterinary medicine, the total administrated dose of the active compound disclosed herein is about 0.01 to 500 mg/kg body weight every 24 hours, preferably 0.01 to 100 mg/kg body weight. If appropriate, the drug is administrated in single dose for multiple times, to achieve the desired effect. The amount of the active compound in a single dose is preferably about 1 to 80 mg, more preferably 1 to 50 mg/kg body weight. Nevertheless, the dose may also be varied according to the kind and the body weight of treatment objects, the nature and the severity of diseases, the type of preparations and the method of administration of drugs, and administration period or time interval.

The pharmaceutical composition provided herein further comprises anti-HBV drugs, and the anti-HBV drug is an HBV polymerase inhibitor, immunomodulator, interferon or other emerging anti-HBV agents such as HBV RNA replication inhibitors, HBsAg secretion inhibitors, HBV capsid inhibitors, antisense oligomers, siRNA, HBV therapeutic vaccines, HBV preventive vaccines, HBV antibody therapy (monoclonal or polyclonal) and agonists for the treatment or prevention of HBV.

The HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon-1b, interferon, interferon-2a, interferon $\beta$-1a, interferon-2, interleukin-2, mivotilate, nitazoxanide, peginterferon alfa-2a, ribavirin, roferon-A, sizofiran, euroavac, rintatolimod, phosphazid, heplisav, interferon-2b, levamisole, or propagermanium, and the like.

In one aspect, provided herein is use of the compound disclosed herein or pharmaceutical compositions thereof in the manufacture of a medicament for preventing, managing, treating or lessening HBV diseases in a patient. The HBV disease is a hepatic disease caused by hepatitis B virus infection or hepatitis B infection, including acute hepatitis, chronic hepatitis, cirrhosis and hepatocellular carcinoma. The symptoms of acute hepatitis B virus infection may be asymptomatic or manifested as acute hepatitis symptoms. A patient with chronic virus infection suffers an active disease, which can progress to cirrhosis and liver cancer.

The compounds or pharmaceutical compositions of the present invention may be used for inhibiting the production or secretion of HBsAg, comprising administering to a patient a pharmaceutically acceptable effective dose.

The compounds or pharmaceutical compositions of the present invention may be used for inhibiting the production of HBV DNA, comprising administering to a patient a pharmaceutically acceptable effective dose.

In one aspect, the compounds or pharmaceutical compositions of the present invention may be used for inhibiting the production of HBV genetic expression, including administering to a patient a pharmaceutically acceptable effective dose.

Those anti-HBV agents may be administered separately from the composition containing the compound disclosed herein as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of the compositions disclosed herein will be no more than the amount of the composition comprising the only active agent as therapeutic agent.

The compounds of the present invention show a strong antiviral effect. Such compounds have unexpected antiviral activity against HBV and are therefore suitable for the treatment of various diseases caused by viruses, in particular diseases caused by acute and chronic persistent HBV viral infections. Chronic viral diseases caused by HBV can lead to various syndromes of varying severity. It is well known that chronic hepatitis B virus infection can lead to cirrhosis and/or hepatocellular carcinoma.

Examples of indications that may be treated with the compounds of the present invention are: treatment of acute and chronic viral infections that can cause infectious hepatitis, such as heterosexual hepatitis virus infections. Particularly preferred treatment are the treatment of chronic hepatitis B infection and the treatment of acute hepatitis B virus infection.

The invention also relates to the use of the compounds and compositions of the invention in the manufacture of a medicament for the treatment and prevention of viral diseases, in particular hepatitis B.

General Synthetic Procedures

For the purpose of describing the invention, the following examples are listed. It should be understood that, the invention is not limited to these examples, and the present invention only provide the method to practice the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (éC). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou X iLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., Qingdao Ocean Chemical Factory.

Nuclear magnetic resonance (NMR) spectra were recorded by a Bruker Avance 400 M Hz spectrometer or Bruker Avance III HD 600 spectrometer, using CDCl$_3$, DMSO-d$_6$, CD$_3$OD or acetone-d$_6$ (reported in ppm) as solvent, and using TMS (0 ppm) or chloroform (7.25 ppm) as the reference standard. When peak multiplicities were reported, the following abbreviations were used: s (singlet), s, s (singlet ⊢ singlet), d (doublet), t (triplet), m (multiplet), br (broadened), dd (doublet of doublets), ddd (doublet of doublet of doublets), dt (doublet of triplets), ddt (doublet of doublet of triplets), td (triplet of doublets), br.s (broadened singlet). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30 éC). G1329A autosampler and G1315B DA D detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30 éC). G1329A autosampler and G1315B DA D detector were applied in the analysis, and an ESI source was used in the LC-MS spectrometer.

Both LC-MS spectrometers above were equipped with an Agilent Zorbax SB-C18 column, 2.1×30 mm, 5≈m. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were shown in Table 1:

TABLE 1

The gradient elution conditions

| Time (min) | A (CH$_3$CN, 0.1% HCOOH) | B (H$_2$O, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series High Performance Liquid Chromatography (HPLC) with UV detection at 210 nm and 254 nm on a Zorbax SB-C18 column with a size of 2.1×30 mm, 4 ≈m, 10 minutes; the flow rate was 0.6 mL/min; the mobile phase was 5-95% (0.1% formic acid in acetonitrile) in (0.1% formic acid in water) and the column temperature was maintained at 40 éC.

The following abbreviations are used throughout the specification:

AcOK potassium acetate
MeCN, CH$_3$CN acetonitrile
MeOH methanol
DCM, CH$_2$Cl$_2$ dichloromethane
D$_2$O deuteroxide
DME dimethyl ether
DMSO dimethylsulfoxide
DMF dimethylformamide
DMAP 4-dimethylaminopyridine
DIBAH diisobutylaluminium hydride
CHCl$_3$ chloroform, trichloromethane
CDCl$_3$ chloroform-d, Deuterated chloroform
CCl$_4$ tetrachloromethane
BOC, Boc tert-butoxycarbonyl
Boc$_2$O di-tert-butyl dicarbonate
Bn benzyl
PE petroleum ether
Pd(dba)$_2$ bis(dibenzylideneacetone)palladium
Pd$_2$(dba)$_3$ tris(dibenzylideneacetone)dipalladium
Ph phenyl
PTSA p-toluenesulfonic acid
EA, EtOAc ethyl acetate
EtOH ethanol
HCl hydrochloric acid
K$_2$CO$_3$ potassium carbonate
NaHCO$_3$ sodium bicarbonate
NH$_4$OAc ammonium acetate
NaOH sodium hydroxide NaBH₃CN sodium cyanoborohydride
NaCl sodium chloride
Na₂SO₄ sodium sulfate
Et₃N, TEA triethylamine
NBS N-bromosuccinimide
H₂O water
mL, ml milliliter
min minute, minutes
m-CPBA m-chloroperoxybenzoic acid
h hour, hours
RT, rt room temperature
Rt retention time
H₂ hydrogen
HATU o-(7-azabenzotriazol-1-yl)-N,N,N',N'-tetramethyluronium hexafluorophosphate
HCl/EtOAc a solution of hydrogen chloride in ethyl acetate
HOAt 1-hydroxy-7-azabenzotriazole
DIPEA N, N-diisopropylethylamine
DCC N,N'-dicylohexylcarbodiimide
DMF dimethylformamide
DME dimethyl ether
THF tetrahydrofuran
TFA trifluoroacetic acid
Tf trifluoromethylsulfonyl
LiOH.H₂O lithium hydroxide monohydrate NaBH₃CN sodium cyanoborohydride
IPA isopropanol
DMSO dimethylsulfoxide
CuCN cuprous cyanide
CH₃OH, MeOH methanol
N₂ nitrogen
NH₄Cl ammonium chloride
NH₄OAc ammonium acetate
Ac₂O acetic anhydride
Xantphos 4,5-bis(diphenylphosphino)-9,9-dimethylxanthene
$t_{1/2}$ half-time
t-BuOH tert-butanol
AUC area under the curve
Vss apparent volume of distribution at steady state
CL, clearance clearance
F, absolute bioavailability bioavailability
Dose dosage
$T_{max}$ time to peak
$C_{max}$ maximum concentration
hr*ng/mL plasma concentration*time Synthetic Method The following schemes list the synthetic steps of the compounds of the invention, wherein, each $R^1$, $R^3$, $R^4$, $R^5$, $R^{6a}$, $R^7$, $R^8$, $R^{10a}$, $R^{10}$, $R^{13}$, $R^a$ and $R^b$ are as defined in the invention, X is halogen.

Scheme 1

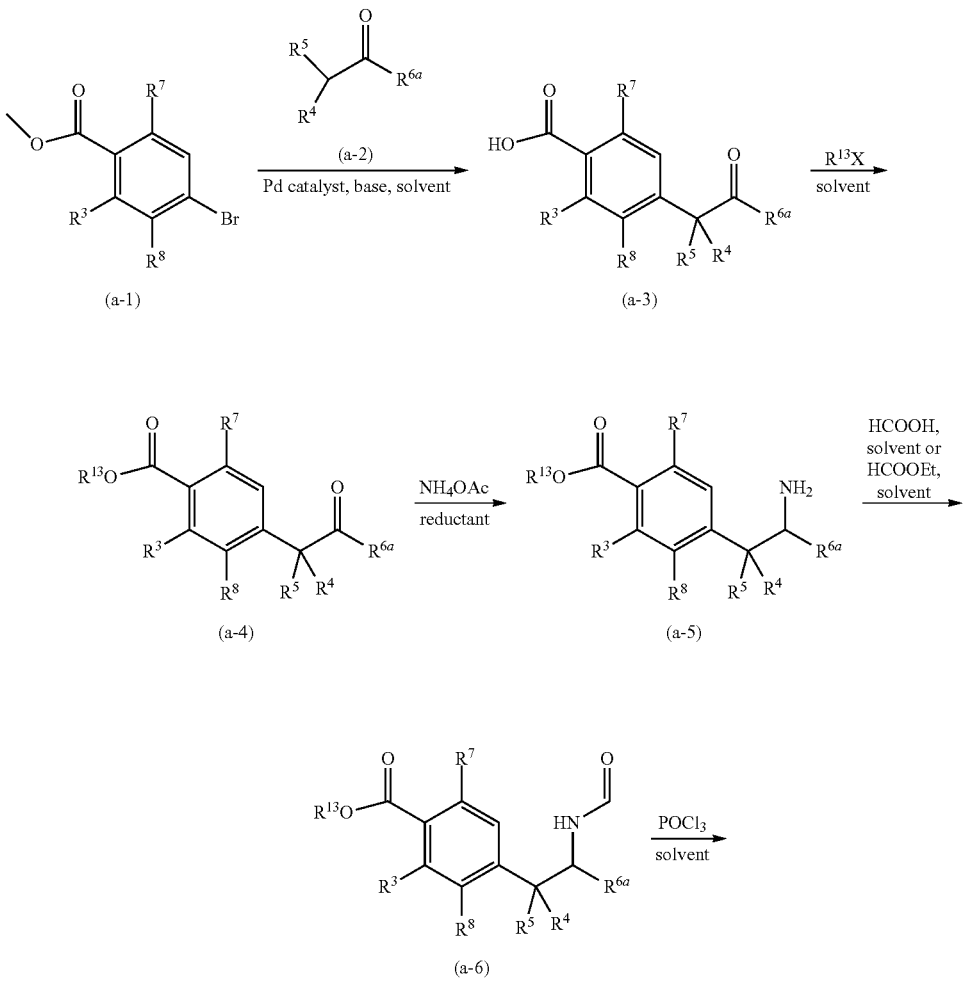

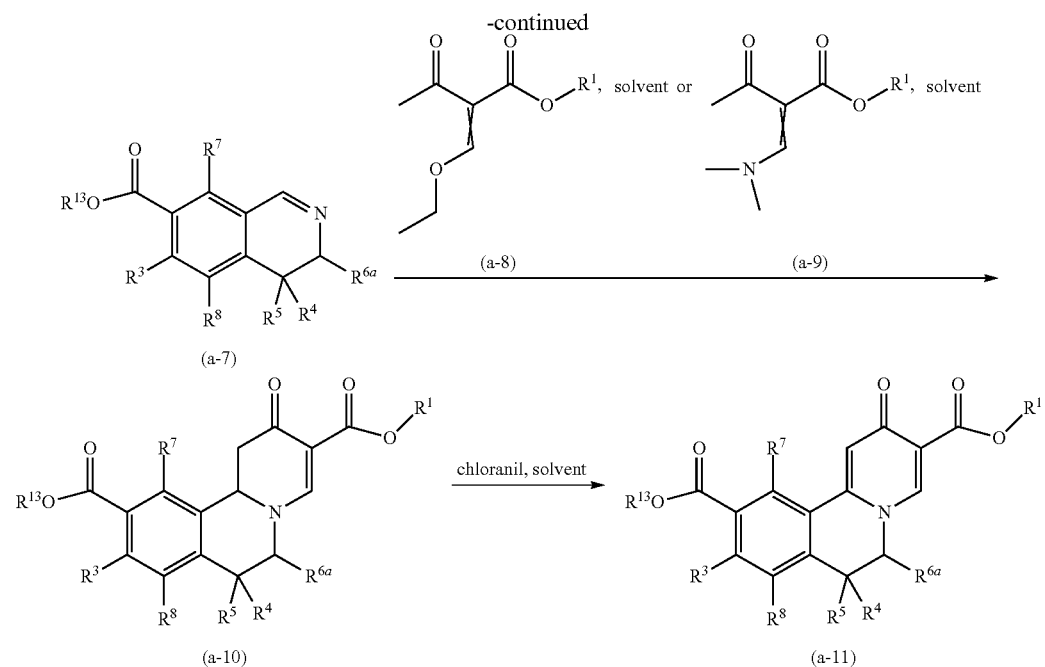

Compound having Formula (a-11) can be prepared by the process illustrated in scheme 1, wherein $R^3$ is as defined in the invention. Firstly, compound (a-1) with compound (a-2) can undergo coupling reaction in the presence of a palladium catalyst (such as $Pd(dba)_2$, $Pd_2(dba)_3$, etc.), a ligand (such as X antphos, etc.), a suitable base (such as sodium tert-butoxide, etc.) and a suitable solvent (such as THF, toluene, and the like) to give compound (a-3). Compound (a-3) with $R^{13}X$ can undergo nucleophilic substitution in the presence of a base (such as $K_2CO_3$, and the like) in a suitable solvent (such as $CH_3CN$, and the like) to give compound (a-4). Compound (a-4) with $NH_4OAc$ can undergo reductive amination in the presence of a reductant (such as $NaBH_3CN$, and the like) in a suitable solvent (such as methanol, and the like) to give compound (a-5). Compound (a-5) can react with formic acid or ethyl formate in a suitable solvent (such as 1,4-dioxane, tetrahydrofuran, and the like) to give compound (a-6). Then, compound (a-6) can react with phosphorus oxychloride in a suitable solvent (such as DCM, and the like) to give compound (a-7). Nextly, compound (a-7) with compound (a-8) or compound (a-9) in a suitable solvent (such as isopropanol, ethanol, DMSO, and the like) can undergo cyclization to give compound (a-10). Lastly, compound (a-10) with chloranil can undergo dehydrogenation reaction in a suitable solvent (such as DME, and the like) to give compound (a-11).

-continued (a-12)

When $R^1$ is benzyl and $R^{13}$ is not benzyl, compound having Formula (a-12) can be prepared by the process illustrated in scheme 2, wherein $R^3$ is as defined in the invention. Benzyl group of compound (a-11) can be removed in the presence of Pd/C catalyst in a suitable solvent (such as THF, methano, and the like) in hydrogen atmosphere (0.1 MPa) to give compound having Formula (a-12).

Scheme 2

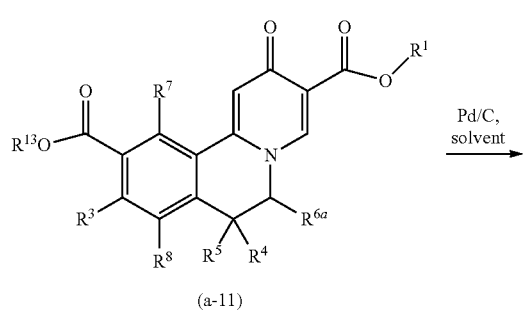

Scheme 3

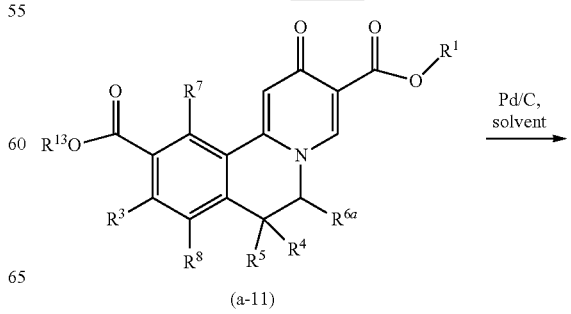

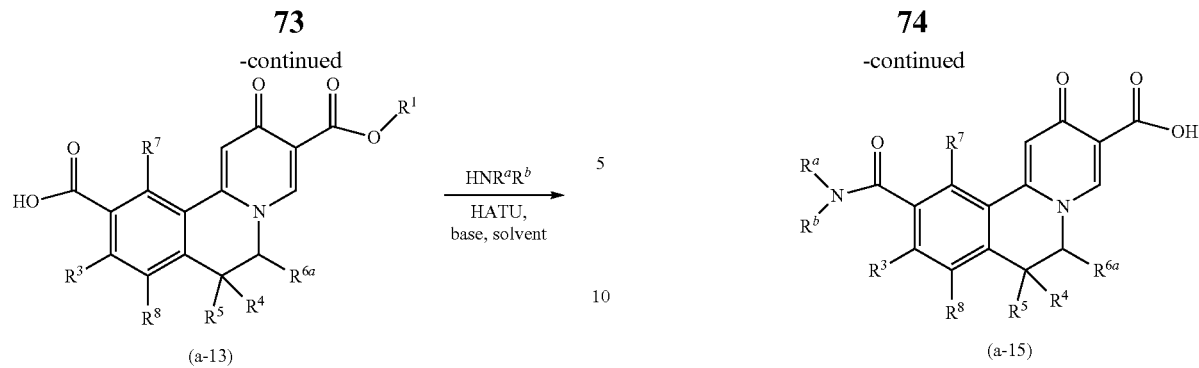

When $R^{13}$ is benzyl and $R^1$ is not benzyl, compound having Formula (a-15) can be prepared by the process illustrated in scheme 3, wherein $R^3$ is as defined in the invention. Firstly, benzyl group of compound (a-11) can be removed in the presence of Pd/C catalyst in a suitable solvent (such as THF, methanol, and the like) in hydrogen atmosphere (0.1 MPa) to give compound having Formula (a-13). Then, compound (a-13) can react with $HNR^aR^b$ in the presence of HATU and a base (such as DIPEA, and the like) in a suitable solvent (such as DMF, and the like) to give compound (a-14). Lastly, compound (a-14) can undergo ester hydrolysis in the presence of a base (such as lithium hydroxide, sodium hydroxide, and the like) in a suitable solvent (such as THF/$H_2O$, EtOH/$H_2O$, MeOH/$H_2O$, MeOH/THF, $H_2O$, and the like), or in the presence of an acid (such as TFA, and the like) in a suitable solvent (such as DCM, and the like) to give compound (a-15)

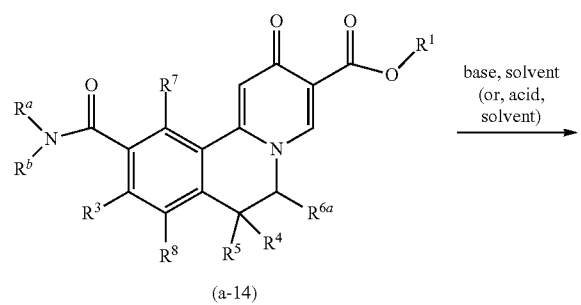

Scheme 4

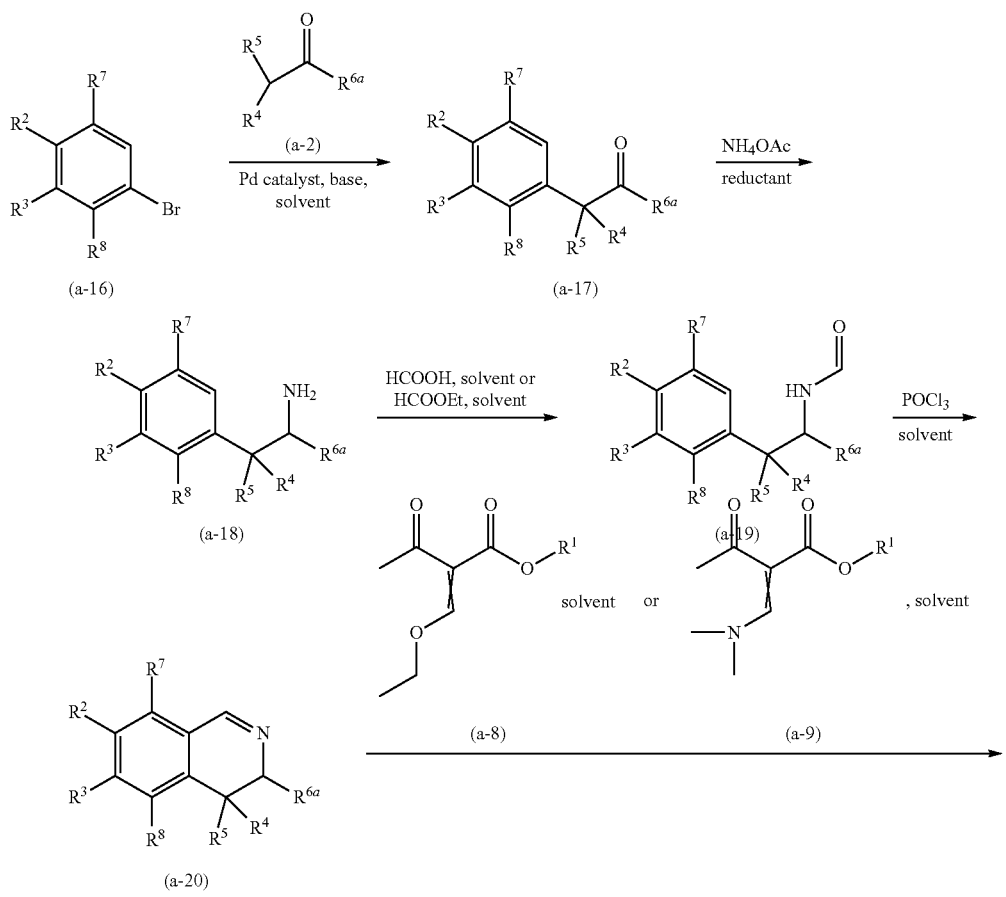

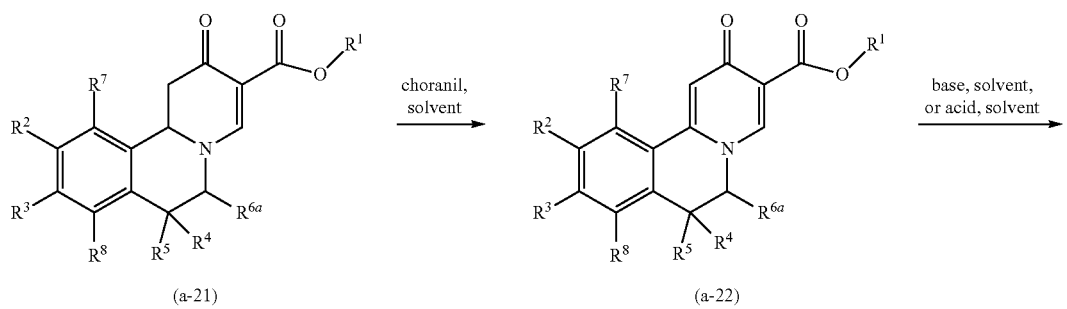

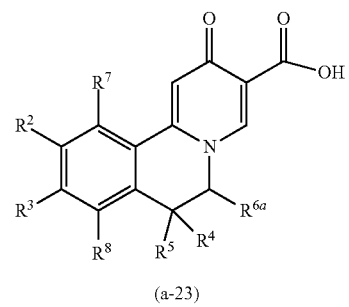

Compound having Formula (a-23) can be prepared by the process illustrated in scheme 4, wherein $R^3$ and $R^2$ are as defined herein, and $R^3$ can also be I or —$NBn_2$, $R^2$ can also be I, phenoxy or —$NBn_2$. Firstly, compound (a-16) with compound (a-2) can undergo coupling reaction in the presence of a palladium catalyst (such as Pd(dba)$_2$, Pd$_2$(dba)$_3$, etc.), a ligand (such as X antphos, etc.), a suitable base (such as sodium tert-butoxide, and the like) in a suitable solvent (such as THF, toluene, etc.) to give compound (a-17). Compound (a-17) with NH$_4$OAc can undergo reductive amination in the presence of a reductant (such as NaBH$_3$CN, and the like) in a suitable solvent (such as methanol, and the like) to give compound (a-18). Compound (a-18) can react with formic acid or ethyl formate in a suitable solvent (such as 1,4-dioxane, tetrahydrofuran, and the like) to give compound (a-19). Then, compound (a-19) can react with phosphorus oxychloride in a suitable solvent (such as DCM, and the like) to give compound (a-20). Nextly, compound (a-20) with compound (a-8) or compound (a-9) in a suitable solvent (such as isopropanol, ethanol, DMSO, and the like) can undergo cyclization to give compound (a-21). Lastly, compound (a-21) with chloranil can undergo dehydrogenation reaction in a suitable solvent (such as DME, and the like) to give compound (a-22). Lastly, compound (a-22) can undergo ester hydrolysis in the presence of a base (such as lithium hydroxide, sodium hydroxide, and the like) in a suitable solvent (such as THF/H$_2$O, EtOH/H$_2$O, MeOH/H$_2$O, MeOH/THF, H$_2$O, and the like), or in the presence of a acid (such as TFA, and the like) in a suitable solvent (such as DCM, and the like) to give compound (a-23).

Scheme 5

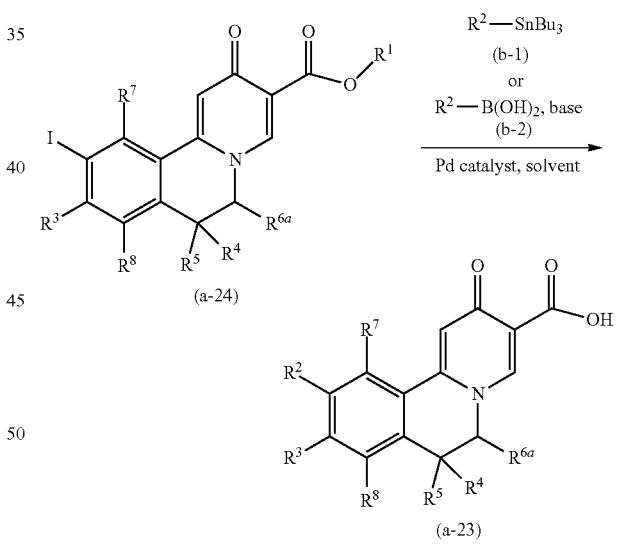

Compound having Formula (a-23) can be prepared by the process illustrated in scheme 5, wherein $R^3$ is as defined herein; $R^2$ is cyclopropyl, $C_{4-7}$ cycloalkyl, 3- to 12-membered heterocyclyl, $C_{6-10}$ aryl or 5- to 10-membered heteroaryl, each of which is unsubstituted or substituted with 1, 2, 3 or 4 $R^w$; and $R^w$ is as defined herein. Compound (a-24) with compound (b-1) or compound (b-2) can undergo coupling reaction in the presence of a Pd catalyst (such as bis(triphenylphosphine)palladium(II) chloride, and the like) in a suitable solvent (such as dioxane, and the like) to give compound (a-23).

Scheme 6

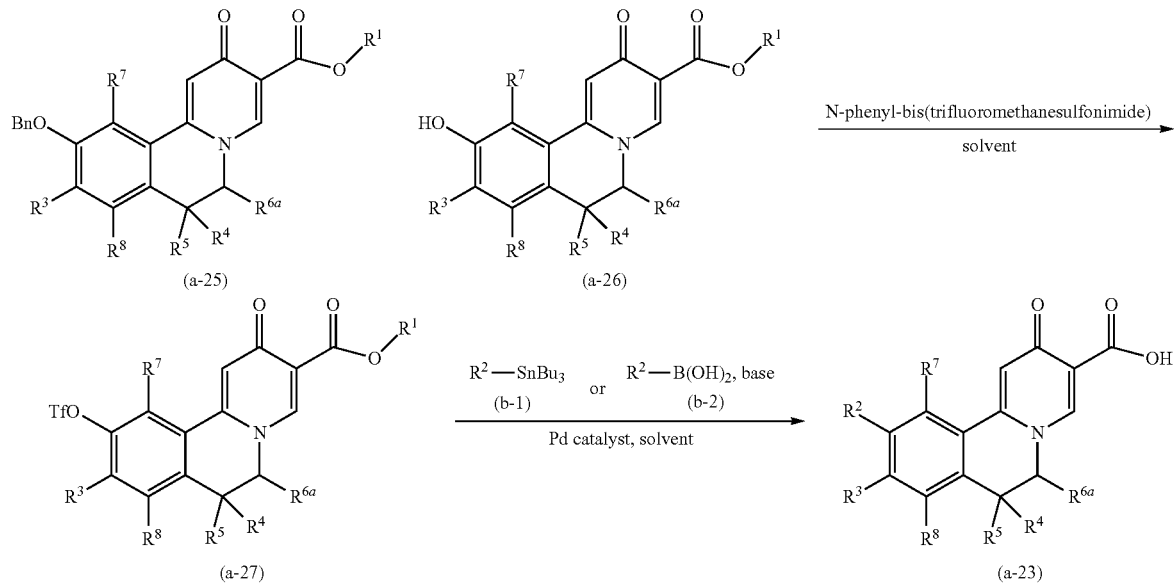

Compound having Formula (a-23) can be prepared by the process illustrated in scheme 6, wherein $R^3$ is as defined herein; $R^2$ is cyclopropyl, $C_{4-7}$ cycloalkyl, 3- to 12-membered heterocyclyl, $C_{6-10}$ aryl or 5- to 10-membered heteroaryl, each of which is unsubstituted or substituted with 1, 2, 3 or 4 $R^w$; and $R^w$ is as defined herein. Firstly, benzyl group on compound (a-25) can be removed to give compound (a-26), then compound (a-26) can react with N-phenyl-bis(trifluoromethanesulfonimide) under a base condition (such as in the presence of triethylamine, and the like) in a suitable solvent (such as dichloromethane, and the like) to give compound (a-27). Lastly, compound (a-27) with compound (b-1) can undergo coupling reaction in the presence of a Pd catalyst (such as bis(triphenylphosphine)palladium (II) chloride, and the like) in a suitable solvent (such as 1,4-dioxane, and the like) to give compound (a-23); or compound (a-27) with compound (b-2) can undergo coupling reaction in the presence of a Pd catalyst (such as tetrakis(triphenylphosphine)palladium(0), and the like), a suitable solvent (such as 1,4-dioxane, and the like) and a suitable base (such as sodium carbonate, potassium phosphate, potassium carbonate, and the like) to give compound (a-23).

Scheme 7

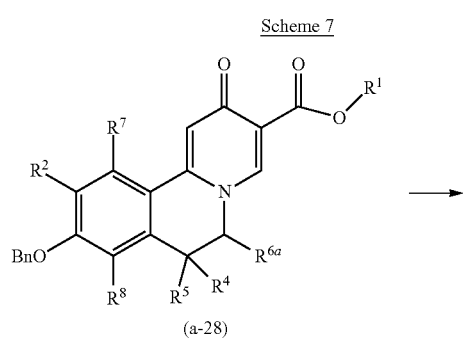

-continued

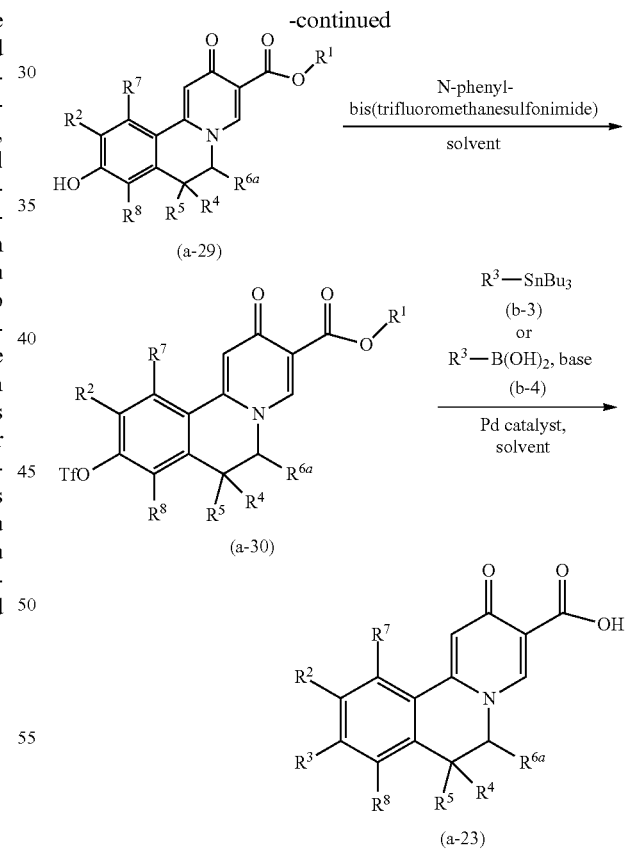

Compound having Formula (a-23) can be prepared by the process illustrated in scheme 7, wherein $R^2$ is as defined herein; $R^3$ is cyclopropyl, $C_{4-7}$ cycloalkyl, 3- to 12-membered heterocyclyl, $C_{6-10}$ aryl or 5- to 10-membered heteroaryl, each of which is unsubstituted or substituted with 1, 2, 3 or 4 $R^w$; and $R^w$ is as defined herein. Firstly, benzyl group on compound (a-28) can be removed to give compound (a-29), then compound (a-29) can react with N-phenyl-bis(trifluoromethanesulfonimide) under a base condition (such as in the presence of triethylamine, and the like) in a suitable solvent (such as dichloromethane, and the like) to give compound (a-30). Lastly, compound (a-30) with compound (b-3) can undergo coupling reaction in the presence of a Pd catalyst (such as bis(triphenylphosphine)palladium (II) chloride, and the like) in a suitable solvent (such as 1,4-dioxane, and the like) to give compound (a-23); or compound (a-30) with compound (1-4) can undergo coupling reaction in the presence of a Pd catalyst (such as tetrakis(triphenylphosphine)palladium(0), and the like), a suitable solvent (such as 1,4-dioxane, and the like) and a suitable base (such as sodium carbonate, potassium phosphate, potassium carbonate, and the like) to give compound (a-23).

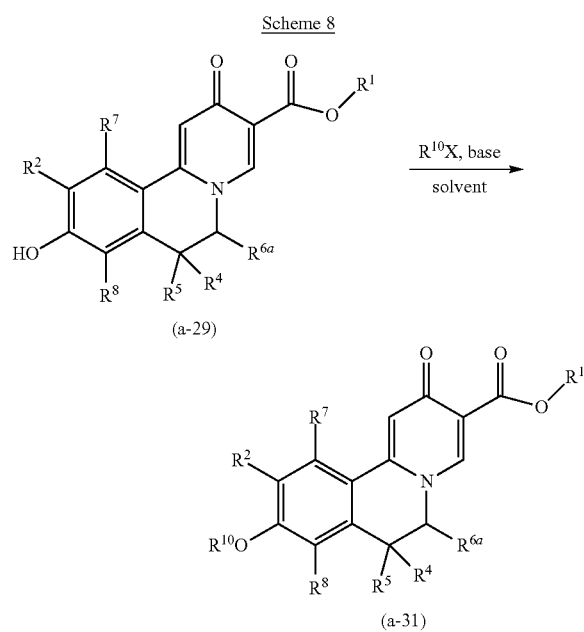

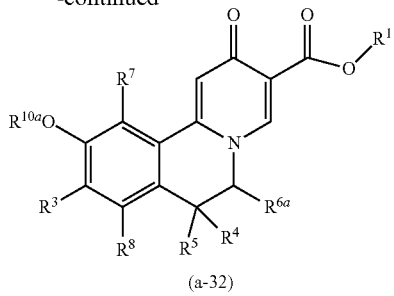

Compound having Formula (a-31) can be prepared by the process illustrated in scheme 8, wherein X is halogen. Compound (a-29) can react with $R^{10}X$ in the presence of a suitable base (such as potassium carbonate, triethylamine, and the like) in a suitable solvent (such as acetonitrile, DMF, DCM, and the like) at a suitable temperature to give compound (a-31).

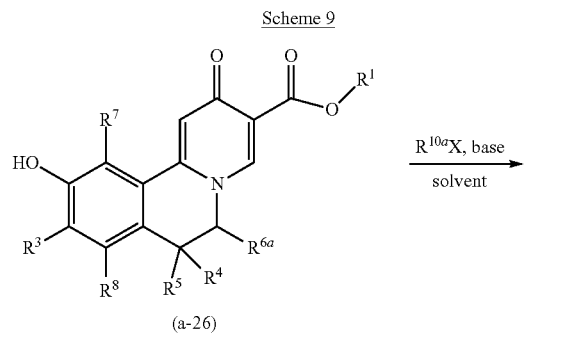

Compound having Formula (a-31) can be prepared by the process illustrated in scheme 9, wherein X is halogen. Compound (a-26) can react with $R^{10}X$ in the presence of a suitable base (such as potassium carbonate, triethylamine, and the like) in a suitable solvent (such as acetonitrile, DMF, DCM, and the like) at a suitable temperature to give compound (a-32).

Description of the Preferred Embodiments

The following examples are used for illustrating the invention, but can not be construed to limit the scope of the invention.

PREPARATION EXAMPLES

In the following preparation examples, the inventors took a part of the compounds of the present invention as examples to describe in detail the preparation process of the compounds of the present invention.

Example 1: 6-isopropyl-10-(methoxycarbonyl)-9-(3-methoxypropoxy)-2-oxo-6,7-dihydro-2H-pyrido[2,1-a]isoquinoline-3-carboxylic Acid

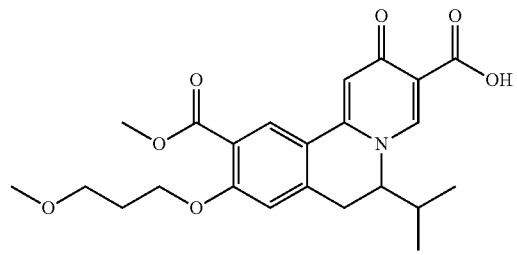 [SMILES: COCCCOc1cc2c(cc1C(=O)OC)-c1cc(=O)c(C(=O)O)cn1C(C(C)C)C2]

Step 1: Methyl 4-bromo-2-hydroxybenzoate

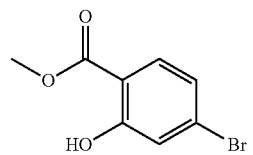

To a three-neck flask were added 4-bromo-2-hydroxybenzoic acid (20 g, 92.16 mmol) and $CH_3OH$ (200 mL). After the mixture was stirred well, to the mixture was added DMF (0.5 mL). The reaction mixture was cooled in an ice-bath, then thionyl chloride (8.02 mL, 111 mmol) was added dropwise slowly into the mixture. After addition, the resulting mixture was heated to reflux and stirred for 12 hours. After the reaction was completed, the mixture was concentrated in vacuo, and the residue was diluted with water (300 mL) and EtOAc (500 mL), then the resulting mixture was stirring, and 5% aqueous sodium hydroxide solution was then added to adjust pH to 6-8, then the mixture was stood for partition. The separated organic layer was washed with saturated brine, dried over anhydrous sodium sulfate, and filtered. The filtrate was concentrated in vacuo to give the title compound as a pale brown solid (20 g, 93.932%).

$^1$H NMR (400 MHz, CDCl$_3$): 10.83 (s, 1H), 7.70 (d, J=8.53 Hz, 1H), 7.20 (s, 1H), 7.04 (d, J=8.50 Hz, 1H), 3.97 (s, 3H).

Step 2: Methyl 4-bromo-2-(3-methoxypropoxy)benzoate

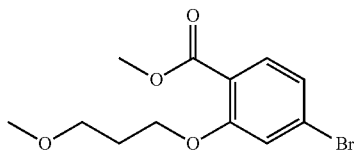 [SMILES: COCCCOc1cc(Br)ccc1C(=O)OC]

To a 1 L single-neck flask were added methyl 4-bromo-2-hydroxybenzoate (44.5 g, 193 mmol) and CH$_3$CN (450 mL). After the solid was dissolved completely by stirring, K$_2$CO$_3$ (39.9 g, 289 mmol) and 1-bromo-3-methoxypropane (45.1 g, 289 mmol) were added in turn. The resulting mixture was heated to 80 éC and stirred for 12 hours at 80 éC. After the reaction was completed, the reaction mixture was cooled to 25 éC and filtered. The filter cake was washed with acetonitrile (100 mL). The combined filtrates was concentrated in vacuo, and the residue was diluted with EtOAc (500 mL). The mixture was washed with saturated brine, dried over anhydrous sodium sulfate and filtered. The filtrate was concentrated in vacuo to give the title compound as orange oil (58 g, 99.3%).

MS (ESI, pos.ion) m/z: 303.2 [M+H]$^+$.

Step 3: 2-(3-methoxypropoxy)-4-(3-methyl-2-oxobutyl)benzoic Acid

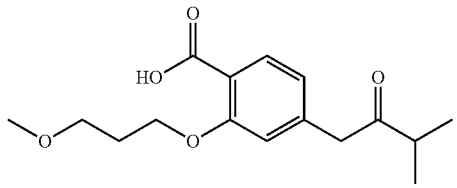 [SMILES: COCCCOc1cc(CC(=O)C(C)C)ccc1C(=O)O]

To a three-neck flask were added sodium tert-butoxide (56 g, 666.0 mmol) and THF (600 mL) in turn. After stirring well, to the mixture was added 4,5-bis(diphenylphosphino)-9,9-dimethylxanthene (3.4 g, 5.9 mmol) and Pd$_2$(dba)$_3$ (4.4 g, 4.8 mmol). The reaction mixture was degassed and refilled with nitrogen for three times, then 3-methylbutan-2-one (33 g, 383.1 mmol) and methyl 4-bromo-2-(3-methoxypropoxy)benzoate (58 g, 191.32 mmol) were added in turn. The mixture was degassed and refilled with nitrogen for three times, then heated to 55 éC and stirred at this temperature for 4 hours. After the addition, the reaction mixture was filtered and the filter cake was washed with THF (100 mL). To the filtrate was added water (100 mL), and the mixture was concentrated in vacuo to remove the solvent. To the residue was added water (800 mL), and the mixture was stirred, then extracted with EtOAc (250 mL B 4), and the organic layer was discarded. To the aqueous layer was added EtOAc (800 mL), then the resulting mixture was stirred, and concentrated hydrochloric acid was then added to adjust pH to 5-6, then the mixture was stood for partition. The separated organic layer was washed with saturated brine, dried over anhydrous sodium sulfate, and filtered. The filtrate was concentrated in vacuo to give the title compound as brown oil (32 g, 56.83%).

MS (ESI, pos.ion) m/z: 295.1 [M+H]$^+$.

Step 4: Methyl 2-(3-methoxypropoxy)-4-(3-methyl-2-oxobutyl)benzoate

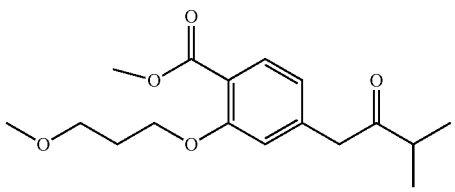 [SMILES: COCCCOc1cc(CC(=O)C(C)C)ccc1C(=O)OC]

To a 500 mL single-neck flask were added 2-(3-methoxypropoxy)-4-(3-methyl-2-oxobutyl)benzoic acid (10 g, 33.98 mmol) and CH$_3$CN (150 mL). After the solid was dissolved by stirring, K$_2$CO$_3$ (7.1 g, 51 mmol) and iodomethane (2.75 mL, 44.2 mmol) were added. The reaction mixture was heated to reflux and stirred for 8 hours, then cooled to 25 èC. The mixture was filtered, and the filtrate was concentrated in vacuo. The residue was diluted with EtOAc (200 mL), and the mixture was washed with saturated brine, dried over anydrous sodium sulfate and filtered. The filtrate was concentrated in vacuo, and the residue was purified by silica gel column chromatography (PE/EtOAc (V/V)=15/1) to give the title compound as light yellow oil (8.9 g, 85%).

MS (ESI, pos.ion) m/z: 309.3 [M+H]$^+$.

Step 5: Methyl 4-(2-amino-3-methylbutyl)-2-(3-methoxypropoxy)benzoate

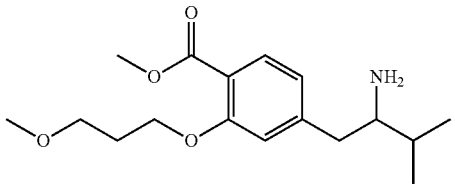 [SMILES: COCCCOc1cc(CC(N)C(C)C)ccc1C(=O)OC]

Methyl 2-(3-methoxypropoxy)-4-(3-methyl-2-oxobutyl)benzoate (6.2 g, 20 mmol) was dissolved in CH$_3$OH (60 mL), then CH$_3$COONH$_4$ (15 g, 194.6 mmol) was added into the mixture. The resulting mixture was stirred for 30 minutes, then cooled to 0 éC, and NaBH$_3$CN (2.5 g, 40 mmol) was added. The reaction mixture was stirred at 25 éC for 20 hours. After the reaction was completed, the reaction mixture was concentrated in vacuo and the residue was diluted with EtOAc (200 mL). The organic layer was washed with saturated brine, dried over anhydrous sodium sulfate and filtered. The filtrate was concentrated in vacuo to give the title compound as colorless oil (6.2 g, 100%).

MS (ESI, pos.ion) m/z: 310.3 [M+H]⁺.

Step 6: Methyl 4-(2-formamido-3-methylbutyl)-2-(3-methoxypropoxy)benzoate

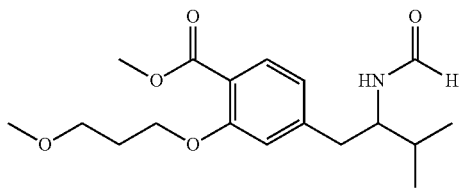 [SMILES: COCCCOc1cc(CC(NC=O)C(C)C)ccc1C(=O)OC]

Methyl 4-(2-amino-3-methylbutyl)-2-(3-methoxy-propoxy)benzoate (1.0 g, 3.23 mmol) was dissolved in dioxane (10 mL), then to the mixture was added formic acid (2.2 g, 42 mmol). The mixture was heated and refluxed for 21 hours. After the reaction was completed, the reaction mixture was cooled to 50 éC, and then concentrated in vacuo. The residue was diluted with EtOAc (100 mL). The organic layer was washed with saturated brine, dried over anhydrous sodium sulfate and filtered. The filtrate was concentrated in vacuo to give the title compound as light yellow oil (1.09 g, 100%).

MS (ESI, pos.ion) m/z: 338.2[M+H]⁺.

Step 7: Methyl 3-isopropyl-6-(3-methoxypropoxy)-3,4-dihydroisoquinoline-7-carboxylate

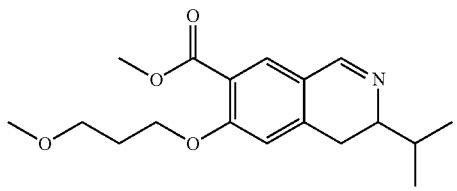 [SMILES: COCCCOc1cc2c(cc1C(=O)OC)C=NC(C(C)C)C2]

To a 100 mL single-neck flask were added dichloromethane (5 mL) and methyl 4-(2-formamido-3-methylbutyl)-2-(3-methoxypropoxy)benzoate (0.45 g, 1.3 mmol), then the mixture was stirred and cooled to 0 éC, and then phosphorus oxychloride (0.2 mL, 2 mmol) was added. The resulting mixture was heated to reflux for 2 hours, then cooled to 0 éC, and DCM (50 mL) was added to dilute the mixture. The resulting mixture was added slowly into the water (20 mL), then the mixture was adjusted with ammonium hydroxide to pH 7-8, and then stood for partition. The aqueous layer was extracted with DCM (30 mL B 2), and the combined organic layers was washed with saturated brine, dried over anhydrous sodium sulfate, and filtered. The filtrate was concentrated in vacuo to give the title compound as a light yellow solid (0.4 g, 90%).

MS (ESI, pos.ion) m/z: 320.2 [M+H]⁺.

Step 8: 3-benzyl 10-methyl 6-isopropyl-9-(3-methoxypropoxy)-2-oxo-2,6,7,11b-tetrahydro-1H-pyrido[2,1-a]isoquinoline-3,10-dicarboxylate

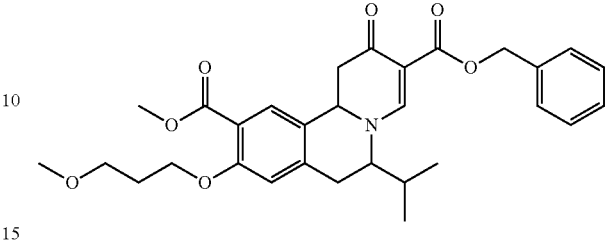

To a dried flask were added ethanol (10 mL), methyl 3-isopropyl-6-(3-methoxypropoxy)-3,4-dihydroisoquinoline-7-carboxylate (0.5 g, 1.57 mmol) and benzyl 2-(ethoxymethylene)-3-oxobutanoate (583 mg, 2.348 mmol) in turn. The reaction mixture was heated and refluxed for 17 hours. After the reaction was completed, the mixture was concentrated in vacuo, and the residue was purified by silica gel column chromatography (DCM/CH₃OH (V/V)=50/1) to give the title compound as brown oil (0.8 g, 98%).

MS (ESI, pos.ion) m/z: 522.2 [M+H]⁺.

Step 9: 3-benzyl 10-methyl 6-isopropyl-9-(3-methoxypropoxy)-2-oxo-6,7-dihydro-2H-pyrido[2,1-a]isoquinoline-3,10-dicarboxylate

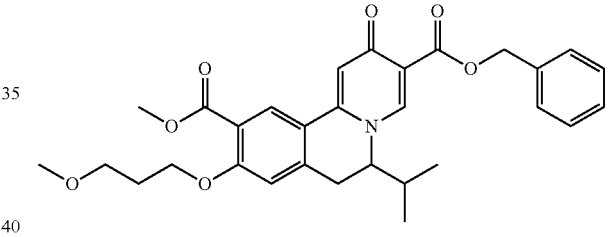

To a dried flask were added 1,2-dimethoxyethane (10 mL) and 3-benzyl 10-methyl 6-isopropyl-9-(3-methoxypropoxy)-2-oxo-2,6,7,11b-tetrahydro-1H-pyrido[2,1-a]isoquinoline-3, 10-dicarboxylate (0.8 g, 1.534 mmol). The mixture was stirred well, then chloranil (380 mg, 1.53 mmol) was added. The reaction mixture was heated and reluxed for 3 hours, then concentrated in vacuo, and the residue was purified by silica gel column chromatography (DCM/CH₃OH(V/V)=50/1) to give the title compound as a gray solid (400 mg, 50.19%).

MS (ESI, pos.ion) m/z: 520.2 [M+H]⁺.

Step 10: 6-isopropyl-10-(methoxycarbonyl)-9-(3-methoxypropoxy)-2-oxo-6,7-dihydro-2H-pyrido[2,1-a]isoquinoline-3-carboxylic Acid

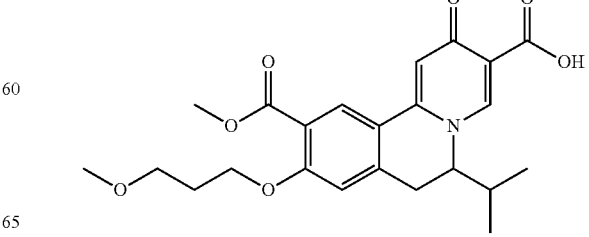

To a 50 mL reaction flask were added 3-benzyl 10-methyl 6-isopropyl-9-(3-methoxypropoxy)-2-oxo-6,7-dihydro-2H-pyrido[2,1-a]isoquinoline-3,10-dicarboxylate (400 mg, 0.77 mmol), methanol (5 mL) and Pd/C (40 mg). The reaction mixture was stirred at rt for 24 hours in a hydrogen atmosphere, then filtered. The filter cake was washed with methanol (10 mL). The filtrate was concentrated, and the residue was purified by silica gel column chromatography (MeOH/DCM(V/V)=50/1) to give the title compound as a gray solid (90 mg, 27.2%).

MS (ESI, pos.ion) m/z: 430.1[M+H]$^+$;

$^1$H NMR (400 MHz, CDCl$_3$) 15.93 (s, 1H), 8.47 (s, 1H), 8.26 (s, 1H), 7.16 (s, 1H), 6.92 (s, 1H), 4.29-4.20 (m, 2H), 3.95 (s, 3H), 3.93-3.90 (m, 1H), 3.67-3.60 (m, 2H), 3.44-3.39 (m, 4H), 3.22 (d, J=16.28 Hz), 1H), 2.19-2.13 (m, 2H), 1.80-1.73 (m, 1H), 0.97 (d, J=6.64 Hz, 3H), 0.85 (d, J=6.71 Hz, 3H).

Example 2: 10-((benzyloxy)carbonyl)-6-isopropyl-9-(3-methoxypropoxy)-2-oxo-6,7-dihydro-2H-pyrido[2,1-a]isoquinoline-3-carboxylic Acid

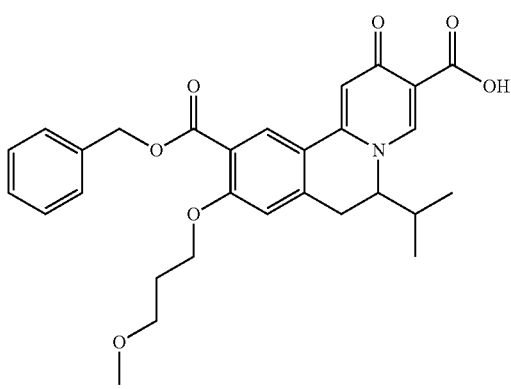 [SMILES: COCCCOc1cc2c(cc1C(=O)OCc1ccccc1)-c1cc(=O)c(C(=O)O)cn1C(C(C)C)C2]

Step 1: benzyl 2-(3-methoxypropoxy)-4-(3-methyl-2-oxobutyl)benzoate

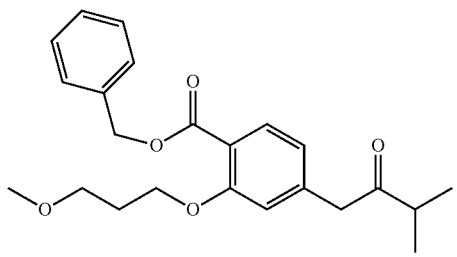 [SMILES: COCCCOc1cc(CC(=O)C(C)C)ccc1C(=O)OCc1ccccc1]

To a 500 mL single-neck flask were added 2-(3-methoxypropoxy)-4-(3-methyl-2-oxobutyl)benzoic acid (14.8 g, 50.3 mmol) and CH$_3$CN (150 mL). After the solid was dissolved completely by stirring, K$_2$CO$_3$ (10.4 g, 75.2 mmol) and benzyl bromide (6.3 mL, 53 mmol) were added in turn. The reaction mixture was heated and refluxed for 8 hours, then cooled to 25 éC, and filtered. The filtrate was concentrated in vacuo, and the residue was diluted with EtOAc (300 mL), then the mixture was washed with saturated brine. The organic layer was dried over anydrous sodium sulfate, and filtered. The filtrate was concentrated in vacuo, and the residue was purified by silica gel column chromatography (PE/EtOAc(V/V)=10/1) to give the title compound as light yellow oil (18 g, 93.1%).

MS (ESI, pos.ion) m/z: 385.6 [M+H]$^+$.

Step 2: Benzyl 4-(2-amino-3-methylbutyl)-2-(3-methoxypropoxy)benzoate

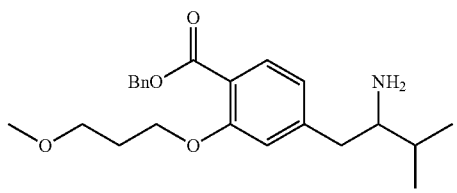 [SMILES: COCCCOc1cc(CC(N)C(C)C)ccc1C(=O)OCc1ccccc1]

To a 500 mL single-neck flask were added benzyl 2-(3-methoxypropoxy)-4-(3-methyl-2-oxobutyl)benzoate (16.27 g, 42.31 mmol) and CH$_3$OH (250 mL). After the solid was dissolved completely by stirring, CH$_3$COONH$_4$ (33 g, 428.1 mmol) was added into the mixture. The reaction mixture was stirred for 30 minutes, then cooled to 0 éC, and NaBH$_3$CN (4 g, 63.65 mmol) was added in three portions. After addition, the reaction mixture was warmed to 25 éC and stirred for 24 hours. After the reaction was completed, the reaction mixture was concentrated in vacuo, and the residue was diluted with EtOAc (400 mL), then the mixture was washed with saturated brine. The organic layer was dried over anydrous sodium sulfate, and filtered. The filtrate was concentrated in vacuo, and the residue was purified by silica gel column chromatography (DCM/CH$_3$OH(V/V)=100/1) to give the title compound as colorless oil (14 g, 85.82%).

MS (ESI, pos.ion) m/z: 386.6 [M+H]$^+$.

Step 3: benzyl 4-(2-formamido-3-methylbutyl)-2-(3-methoxypropoxy)benzoate

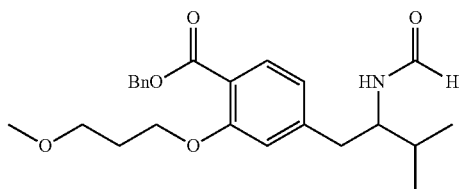 [SMILES: COCCCOc1cc(CC(NC=O)C(C)C)ccc1C(=O)OCc1ccccc1]

To a 50 mL single-neck flask were added benzyl 4-(2-amino-3-methylbutyl)-2-(3-methoxypropoxy)benzoate (2.7 g, 7.0 mmol), dioxane (12 mL) and formic acid (5.2 g, 110 mmol). The mixture was stirred at 110 éC for 24 hours under N$_2$ protection. After the reaction was completed, the reaction mixture was concentrated in vacuo, and to the residue was added saturated brine (15 mL). The residue was extracted with DCM (30 mL B 4). The combined organic layers were washed with saturated brine, dried over anhydrous sodium sulfate and filtered. The filtrate was concentrated in vacuo to give the title compound as brown oil (2.9 g, 100%).

MS (ESI, pos.ion) m/z: 414.2[M+H]$^+$.

Step 4: Benzyl 3-isopropyl-6-(3-methoxypropoxy)-3,4-dihydroisoquinoline-7-carboxylate

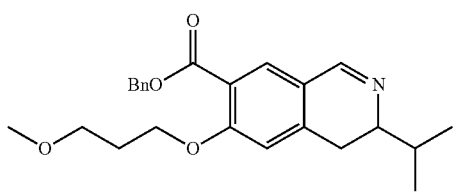 [SMILES: COCCCOc1cc2c(cc1C(=O)OCc1ccccc1)C=NC(C(C)C)C2]

To a 100 mL single-neck flask were added benzyl 4-(2-formamido-3-methylbutyl)-2-(3-methoxypropoxy)benzoate (2.9 g, 7.0 mmol) and DCM (30 mL). The mixture was stirred well, then cooled to 0 ëC, and POCl$_3$ (1.3 mL, 14 mmol) was added into the mixture. The reaction mixture was heated to 50 ëC under N$_2$ protection, then stirred for 3 hours. After the reaction was completed, the reaction mixture was concentrated in vacuo, and to the residue was added ice-water (40 mL). The resulting mixture was extracted with EtOAc (50 mL B3). The combined organic layers were washed with saturated brine, dried over anydrous sodium sulfate, and filtered. The filtrate was concentrated in vacuo to give the title compound as a light yellow solid (2.7 g, 97%).

MS (ESI, pos.ion) m/z: 396.5[M+H]$^+$.

Step 5: 10-benzyl 3-tert-butyl 6-isopropyl-9-(3-methoxypropoxy)-2-oxo-2,6,7,11b-tetrahydro-1H-pyrido[2,1-a]isoquinoline-3,10-dicarboxylate

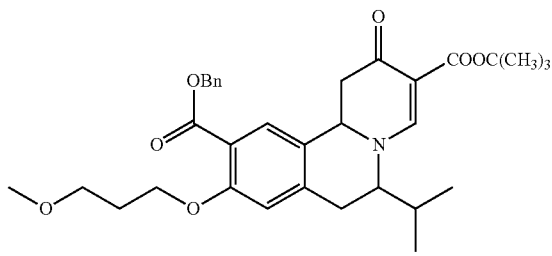

To a 100 mL single-neck flask were added benzyl 3-isopropyl-6-(3-methoxypropoxy)-3,4-dihydroisoquinoline-7-carboxylate (1.9 g, 4.8 mmol), tert-butyl 2-((dimethylamino)methylene)-3-oxobutanoate (1.5 g, 7 mmol) and tert-butanol (50 mL) in turn. The reaction mixture was stirred at 85 ëC for 24 hours under N$_2$ protection, then concentrated in vacuo. The residue was purified by silica gel column chromatography (EtOAc/MeOH (V/V)=20/1) to give the title compound as a light brown solid (1.62 g, 60%).

MS (ESI, pos.ion) m/z: 564.3[M+H]$^+$.

Step 6: 10-benzyl 3-tert-butyl 6-isopropyl-9-(3-methoxypropoxy)-2-oxo-6,7-dihydro-2H-pyrido[2,1-a]isoquinoline-3,10-dicarboxylate

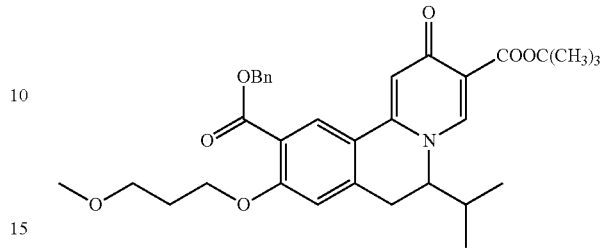

To a 250 mL three-neck flask were added 10-benzyl 3-tert-butyl 6-isopropyl-9-(3-methoxypropoxy)-2-oxo-2,6,7,11b-tetrahydro-1H-pyrido[2,1-a]isoquinoline-3, 10-dicarboxylate (12.2 g, 21.6 mmol) and DME (90 mL). After stirring well, chloranil (5.0 g, 20 mmol) was added into the mixture, and the reaction mixture was stirred at 25 ëC for 12 hours. After the reaction was completed, the mixture was concentrated in vacuo, and the residue was purified by silica gel column chromatography (DCM/MeOH(V/V)=10/1) to give the title compound as a light brown solid (12.2 g, 100%).

MS (ESI, pos.ion) m/z: 562.4[M+H]$^+$.

Step 7: 10-((benzyloxy)carbonyl)-6-isopropyl-9-(3-methoxypropoxy)-2-oxo-6,7-dihydro-2H-pyrido[2,1-a]isoquinoline-3-carboxylic Acid

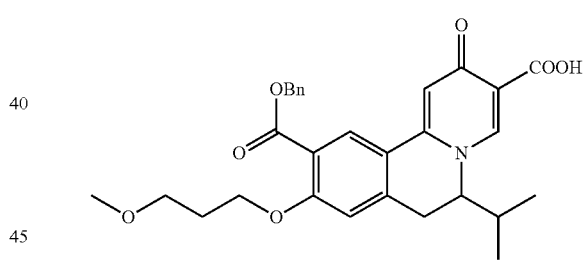

To a 50 mL single-neck flask were added 10-benzyl 3-tert-butyl 6-isopropyl-9-(3-methoxypropoxy)-2-oxo-6,7-dihydro-2H-pyrido[2,1-a]isoquinoline-3,10-dicarboxylate (0.4 g, 0.71 mmol) and DCM (5 mL). After dissolving completely by stirring, to the reaction mixture was added TFA (3 mL). The reaction mixture was stirred at 25 ëC for 12 hours, then concentrated in vacuo. The residue was diluted with EtOAc (100 mL), and the mixture was washed with saturated brine. The organic layer was dried over anydrous sodium sulfate, and filtered. The filtrate was concentrated in vacuo, and the residue was purified by silica gel column chromatography (DCM/CH$_3$OH(V/V)=50/1) to give the title compound as a white solid (0.2 g, 56%).

MS (ESI, pos.ion) m/z: 506.6 [M+H]$^+$;

$^1$H NMR (400 MHz, CDCl$_3$) 15.95 (s, 1H), 8.47 (s, 1H), 8.26 (s, 1H), 7.49-7.41 (m, 5H), 7.13 (s, 1H), 6.91 (s, 1H), 5.39 (s, 2H), 4.24-4.19 (m, 2H), 3.96-3.91 (m, 1H), 3.55-3.45 (m, 2H), 3.44-3.39 (m, 1H), 3.33 (s, 3H), 3.19 (d, J=15.90 Hz, 1H), 2.10-2.08 (m, 3H), 0.96 (d, J=6.19 Hz 3H), 0.84 (d, J=6.35 Hz, 3H).

Example 3: 10-((cyclopentyloxy)carbonyl)-6-isopropyl-9-(3-methoxypropoxy)-2-oxo-6,7-dihydro-2H-pyrido[2,1-a]isoquinoline-3-carboxylic Acid

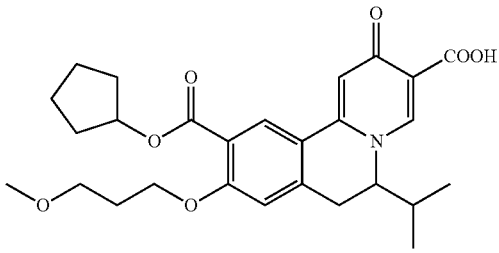 [SMILES: COCCCOc1cc2c(cc1C(=O)OC1CCCC1)-c1cc(=O)c(C(=O)O)cn1C(C(C)C)C2]

Step 1: 3-(tert-butoxycarbonyl)-6-isopropyl-9-(3-methoxypropoxy)-2-oxo-6,7-dihydro-2H-pyrido[2,1-a]isoquinoline-10-carboxylic Acid

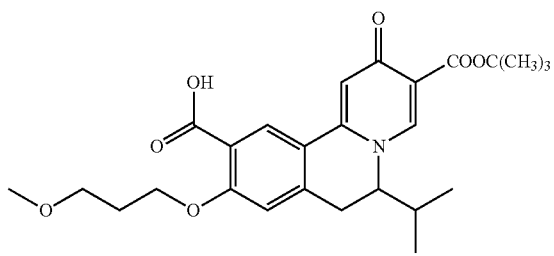

To a 100 mL single-neck flask were added 10-benzyl 3-tert-butyl 6-isopropyl-9-(3-methoxypropoxy)-2-oxo-6,7-dihydro-2H-pyrido[2,1-a]isoquinoline-3,10-dicarboxylate (4.0 g, 7.1 mmol), THF (40 mL) and Pd/C (0.4 g, 10%). The reaction mixture was stirred at 25 ěC for 12 hours under an hydrogen atmosphere of 0.1 MPa. After the reaction was completed, the mixture was filtered, and the filter cake was washed with DCM (50 mL). The filtrate was concentrated in vacuo, and the residue was purified by silica gel column (DCM/MeOH(V/V)=10/1) to give the title compound as a light brown solid (3.0 g, 89%).

MS (ESI, pos.ion) m/z₁ⁱ 472.3 [M+H]⁺.

Step 2: 3-tert-butyl 10-cyclopentyl 6-isopropyl-9-(3-methoxypropoxy)-2-oxo-6,7-dihydro-2H-pyrido[2,1-a]isoquinoline-3,10-dicarboxylate

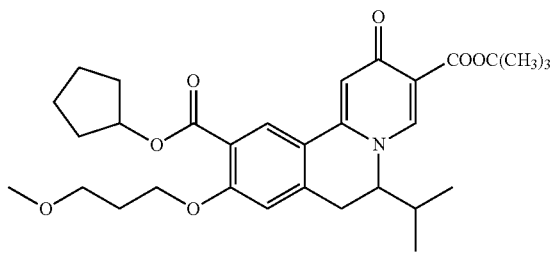

To a 50 mL single-neck flask were added 3-(tert-butoxycarbonyl)-6-isopropyl-9-(3-methoxypropoxy)-2-oxo-6,7-dihydro-2H-pyrido[2,1-a]isoquinoline-10-carboxylic acid (0.3 g, 0.6 mmol), bromocyclopentane (0.379 g, 2.54 mmol), K₂CO₃ (0.351 g, 2.54 mmol) and DMF (5 mL). The reaction mixture was heated to 50 ěC, and stirred at this temperature for 12 hours, then cooled to 0 ěC and diluted with water (10 mL). The mixture was extracted with DCM (20 mL B 4). The combined organic layers were washed with saturated brine, dried over anhydrous sodium sulfate and filtered. The filtrate was concentrated in vacuo to give the title compound as a light brown solid (0.343 g, 100%).

MS (ESI, pos.ion) m/z: 540.2 [M+H]⁺.

Step 3: 10-((cyclopentyloxy)carbonyl)-6-isopropyl-9-(3-methoxypropoxy)-2-oxo-6,7-dihydro-2H-pyrido[2,1-a]isoquinoline-3-carboxylic Acid

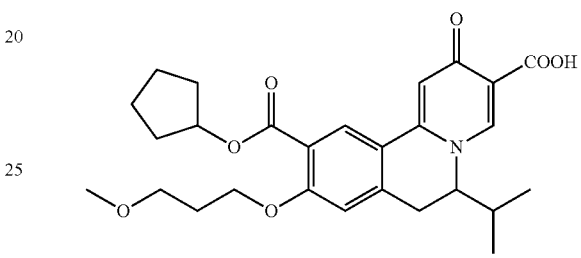

To a 50 mL single-neck flask were added 3-tert-butyl 10-cyclopentyl 6-isopropyl-9-(3-methoxypropoxy)-2-oxo-6,7-dihydro-2H-pyrido[2,1-a]isoquinoline-3,10-dicarboxylate (0.343 g, 0.636 mmol), DCM (3 mL) and TFA (3 mL). The reaction mixture was stirred at 50 ěC for 12 hours in a hydrogen atmosphere, then concentrated in vacuo, and the residue was purified by silica gel column chromatography (DCM/MeOH(V/V)=10/1) to give the title compound as a gray solid (120 mg, 39.0%).

MS (ESI, pos.ion) m/z: 484.3[M+H]⁺;

¹H NMR (400 MHz, CDCl₃) 15.98 (s, 1H), 8.48 (s, 1H), 8.17 (s, 1H), 7.14 (s, 1H), 6.90 (s, 1H), 4.47-4.35 (m, 1H), 4.27-4.17 (m, 2H), 3.96-3.91 (s, 1H), 3.70-3.55 (m, 2H), 3.44-3.33 (m ⊢ 4H), 3.23-3.14 (m, 1H), 2.16-2.13 (m, 2H), 2.08-1.94 (m, 3H), 1.90-1.78 (m, 6H), 0.96 (d, J=5.77 Hz, 3H), 0.84 (d, J=5.95 Hz, 3H).

Example 4: 10-(isopropoxycarbonyl)-6-isopropyl-9-(3-methoxypropoxy)-2-oxo-6,7-dihydro-2H-pyrido[2,1-a]isoquinoline-3-carboxylic Acid

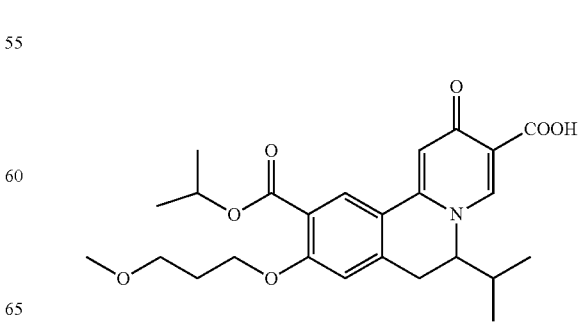

Step 1: 3-tert-butyl 10-isopropyl 6-isopropyl-9-(3-methoxypropoxy)-2-oxo-6,7-dihydro-2H-pyrido[2,1-a]isoquinoline-3,10-dicarboxylate

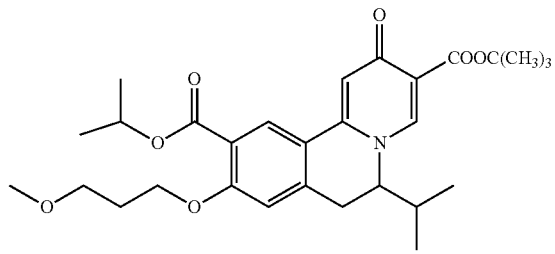

The title compound was prepared according to the synthetic method of step 2 in example 3 by using 3-(tert-butoxycarbonyl)-6-isopropyl-9-(3-methoxypropoxy)-2-oxo-6,7-dihydro-2H-pyrido[2,1-a]isoquinoline-10-carboxylic acid (0.47 g, 1 mmol), isopropyl iodide (0.34 g, 2 mmol), potassium carbonate (0.28 g, 2 mmol) and DMF (10 mL) as raw materials to give the title compound as a gray solid (0.33 g, 64%).

MS (ESI, pos.ion) m/z: 514.3 [M+H]$^+$.

Step 2: 10-(isopropoxycarbonyl)-6-isopropyl-9-(3-methoxypropoxy)-2-oxo-6,7-dihydro-2H-pyrido[2,1-a]isoquinoline-3-carboxylic Acid

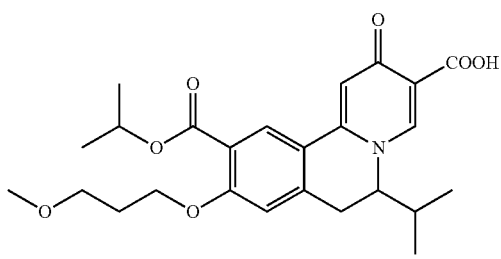 [SMILES: COCCCOc1cc2c(cc1C(=O)OC(C)C)-c1cc(=O)c(C(=O)O)cn1C(C(C)C)C2]

The title compound was prepared according to the synthetic method of step 3 in example 3 by using 3-tert-butyl 10-isopropyl 6-isopropyl-9-(3-methoxypropoxy)-2-oxo-6,7-dihydro-2H-pyrido[2,1-a]isoquinoline-3,10-dicarboxylate (0.26 g, 0.5 mmol), DCM (3 mL) and TFA (3 mL) as raw materials to give the title compound as an offwhite solid (112 mg, 49%).

MS (ESI, pos.ion) m/z: 458.1 [M+H]$^+$;

$^1$H NMR (400 MHz, CDCl$_3$) 16.07 (s, 1H), 8.53 (s, 1H), 8.15 (s, 1H), 7.12 (s, 1H), 6.90 (s, 1H), 5.32-5.23 (m, 1H), 4.25-4.16 (m, 2H), 4.04 (dd, J=9.4, 4.4 Hz, 1H), 3.64-3.584 (m, 2H), 3.43 (dd, J=4.84, 16.46 Hz, 1H), 3.35 (s, 3H), 3.18 (d, J=16.32 Hz, 1H), 2.15-2.09 (m, 2H), 1.78-1.69 (m, 1H), 1.39-1.35 (m, 6H), 0.94 (d, 3H), 0.80 (d, 3H).

Example 5: 6-isopropyl-9-(3-methoxypropoxy)-10-(methylcarbamoyl)-2-oxo-6,7-dihydro-2H-pyrido[2,1-a]isoquinoline-3-carboxylic Acid

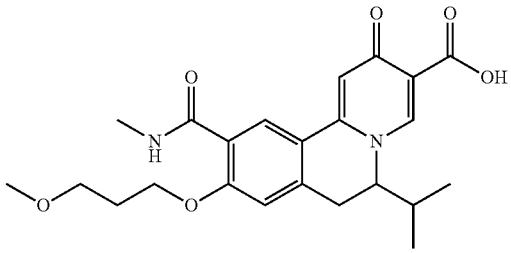 [SMILES: CNC(=O)c1cc2c(cc1OCCCOC)CC(C(C)C)n1cc(C(=O)O)c(=O)cc1-2]

Step 1: 10-benzyl 3-ethyl 6-isopropyl-9-(3-methoxypropoxy)-2-oxo-2,6,7,11b-tetrahydro-1H-pyrido[2,1-a]isoquinoline-3,10-dicarboxylate

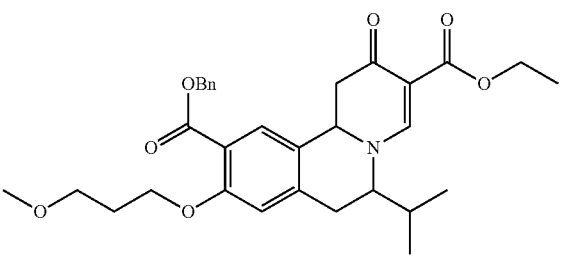 [SMILES: CCOC(=O)C1=CN2C(CC1=O)c1cc(C(=O)OCc3ccccc3)c(OCCCOC)cc1CC2C(C)C]

The title compound was prepared according to the synthetic method of step 8 in example 1 by using benzyl 3-isopropyl-6-(3-methoxypropoxy)-3,4-dihydroisoquinoline-7-carboxylate (1.9 g, 4.8 mmol), ethyl 2-(ethoxymethylene)-3-oxobutanoate (1.34 g, 7.2 mmol) and anhydrous ethanol (15 mL) as raw materials to give light yellow oil (1.8 g, 70%).

MS (ESI, pos.ion) m/z: 536.2 [M+H]$^+$.

Step 2: 10-benzyl 3-ethyl 6-isopropyl-9-(3-methoxypropoxy)-2-oxo-6,7-dihydro-2H-pyrido[2,1-a]isoquinoline-3,10-dicarboxylate

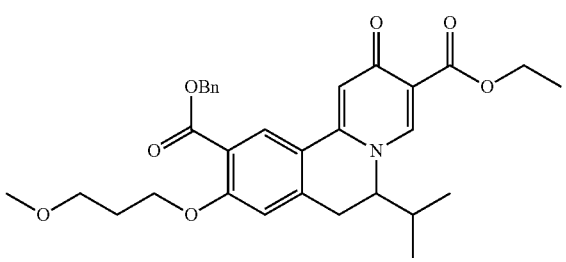 [SMILES: CCOC(=O)c1cn2c(cc1=O)-c1cc(C(=O)OCc3ccccc3)c(OCCCOC)cc1CC2C(C)C]

The title compound was prepared according to the synthetic method of step 9 in example 1 by using 10-benzyl 3-ethyl 6-isopropyl-9-(3-methoxypropoxy)-2-oxo-2,6,7,11b-tetrahydro-1H-pyrido[2,1-a]isoquinoline-3,10-dicarboxylate (1.6 g, 3 mmol), chloranil (0.74 g, 3 mmol) and DME (20 mL) as raw materials to give a brown solid (1.31 g, 82%).

MS (ESI, pos.ion) m/z$_1^i$ 534.1 [M+H]$^+$.

Step 3: 3-(ethoxycarbonyl)-6-isopropyl-9-(3-methoxypropoxy)-2-oxo-6,7-dihydro-2H-pyrido[2,1-a]isoquinoline-10-carboxylic Acid

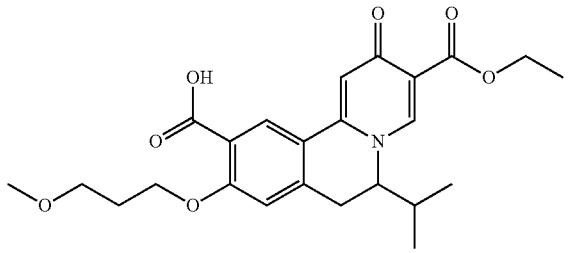 [SMILES: CCOC(=O)c1cn2c(cc1=O)-c1cc(C(=O)O)c(OCCCOC)cc1CC2C(C)C]

The title compound was prepared according to the synthetic method of step 10 in example 1 by using 10-benzyl 3-ethyl 6-isopropyl-9-(3-methoxypropoxy)-2-oxo-6,7-dihydro-2H-pyrido[2,1-a]isoquinoline-3,10-dicarboxylate (1.3 g, 2.44 mmol) and Pd/C (0.2 g, 10%) as raw materials to give a gray solid (0.97 g, 90%).

MS (ESI, pos.ion) m/z: 444.1 [M+H]$^+$.

Step 4: Ethyl 6-isopropyl-9-(3-methoxypropoxy)-10-(methylcarbamoyl)-2-oxo-6,7-dihydro-2H-pyrido[2,1-a]isoquinoline-3-carboxylate

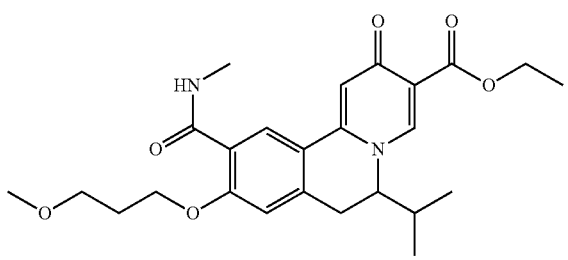 [SMILES: CCOC(=O)c1cn2c(cc1=O)-c1cc(C(=O)NC)c(OCCCOC)cc1CC2C(C)C]

To a 100 mL single-neck flask were added 3-(ethoxycarbonyl)-6-isopropyl-9-(3-methoxypropoxy)-2-oxo-6,7-dihydro-2H-pyrido[2,1-a]isoquinoline-10-carboxylic acid (0.55 g, 1.2 mmol), DMF (12 mL), DIPEA (0.41 mL, 2.5 mmol), HATU (0.57 g, 1.5 mmol) and methylamine hydrochloride (0.13 g, 1.9 mmol). The reaction mixture was stirred at 25 ёC for 12 hours, then to the reaction mixture was added EtOAc (150 mL) and water (100 mL). The resulting mixture was stirred, and concentrated hydrochloric acid was then added to adjust pH to 6-7, then the mixture was stood for partition. The separated organic layer was washed with saturated brine, dried over anhydrous sodium sulfate, and filtered. The filtrate was concentrated in vacuo, and the residue was purified by silica gel column chromatography (DCM/CH$_3$OH(V/V)=50/1) to give the title compound as a purply solid (0.25 g, 44%).

MS (ESI, pos.ion) m/z: 457.3[M+H]$^+$.

Step 5: 6-isopropyl-9-(3-methoxypropoxy)-10-(methyl carbamoyl)-2-oxo-6,7-dihydro-2H-pyrido[2,1-a]isoquinoline-3-carboxylic Acid

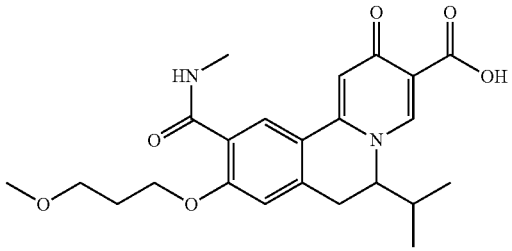 [SMILES: CNC(=O)c1cc2c(cc1OCCCOC)CC(C(C)C)n1cc(C(=O)O)c(=O)cc1-2]

To a 100 mL single-neck flask were added ethyl 6-isopropyl-9-(3-methoxypropoxy)-10-(methyl carbamoyl)-2-oxo-6,7-dihydro-2H-pyrido[2,1-a]isoquinoline-3-carboxylate (0.24 g, 0.53 mmol), ethanol (6 mL) and THF (6 mL). The reaction mixture was stirred to dissolve the solid, and then a solution of NaOH (0.11 g, 2.8 mmol) in H$_2$O (4 mL) was added. The reaction mixture was continued to stir for 2 hours at room temperature. After the reaction was completed, the reaction mixture was concentrated in vacuo, and the residue was diluted with water (30 mL) and EtOAc (50 mL), then the resulting mixture was stirred, and concentrated hydrochloric acid was then added to adjust pH to 5-7. Then the mixture was stood for partition. The separated organic layer was washed with saturated brine, dried over anhydrous sodium sulfate, and filtered. The filtrate was concentrated in vacuo. To the residue was added IPA (2 mL), then the mixture was treated by ultraphonic, and then filtered. The filter cake was washed with IPA (1 mL) to give the title compound as a white solid (100 mg, 44%).

MS (ESI, pos.ion) m/z: 429.3 [M+H]$^+$;

$^1$H NMR (400 MHz, CDCl$_3$) 16.12 (s, 1H), 8.61 (s, 1H), 8.46 (s, 1H), 8.15 (br, 1H), 7.17 (s, 1H), 6.90 (s, 1H), 4.33 (t, J=5.8 Hz, 2H), 3.98 (dd, J=9.1, 4.8 Hz, 1H), 3.64 (t, J=5.4 Hz, 2H), 3.47 (dd, J=16.4, 4.8 Hz, 1H), 3.40 (s, 3H), 3.20 (d, 1H), 3.02 (d, 3H), 2.24-2.18 (m, 2H), 1.77-1.70 (m, 1H), 0.95 (d, J=6.6 Hz, 3H), 0.81 (d, J=6.7 Hz, 3H).

Example 6: 10-acetyl-6-isopropyl-9-(3-methoxypropoxy)-2-oxo-6,7-dihydro-2H-pyrido[2,1-a]isoquinoline-3-carboxylic Acid

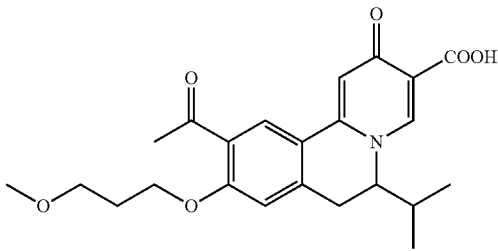 [SMILES: COCCCOc1cc2c(cc1C(C)=O)-c1cc(=O)c(C(=O)O)cn1C(C(C)C)C2]

Step 1: 2-(4-bromo-2-(3-methoxypropoxy)phenyl)-2-methyl-1,3-dioxolane

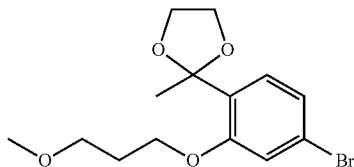 [SMILES: COCCCOc1cc(Br)ccc1C1(C)OCCO1]

To a dried reaction flask were added 1-(4-bromo-2-(3-methoxypropoxy) phenyl)ethanone (5.0 g, 17 mmol), ethanediol (8.4 mL), p-toluenesulfonic acid (0.5 g), trimethyl orthoformate (12 mL) and toluene (25 mL) in turn. The reaction mixture was heated to 60 ěC and stirred for 8 hours. After the reaction was completed, the reaction mixture was cooled to 25 ěC, then saturated aqueous sodium bicarbonate solution (50 mL) was added. The reaction mixture was stood for partition, and the aqueous layer was extracted with EtOAc (50 mL). The combined organic layer was dried over anhydrous sodium sulfate and filtered. The filtrate was concentrated in vacuo to give the title compound as light yellow oil (3.93 g, 70%).

MS (ESI, pos.ion) m/z: 331.0. [M+H]$^+$.

Step 2: 1-(3-(3-methoxypropoxy)-4-(2-methyl-1,3-dioxolan-2-yl)phenyl)-3-methylbutan-2-one

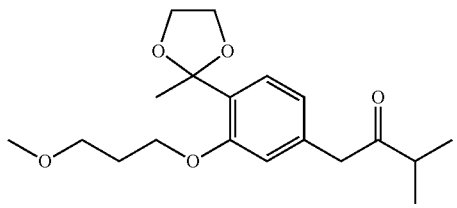 [SMILES: COCCCOc1cc(CC(=O)C(C)C)ccc1C1(C)OCCO1]

To a dried flask were added 2-(4-bromo-2-(3-methoxypropoxy) phenyl)-2-methyl-1,3-dioxolane (6.0 g, 18 mmol), 3-methylbutan-2-one (3.9 g, 45 mmol), THF (50 mL), 4,5-bis(diphenylphosphino)-9,9-dimethylxanthene (0.39 g, 0.67 mmol), sodium tert-butoxide (5.0 g, 52 mmol) and Pd(dba)$_2$ (0.35 g, 0.61 mmol) in turn. The reaction mixture was stirred at rt for 1 hour under nitrogen protection, then heated to 60 ěC and stirred for 3 hours. After the reaction was completed, the reaction mixture was cooled to rt and concentrated in vacuo. To the residue were added EtOAc (50 mL) and aqueous NaOH solution (50 mL, 1 M). The mixture was stood for partition, and the aqueous layer was extracted with EtOAc (50 mL B3). The combined organic layers were dried over anydrous sodium sulfate and filtered. The filtrate was concentrated in vacuo, and the residue was purified by silica gel column chromatography (PE/EtOAc (V/V)=2/1) to give the title compound as light brown oil (5.0 g, 82%).

MS (ESI, pos.ion) m/z: 337.5[M+H]$^+$.

Step 3: 1-(3-(3-methoxypropoxy)-4-(2-methyl-1,3-dioxolan-2-yl)phenyl)-3-methylbutan-2-amine

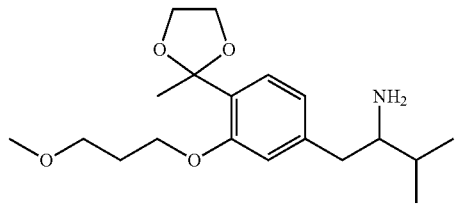 [SMILES: COCCCOc1cc(CC(N)C(C)C)ccc1C1(C)OCCO1]

The title compound was prepared according to the synthetic method of step 5 in example 1 by using 1-(3-(3-methoxypropoxy)-4-(2-methyl-1,3-dioxolan-2-yl) phenyl)-3-methylbutan-2-one (1.7 g, 5.1 mmol), NH$_4$OAc (4.5 g, 58 mmol), MeOH (10 mL) and NaBH$_3$CN (0.91 g, 14 mmol) as raw materials to give light yellow oil (1.7 g, 100%).

MS: (ESI, pos.ion) m/z: 338.6. [M+H]$^+$.

Step 4: N-(1-(4-acetyl-3-(3-methoxypropoxy)phenyl)-3-methylbutan-2-yl)formamide

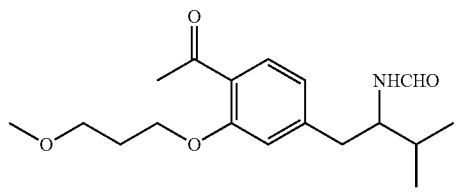

The title compound was prepared according to the synthetic method of step 6 in example 1 by using 1-(3-(3-methoxypropoxy)-4-(2-methyl-1,3-dioxolan-2-yl)phenyl)-3-methylbutan-2-amine (1.7 g, 5.0 mmol), dioxane (8 mL) and formic acid (3.7 g, 80 mmol) as raw materials to give light brown oil (1.03 g, 64%).

MS (ESI, pos.ion) m/z: 322.2. [M+H]$^+$.

Step 5: 1-(3-isopropyl-6-(3-methoxypropoxy)-3,4-dihydroisoquinolin-7-yl)ethanone

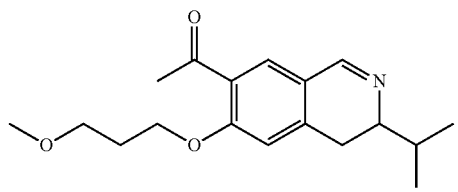 [SMILES: COCCCOc1cc2c(cc1C(C)=O)C=NC(C(C)C)C2]

The title compound was prepared according to the synthetic method of step 7 in example 1 by using N-(1-(4-acetyl-3-(3-methoxypropoxy)phenyl)-3-methylbutan-2-yl) formamide (0.21 g, 0.65 mmol), DCM (6 mL) and POCl$_3$ (0.12 mL, 1.3 mmol) as raw materials to give light brown oil (0.18 g, 91%).

MS (ESI, pos.ion) m/z: 304.5[M+H]$^+$.

Step 6: Ethyl 10-acetyl-6-isopropyl-9-(3-methoxypropoxy)-2-oxo-2,6,7,11b-tetrahydro-1H-pyrido[2,1-a]isoquinoline-3-carboxylate

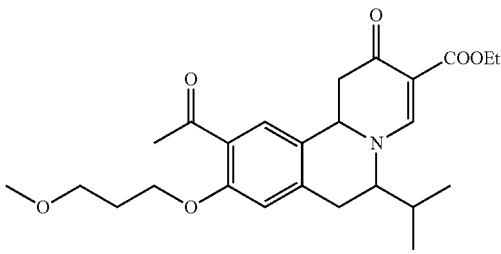 [SMILES: CCOC(=O)C1=CN2C(CC1=O)c1cc(C(C)=O)c(OCCCOC)cc1CC2C(C)C]

The title compound was prepared according to the synthetic method of step 8 in example 1 by using 1-(3-isopropyl-6-(3-methoxypropoxy)-3,4-dihydroisoquinolin-7-yl)ethanone (0.20 g, 0.66 mmol), ethyl 2-(ethoxymethylene)-3-oxobutanoate (0.2 g, 1 mmol) and EtOH (5 mL) as raw materials to give a gray solid (0.18 g, 62%).

MS (ESI, pos.ion) m/z: 444.2[M+H]$^+$.

Step 7: Ethyl 10-acetyl-6-isopropyl-9-(3-methoxypropoxy)-2-oxo-6,7-dihydro-2H-pyrido[2,1-a]isoquinoline-3-carboxylate

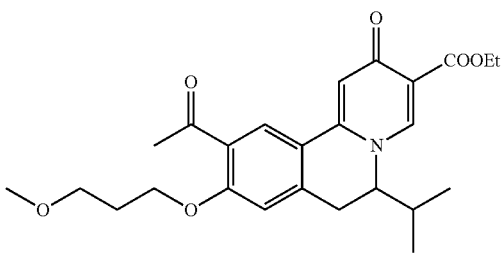 [SMILES: CCOC(=O)c1cn2c(cc1=O)-c1cc(C(C)=O)c(OCCCOC)cc1CC2C(C)C]

The title compound was prepared according to the synthetic method of step 9 in example 1 by using ethyl 10-acetyl-6-isopropyl-9-(3-methoxypropoxy)-2-oxo-2,6,7,11b-tetrahydro-1H-pyrido[2,1-a]isoquinoline-3-carboxylate (0.37 g, 0.834 mmol), THF (6 mL) and chloranil (205 mg, 0.834 mmol) as raw materials to give an offwhite solid (0.32 g, 87%).

MS (ESI, pos.ion) m/z: 442.1. [M+H]$^+$.

Step 8: 10-acetyl-6-isopropyl-9-(3-methoxypropoxy)-2-oxo-6,7-dihydro-2H-pyrido[2,1-a]isoquinoline-3-carboxylic Acid

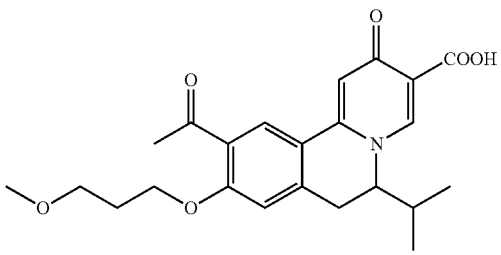 [SMILES: COCCCOc1cc2c(cc1C(C)=O)-c1cc(=O)c(C(=O)O)cn1C(C(C)C)C2]

The title compound was prepared according to the synthetic method of step 5 in example 5 by using ethyl 10-acetyl-6-isopropyl-9-(3-methoxypropoxy)-2-oxo-6,7-dihydro-2H-pyrido[2,1-a]isoquinoline-3-carboxylate (0.15 g, 0.34 mmol), THF (2 mL), EtOH (1 mL), H$_2$O (0.5 mL) and LiOH.H$_2$O (57 mg, 1.36 mmol) as raw materials to give an offwhite solid (32 mg, 23%).

MS (ESI, pos.ion) m/z: 414.4 [M+H]$^+$;
$^1$H NMR (400 MHz, CDCl$_3$) 15.98 (br, 1H), 8.47 (s, 1H), 8.20 (s, 1H), 7.17 (s, 1H), 6.92 (s, 1H), 4.34-4.25 (m, 2H), 3.97-3.89 (m, 1H), 3.66-3.58 (m, 2H), 3.45-3.40 (m ⊢4H), 3.21 (d, J=16.52 Hz, 1H), 2.67 (s, 3H), 2.24-2.15 (m, 2H), 1.81-1.71 (m, 1H), 0.97 (d, J=6.28 Hz, 3H), 0.84 (d, J=6.30 Hz, 3H).

Example 7: 10-(ethoxymethyl)-6-isopropyl-9-(3-methoxypropoxy)-2-oxo-6,7-dihydro-2H-pyrido[2,1-a]isoquinoline-3-carboxylic Acid

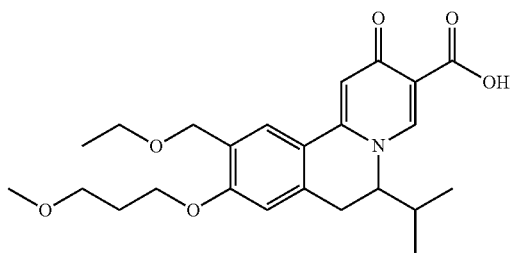 [SMILES: CCOCc1cc2c(cc1OCCCOC)CC(C(C)C)n1cc(C(=O)O)c(=O)cc1-2]

Step 1: (4-bromo-2-(3-methoxypropoxy)phenyl)methanol

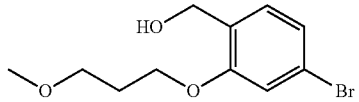

To a dried reaction flask were added methyl 4-bromo-2-(3-methoxypropoxy)benzoate (5 g, 16.493 mmol) and THF (50 mL) in turn, then the mixture was cooled under an ice-bath condition, and then borane-tetrahydrofuran complex (66 mL, 66 mmol) was added dropwise slowly. The reaction mixture was heated to 70 ĕC and stirred for 16 hours. Then the mixture was cooled to 0 ĕC, ethanol (30 mL) and water (30 mL) were added slowly to quench the reaction. The mixture was concentrated in vacuo, and the residue was diluted with ethyl acetate (100 mL). The resulting mixture was washed with aqueous sodium hydroxide solution (50 mL B 2), and the combined organic layers were dried over anhydrous sodium sulfate, and filtered. The filtrate was concentrated in vacuo to give the title compound as colorless oil (4.5 g, 100%).

MS (ESI, pos.ion) m/z: 298.0[M+Na]$^+$.

Step 2: 4-bromo-1-(ethoxymethyl)-2-(3-methoxypropoxy)benzene

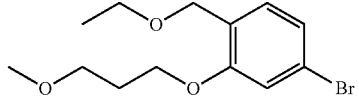 [SMILES: CCOCc1ccc(Br)cc1OCCCOC]

To a reaction flask was added DMF (20 mL), and DMF was cooled under an ice-bath condition, then sodium hydride (2.8 g, 70 mmol, 60%) was added. The mixture was stirred for 10 minutes, then a solution of (4-bromo-2-(3-methoxypropoxy)phenyl)methanol (4.8 g, 17 mmol) in DMF (20 mL) was added dropwise. After addition, bromoethane (3.5 mL, 47 mmol) was added. After addition, the reaction mixture was stirred for 15 minutes at this temperature, then stirred at 25 ēC for 12 hours. After the reaction was completed, to the mixture was added saturated aqueous sodium bisulfate solution to quench the reaction under an ice-bath cooling condition. The resulting mixture was extracted with ethyl acetate (100 mL B 2). The combined organic layers were washed with saturated brine, dried over anhydrous sodium sulfate and filtered. The filtrate was concentrated in vacuo to give the title compound as pale brown oil (4 g, 76%).

MS (ESI, pos.ion) m/z: 326.1[M+Na]+.

Step 3: 1-(4-(ethoxymethyl)-3-(3-methoxypropoxy)phenyl)-3-methylbutan-2-one

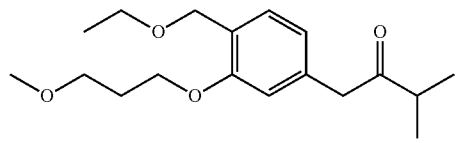 [SMILES: CCOCc1ccc(CC(=O)C(C)C)cc1OCCCOC]

The title compound was prepared according to the synthetic method of step 1 in example 7 by using 4-bromo-1-(ethoxymethyl)-2-(3-methoxypropoxy)benzene (2 g, 6.596 mmol), 3-methylbutan-2-one (0.85 g, 9.9 mmol), sodium tert-butoxide (1.3 g, 13 mmol), 1,4-dioxane (30 mL), 4,5-bis(diphenylphosphino)-9,9-dimethylxanthene (0.4 g, 0.7 mmol) and Pd$_2$(dba)$_3$ (0.3 g, 0.3 mmol) as raw materials to give light brown oil (1.22 g, 60%).

MS (ESI, pos.ion) m/z: 331.6[M+Na]+.

Step 4: 1-(4-(ethoxymethyl)-3-(3-methoxypropoxy)phenyl)-3-methylbutan-2-amine

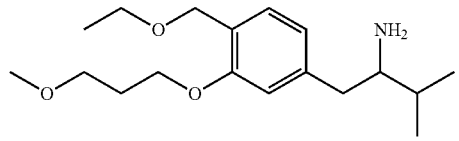 [SMILES: CCOCc1ccc(CC(N)C(C)C)cc1OCCCOC]

The title compound was prepared according to the synthetic method of step 2 in example 2 by using 1-(4-(ethoxymethyl)-3-(3-methoxypropoxy)phenyl)-3-methylbutan-2-one (2 g, 6.485 mmol), methanol (30 mL), ammonium acetate (5 g, 64.87 mmol) and sodium cyanoborohydride (2 g, 31.83 mmol) as raw materials to give colorless oil (1.09 g, 54.5%).

MS (ESI, pos.ion) m/z: 310.6[M+H]+.

Step 5: N-(1-(4-(ethoxymethyl)-3-(3-methoxypropoxy)phenyl)-3-methylbutan-2-yl)formamide

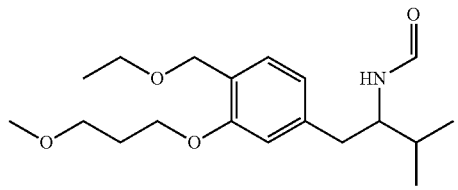 [SMILES: CCOCc1ccc(CC(NC=O)C(C)C)cc1OCCCOC]

The title compound was prepared according to the synthetic method of step 6 in example 1 by using 1-(4-(ethoxymethyl)-3-(3-methoxypropoxy)phenyl)-3-methylbutan-2-amine (1.5 g, 4.8 mmol), 1,4-dioxane (15 mL) and formic acid (24 mL, 64 mmol) as raw materials to give pale brown oil (1.3 g, 79%).

MS (ESI, pos.ion) m/z: 338.6 [M+H]+.

Step 6: 7-(ethoxymethyl)-3-isopropyl-6-(3-methoxypropoxy)-3,4-dihydroisoquinoline

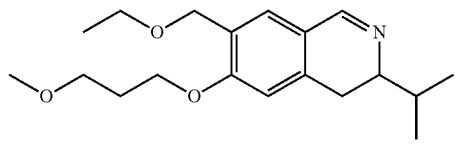 [SMILES: CCOCc1cc2c(cc1OCCCOC)CC(C(C)C)N=C2]

The title compound was prepared according to the synthetic method of step 7 in example 1 by using N-(1-(4-(ethoxymethyl)-3-(3-methoxypropoxy)phenyl)-3-methylbutan-2-yl)formamide (1 g, 2.964 mmol), dichloromethane (10 mL) and phosphorus oxychloride (0.83 mL, 8.9 mmol) as raw materials to give pale brown oil (0.66 g, 70%).

MS (ESI, pos.ion) m/z: 320.2 [M+H]+.

Step 7: Ethyl 10-(ethoxymethyl)-6-isopropyl-9-(3-methoxypropoxy)-2-oxo-2,6,7,11b-tetrahydro-1H-pyrido[2,1-a]isoquinoline-3-carboxylate

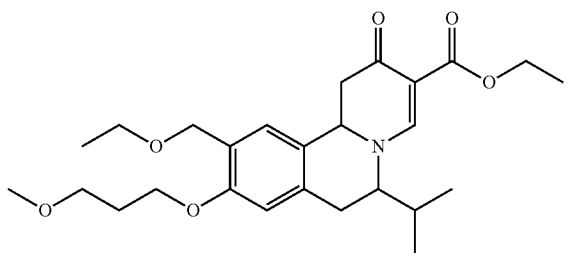 [SMILES: CCOCc1cc2c(cc1OCCCOC)CC(C(C)C)N1C=C(C(=O)OCC)C(=O)CC21]

The title compound was prepared according to the synthetic method of step 8 in example 1 by using 7-(ethoxymethyl)-3-isopropyl-6-(3-methoxypropoxy)-3,4-dihydroisoquinoline (0.94 g, 2.9 mmol), ethyl 2-(ethoxymethylene)-3-oxobutanoate (1.1 g, 5.9 mmol) and ethanol (20 mL) as raw materials to give pale brown oil (1.09 g, 81%).

MS (ESI, pos.ion) m/z: 460.2 [M+H]+.

Step 8: Ethyl 10-(ethoxymethyl)-6-isopropyl-9-(3-methoxypropoxy)-2-oxo-6,7-dihydro-2H-pyrido[2,1-a]isoquinoline-3-carboxylate

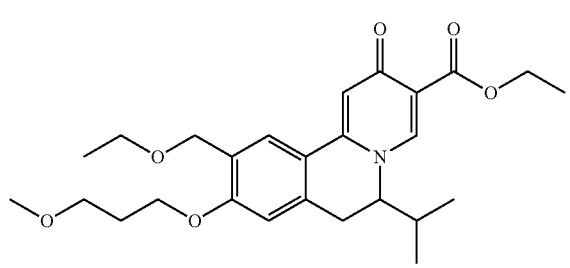 [SMILES: CCOCc1cc2c(cc1OCCCOC)CC(C(C)C)n1cc(C(=O)OCC)c(=O)cc1-2]

The title compound was prepared according to the synthetic method of step 9 in example 1 by using ethyl 10-(ethoxymethyl)-6-isopropyl-9-(3-methoxypropoxy)-2-oxo-2,6,7,11b-tetrahydro-1H-pyrido[2,1-a]isoquinoline-3-carboxylate (1.4 g, 3.0 mmol), chloranil (0.76 g, 3.1 mmol) and DME (20 mL) as raw materials to give a pale brown solid (0.61 g, 44%).

MS-ESI: (ESI, pos.ion) m/z: 458.8[M+H]$^+$.

Step 9: 10-(ethoxymethyl)-6-isopropyl-9-(3-methoxypropoxy)-2-oxo-6,7-dihydro-2H-pyrido[2,1-a]isoquinoline-3-carboxylic Acid

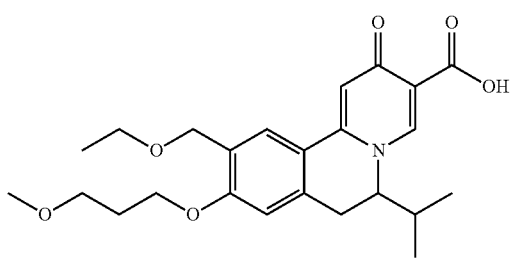 [SMILES: CCOCc1cc2c(cc1OCCCOC)CC(C(C)C)n1cc(C(=O)O)c(=O)cc1-2]

The title compound was prepared according to the synthetic method of step 5 in example 5 by using ethyl 10-(ethoxymethyl)-6-isopropyl-9-(3-methoxypropoxy)-2-oxo-6,7-dihydro-2H-pyrido[2,1-a]isoquinoline-3-carboxylate (470 mg, 1.027 mmol), THF (4 mL), ethanol (2 mL), water (1 mL) and lithium hydroxide monohydrate (0.17 g, 4.1 mmol) as raw materials to give a white solid (28 mg, 6.4%).

MS (ESI, pos.ion) m/z: 430.1 [M+H]$^+$;

$^1$H NMR (400 MHz, DMSO-d$_6$) 8.77 (s, 1H), 7.90 (s, 1H), 7.20 (s, 1H), 7.13 (s, 1H), 4.52 (overlap, 3H), 4.19-4.09 (m, 2H), 3.56-3.49 (m, 4H), 3.25 (overlap, 4H), 2.02-1.96 (m, 2H), 1.62-1.57 (m, 1H), 1.18 (t, J=6.97 Hz, 3H), 0.88 (d, J=6.58 Hz, 3H), 0.70 (d, J=6.61 Hz, 3H).

Example 8: 10-(2-aminothiazol-4-yl)-6-isopropyl-9-(3-methoxypropoxy)-2-oxo-6,7-dihydro-2H-pyrido[2,1-a]isoquinoline-3-carboxylic Acid

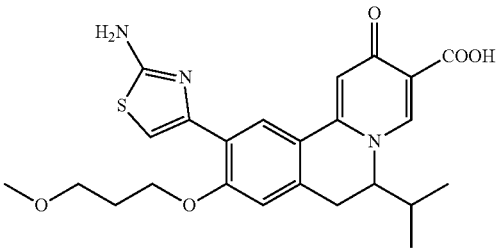 [SMILES: COCCCOc1cc2c(cc1-c1csc(N)n1)-c1cc(=O)c(C(=O)O)cn1C(C(C)C)C2]

Step 1: 1-(4-bromo-2-(3-methoxypropoxy)phenyl)ethanone

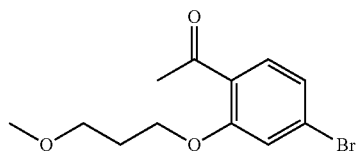 [SMILES: COCCCOc1cc(Br)ccc1C(C)=O]

To a 100 mL single-neck flask were added 1-(4-bromo-2-hydroxyphenyl)ethanone (5 g, 23.251 mmol), DMF (20 mL), 1-bromo-3-methoxypropane (11.06 g, 72.28 mmol) and K$_2$CO$_3$ (4.813 g, 34.88 mmol). The mixture was stirred at rt overnight. The reaction monitored by TLC was completed, then water (100 mL) was added into reaction mixture. The resulting mixture was extracted with ethyl acetate (100 mL B 4), and the combined organic layer was washed with saturated brine (100 mL B 2). The organic layer was concentrated in vacuo, and the residue was purified by silica gel column chromatography (PE/EA (V/V)=1/1) to give the title compound as colorless oil (6.6 g, 99%).

MS (ESI, Pos.ion) m/z: 287.4 [M+H]$^+$.

Step 2: 2-bromo-1-(4-bromo-2-(3-methoxypropoxy)phenyl)ethanone

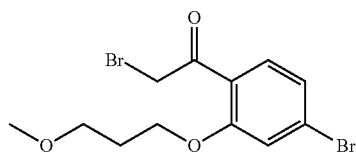 [SMILES: COCCCOc1cc(Br)ccc1C(=O)CBr]

To a 50 mL single-neck flask were added 1-(4-bromo-2-(3-methoxypropoxy)phenyl)ethanone (6 g, 20.90 mmol), then CHCl$_3$ (30 mL), ethyl acetate (30 mL) and cupric bromide (9.33 g, 41.79 mmol) were added. The mixture was heated to 85 èC under nitrogen protection and stirred for 3 hours. The reaction monitored by TLC was completed, and the reaction mixture was filtered to remove the solid. The filtrate was concentrated in vacuo to give the title compound as a white solid (7.64 g, 99%), which was used in the next step without further purification.

MS (ESI, pos.ion) m/z: 366.9 [M+H]$^+$.

Step 3: 4-(4-bromo-2-(3-methoxypropoxy)phenyl)thiazol-2-amine

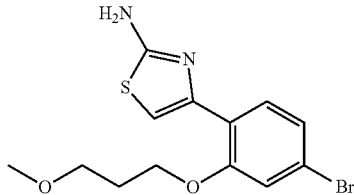 [SMILES: COCCCOc1cc(Br)ccc1-c1csc(N)n1]

2-Bromo-1-(4-bromo-2-(3-methoxypropoxy)phenyl)ethanone (7.64 g, 20.9 mmol) and thiourea (1.75 g, 23.0 mmol) were added into a 100 mL single-neck flask, then EtOH (50 mL) was added, and the mixture was stirred overnight at room temperature. The reaction monitored by TLC was completed. The reaction mixture was diluted with ethyl acetate (200 mL) and saturated aqueous sodium bicarbonate solution (100 mL), and the resulting mixture was extracted with EtOAc (200 mL B 4). The combined organic layers were washed with saturated brine (100 mL), dried over anhydrous sodium sulfate, and filtered. The filtrate was concentrated in vacuo, and the residue was purified by silica gel column chromatography (PE/EA (V/V)=1/1) to give the title compound as a light yellow solid (5.8 g, 17 mmol, 81%).

MS (ESI, pos.ion) m/z: 343.0 [M+H]+.

Step 4: Tert-butyl (4-(4-bromo-2-(3-methoxypropoxy)phenyl)thiazol-2-yl)carbamate

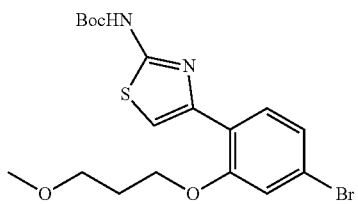 [SMILES: COCCCOc1cc(Br)ccc1-c1csc(NC(=O)OC(C)(C)C)n1]

4-(4-Bromo-2-(3-methoxypropoxy)phenyl)thiazol-2-amine (5.1 g, 15 mmol) was added into a 100 mL single-neck flask, then THF (30 mL), pyridine (20 mL), Boc$_2$O (4.9 g, 22 mmol) and DMAP (50 mg, 0.41 mmol) were added. The reaction mixture was stirred at 50 ěC for 48 hours. After the reaction was completed, the reaction mixture was cooled to room temperature, and concentrated in vacuo. The residue was diluted with ethyl acetate (50 mL) and water (50 mL) in turn, then the mixture was stood for partition. The separated organic layer was washed with saturated brine (50 mL), dried over anhydrous sodium sulfate, and filtered. The filtrate was concentrated in vacuo, and the residue was purified by silica gel column chromatography (PE/EA (V/V)=8/1) to give the title compound as a white solid (5.23 g, 11.8 mmol, 79%).

MS (ESI, pos.ion) m/z: 443.0 [M+H]+.

Step 5: Tert-butyl (4-(2-(3-methoxypropoxy)-4-(3-methyl-2-oxobutyl)phenyl)thiazol-2-yl)carbamate

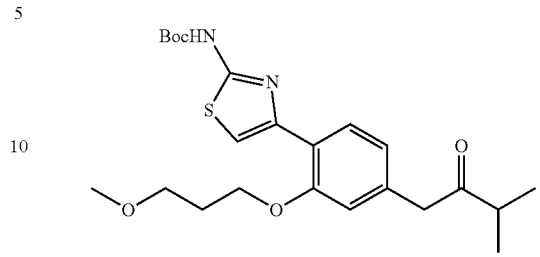

tert-Butyl (4-(4-bromo-2-(3-methoxypropoxy)phenyl)thiazol-2-yl)carbamate (5.2 g, 12 mmol) was added into a 50 mL two-neck flask, then THF (52 mL), 3-methylbutan-2-one (3.0 g, 35 mmol), X antPhos (0.31 g, 0.54 mmol), sodium tert-butoxide (3.9 g, 41 mmol) and Pd(dba)$_2$ (0.27 g, 0.47 mmol) were added. The reaction mixture was stirred at room temperature for 1 hour under nitrogen protection, then heated to 55 ěC and stirred for 2 hours, then the reaction monitored by TLC was completed. The mixture was cooled to rt, and poured into water (100 mL). The mixture was extracted with ethyl acetate (100 mL B4). The combined organic layers were dried over anydrous sodium sulfate and filtered. The filtrate was concentrated in vacuo, and the residue was purified by silica gel column chromatography (PE/EA (V/V)=1/1) to give the title compound as light yellow oil (4.39 g, 9.79 mmol, 83%).

MS (ESI, pos.ion) m/z: 449.1 [M+H]+.

Step 6: Tert-butyl (4-(4-(2-amino-3-methylbutyl)-2-(3-methoxypropoxy)phenyl)thiazol-2-yl)carbamate

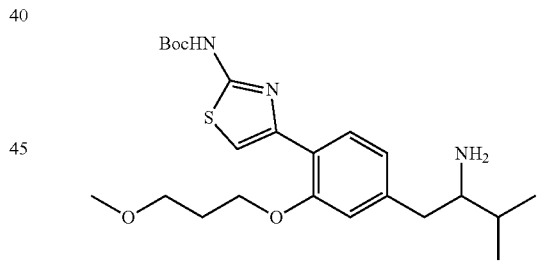

tert-Butyl (4-(2-(3-methoxypropoxy)-4-(3-methyl-2-oxobutyl)phenyl)thiazol-2-yl) carbamate (1.45 g, 3.23 mmol) was added into a 20 mL single-neck flask, then NH$_4$OAc (2.99 g, 38.8 mmol) and MeOH (15 mL) were added. The reaction mixture was stirred at rt for 1 hours, then cooled to 0 ěC and NaBH$_3$CN (0.609 g, 9.69 mmol) was added. The mixture was continued to stir overnight at 55 ěC. After the reaction was completed, the reaction mixture was concentrated in vacuo, then ethyl acetate (50 mL) and aqueous NaOH solution (1 M, 30 mL) was added in turn to dilute the residue. The mixture was stood for partition, and the aqueous layer were extracted with ethyl acetate (30 mL B 3). The combined organic layer was concentrated in vacuo to give the title compound as light yellow oil (1.4 g, 3.1 mmol, 96%).

MS (ESI, pos.ion) m/z: 450.6 [M+1]+.

Step 7: Tert-butyl (4-(4-(2-formamido-3-methyl-butyl)-2-(3-methoxypropoxy)phenyl)thiazol-2-yl)carbamate

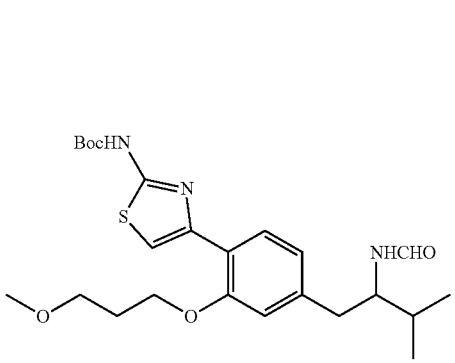

tert-Butyl (4-(4-(2-amino-3-methylbutyl)-2-(3-methoxypropoxy)phenyl)thiazol-2-yl) carbamate (0.724 g, 1.61 mmol) was added into a 25 mL single-neck flask, then methyl acetate (15 mL) was added. The mixture was refluxed overnight under nitrogen protection. After the reaction was completed, the reaction mixture was concentrated in vacuo to give the title compound as a light yellow solid (0.75 g, 1.6 mmol, 98%), which was used in the next step without further purification.

MS (ESI, pos.ion) m/z: 478.1 [M+H]$^+$.

Step 8: Tert-butyl (4-(3-isopropyl-6-(3-methoxy-propoxy)-3,4-dihydroisoquinolin-7-yl)thiazol-2-yl)carbamate

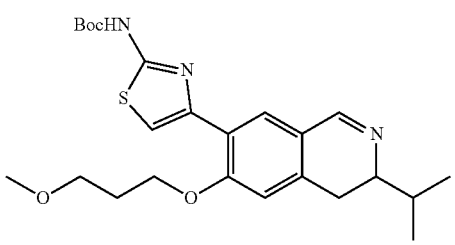 [SMILES: COCCCOc1cc2c(cc1-c1csc(NC(=O)OC(C)(C)C)n1)C=NC(C(C)C)C2]

tert-Butyl (4-(4-(2-formamido-3-methylbutyl)-2-(3-methoxypropoxy)phenyl)thiazol-2-yl)carbamate (2.31 g, 4.84 mmol) was added in a 100 mL single-neck flask, then DCM (23 mL) was added. The mixture was cooled to 0 ěC, and POCl$_3$ (0.902 mL, 9.68 mmol) was added. The resulting mixture was degassed and filled with nitrogen for three times, then heated to reflux and stirred for 3 hours. After the reaction was completed, the reaction mixture was cooled to rt, and ammonium hydroxide (15 mL) was added. The mixture was extracted with ethyl acetate (30 mL B 3). The combined organic layers were dried over anydrous sodium sulfate, and filtered. The filtrate was concentrated in vacuo to give the title compound as light yellow oil (2.0 g, 4.4 mmol, 90%), which was used directly in the next step.

MS (ESI, pos.ion) m/z: 460.1 [M+1]$^+$.

Step 9: Ethyl 10-(2-((tert-butoxycarbonyl)amino)thiazol-4-yl)-6-isopropyl-9-(3-methoxypropoxy)-2-oxo-2,6,7,11b-tetrahydro-1H-pyrido[2,1-a]isoquinoline-3-carboxylate

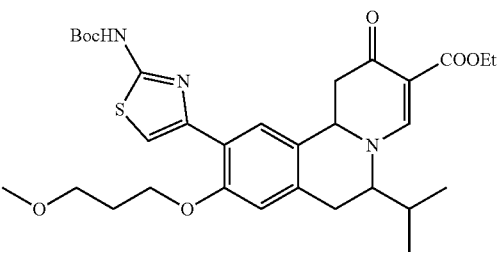 [SMILES: CCOC(=O)C1=CN2C(CC1=O)c1cc(-c3csc(NC(=O)OC(C)(C)C)n3)c(OCCCOC)cc1CC2C(C)C]

tert-Butyl (4-(3-isopropyl-6-(3-methoxypropoxy)-3,4-dihydroisoquinolin-7-yl)thiazol-2-yl)carbamate (0.5 g, 1 mmol) was added into a 50 mL single-neck flask, then ethyl 2-(ethoxymethylene)-3-oxobutanoate (0.4 g, 2 mmol) and EtOH (5 mL) were added. The mixture was refluxed overnight under nitrogen protection. After the reaction was completed, the mixture was concentrated in vacuo, and the residue was purified by silica gel column chromatography (EA) to give the title compound as a brown solid (0.12 g, 0.20 mmol, 20%).

MS (ESI, pos.ion) m/z: 600.1 [M+1]$^+$.

Step 10: Ethyl 10-(2-((tert-butoxycarbonyl)amino)thiazol-4-yl)-6-isopropyl-9-(3-methoxypropoxy)-2-oxo-6,7-dihydro-2H-pyrido[2,1-a]isoquinoline-3-carboxylate

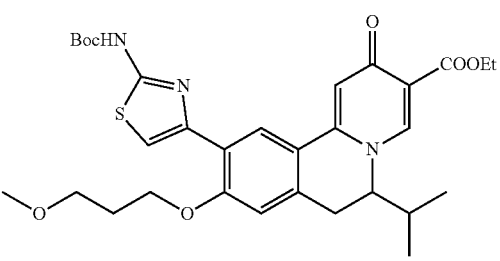 [SMILES: CCOC(=O)c1cn2c(cc1=O)-c1cc(-c3csc(NC(=O)OC(C)(C)C)n3)c(OCCCOC)cc1CC2C(C)C]

Ethyl 10-(2-((tert-butoxycarbonyl)amino)thiazol-4-yl)-6-isopropyl-9-(3-methoxy propoxy)-2-oxo-2,6,7,11b-tetrahydro-1H-pyrido[2,1-a]isoquinoline-3-carboxylate (0.290 g, 0.484 mmol) was added into a 25 mL single-neck flask, then DME (10 mL) and chloranil (0.119 g, 0.484 mmol) were added. The mixture was heated to 90 ěC and stirred for 1 hour. The reaction mixture was cooled to rt, and concentrated in vacuo. The residue was purified by silica gel column chromatography (DCM/MeOH (V/V)=10/1) to give the title compound as a brown solid (0.20 g, 0.33 mmol, 69%).

MS (ESI, pos.ion) m/z: 598.2 [M+1]$^+$.

Step 11: Ethyl 10-(2-aminothiazol-4-yl)-6-isopropyl-9-(3-methoxypropoxy)-2-oxo-6,7-dihydro-2H-pyrido[2,1-a]isoquinoline-3-carboxylate

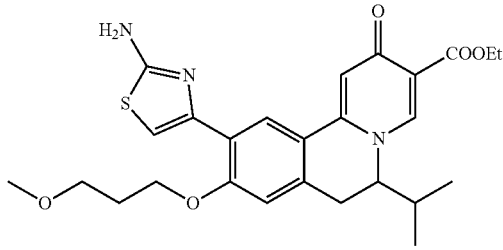 [SMILES: CCOC(=O)c1cn2c(cc1=O)-c1cc(-c3csc(N)n3)c(OCCCOC)cc1CC2C(C)C]

Ethyl 10-(2-((tert-butoxycarbonyl)amino)thiazol-4-yl)-6-isopropyl-9-(3-methoxy propoxy)-2-oxo-6,7-dihydro-2H-pyrido[2,1-a]isoquinoline-3-carboxylate (0.30 g, 0.50 mmol) was added into a 25 mL single-neck flask, then a solution of hydrogen chloride in 1,4-dioxane (5 mL) was added. The mixture was stirred at rt for 3 hours under nitrogen protection. After the reaction was completed, the reaction mixture was concentrated in vacuo, and the residue was dissolved in DCM (20 mL). The mixture was washed with saturated aqueous sodium bicarbonate (10 mL B 2) and saturated brine (10 mL), dried over anhydrous sodium sulfate, and filtered. The filtrate was concentrated in vacuo, and the residue was purified by silica gel column chromatography column chromatography (DCM/MeOH (V/V)=10/1) to give the title compound as a brown solid (0.21 g, 0.42 mmol, 84%).

MS (ESI, pos.ion) m/z: 498.3 [M+1]$^+$.

Step 12: 10-(2-aminothiazol-4-yl)-6-isopropyl-9-(3-methoxypropoxy)-2-oxo-6,7-dihydro-2H-pyrido[2,1-a]isoquinoline-3-carboxylic Acid

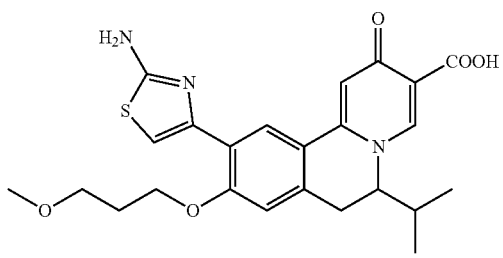 [SMILES: COCCCOc1cc2c(cc1-c1csc(N)n1)-c1cc(=O)c(C(=O)O)cn1C(C(C)C)C2]

Ethyl 10-(2-aminothiazol-4-yl)-6-isopropyl-9-(3-methoxypropoxy)-2-oxo-6,7-dihydro-2H-pyrido[2,1-a]isoquinoline-3-carboxylate (0.21 g, 0.42 mmol) was added into a 25 mL single-neck flask, then THF (2 mL), EtOH (1 mL), H$_2$O (0.5 mL) and LiOH.H$_2$O (71 mg, 1.69 mmol) was added. The reaction mixture was stirred at rt for 5 hours, then concentrated in vacuo, and the residue was adjusted with hydrochloric acid (1 M) to pH=3, then the mixture was extracted with DCM (30 mL B 2). The combined organic layers were concentrated in vacuo, and the residue was recrystallized from methanol (2 mL) to give the title compound as an offwhite solid (50 mg, 0.10 mmol, 25%).

MS (ESI, pos.ion) m/z: 470.3 [M+1]$^+$;

$^1$H NMR (400 MHz, CDCl$_3$) 16.197 (br, 1H), 8.665 (s, 1H), 8.458 (s, 1H), 7.292 (s, 1H), 6.866 (s, 1H), 4.996 (s, 2H). 4.345-4.257 (m, 2H), 3.932-3.873 (m, 1H), 3.63 (t, J=6 Hz, 2H), 3.460-3.391 (m, 4H), 3.189-3.112 (m, 1H), 2.255-2.194 (m, 2H), 1.879-1.786 (m, 1H), 0.963 (d, J=6.4 Hz, 3H), 0.828 (d, J=6.8 Hz, 3H).

Example 9: 6-isopropyl-9-(3-methoxypropoxy)-2-oxo-10-(thiazol-2-yl)-6,7-dihydro-2H-pyrido[2,1-a]isoquinoline-3-carboxylic Acid

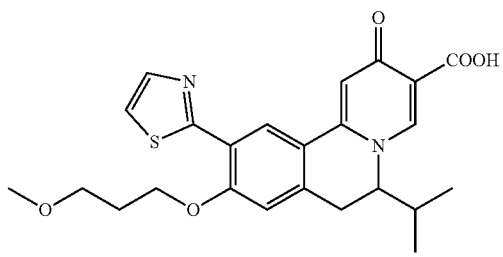 [SMILES: COCCCOc1cc2c(cc1-c1nccs1)-c1cc(=O)c(C(=O)O)cn1C(C(C)C)C2]

Step 1: 4-bromo-2-(3-methoxypropoxy)-1-nitrobenzene

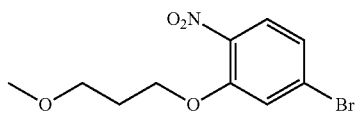 [SMILES: COCCCOc1cc(Br)ccc1[N+](=O)[O-]]

5-Bromo-2-nitrophenol (5.0 g, 23 mmol) was added into a 100 mL single-neck flask, then DMF (50 mL), K$_2$CO$_3$ (7.9 g, 57 mmol) and 1-bromo-3-methoxypropane (5.3 g, 35 mmol) were added in turn. The reaction mixture was stirred at 50 ěC overnight. After the reaction was completed, the reaction mixture was cooled to room temperature, and diluted with water (50 mL), then the mixture was extracted with EA (40 mL B 4). The combined organic layers were concentrated in vacuo, and the residue was purified by silica gel column chromatography (PE/EA (V/V)=4/1) to give the title compound as brown oil (6.7 g, 23 mmol, 99%).

MS (ESI, pos.ion) m/z: 290.0 [M+H]$^+$.

Step 2: 4-bromo-2-(3-methoxypropoxy)aniline

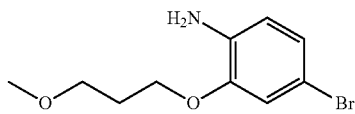

4-Bromo-2-(3-methoxypropoxy)-1-nitrobenzene (2.4 g, 8.3 mmol), H$_2$O (6 mL) and MeOH (12 mL) were added into a 100 mL two-neck flask, then ferrous powder (3.9 g, 70 mmol) and NH$_4$Cl (3.9 g, 74 mmol) were added in turn. The reaction mixture was heated to 80 ěC and stirred for 40 minutes under nitrogen protection. After the reaction was completed, the reaction mixture was cooled to rt and filtered by suction. The filter cake was washed with EA/MeOH(V/V=1/1), and the combined filtrates were concentrated. The residue was dissolved in ethyl acetate (50 mL), and the mixture was washed with saturated brine (10 mL). The organic layer was dried over anydrous sodium sulfate, filtered, and the filtrate was concentrated in vacuo to give the title compound as a gray solid (1.7 g, 6.5 mmol, 78%).

MS (ESI, pos.ion) m/z: 260.0 [M+H]⁺.

Step 3: N, N-dibenzyl-4-bromo-2-(3-methoxypropoxy)aniline

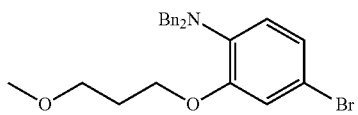

4-Bromo-2-(3-methoxypropoxy)aniline (1.2 g, 4.6 mmol) was added into a 100 mL single-neck flask, then DMF (10 mL), Na₂CO₃ (1.9 g, 14 mmol), benzyl bromide (1.7 g, 10.1 mmol) and THF (10 mL) were added in turn. The reaction mixture was stirred for 10 min, then heated to 80 ěC and stirred overnight. After the reaction was completed, to the reaction mixture was added water (50 mL), and the resulting mixture was extracted with ethyl acetate (50 mL B 3). The combined organic layers were dried over anhydrous sodium sulfate, filtered and the filtrate was concentrated in vacuo. The residue was purified by silica gel column chromatography (PE/EA (V/V)=10/1) to give the title compound as colorless oil (1.98 g, 4.50 mmol, 97%).

MS (ESI, pos.ion) m/z: 440.2 [M+H]⁺.

Step 4: 1-(4-(dibenzylamino)-3-(3-methoxypropoxy) phenyl)-3-methylbutan-2-one

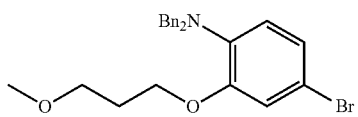

N,N-Dibenzyl-4-bromo-2-(3-methoxypropoxy)aniline (1.00 g, 2.27 mmol) was added into a 50 mL single-neck flask, then 3-methylbutan-2-one (0.59 g, 6.9 mmol), THF (10 mL), X antPhos (59 mg, 0.10 mmol), sodium tert-butoxide (0.75 g, 7.8 mmol) and Pd(dba)₂ (46 mg, 0.08 mmol) were added. The reaction mixture was degassed and filled with nitrogen for three times, and then stirred at rt for 30 min, then heated to 60 ěC and stirred for 3 hours. After the reaction was completed, the reaction mixture was cooled to rt, and ethyl acetate (50 mL) was added into the mixture, then aqueous NaOH solution (1 M, 50 mL) was added. The resulting mixture was partitioned, and the aqueous layer was extracted with ethyl acetate (50 mL B 3). The combined organic layers were dried over anhydrous sodium sulfate, filtered and the filtrate was concentrated. The residue was purified by silica gel column chromatography (PE/EA (V/V)=10/1) to give the title compound as colorless oil (0.70 g, 1.6 mmol, 69%).

MS (ESI, pos.ion) m/z: 446.4 [M+H]⁺.

Step 5: 4-(2-amino-3-methylbutyl)-N,N-dibenzyl-2-(3-methoxypropoxy)aniline

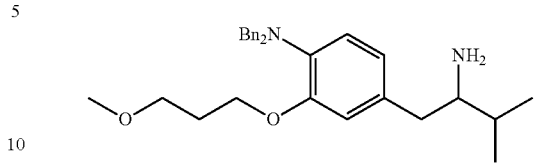

1-(4-(Di benzyl amino)-3-(3-methoxypropoxy)phenyl)-3-methylbutan-2-one (0.70 g, 1.6 mmol) was added into a 50 mL single-neck flask, then NH₄OAc (1.5 g, 19 mmol) and MeOH (10 mL) were added. The reaction mixture was stirred at rt for 30 minutes, then cooled to 0 ěC and NaBH₃CN (0.30 g, 4.8 mmol) was added. The mixture was gradually heated to 50 ěC and stirred overnight. After the reaction, the reaction mixture was concentrated in vacuo, and the residue was diluted with water (30 mL), then the mixture was extracted with ethyl acetate (30 mL B 3). The combined organic layers were dried over anydrous sodium sulfate, and filtered. The filtrate was concentrated in vacuo to give the title compound as light yellow oil (0.7 g, 2 mmol, 100%), which was directly used in the next step.

MS (ESI, pos.ion) m/z: 447.4 [M+H]⁺.

Step 6: N-(1-(4-(dibenzylamino)-3-(3-methoxypropoxy)phenyl)-3-methylbutan-2-yl)formamide

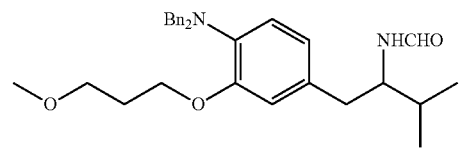

To a 50 mL single-flask were added 4-(2-amino-3-methylbutyl)-N, N-dibenzyl-2-(3-methoxypropoxy)aniline (0.58 g, 1.3 mmol), then 1,4-dioxane (5 mL) and formic acid (0.96 g, 21 mmol) were added. The reaction mixture was heated to 110 ěC and stirred for 24 hours under nitrogen protection. After the reaction was completed, the reaction mixture was concentrated in vacuo, and the residue was dissolved in EA (20 mL). Then the mixture was washed with saturated brine (20 mL), and the aqueous layer was extracted with EA (20 mL). The organic layers were combined, dried over anydrous sodium sulfate and filtered. The filtrated was concentrated in vacuo to give the titile compound as a white solid (0.62 g, 1.3 mmol, 100%).

MS (ESI, pos.ion) m/z: 475.2 [M+H]⁺.

Step 7: N-(1-(4-amino-3-(3-methoxypropoxy)phenyl)-3-methylbutan-2-yl)formamide

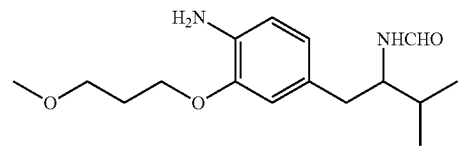

N-(1-(4-(Dibenzylamino)-3-(3-methoxypropoxy)phenyl)-3-methylbutan-2-yl)formamide (0.17 g, 0.36 mmol) was added into a 50 mL single-neck flask, then THF (20 mL) and Pd/C (17 mg, 10%) was added in turn. The reaction mixture was heated to 60 °C and stirred overnight under hydrogen atmosphere. After the reaction was completed, the reaction mixture was filtered. The filter cake was washed with EA (30 mL), and the filtrate was concentrated in vacuo to give the title compound as a gray solid (0.1 g, 0.3 mmol, 90%), which was directly used in the next step.

MS (ESI, pos.ion) m/z: 295.2 [M+H]$^+$.

Step 8: N-(1-(4-iodo-3-(3-methoxypropoxy)phenyl)-3-methylbutan-2-yl)formamide

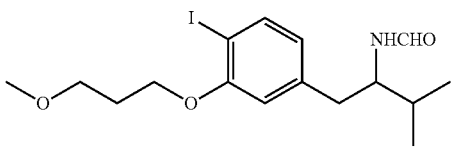

N-(1-(4-Amino-3-(3-methoxypropoxy)phenyl)-3-methylbutan-2-yl)formamide (8.00 g, 27.2 mmol) was added into a 100 mL single-neck flask, then H$_2$O (40 mL) and H$_2$SO$_4$ (13.3 g, 136 mmol) was added in turn. The reaction mixture was stirred for 10 min, then cooled to 0 °C, and a solution of NaNO$_2$ (1.87 g, 27.1 mmol) in H$_2$O (10 mL) was added. The mixture was stirred at 0 °C for 20 min, then transferred to a dropping funnel. A dried 500 mL single-neck flask was took, then KI (5.87 g, 35.4 mmol), NaHSO$_3$ (792 mg, 7.6110 mmol) and H$_2$O (40 mL) were added into the flask. The mixture was heated to 40 °C, and the mixture in the dropping funnel was added dropwise slowly into the flask for about 15 min. After addition, the reaction mixture was heated to 80 °C and stirred for 1 hour. After the reaction was completed, the reaction mixture was cooled to rt, and extracted with ethyl acetate (100 mL B 4). The combined organic layer was concentrated. The residue was purified by silica gel column chromatography (PE/EA (V/V)=1/1) to give the title compound as red brown oil (4.5 g, 11 mmol, 41%).

MS (ESI, pos.ion) m/z: 406.1 [M+H]$^+$.

Step 9: 7-iodo-3-isopropyl-6-(3-methoxypropoxy)-3,4-dihydroisoquinoline

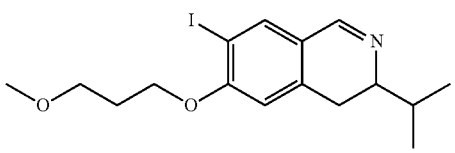 [SMILES: COCCCOc1cc2c(cc1I)C=NC(C(C)C)C2]

To a 50 mL dried single-neck flask were added N-(1-(4-iodo-3-(3-methoxypropoxy)phenyl)-3-methylbutan-2-yl)formamide (0.34 g, 0.85 mmol) and DCM (6 mL). The mixture was cooled to 0 °C, then POCl$_3$ (0.159 mL, 1.71 mmol) was added. After addition, the reaction mixture was heated to 50 °C and stirred for 2 hours. After the reaction was completed, the reaction mixture was cooled to rt, and poured into ice-water (20 mL). The mixture was extracted with ethyl acetate (30 mL B3), and the combined organic layers were washed with saturated brine (10 mL), dried over anydrous sodium sulfate, and filtered. The filtrate was concentrated in vacuo to give the title compound as brown oil (0.282 g, 0.728 mmol, 85.1%), which was directly used in the next step.

MS (ESI, pos.ion) m/z: 387.9 [M+H]$^+$.

Step 10: Ethyl 10-iodo-6-isopropyl-9-(3-methoxypropoxy)-2-oxo-2,6,7,11b-tetrahydro-1H-pyrido[2,1-a]isoquinoline-3-carboxylate

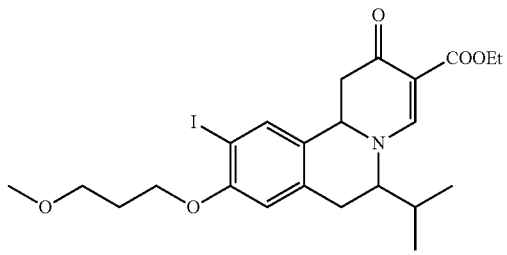 [SMILES: CCOC(=O)C1=CN2C(CC1=O)c1cc(I)c(OCCCOC)cc1CC2C(C)C]

7-Iodo-3-isopropyl-6-(3-methoxypropoxy)-3,4-dihydroisoquinoline (0.282 g, 0.7281 mmol), ethyl 2-(ethoxymethylene)-3-oxobutanoate (0.393 g, 2.11 mmol) and EtOH (10 mL) were added into a 100 mL single-neck flask. The mixture was stirred at 90 °C overnight under nitrogen protection. After the reaction was completed, the reaction mixture was cooled to rt and concentrated in vacuo. The residue was purified by silica gel column chromatography (EA) to give the title compound as brown oil (0.195 g, 0.370 mmol, 50.8%).

MS (ESI, pos.ion) m/z: 528.0 [M+H]$^+$.

Step 11: Ethyl 10-iodo-6-isopropyl-9-(3-methoxypropoxy)-2-oxo-6,7-dihydro-2H-pyrido[2,1-a]isoquinoline-3-carboxylate

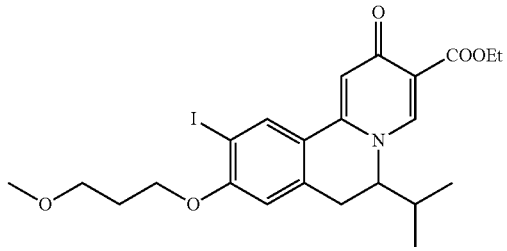 [SMILES: CCOC(=O)c1cn2c(cc1=O)-c1cc(I)c(OCCCOC)cc1CC2C(C)C]

To a 100 mL single-neck flask were added ethyl 10-iodo-6-isopropyl-9-(3-methoxypropoxy)-2-oxo-2,6,7,11b-tetrahydro-1H-pyrido[2,1-a]isoquinoline-3-carboxylate (0.20 g, 0.38 mmol), DME (10 mL) and chloranil (0.09 g, 0.38 mmol). The reaction mixture was heated to 90 °C and stirred for 1 hour, then concentrated in vacuo. The residue was purified by silica gel column chromatography (DCM/MeOH (V/V)=6/1) to give the title compound as brown oil (0.199 g, 0.38 mmol, 99.9%).

MS (ESI, pos.ion) m/z$_1^I$ 526.2 [M+H]$^+$.

Step 12: 6-isopropyl-9-(3-methoxypropoxy)-2-oxo-10-(thiazol-2-yl)-6,7-dihydro-2H-pyrido[2,1-a]isoquinoline-3-carboxylic Acid

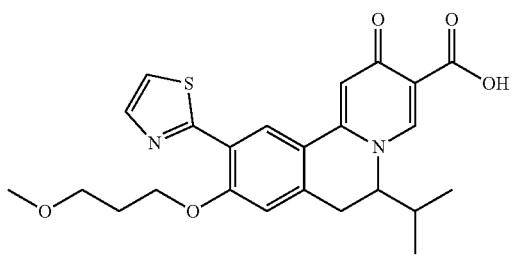 [SMILES: COCCCOc1cc2c(cc1-c1nccs1)-c1cc(=O)c(C(=O)O)cn1C(C(C)C)C2]

To a 25 mL single-neck flask were added ethyl 10-iodo-6-isopropyl-9-(3-methoxypropoxy)-2-oxo-6,7-dihydro-2H-pyrido[2,1-a]isoquinoline-3-carboxylate (0.3 g, 0.57 mmol), 2-(tributylstannyl)thiazole (0.427 g, 1.14 mmol), anhydrous dioxane (10 mL) and bis(triphenylphosphine)palladium(II) chloride (99 mg, 0.14 mmol). The reaction mixture was heated to 110 °C and stirred for 24 h under nitrogen protection. After the reaction was completed, the reaction mixture was concentrated in vacuo. The residue was purified by silica gel column chromatography (DCM/MeOH (V/V) =10/1) to give the title compound as a white solid (50 mg, 0.11 mmol, 19.3%).

MS (ESI, pos.ion) m/z: 455.1 [M+H]$^+$;
$^1$H NMR (400 MHz, CDCl$_3$) 16.106 (br ⊢1H), 8.915 (s, 1H), 8.470 (s, 1H), 7.971 (d, J=2.4 Hz, 1H), 7.477 (d, J=2.4 Hz, 1H), 7.320 (s, 1H), 6.974 (s, 1H), 4.467-4.357 (m, 2H), 3.991-3.877 (m, 1H), 3.760-3.660 (m, 2H), 3.515-3.352 (m, 4H), 3.258-3.166 (m, 1H), 2.358-2.248 (m, 2H), 2.089-1.973 (m, 1H), 0.978 (d, J=6.4 Hz, 3H), 0.847 (d, J=6.0 Hz, 3H).

Example 10: 6-isopropyl-9-(3-methoxypropoxy)-10-(oxazol-2-yl)-2-oxo-6,7-dihydro-2H-pyrido[2,1-a]isoquinoline-3-carboxylic Acid

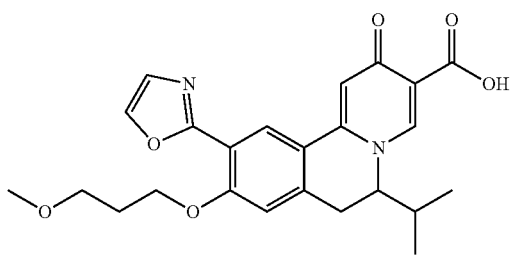 [SMILES: COCCCOc1cc2c(cc1-c1ncco1)-c1cc(=O)c(C(=O)O)cn1C(C(C)C)C2]

To a 25 mL single-neck flask were added ethyl 10-iodo-6-isopropyl-9-(3-methoxypropoxy)-2-oxo-6,7-dihydro-2H-pyrido[2,1-a]isoquinoline-3-carboxylate (0.330 g, 0.63 mmol), 2-(tributylstannyl)oxazole (0.562 g, 1.57 mmol), anhydrous dioxane (10 mL) and bis(triphenylphosphine) palladium(II) chloride (0.11 g, 0.16 mmol). The reaction mixture was heated to 110 °C and stirred for 24 h under nitrogen protection. After the addition, the reaction mixture was concentrated in vacuo. The residue was purified by silica gel column chromatography (DCM/MeOH (V/V)=10/1) to give the title compound as a white solid (40 mg, 0.11 mmol, 15%).

MS (ESI, pos.ion) m/z: 438.9 [M+H]$^+$;
$^1$H NMR (400 MHz, CDCl$_3$) 15.988 (br, 1H), 8.476 (s, 1H), 8.407 (s, 1H), 7.802 (d, 1H), 7.325 (d, 1H), 7.221 (s, 1H), 6.966 (s, 1H), 4.347-4.256 (m, 2H), 3.954-3.919 (m, 1H), 3.693-3.610 (m, 2H), 3.470-3.416 (m, 1H), 3.377 (s, 3H), 3.243-3.173 (m, 1H), 2.220-2.151 (m, 2H), 2.053-2.004 (m, 1H), 0.985 (d, J=6.8 Hz, 3H), 0.858 (d, J=6.8 Hz, 3H).

Example 11: 10-(furan-2-yl)-6-isopropyl-9-(3-methoxypropoxy)-2-oxo-6,7-dihydro-2H-pyrido[2,1-a]isoquinoline-3-carboxylic Acid

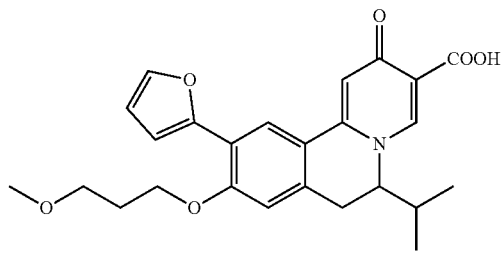 [SMILES: COCCCOc1cc2c(cc1-c1ccco1)-c1cc(=O)c(C(=O)O)cn1C(C(C)C)C2]

Step 1: 2-(benzyloxy)-5-bromobenzaldehyde

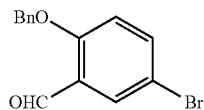 [SMILES: O=Cc1cc(Br)ccc1OCc1ccccc1]

5-Bromo-2-hydroxybenzaldehyde (10.045 g, 49.970 mmol), benzyl bromide (12.82 g, 74.96 mmol), K$_2$CO$_3$ (13.79 g, 99.94 mmol) and DMF (50 mL) were added into a 100 mL two-neck flask. The reaction mixture was heated to 60 °C and stirred for 12 h under nitrogen protection. After the reaction was completed, to the reaction mixture was added water (100 mL), and the resulting mixture was extracted with ethyl acetate (50 mL B 4). The combined organic layers were washed with saturated brine (50 mL B 2), dried over anhydrous sodium sulfate, and filtered. The filtrate was concentrated in vacuo to give the title compound as a white solid (14.2 g, 48.8 mmol, 97.6%).

MS (ESI, pos.ion) m/z: 312.9 [M+Na]$^+$.

Step 2: 2-(benzyloxy)-5-bromophenyl Formate

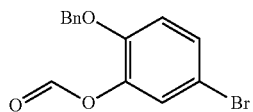

To a 500 mL single-neck flask was added 2-(benzyloxy)-5-bromobenzaldehyde (13.2 g, 45.3 mmol) and ethyl acetate (130 mL), then the mixture was cooled to 0 °C, and m-CPBA (11.7 g, 67.8 mmol) were added into the flask in portions. After addition, the reaction mixture was stirred for 30 min at 0 °C, then heated to rt and stirred overnight. After the reaction was completed, the reaction mixture was diluted with ethyl acetate (50 mL), then washed with aqueous NaOH solution (mass percent: 3%, 100 mL), and the aqueous layer was extracted with ethyl acetate (50 mL B 3). The combined organic layers were washed with saturated brine (50 mL B 3), dried over anhydrous sodium sulfate and filtered. The filtrate was concentrated in vacuo, and the residue was purified by silica gel column chromatography (PE/EA (V/V)=1/1) to give the title compound as brown oil (13.31 g, 43.34 mmol, 95.6%).

MS (ESI, pos.ion) m/z: 329.0 [M+Na]$^+$.

Step 3: 2-(benzyloxy)-5-bromophenol

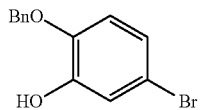

2-(Benzyloxy)-5-bromophenyl formate (13.31 g, 43.34 mmol) was added into a 500 mL single-neck flask, then the solvent in the flask was degassed and filled with nitrogen for three times, then anydrous THF (130 mL) was added. The mixture was cooled to 0 èC, and DIBAH (46 mL, 69 mmol) was added into the mixture. The reaction mixture was stirred at 0 èC for 1 hour, then ethyl acetate (100 mL) was added into the mixture, and water (100 mL) was added to quench the reaction. The mixture was adjusted with concentrated hydrochloric acid to pH=7, then extracted with ethyl acetate (200 mL B 3). The combined organic layers were concentrated in vacuo, and the residue was purified by silica gel column chromatography (PE/EA (V/V)=1/1) to give the title compound as colorless oil (11.58 g, 41.49 mmol, 95.73%).

MS (ESI, neg.ion) m/z: 276.9 [M–H]$^-$.

Step 4: 1-(benzyloxy)-4-bromo-2-(3-methoxypropoxy)benzene

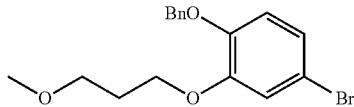 [SMILES: COCCCOc1cc(Br)ccc1OCc1ccccc1]

2-(Benzyloxy)-5-bromophenol (11.58 g, 41.49 mmol) was added into a 100 mL single-neck flask, then DMF (60 mL), K$_2$CO$_3$ (11.45 g, 82.97 mmol) and 1-bromo-3-methoxypropane (9.523 g, 62.23 mmol) were added in turn. The reaction mixture was stirred at 50 èC overnight, then diluted with water (50 mL), and the mixture was extracted with ethyl acetate (50 mL B 3). The combined organic layers were washed with saturated brine (30 mL B 2), dried over anhydrous sodium sulfate and filtered. The filtrate was concentrated in vacuo, and the residue was purified by silica gel column chromatography (PE/EA (V/V)=10/1) to give the title compound as colorless oil (14.3 g, 40.7 mmol, 98.1%).

MS (ESI, pos.ion) m/z: 351.1 [M+H]$^+$.

Step 5:1-(4-(benzyloxy)-3-(3-methoxypropoxy)phenyl)-3-methylbutan-2-one

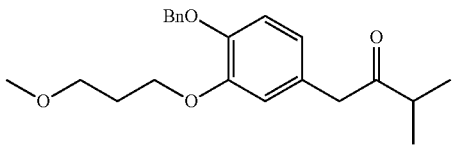 [SMILES: COCCCOc1cc(CC(=O)C(C)C)ccc1OCc1ccccc1]

1-(Benzyloxy)-4-bromo-2-(3-methoxypropoxy)benzene (12.50 g, 35.59 mmol), Pd(dba)$_2$ (0.818 g, 1.42 mmol), sodium tert-butoxide (11.73 g, 122.1 mmol), X anPhos (0.926 g, 1.60 mmol), THF (100 mL) and 3-methylbutan-2-one (9.917 g, 115.1 mmol) were added into a 250 mL two-neck flask. The reaction mixture was stirred at rt for 30 min under nitrogen protection, then heated to 60 èC and stirred overnight. After the reaction was completed, the mixture was diluted with water (100 mL), and the mixture was extracted with EA (200 mL B 3). The combined organic layers were concentrated in vacuo, and the residue was purified by silica gel column chromatography (EA) to give the title compound as yellow oil (12.0 g, 33.7 mmol, 94.6%).

MS (ESI, pos.ion) m/z: 357.2 [M+H]$^+$.

Step 6: 1-(4-(benzyloxy)-3-(3-methoxypropoxy) phenyl)-3-methylbutan-2-amine

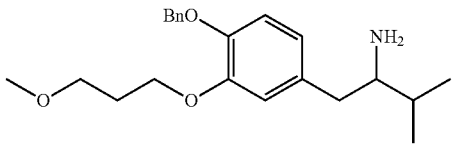 [SMILES: COCCCOc1cc(CC(N)C(C)C)ccc1OCc1ccccc1]

1-(4-(Benzyloxy)-3-(3-methoxypropoxy)phenyl)-3-methylbutan-2-one (13.28 g, 37.25 mmol) was added into a 500 mL single-neck flask, then NH$_4$OAc (34.46 g, 447.1 mmol) and MeOH (130 mL) were added. The reaction mixture was stirred at rt to dissolve the solid, then cooled to 0 èC and NaBH$_3$CN (7.023 g, 111.8 mmol) was added. The reaction mixture was stirred at rt for 12 h. After the reaction was completed, the mixture was concentrated in vacuo, and to the residue was added saturated aqueous ammonium chloride solution (50 mL), EA (100 mL) and saturated sodium chloride (50 mL). The mixture was partitioned, and the aqueous layer was extracted with ethyl acetate (100 mL B 3). The combined organic layers were concentrated in vacuo, and the residue was purified by silica gel column chromatography (DCM/MeOH (V/V)=10/1) to give the title compound as yellow oil (13.0 g, 36.4 mmol, 97.6%).

MS (ESI, pos.ion) m/z: 358.3 [M+H]$^+$.

Step 7: N-(1-(4-(benzyloxy)-3-(3-methoxypropoxy) phenyl)-3-methylbutan-2-yl)formamide

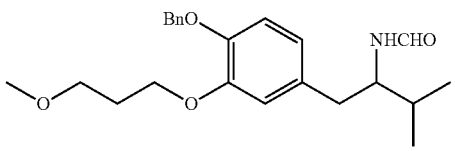

1-(4-(Benzyloxy)-3-(3-methoxypropoxy)phenyl)-3-methylbutan-2-amine (13 g, 36.36 mmol) was added into a 500 mL single-neck flask, then dioxane (130 mL) and formic acid (26.78 g, 581.9 mmol) were added in turn. The reaction mixture was heated to 110 ěC and stirred for 12 hours under nitrogen protection. After the reaction was completed, the reaction mixture was concentrated in vacuo, and the residue was diluted with water (50 mL). The mixture was extracted with EA (100 mL B 4). The combined organic layers were concentrated in vacuo, and the residue was purified by silica gel column chromatography (PE/EA (V/V)=1/1) to give the title compound as a white solid (9.5 g, 25 mmol, 68%).

MS (ESI, pos.ion) m/z: 386.4 [M+H]$^+$.

Step 8: 7-(benzyloxy)-3-isopropyl-6-(3-methoxy-propoxy)-3,4-dihydroisoquinoline

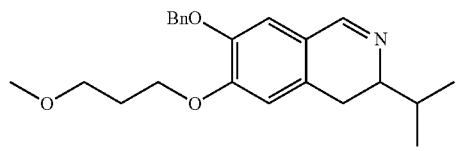 [SMILES: COCCCOc1cc2c(cc1OCc1ccccc1)C=NC(C(C)C)C2]

N-(1-(4-(benzyloxy)-3-(3-methoxypropoxy)phenyl)-3-methylbutan-2-yl)formamide (5.0 g, 13 mmol) was added into a 100 mL two-neck flask, then DCM (50 mL) was added. The reaction mixture was cooled to 0 ěC, then POCl$_3$ (2.4 mL, 26 mmol) was added, and the mixture was stirred at 50 ěC for 3 hours. After the reaction was completed, the reaction mixture was concentrated in vacuo, and the residue was diluted with ethyl acetate (50 mL) and water (50 mL). The mixture was partitioned, and the aqueous layer was extracted with EA (50 mL B 4). The combined organic layers were concentrated in vacuo, and the residue was purified by silica gel column chromatography (EA) to give the title compound as a yellow solid (3.8 g, 10 mmol, 80%).

MS (ESI, pos.ion) m/z: 368.2 [M+H]$^+$.

Step 9: Ethyl 10-(benzyloxy)-6-isopropyl-9-(3-methoxypropoxy)-2-oxo-2,6,7,11b-tetrahydro-1H-pyrido[2,1-a]isoquinoline-3-carboxylate

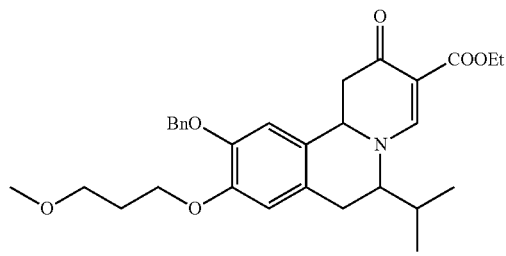 [SMILES: CCOC(=O)C1=CN2C(CC1=O)c1cc(OCc3ccccc3)c(OCCCOC)cc1CC2C(C)C]

7-(Benzyloxy)-3-isopropyl-6-(3-methoxypropoxy)-3,4-dihydroisoquinoline (4.5 g, 12 mmol), EtOH (10 mL) and ethyl 2-(ethoxymethylene)-3-oxobutanoate (3.4 g, 18 mmol) were added into a 100 mL single-neck flask. The mixture was stirred at 90 ěC overnight under nitrogen protection. After the reaction was completed, the reaction mixture was concentrated in vacuo, and the residue was purified by silica gel column chromatography (EA) to give the title compound as a brown solid (4.3 g, 8.5 mmol, 69%).

MS (ESI, pos.ion) m/z: 508.3 [M+H]$^+$.

Step 10: Ethyl 10-(benzyloxy)-6-isopropyl-9-(3-methoxypropoxy)-2-oxo-6,7-dihydro-2H-pyrido[2,1-a]isoquinoline-3-carboxylate

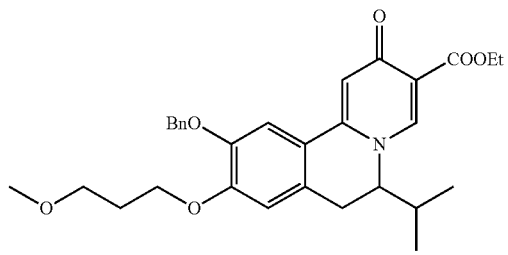 [SMILES: CCOC(=O)c1cn2c(cc1=O)-c1cc(OCc3ccccc3)c(OCCCOC)cc1CC2C(C)C]

Ethyl 10-(benzyloxy)-6-isopropyl-9-(3-methoxypropoxy)-2-oxo-2,6,7,11b-tetrahydro-1H-pyrido[2,1-a]isoquinoline-3-carboxylate (3.648 g, 7.187 mmol) was added into a 100 mL single-neck flask, then DME (36 mL) and chloranil (1.767 g, 7.186 mmol) were added. The reaction mixture was stirred at 90 ěC for 1 h under nitrogen protection. After the reaction was completed, the reaction mixture was concentrated in vacuo, and the residue was purified by silica gel column chromatography (DCM/MeOH (V/V)=10/1) to give the title compound as a brown solid (3.2 g, 6.3 mmol, 88%).

MS (ESI, pos.ion) m/z: 506.4 [M+H]$^+$.

Step 11: Ethyl 10-hydroxy-6-isopropyl-9-(3-methoxypropoxy)-2-oxo-6,7-dihydro-2H-pyrido[2,1-a]isoquinoline-3-carboxylate

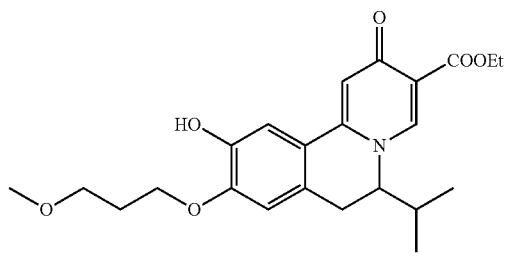 [SMILES: CCOC(=O)c1cn2c(cc1=O)-c1cc(O)c(OCCCOC)cc1CC2C(C)C]

Ethyl 10-(benzyloxy)-6-isopropyl-9-(3-methoxypropoxy)-2-oxo-6,7-dihydro-2H-pyrido[2,1-a]isoquinoline-3-carboxylate (2.347 g, 4.642 mmol), Pd/C (0.237 g) and THF (12 mL) were added into a 100 mL single-neck flask. The mixture was stirred at 50 ěC overnight under nitrogen protection. After the reaction was completed, the reaction mixture was filtered through a celite pad, and the residue was purified by silica gel column chromatography (DCM/MeOH (V/V)=10/1) to give the title compound as a brown solid (1.9 g, 4.6 mmol, 99%).

MS (ESI, pos.ion) m/z: 416.3 [M+H]$^+$.

Step 12: Ethyl 6-isopropyl-9-(3-methoxypropoxy)-2-oxo-10-(((trifluoromethyl)sulfonyl) oxy)-6,7-dihydro-2H-pyrido[2,1-a]isoquinoline-3-carboxylate

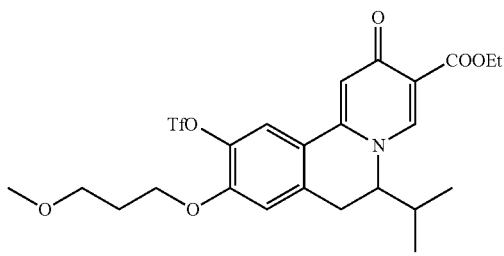 [SMILES: CCOC(=O)c1cn2c(cc1=O)-c1cc(OS(=O)(=O)C(F)(F)F)c(OCCCOC)cc1CC2C(C)C]

To a 50 mL dried single-neck flask were added ethyl 10-hydroxy-6-isopropyl-9-(3-methoxypropoxy)-2-oxo-6,7-dihydro-2H-pyrido[2,1-a]isoquinoline-3-carboxylate (250 mg, 0.60 mmol), TEA (0.16 mL, 1.2 mmol) and DCM (5 mL). The reaction mixture was cooled to 0 ěC, then N,N-bis(trifluoromethylsulfonyl)aniline (429 mg, 1.201 mmol) was added. The resulting mixture was warmed to rt and stirred overnight. After the reaction was completed, the reaction mixture was washed with hydrochloric acid (20 mL, 1 M) and saturated brine (20 mL), dried over anydrous sodium sulfate, and filtered. The filtrate was concentrated in vacuo, and the residue was purified by silica gel column chromatography (DCM/CH$_3$OH(V/V)=50/1 to 30/1) to give the title compound as gray powder (310 mg, 94.10%).

MS (ESI, pos.ion) m/z: 547.8 [M+H]$^+$.

Step 13: 10-(furan-2-yl)-6-isopropyl-9-(3-methoxypropoxy)-2-oxo-6,7-dihydro-2H-pyrido[2,1-a]isoquinoline-3-carboxylic Acid

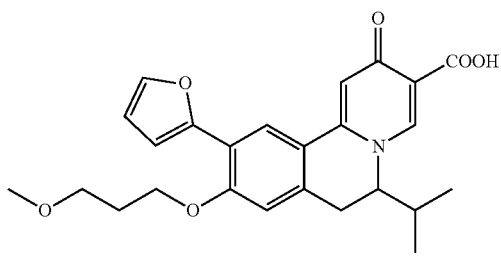 [SMILES: COCCCOc1cc2c(cc1-c1ccco1)-c1cc(=O)c(C(=O)O)cn1C(C(C)C)C2]

To a 50 mL single-neck flask were added 2-furanboronic acid (81 mg, 0.72 mmol), ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (200 mg, 0.36 mmol), tetrakis(triphenylphosphine)palladium (42 mg, 0.036 mmol) and sodium carbonate (193 mg, 1.82 mmol). The reaction mixture was degassed and filled with nitrogen for three times, then 1,4-dioxane (4 mL) and water (1 mL) were added. The resulting mixture was stirred at 100 ěC overnight. After the reaction was completed, the reaction mixture was adjusted with hydrochloric acid (1 M) to pH 5, then the mixture was extracted with ethyl acetate (10 mL B 3). The combined organic layer was concentrated in vacuo. The residue was purified by silica gel column chromatography (DCM/MeOH (V/V)=10/1) to give the title compound as an off-white solid (100 mg, 0.23 mmol, 62.57%).

MS (ESI, pos.ion) m/z: 438.3[M+H]$^+$;

$^1$H NMR (400 MHz, CDCl$_3$) 8.58 (s, 1H), 8.28 (s, 1H), 7.54 (s, 1H), 7.30 (s, 1H), 6.99 (d, J=3.2 Hz, 1H), 6.89 (s, 1H), 6.54 (dd, J=3.1, 1.7 Hz, 1H), 4.39-4.24 (m, 2H), 4.02 (s, 1H), 3.66 (t, J=5.3 Hz, 2H), 3.48-3.36 (m, 4H), 3.17 (d, J=16.2 Hz, 1H), 2.29-2.19 (m, 2H), 1.84 (dd, J=15.8, 6.7 Hz, 1H), 0.98 (d, J=6.6 Hz, 3H), 0.84 (d, J=6.6 Hz, 3H).

Example 12: 6-isopropyl-9-(3-methoxypropoxy)-2-oxo-10-(pyrimidin-5-yl)-6,7-dihydro-2H-pyrido[2,1-a]isoquinoline-3-carboxylic Acid

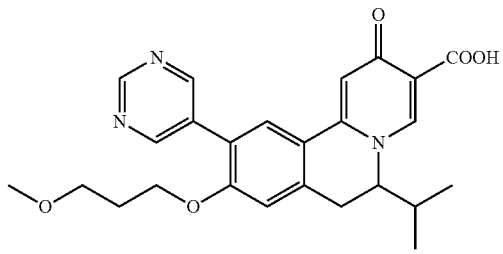 [SMILES: COCCCOc1cc2c(cc1-c1cncnc1)-c1cc(=O)c(C(=O)O)cn1C(C(C)C)C2]

To a microwave tube were added (pyrimidin-5-yl)boric acid (54 mg, 0.43580 mmol), ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (200 mg, 0.36 mmol), K$_3$PO$_4$ (232 mg, 1.09 mmol), Pd(dppf)Cl$_2$ (53 mg, 0.072 mmol), DME (6 mL), EtOH (2 mL) and H$_2$O (2 mL). The reaction mixture was bubbled with nitrogen for 5 min under ultraphonic condition, then the microwave tube was sealed and stirred at 135 ěC under microwave heating for 30 min. Then the reaction mixture was cooled to rt, and lithium hydroxide monohydrate (153 mg, 3.64 mmol) was added. The mixture was stirred at rt overnight. After the reaction, the reaction mixture was concentrated in vacuo, and to the residue was added hydrochloric acid (1 M) to adjust pH=5. The mixture was extracted with ethyl acetate (20 mL B 3). The combined organic layers were dried over anhydrous sodium sulfate, filtered and the filtrate was concentrated in vacuo. The residue was purified by silica gel column chromatography (DCM/CH$_3$OH (V/V)=10/1) to give the title compound as a gray solid (50 mg, 0.1112 mmol, 30.45%).

MS (ESI, pos.ion) m/z: 450.3 [M+H]$^+$;

1H NMR (400 MHz, CDCl$_3$) 15.96 (s, 1H), 9.23 (s, 1H), 8.94 (s, 2H), 8.54 (s, 1H), 7.72 (s, 1H), 7.13 (s, 1H), 6.97 (s, 1H), 4.33-4.16 (m, 2H), 4.02 (s, 1H), 3.48 (t, J=5.6 Hz, 3H), 3.33 (s, 3H), 3.24 (d, J=13.0 Hz, 1H), 2.12-1.99 (m, 2H), 1.85 (s, 1H), 1.01 (d, J=6.2 Hz, 3H), 0.87 (d, J=6.5 Hz, 3H).

Example 13: 6-isopropyl-9-(3-methoxypropoxy)-2-oxo-10-(thiazol-4-yl)-6,7-dihydro-2H-pyrido[2,1-a]isoquinoline-3-carboxylic Acid

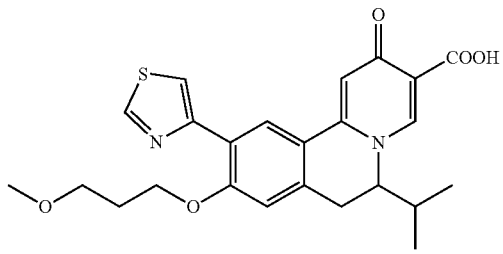 [SMILES: COCCCOc1cc2c(cc1-c1cscn1)-c1cc(=O)c(C(=O)O)cn1C(C(C)C)C2]

To a 25 mL single-neck flask were added ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (0.300 g, 0.510 mmol), 4-(tributylstannyl)thiazole (0.913 mmol, 1 mmol), anhydrous dioxane (10 mL) and bis(triphenylphosphine)palladium(II) chloride (79 mg, 0.112 mmol). The reaction mixture was heated to 110 ěC and stirred for 12 h under nitrogen protection. After the reaction was completed, the reaction mixture was purified by silica gel column chromatography (DCM/MeOH (V/V)=15/1) to give the title compound as a gray solid (50 mg, 0.110 mmol, 24.09%).

MS (ESI, pos.ion) m/z: 455.0 [M+H]$^+$;

$^1$H NMR (400 MHz, CDCl$_3$) 16.151 (br, 1H), 8.896 (s, 1H), 8.838 (s, 1H), 8.468 (s, 1H), 8.078 (s, 1H), 7.310 (s, 1H), 6.938 (s, 1H), 4.389-4.303 (m, 2H), 3.962-3.874 (m, 1H), 3.683-3.601 (m, 2H), 3.483-3.422 (m, 1H), 3.393 (s, 3H), 3.229-3.133 (m, 1H), 2.314-2.177 (m, 2H), 1.896-1.812 (m, 1H), 0.983 (d, J=6.4 Hz, 3H), 0.851 (d, J=6.4 Hz, 3H).

Example 14: 6-isopropyl-9-(3-methoxypropoxy)-10-(2-methylthiazol-4-yl)-2-oxo-6,7-dihydro-2H-pyrido[2,1-a]isoquinoline-3-carboxylic Acid

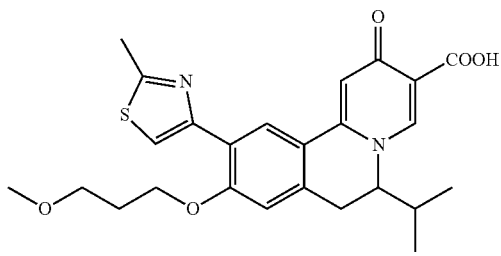 [SMILES: COCCCOc1cc2c(cc1-c1csc(C)n1)-c1cc(=O)c(C(=O)O)cn1C(C(C)C)C2]

Step 1: Methyl 4-bromo-2-(3-methoxypropoxy)benzoate

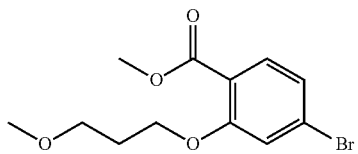 [SMILES: COCCCOc1cc(Br)ccc1C(=O)OC]

To a dried reaction flask were added DMF (50 mL), methyl 4-bromo-2-hydroxybenzoate (10 g, 43.283 mmol), 1-bromo-3-methoxypropane (7.95 g, 52 mmol) and potassium carbonate (9.06 g, 64.9 mmol). The mixture was heated to 50 ěC and stirred for 16 hours. After the reaction was completed, the reaction mixture was diluted with water, and the mixture was extracted with ethyl acetate (50 mL В 3). The combined organic layers were dried over anhydrous sodium sulfate and filtered. The filtrate was concentrated in vacuo to give the title compound as colorless oil (13 g, 99.1%).

MS (ESI, pos.ion) m/z: 303.2 [M+H]$^+$.

Step 2: 2-(3-methoxypropoxy)-4-(3-methyl-2-oxobutyl)benzoic Acid

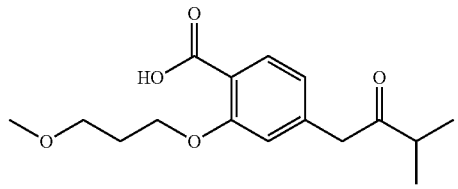 [SMILES: COCCCOc1cc(CC(=O)C(C)C)ccc1C(=O)O]

To a 250 mL three-neck flask were added methyl 4-bromo-2-(3-methoxypropoxy)benzoate (6 g, 19.792 mmol), 3-methyl-2-butan-one (2.56 g, 29.72 mmol), tetrahydrofuran (60 mL), xantphos (354 mg, 0.593 mmol) and sodium tert-butoxide (5.882 g, 59.36 mmol). The reaction mixture was degassed and filled with nitrogen for three times, and Pd(dba)$_2$ (440 mg, 0.466 mmol) was added into the mixture under nitrogen protection, then the resulting mixture was degassed and filled with nitrogen for three times. The mixture was heated to 55 ěC and stirred for 2 hours. After the reaction was completed, the reaction mixture was diluted with water (100 mL), and washed with ethyl acetate (50 mL) and ethyl acetate (20 mL) in turn. The aqueous layer was diluted with ethyl acetate (80 mL), and the mixture was adjusted with diluted aqueous HCl solution (mass percent: 10%) to pH=5-7. The mixture was partitioned, and the aqueous layer was extracted with ethyl acetate (30 mL В 2). The combined organic layers were dried over anhydrous sodium sulfate and filtered. The filtrate was concentrated in vacuo to give the title compound as colorless oil (3.2 g, 10.88 mmol, 55%).

MS (ESI, pos.ion) m/z: 317.1 [M+Na]$^+$.

Step 3: N-methoxy-2-(3-methoxypropoxy)-N-methyl-4-(3-methyl-2-oxobutyl)benzamide

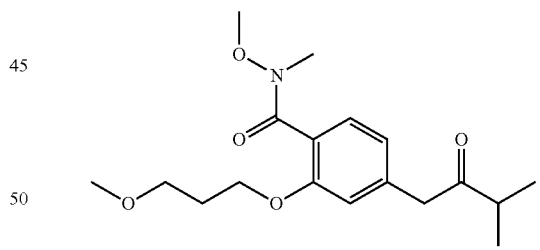

To a 50 mL single-neck flask were added 2-(3-methoxypropoxy)-4-(3-methyl-2-oxobutyl)benzoic acid (1 g, 3.398 mmol), DMF (6 mL), DIPEA (1.78 mL, 10.2 mmol), N,O-dimethylhydroxylamine hydrochloride (500 mg, 5.126 mmol) and HATU (2 g, 5.2598 mmol). The reaction mixture was stirred at rt for 24 h, then to the mixture was added hydrochloric acid (1 M) to adjust pH=5. The mixture was extracted with ethyl acetate (20 mL В 3). The combined organic layers were dried over anydrous sodium sulfate and filtered. The filtrate was concentrated in vacuo, and the residue was purified by silica gel column chromatography (PE/EA (V/V)=1/1) to give the title compound as colorless oil (200 mg, 0.59 mmol, 17.45%).

MS (ESI, pos.ion) m/z: 338.3 [M+H]$^+$.

Step 4: 4-(2-amino-3-methylbutyl)-N-methoxy-2-(3-methoxypropoxy)-N-methylbenzamide

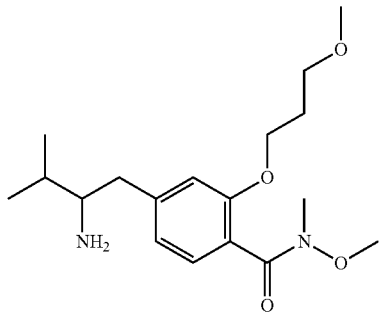 [SMILES: COCCCOc1cc(CC(N)C(C)C)ccc1C(=O)N(C)OC]

To a 100 mL single-neck flask were added methanol (45 mL), N-methoxy-2-(3-methoxypropoxy)-N-methyl-4-(3-methyl-2-oxobutyl)benzamide (4.5 g, 13 mmol) and ammonium acetate (7.2 g, 93 mmol). The reaction mixture was stirred at rt for 1 h, then cooled to 0 ěC, and sodium cyanoborohydride (1.7 g, 27 mmol) was added slowly. The resulting mixture was stirred at rt for 24 h. After the reaction was completed, the reaction mixture was concentrated in vacuo to remove the solvent, the reaction mixture was quenched with saturated aqueous sodium bicarbonate solution (50 mL), and extracted with ethyl acetate (50 mL B 3). The combined organic layer was concentrated in vacuo. The combined organic layers were dried over anydrous sodium sulfate and filtered. The filtrate was concentrated in vacuo to give the title compound as colorless oil (4 g, 11.82 mmol, 89%).

MS (ESI, pos.ion) m/z: 339.1 [M+H]$^+$.

Step 5: Tert-butyl (1-(4-(methoxy(methyl)carbamoyl)-3-(3-methoxypropoxy)phenyl)-3-methylbutan-2-yl)carbamate

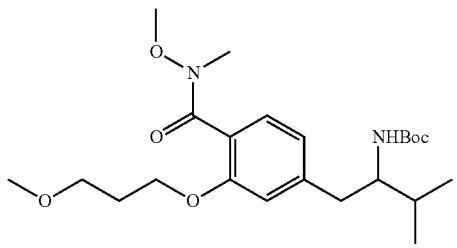 [SMILES: COCCCOc1cc(CC(NC(=O)OC(C)(C)C)C(C)C)ccc1C(=O)N(C)OC]

To a 250 mL single-neck flask were added 4-(2-amino-3-methylbutyl)-N-methoxy-2-(3-methoxypropoxy)-N-methylbenzamide (4 g, 11.82 mmol), TEA (3.7 mL, 27 mmol), DCM (50 mL) in turn, then Boc$_2$O (5.8 g, 27 mmol) was added dropwise. The resulting mixture was stirred at rt for 2 h. After the reaction was completed, the reaction mixture was concentrated in vacuo. To the residue was added hydrochloric acid (1 M) to pH=5, then the mixture was extracted with ethyl acetate (20 mL B 3). The combined organic layers were dried over anydrous sodium sulfate and filtered. The filtrate was concentrated in vacuo. The residue was purified by silica gel column chromatography (PE/EA (V/V)=1/1) to give the title compound as colorless oil (3.2 g, 7.3 mmol, 62%).

$^1$H NMR (600 MHz, CDCl$_3$) 7.20 (d, J=7.3 Hz, 1H), 6.83-6.77 (m, 2H), 4.37 (d, J=9.3 Hz, 1H), 4.10 (t, J=6.2 Hz, 2H), 3.76 (s, 1H), 3.67-3.44 (m, 5H), 3.39-3.20 (m, 6H), 2.93 (q, J=7.3 Hz, 1H), 2.83-2.76 (m, 1H), 2.72-2.65 (m, 1H), 2.06-2.01 (m, 1H), 1.79-1.71 (m, 1H), 1.40 (s, 9H), 0.98 (d, J=6.8 Hz, 3H), 0.93 (d, J=6.8 Hz, 3H).

Step 6: Tert-butyl (1-(4-acetyl-3-(3-methoxypropoxy)phenyl)-3-methylbutan-2-yl)carbamate

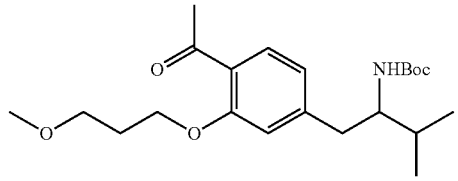 [SMILES: COCCCOc1cc(CC(NC(=O)OC(C)(C)C)C(C)C)ccc1C(C)=O]

To a dried flask were added tert-butyl (1-(4-(methoxy(methyl)carbamoyl)-3-(3-methoxypropoxy)phenyl)-3-methylbutan-2-yl)carbamate (21 g, 47.88 mmol) and THF (200 mL). The mixture was degassed and filled with nitrogen for three times, then cooled to −5 ěC, and a solution of methyl magnesium bromide in tetrahydrofuran (64 mL, 192 mmol, 3 mol/L) was added dropwise slowly. The reaction mixture was stirred at −5 ěC for 12 h, then saturated aqueous ammonium chloride (100 mL), ethyl acetate (200 mL) and water (200 mL) were added. The mixture was partitioned, and the aqueous layer was extracted with ethyl acetate (100 mL). The combined organic layers were concentrated in vacuo to remove the solvent, and the residue was purified by silica gel column chromatography (PE/EA (V/V)=2/1) to give the title compound as a white solid (17 g, 43.20 mmol, 90.23%).

MS (ESI, pos.ion) m/z: 394.3 [M+H]$^+$.

Step 7: 1-(4-(2-amino-3-methylbutyl)-2-(3-methoxypropoxy)phenyl)ethanone

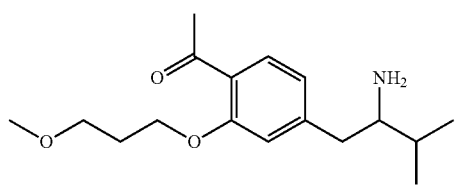 [SMILES: COCCCOc1cc(CC(N)C(C)C)ccc1C(C)=O]

To a 50 mL single-neck flask were added tert-butyl (1-(4-acetyl-3-(3-methoxypropoxy)phenyl)-3-methylbutan-2-yl)carbamate (5 g, 12.71 mmol), DCM (10 mL) and TFA (10 mL). The reaction mixture was stirred at rt for 3 h, then concentrated by rotary evaporation. To the residue was added saturated aqueous sodium bicarbonate solution to pH=8, then the mixture was extracted with ethyl acetate (20 mL B 3). The combined organic layers were dried over anydrous sodium sulfate and filtered. The filtrate was concentrated in vacuo to give the title compound as colorless oil (3.3 g, 11 mmol, 89%).

MS (ESI, pos.ion) m/z: 294.3[M+H]$^+$.

Step 8: N-(1-(4-acetyl-3-(3-methoxypropoxy)phenyl)-3-methylbutan-2-yl)formamide

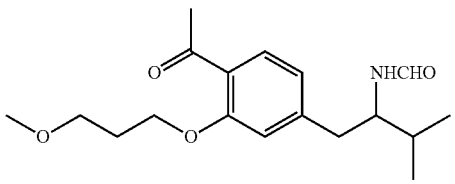

To a 50 mL single-neck flask were added 1-(4-(2-amino-3-methylbutyl)-2-(3-methoxypropoxy)phenyl)ethanone (3.3 g, 11 mmol), 1,4-dioxane (33 mL) and formic acid (6.4 mL, 170 mmol). The mixture was heated and refluxed for 20 hours, then concentrated in vacuo, and the residue was purified by silica gel column chromatography (DCM/CH$_3$OH (V/V)=20/1) to give the title compound as a white solid (2.35 g, 7.31 mmol, 65%).

MS (ESI, pos.ion) m/z: 322.3[M+H]$^+$.

Step 9: N-(1-(4-(2-bromoacetyl)-3-(3-methoxypropoxy)phenyl)-3-methylbutan-2-yl)formamide

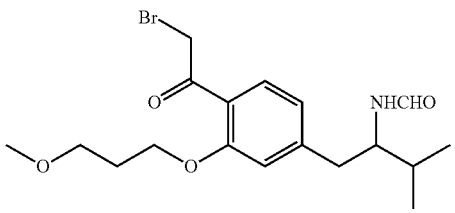

To a 50 mL single-neck flask were added N-(1-(4-acetyl-3-(3-methoxypropoxy)phenyl)-3-methylbutan-2-yl)formamide (200 mg, 0.62 mmol), methanol (10 mL) and montmorillonite K 10 (20 mg). The mixture was heated to 60 ěC, and NBS (130 mg, 0.73 mmol) was added in six portions for 15 min. Then the resulting mixture was stirred for 30 min. After the reaction was completed, the reaction mixture was filtered to remove the solid, and the filtrate was concentrated in vacuo. The residue was purified by silica gel column chromatography (PE/EA (V/V)=2/1) to give the title compound as a white solid (237 mg, 0.5921 mmol, 95.14%).

MS (ESI, pos.ion) m/z: 400.2 [M+H]$^+$.

Step 10: N-(1-(3-(3-methoxypropoxy)-4-(2-methylthiazol-4-yl)phenyl)-3-methylbutan-2-yl)formamide

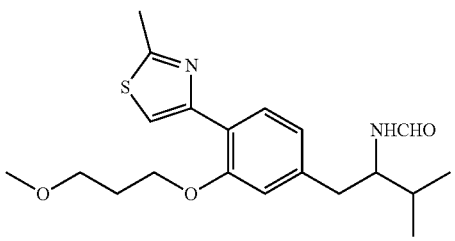

N-(1-(4-(2-Bromoacetyl)-3-(3-methoxypropoxy)phenyl)-3-methylbutan-2-yl)formamide (1.22 g, 3.05 mmol), thioacetamide (0.252 g, 3.35 mmol) and EtOH (10 mL) was added into a 100 mL single-neck flask. The mixture was stirred at rt overnight, then concentrated, and the residue was purified by silica gel column chromatography (DCM/CH$_3$OH (V/V)=10/1) to give the title compound as black brown oil (1.1 g, 2.9 mmol, 96%).

MS (ESI, pos.ion) m/z: 377.4 [M+H]$^+$.

Step 11: 4-(3-isopropyl-6-(3-methoxypropoxy)-3,4-dihydroisoquinolin-7-yl)-2-methylthiazole

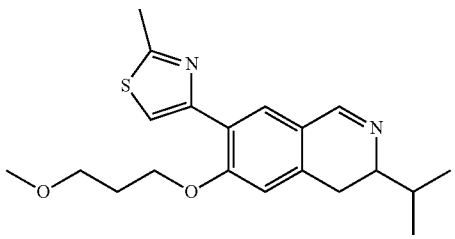 [SMILES: COCCCOc1cc2c(cc1-c1csc(C)n1)C=NC(C(C)C)C2]

N-(1-(3-(3-M ethoxypropoxy)-4-(2-methylthiazol-4-yl)phenyl)-3-methylbutan-2-yl) formamide (1.22 g, 3.05 mmol) and DCM (22 mL) was added into a 100 mL single-neck flask. The mixture was cooled to 0 ěC, then POCl$_3$ (0.54 mL, 5.8 mmol) was added into the mixture. The reaction mixture was stirred at rt overnight, and poured into ice-water (20 g). The resulting mixture was adjusted with ammonium hydroxide to pH=10. The mixture was extracted with ethyl acetate (30 mL B 4). The combined organic layers were washed with saturated brine (30 mL B 2), and the organic layer was concentrated in vacuo. The residue was purified by silica gel column chromatography (PE/EA (V/V)=1/1) to give the title compound as brown oil (0.385 g, 1.07 mmol, 37%).

MS (ESI, pos.ion) m/z: 359.3 [M+H]$^+$.

Step 12: Ethyl 6-isopropyl-9-(3-methoxypropoxy)-10-(2-methylthiazol-4-yl)-2-oxo-2,6,7,11b-tetrahydro-1H-pyrido[2,1-a]isoquinoline-3-carboxylate

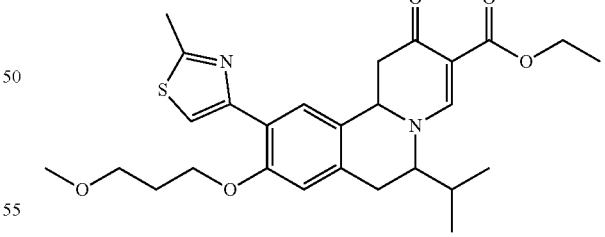

4-(3-Isopropyl-6-(3-methoxypropoxy)-3,4-dihydroisoquinolin-7-yl)-2-methylthiazole (0.385 g, 1.07 mmol), ethyl 2-(ethoxymethylene)-3-oxobutanoate (0.400 g, 2.15 mmol) and EtOH (10 mL) were added into a 100 mL single-neck flask. The mixture was stirred at 85 ěC overnight. The reaction mixture was cooled to rt, and concentrated in vacuo. The residue was purified by silica gel column chromatography (EA) to give the title compound as brown oil (0.31 g, 0.62 mmol, 50%).

MS (ESI, pos.ion) m/z: 499.4 [M+H]$^+$.

Step 13: Ethyl 6-isopropyl-9-(3-methoxypropoxy)-10-(2-methylthiazol-4-yl)-2-oxo-6,7-dihydro-2H-pyrido[2,1-a]isoquinoline-3-carboxylate

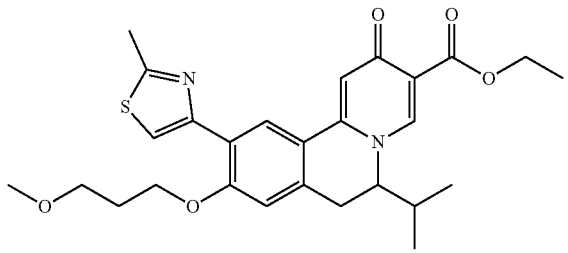 [SMILES: CCOC(=O)c1cn2c(cc1=O)-c1cc(-c3csc(C)n3)c(OCCCOC)cc1CC2C(C)C]

Ethyl 6-isopropyl-9-(3-methoxypropoxy)-10-(2-methylthiazol-4-yl)-2-oxo-2,6,7,11b-tetrahydro-1H-pyrido[2,1-a]isoquinoline-3-carboxylate (0.31 g, 0.62 mmol) was added into a 50 mL single-neck flask, then chloranil (0.15 g, 0.61 mmol) and 1,2-dimethoxyethane (10 mL) were added. The reaction mixture was heated to 90 ěC and stirred for 1 h under nitrogen protection, then concentrated in vacuo. The residue was purified by silica gel column chromatography (DCM/MeOH (V/V)=8/1) to give the title compound as a brown solid (0.30 g, 0.60 mmol, 97%).

MS (ESI, pos.ion) m/z: 497.3 [M+H]$^+$.

Step 14: 6-isopropyl-9-(3-methoxypropoxy)-10-(2-methylthiazol-4-yl)-2-oxo-6,7-dihydro-2H-pyrido[2,1-a]isoquinoline-3-carboxylic Acid

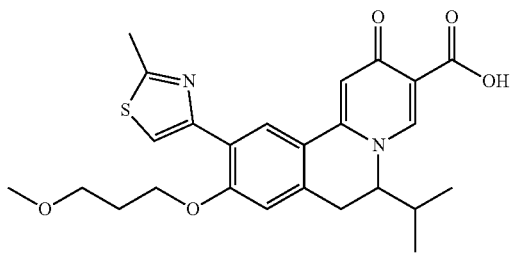 [SMILES: COCCCOc1cc2c(cc1-c1csc(C)n1)-c1cc(=O)c(C(=O)O)cn1C(C(C)C)C2]

Ethyl 6-isopropyl-9-(3-methoxypropoxy)-10-(2-methylthiazol-4-yl)-2-oxo-6,7-dihydro-2H-pyrido[2,1-a]isoquinoline-3-carboxylate (0.300 g, 0.604 mmol) was added into a 50 mL single-neck flask, then THF (6 mL), EtOH (3 mL) and H$_2$O (1.5 mL) were added. The mixture was stirred to dissolve the solid, then LiOH.H$_2$O (50 mg, 1.1905 mmol) was added. The reaction mixture was stirred at rt for 6 hours, then concentrated in vacuo, and the residue was dissolved in water (5 mL). Then the mixture adjusted with hydrochloric acid (1 M) to pH=2-3, and the mixture was extracted with DCM (20 mL B 4). The combined organic layers were concentrated in vacuo, and the residue was recrystallized from methanol (5 mL) to give the title compound as a white solid (170 mg, 0.3628 mmol, 60.1%).

MS (ESI, pos.ion) m/z: 469.3 [M+H]$^+$;

$^1$H NMR (400 MHz, CDCl$_3$) 16.172 (br, 1H), 8.796 (s, 1H), 8.463 (s, 1H), 7.821 (s, 1H), 7.322 (s, 1H), 6.904 (s, 1H), 4.270-4.361 (m, 2H), 3.911-3.889 (m, 1H), 3.669-3.593 (m, 2H), 3.469-3.406 (m, 1H), 3.388 (s, 3H), 3.321-3.122 (m, 1H), 2.810 (s, 3H), 2.261-2.200 (m, 2H), 1.886-1.787 (m, 1H), 0.973 (d, J=6.4 Hz, 3H), 0.835 (d, J=6.8 Hz, 3H).

Example 15: 6-isopropyl-9-(3-methoxypropoxy)-2-oxo-10-(thiophen-2-yl)-6,7-dihydro-2H-pyrido[2,1-a]isoquinoline-3-carboxylic Acid

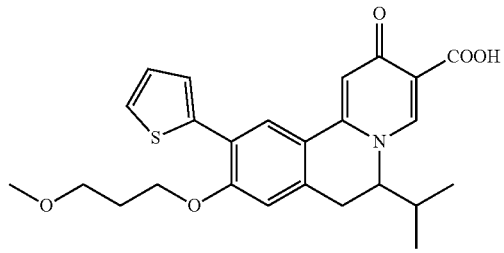

To a 50 mL two-neck flask were added 2-(tributylstannyl)thiazole (0.378 g, 1.01 mmol), ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (0.22 g, 0.40 mmol), bis(triphenylphosphine)palladium (II) (71 mg, 0.10 mmol) and anhydrous dioxane (10 mL). The reaction mixture was stirred at 110 ěC overnight under nitrogen protection, then distilled under reduced pressure to remove the solvent. The residue was recrystallized from methanol (5 mL) to give the title compound as a gray solid (40 mg, 0.09 mmol).

MS (ESI, pos.ion) m/z: 454.3 [M+H]$^+$;

$^1$H NMR (400 MHz, CDCl$_3$) 16.049 (br, 1H), 8.489 (s, 1H), 8.040 (s, 1H), 7.559 (d, J=2.8 Hz, 1H), 7.423 (d, J=4.2 Hz, 1H), 7.185 (s, 1H), 7.168-7.146 (m, 1H), 6.907 (s, 1H), 4.341-4.248 (m, 2H), 3.948-3.914 (m, 1H), 3.691-3.636 (m, 2H), 3.461-3.405 (m, 1H), 3.390 (s, 3H), 3.226-3.120 (m, 1H), 2.2594-2.198 (m, 2H), 1.902-1.799 (m, 1H), 0.991 (d, J=6.8 Hz, 3H), 0.864 (d, J=6.8 Hz, 3H).

Example 16: 9-(furan-2-yl)-6-isopropyl-10-methoxy-2-oxo-6,7-dihydro-2H-pyrido[2,1-a]isoquinoline-3-carboxylic Acid

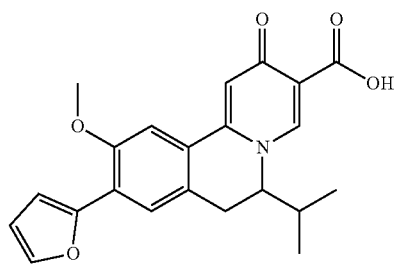 [SMILES: COc1cc2c(cc1-c1ccco1)CC(C(C)C)n1cc(C(=O)O)c(=O)cc1-2]

Step 1: 2-(benzyloxy)-4-bromo-1-methoxybenzene

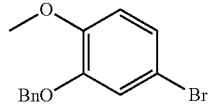

To a 500 mL two-neck flask were added 5-bromo-2-methoxyphenol (20 g, 98.50 mmol), benzyl bromide (12.3 mL, 104 mmol), acetone (200 mL) and potassium carbonate (20 g, 144.71 mmol). The mixture was stirred at 50 °C overnight, then cooled to rt and filtered. The filter cake was washed with dichloromethane, and the combined filtrates were concentrated in vacuo to give the title compound as a white solid (23 g, 78.4 mmol).

$^1$H NMR (400 MHz, DMSO-d$_6$) 7.42 (dt, J=15.3, 7.1 Hz, 4H), 7.37-7.31 (m, 1H), 7.21 (d, J=2.3 Hz, 1H), 7.08 (dd, J=8.6, 2.3 Hz, 1H), 6.94 (d, J=8.6 Hz, 1H), 5.10 (s, 2H), 3.76 (s, 3H).

Step 2: 1-(3-(benzyloxy)-4-methoxyphenyl)-3-methylbutan-2-one

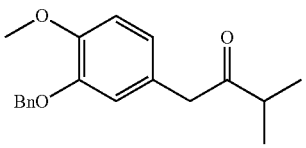 [SMILES: COc1ccc(CC(=O)C(C)C)cc1OCc1ccccc1]

To a 500 mL three-neck flask were added 2-(benzyloxy)-4-bromo-1-methoxybenzene (22 g, 75.03 mmol) and sodium tert-butoxide (22 g, 222.05 mmol), then the mixture was stirred under nitrogen protection, and then X antPhos (4.5 g, 7.5 mmol) and Pd$_2$(dba)$_3$ (7 g, 7.41 mmol) were added into the mixture. The reaction mixture was degassed and filled with nitrogen for three times, then THF (200 mL) and 3-methyl-2-butan-one (16 g, 185.8 mmol) were added. The mixture was heated to 60 °C and stirred for 3 h. After the reaction was completed, the reaction mixture was cooled to rt, and concentrated in vacuo. The residue was purified by silica gel column chromatography (PE/EA (V/V)=20/1) to give the title compound as red brown oil (14.65 g, 49.10 mmol, 65%).

MS (ESI, pos.ion) m/z: 299.1 [M+H]$^+$.

Step 3: 1-(3-(benzyloxy)-4-methoxyphenyl)-3-methylbutan-2-amine

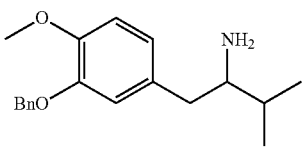 [SMILES: COc1ccc(CC(N)C(C)C)cc1OCc1ccccc1]

To a 500 mL single-neck flask were added 1-(3-(benzyloxy)-4-methoxyphenyl)-3-methylbutan-2-one (19.5 g, 65.3 mmol), MeOH (200 mL) and NH$_4$OAc (30 g, 389.2 mmol). The mixture was stirred at rt for 1 h, then NaBH$_3$CN (12 g, 191.0 mmol) was added at 0 °C with stirring. After addition, the mixture was heated to 60 °C and stirred for 8 hours, then concentrated in vacuo. The residue was purified by silica gel column chromatography (DCM/CH$_3$OH (V/V)=20/1) to give the title compound as a white solid (15.2 g, 50.8 mmol, 78%).

MS (ESI, pos.ion) m/z: 300.1 [M+H]$^+$.

Step 4: N-(1-(3-(benzyloxy)-4-methoxyphenyl)-3-methylbutan-2-yl)formamide

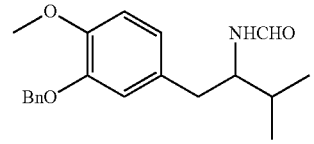

To a 250 mL single-neck flask were added 1-(3-(benzyloxy)-4-methoxyphenyl)-3-methylbutan-2-amine (6.8 g, 23 mmol), 1,4-dioxane (70 mL) and formic acid (21 mL, 557 mmol). The mixture was heated to 100 °C and stirred for 24 h, then concentrated in vacuo. The residue was purified by silica gel column chromatography (PE/EA (V/V)=1/1) to give the title compound as brown oil (7.26 g, 22.2 mmol, 98%).

MS (ESI, pos.ion) m/z: 328.2 [M+H]$^+$.

Step 5: 6-(benzyloxy)-3-isopropyl-7-methoxy-3,4-dihydroisoquinoline

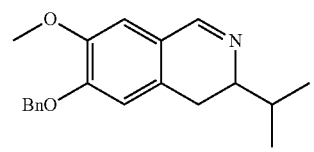 [SMILES: COc1cc2c(cc1OCc1ccccc1)CC(C(C)C)N=C2]

To a 250 mL single-neck flask were added N-(1-(3-(benzyloxy)-4-methoxyphenyl)-3-methylbutan-2-yl)formamide (11.7 g, 35.7 mmol) and DCM (120 mL), then the mixture was stirred at 0 °C, and POCl$_3$ (10 mL, 107.3 mmol) was added. After addition, the mixture was heated to 50 °C and stirred overnight under nitrogen protection. The mixture was cooled naturally to rt, then added into ice-water (300 mL). The mixture was adjusted with ammonium hydroxide to pH=11, and then partitioned. The organic layer was concentrated in vacuo, and the residue was diluted with ethyl acetate (300 mL) and water (300 mL). The mixture was partitioned, then the organic layer was dried over anhydrous sodium sulfate and filtered. The filtrate was concentrated in vacuo, and the residue was purified by silica gel column chromatography (PE/EA (V/V)=5/1-1/1) to give the title compound as a white solid (9.2 g, 35.7 mmol, 83%).

MS (ESI, pos.ion) m/z: 310.1 [M+H]$^+$.

Step 6: Ethyl 9-(benzyloxy)-6-isopropyl-10-methoxy-2-oxo-2,6,7,11b-tetrahydro-1H-pyrido[2,1-a]isoquinoline-3-carboxylate

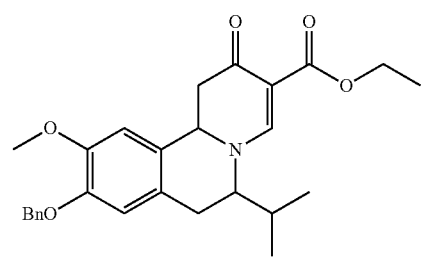 [SMILES: CCOC(=O)C1=CN2C(CC1=O)c1cc(OC)c(OCc3ccccc3)cc1CC2C(C)C]

6-(Benzyloxy)-3-isopropyl-7-methoxy-3,4-dihydroisoquinoline (9.2 g, 30 mmol), EtOH (10 mL) and ethyl 2-(ethoxymethylene)-3-oxobutanoate (11 g, 59.076 mmol) were added into a 250 mL single-neck flask. The reaction mixture was heated to 90 ėC and stirred for 24 hours under nitrogen protection, then concentrated in vacuo. The residue was purified by silica gel column chromatography (EA) to give the title compound as an aubergine solid (10.8 g, 24 mmol, 81%).

MS (ESI, pos.ion) m/z: 450.2 [M+H]$^+$.

Step 7: Ethyl 9-(benzyloxy)-6-isopropyl-10-methoxy-2-oxo-6,7-dihydro-2H-pyrido[2,1-a]isoquinoline-3-carboxylate

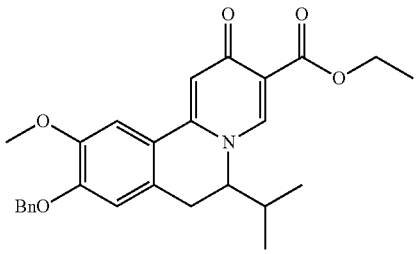 [SMILES: CCOC(=O)c1cn2c(cc1=O)-c1cc(OC)c(OCc3ccccc3)cc1CC2C(C)C]

To a 250 mL single-neck flask were added ethyl 9-(benzyloxy)-6-isopropyl-10-methoxy-2-oxo-2,6,7,11b-tetrahydro-1H-pyrido[2,1-a]isoquinoline-3-carboxylate (10.8 g, 24.0 mmol), DME (100 mL) and chloranil (6 g, 24.1585 mmol). The reaction mixture was heated to 90 ėC and stirred for 1 hours, then concentrated in vacuo. The residue was purified by silica gel column chromatography (DCM/CH$_3$OH (V/V)=10/1) to give the title compound as brown oil (10.1 g, 22.6 mmol, 93.9%).

MS (ESI, pos.ion) m/z: 448.3 [M+H]$^+$.

Step 8: Ethyl 9-hydroxy-6-isopropyl-10-methoxy-2-oxo-6,7-dihydro-2H-pyrido[2,1-a]isoquinoline-3-carboxylate

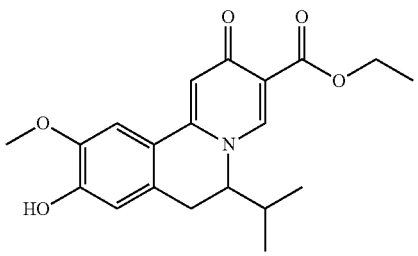 [SMILES: CCOC(=O)c1cn2c(cc1=O)-c1cc(OC)c(O)cc1CC2C(C)C]

To a 250 mL single-neck flask were added ethyl 9-(benzyloxy)-6-isopropyl-10-methoxy-2-oxo-6,7-dihydro-2H-pyrido[2,1-a]isoquinoline-3-carboxylate (10.1 g, 22.6 mmol), THF (100 mL) and Pd/C (1 g, mass percent: 10%). The reaction mixture was degassed and filled with hydrogen for three times, then stirred at 50 ėC for 12 h in a hydrogen atmosphere. After the reaction was completed, the reaction mixture was cooled to rt, and filtered through a celite pad to remove Pd/C. The filter cake was washed with ethyl acetate and the filtrate was concentrated to give the title compound as a reddish brown solid (7.2 g, 22.6 mmol, 89%).

MS (ESI, pos.ion) m/z: 358.1 [M+H]$^+$.

Step 9: Ethyl 6-isopropyl-10-methoxy-2-oxo-9-((((trifluoromethyl)sulfonyl)oxy)-6,7-dihydro-2H-pyrido[2,1-a]isoquinoline-3-carboxylate

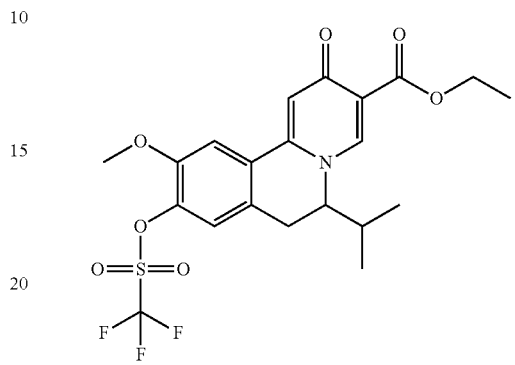

To a 50 mL dried single-neck flask were added ethyl 9-hydroxy-6-isopropyl-10-methoxy-2-oxo-6,7-dihydro-2H-pyrido[2,1-a]isoquinoline-3-carboxylate (1 g, 2.80 mmol), TEA (1.5 mL, 11 mmol) and DCM (10 mL). The mixture was cooled to 0 ėC, and N-phenylbis(trifluoromethanesulfon)imide (1.5 g, 4.2 mmol) was added. The reaction mixture was stirred at rt for 8 h, then washed with aqueous hydrochloric acid solution (1 M, 20 mL) and saturated brine (20 mL). The combined organic layers were dried over anhydrous sodium sulfate, filtered and the filtrate was concentrated in vacuo. The residue was purified by silica gel column chromatography (DCM/CH$_3$OH (V/V)=30/1) to give the title compound as black green powder (790 mg, 1.614 mmol, 57.68%).

MS (ESI, pos.ion) m/z: 490.3 [M+H]$^+$.

Step 10: 9-(furan-2-yl)-6-isopropyl-10-methoxy-2-oxo-6,7-dihydro-2H-pyrido[2,1-a]isoquinoline-3-carboxylic Acid

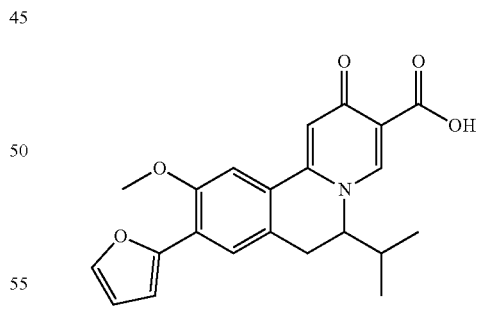

To a 50 mL single-neck flask were added 2-furanboronic acid (91 mg, 0.81 mmol), ethyl 6-isopropyl-10-methoxy-2-oxo-9-(((trifluoromethyl)sulfonyl)oxy)-6,7-dihydro-2H-pyrido[2,1-a]isoquinoline-3-carboxylate (200 mg, 0.41 mmol), tetrakis(triphenylphosphine)palladium (47 mg, 0.04 mmol) and sodium carbonate (216 mg, 2.04 mmol). The reaction mixture was degassed and filled with nitrogen for three times, then 1,4-dioxane (4 mL) and water (1 mL) were added. The resulting mixture was stirred at 100 ėC for 24 h, then adjusted with hydrochloric acid (1 M) to pH=5. The mixture was extracted with ethyl acetate (3 B 20 mL). The combined organic layers were dried over anhydrous sodium sulfate, filtered and the filtrate was concentrated in vacuo. The residue was purified by silica gel column chromatography (DCM/MeOH (V/V)=20/1) to give the title compound as an off-white solid (100 mg, 0.26 mmol, 64.51%).

MS (ESI, pos.ion) m/z: 380.2 [M+H]$^+$;

$^1$H NMR (400 MHz, CDCl$_3$) 15.92 (s, 1H), 8.52 (s, 1H), 7.80 (s, 1H), 7.55 (s, 1H), 7.25-7.10 (m, 2H), 6.57 (s, 1H), 5.32 (s, 1H), 4.22-3.87 (m, 4H), 3.42-3.14 (m, 2H), 2.06 (s, 1H), 1.05-0.75 (m, 6H).

Example 17: 6-isopropyl-10-methoxy-2-oxo-9-(thiophen-2-yl)-6,7-dihydro-2H-pyrido[2,1-a]isoquinoline-3-carboxylic Acid

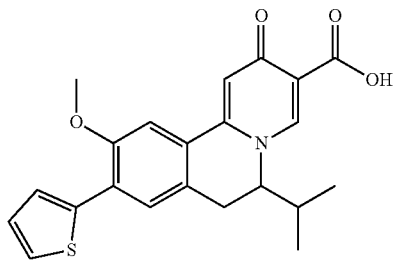 [SMILES: COc1cc2c(cc1-c1cccs1)CC(C(C)C)n1cc(C(=O)O)c(=O)cc1-2]

To a dried reaction flask were added ethyl 6-isopropyl-10-methoxy-2-oxo-9-(((trifluoromethyl)sulfonyl)oxy)-6,7-dihydro-2H-pyrido[2,1-a]isoquinoline-3-carboxylate (200 mg, 0.41 mmol), tributyl(thiophen-2-yl)stannane (300 mg, 0.82 mmol), bis(triphenylphosphine)palladium(II) chloride (71 mg, 0.10 mmol) and 1,4-dioxane (10 mL). The reaction mixture was degassed and filled with nitrogen for three times, then heated to 110 ěC and stirred for 12 hours. The reaction mixture was concentrated in vacuo, and the residue was purified by silica gel column chromatography (DCM/MeOH (V/V)=20/1) to give the title compound as an light yellow solid (75 mg, 0.41 mmol, 46.41%).

MS (ESI, pos.ion) m/z: 396.3 [M+1]$^+$;

$^1$H NMR (400 MHz, DMSO-d$_6$) 8.82 (s, 1H), 7.86 (s, 1H), 7.76 (d, J=2.7 Hz, 1H), 7.73-7.58 (m, 3H), 7.19-7.13 (m, 1H), 4.48 (d, J=5.7 Hz, 1H), 4.04 (s, 3H), 3.34-3.20 (m, 2H), 1.74-1.50 (m, 1H), 0.88 (d, J=6.52 Hz, 3H), 0.88 (d, J=6.59 Hz, 3H).

Example 18: 9-(benzyloxy)-6-isopropyl-2-oxo-10-(thiazol-2-yl)-6,7-dihydro-2H-pyrido[2,1-a]isoquinoline-3-carboxylic Acid

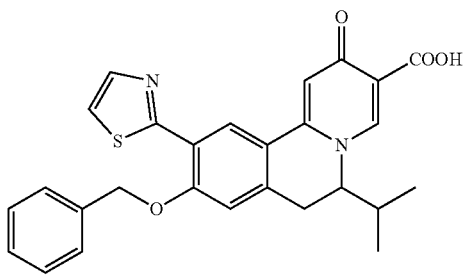 [SMILES: CC(C)C1Cc2cc(OCc3ccccc3)c(-c3nccs3)cc2-c2cc(=O)c(C(=O)O)cn21]

Step 1: 2-(benzyloxy)-1-bromo-4-iodobenzene

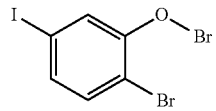

To a single-neck flask were added 2-bromo-5-iodophenol (20 g, 66.9 mmol), potassium carbonate (18.5 g, 134 mmol), acetonitrile (100 mL) and benzyl bromide (8.74 mL, 73.6 mmol). The mixture was heated to 80 ěC and stirred for 2 h, then filtered to remove the solid. The filtrated was concentrated by reduced pressure distillation to give the title compound as a white solid (26.0 g, 99.9%).

MS (ESI, neg.ion) m/z: 386.9, 388.9 [M−H]$^-$.

Step 2: 1-(3-(benzyloxy)-4-bromophenyl)-3-methylbutan-2-one

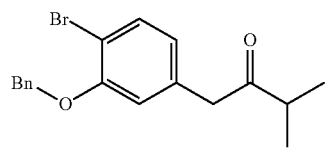 [SMILES: CC(C)C(=O)Cc1ccc(Br)c(OCc2ccccc2)c1]

To a single-neck flask were added 2-(benzyloxy)-1-bromo-4-iodobenzene (10.0 g, 25.7 mmol), 3-methyl-butan-2-one (4.14 mL, 38.6 mmol), sodium tert-butoxide (4.94 g, 51.4 mmol), tetrahydrofuran (100 mL), bis(dibenzylideneacetone)palladium (1.06 g, 1.81 mmol) and 4,5-bis(diphenylphosphino)-9,9-dimethylxanthene (1.07 g, 1.79 mmol). The mixture was degassed and filled with nitrogen for three times, then heated to 60 ěC and stirred for 10 h. After the reaction was completed, the reaction mixture was concentrated in vacuo, and the residue was purified by silica gel column chromatography (PE/EA (V/V)=10/1) to give the title compound as a light yellow solid (7.10 g, 79.5%).

$^1$H NMR (400 MHz, CDCl$_3$) 7.54-7.48 (m, 3H), 7.41 (t, J=7.4 Hz, 2H), 7.37-7.32 (m, 1H), 6.82 (d, J=1.6 Hz, 1H), 6.71 (dd, J=8.0, 1.7 Hz, 1H), 5.17 (s, 2H), 3.69 (s, 2H), 2.76-2.62 (m, 1H), 1.10 (s, 3H), 1.09 (s, 3H).

Step 3: 1-(3-(benzyloxy)-4-bromophenyl)-3-methylbutan-2-amine

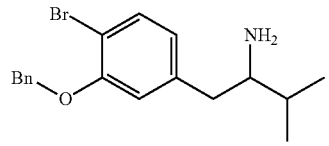 [SMILES: CC(C)C(N)Cc1ccc(Br)c(OCc2ccccc2)c1]

To a single-neck flask were added 1-(3-(benzyloxy)-4-bromophenyl)-3-methylbutan-2-one (5.20 g, 15.0 mmol), methanol (50 mL) and ammonium acetate (5.77 g, 74.9 mmol). The mixture was stirred at rt for 1 h, then sodium cyanoborohydride (1.41 g, 22.4 mmol) was added, and the resulting mixture was stirred at rt for 12 h. After the reaction was completed, the reaction mixture was concentrated by reduced pressure distillation, and the residue was diluted with water (50 mL) and aqueous sodium hydroxide solution (10 mL, 10%). The mixture was extracted with dichloromethane (50 mL B 2). The combined organic layers were washed with saturated brine (50 mL B 1), dried over anhydrous sodium sulfate and concentrated in vacuo to give the title compound as colorless oil (5.0 g, 96%).

MS (ESI, pos.ion) m/z: 348.0 [M+H]$^+$.

Step 4: N-(1-(3-(benzyloxy)-4-bromophenyl)-3-methylbutan-2-yl)formamide

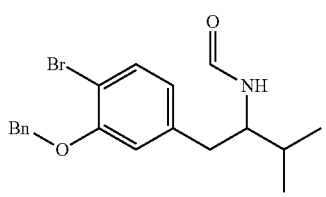 [SMILES: CC(C)C(Cc1ccc(Br)c(OCc2ccccc2)c1)NC=O]

To a single-neck flask were added 1-(3-(benzyloxy)-4-bromophenyl)-3-methylbutan-2-amine (13.0 g, 37.3 mmol) and ethyl formate (100 mL). The reaction mixture was heated and refuxed for 12 h, then cooled to rt, and concentrated in vacuo to give the title compound as a light yellow solid (14 g, 99.7%).

MS (ESI, pos.ion) m/z: 376.5 [M+H]$^+$.

Step 5: 6-(benzyloxy)-7-bromo-3-isopropyl-3,4-dihydroisoquinoline

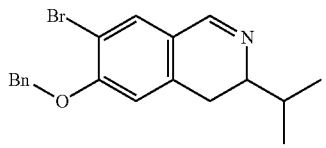 [SMILES: CC(C)C1Cc2cc(OCc3ccccc3)c(Br)cc2C=N1]

To a single-neck flask were added N-(1-(3-(benzyloxy)-4-bromophenyl)-3-methylbutan-2-yl)formamide (14 g, 37.2 mmol) and dichloromethane (100 mL). To the mixture was added phosphorus oxychloride (17 mL, 182.4 mmol) under a 0 ěC cold-bath condition. After the addition, the reaction mixture stirred at rt for 12 hours. After the reaction was completed, the reaction mixture was adjusted with saturated aqueous sodium bicarbonate to neutral. Then the mixture was extracted with dichloromethane (40 mL B 2). The combined organic layers were washed with saturated sodium chloride (100 mL), dried over anhydrous sodium sulfate and concentrated in vacuo to give the title compound as brown viscous product (11.0 g, 82.5%).

MS (ESI, pos.ion) m/z: 358.5[M+H]$^+$.

Step 6: Ethyl 9-(benzyloxy)-10-bromo-6-isopropyl-2-oxo-2,6,7,11b-tetrahydro-1H-pyrido[2,1-a]isoquinoline-3-carboxylate

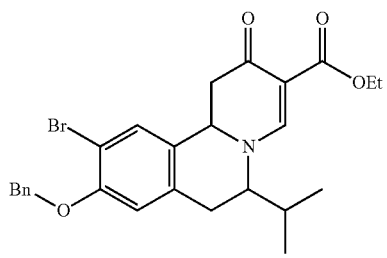 [SMILES: CCOC(=O)C1=CN2C(CC1=O)c1cc(Br)c(OCc3ccccc3)cc1CC2C(C)C]

To a single-neck flask were added 6-(benzyloxy)-7-bromo-3-isopropyl-3,4-dihydroisoquinoline (10.0 g, 28 mmol), ethyl 2-(ethoxymethylene)-3-oxobutanoate (10.4 g, 56 mmol) and tertiary butanol (50 mL). The reaction mixture was heated to 100 ěC and stirred for 12 h. After the reaction was completed, the reaction mixture was concentrated in vacuo, and the residue was purified by silica gel column chromatography (PE/EA (V/V)=1/1) to give the title compound as a brown solid (6.0 g, 43%).

MS: (ESI, pos.ion) m/z: 498.1/500.1 [M+H]$^+$.

Step 7: Ethyl 9-(benzyloxy)-6-isopropyl-2-oxo-10-(thiazol-2-yl)-2,6,7,11b-tetrahydro-1H-pyrido[2,1-a]isoquinoline-3-carboxylate

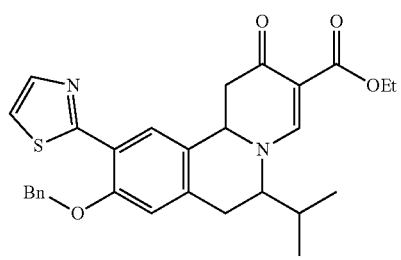 [SMILES: CCOC(=O)C1=CN2C(CC1=O)c1cc(-c3nccs3)c(OCc3ccccc3)cc1CC2C(C)C]

To a single-neck flask were added ethyl 9-(benzyloxy)-10-bromo-6-isopropyl-2-oxo-2,6,7,11b-tetrahydro-1H-pyrido[2,1-a]isoquinoline-3-carboxylate (4.0 g, 8.0 mmol), bis(triphenylphosphine)palladium (II) (1.1 g, 1.6 mmol), 2-(tributylstannyl)thiazole (4.5 g, 12 mmol) and dioxane (20 mL). The reaction mixture was degassed and filled with nitrogen for three times, then heated to 100 ěC and stirred for 12 h. After the reaction was completed, the mixture was concentrated in vacuo, and the residue was purified by silica gel column chromatography (DCM/MeOH(V/V)=10/1) to give the title compound as a brown solid (3.80 g, 94%).

MS (ESI, pos.ion) m/z: 503.2 [M+H H]$^+$.

Step 8: Ethyl 9-(benzyloxy)-6-isopropyl-2-oxo-10-(thiazol-2-yl)-6,7-dihydro-2H-pyrido[2,1-a]isoquinoline-3-carboxylate

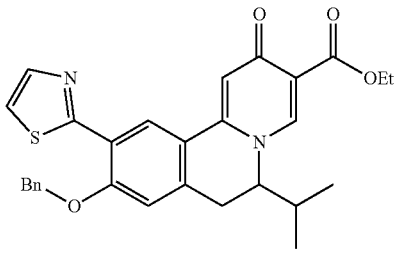 [SMILES: CCOC(=O)c1cn2c(cc1=O)-c1cc(-c3nccs3)c(OCc3ccccc3)cc1CC2C(C)C]

To a single-neck flask were added ethyl 9-(benzyloxy)-6-isopropyl-2-oxo-10-(thiazol-2-yl)-2,6,7,11b-tetrahydro-1H-pyrido[2,1-a]isoquinoline-3-carboxylate (3.80 g, 7.56 mmol), chloranil (2.04 g, 8.30 mmol) and DME (40 mL). The reaction mixture was stirred at 80 ěC for 2 hours, then cooled to rt, and concentrated in vacuo to remove the solvent. The residue was purified by silica gel column chromatography (DCM/MeOH(V/V)=10/1) to give the title compound as a gray solid (3.0 g, 79%).

MS (ESI, pos.ion) m/z: 501.1 [M+H]$^+$.

Step 9: 9-(benzyloxy)-6-isopropyl-2-oxo-10-(thiazol-2-yl)-6,7-dihydro-2H-pyrido[2,1-a]isoquinoline-3-carboxylic Acid

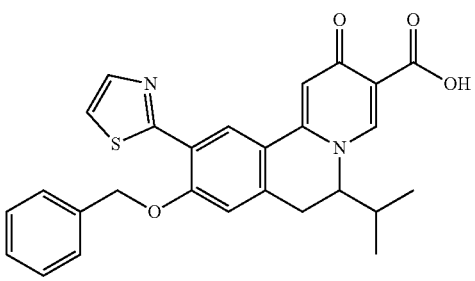 [SMILES: CC(C)C1Cc2cc(OCc3ccccc3)c(-c3nccs3)cc2-c2cc(=O)c(C(=O)O)cn21]

To a single-neck flask were added ethyl 9-(benzyloxy)-6-isopropyl-2-oxo-10-(thiazol-2-yl)-6,7-dihydro-2H-pyrido[2,1-a]isoquinoline-3-carboxylate (70 mg, 0.14 mmol), lithium hydroxide monohydrate (18 mg, 4.3 mmol) and methanol (1 mL). The reaction mixture was stirred at rt for 4 h, then hydrochloric acid (1 M) was added to adjust the pH to 5, and there was a solid precipitated out. The mixture was filtered to give the title compound as a yellow solid (28 mg 42%).

MS (ESI, pos.ion) m/z: 473.1525 [M+H]$^+$;

$^1$H NMR (400 MHz, CDCl$_3$) 16.11 (s, 1H), 8.91 (s, 1H), 8.46 (s, 1H), 7.94 (d, J=3.2 Hz, 1H), 7.52 (d, J=6.7 Hz, 2H), 7.47-7.37 (m, 4H), 7.31 (s, 1H), 7.00 (s, 1H), 5.40 (s, 2H), 3.92 (dd, J=9.4, 4.4 Hz, 1H), 3.43 (dd, J=16.2, 4.8 Hz, 1H), 3.17 (d, J=16.2 Hz, 1H), 1.84-1.57 (m, 2H), 0.92 (d, J=6.6 Hz, 3H), 0.82 (d, J=6.7 Hz, 3H).

Example 19: 9-(heptan-4-yloxy)-6-isopropyl-2-oxo-10-(thiazol-2-yl)-6,7-dihydro-2H-pyrido[2,1-a]isoquinoline-3-carboxylic Acid

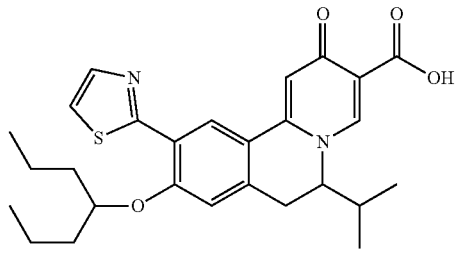 [SMILES: CCCC(CCC)Oc1cc2c(cc1-c1nccs1)-c1cc(=O)c(C(=O)O)cn1C(C(C)C)C2]

Step 1: Ethyl 9-(benzyloxy)-10-bromo-6-isopropyl-2-oxo-6,7-dihydro-2H-pyrido[2,1-a]isoquinoline-3-carboxylate

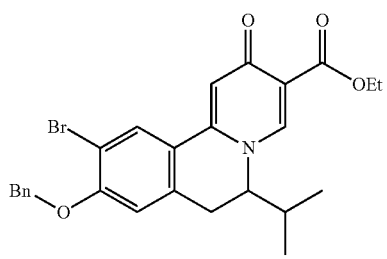 [SMILES: CCOC(=O)c1cn2c(cc1=O)-c1cc(Br)c(OCc3ccccc3)cc1CC2C(C)C]

To a single-neck flask were added ethyl 9-(benzyloxy)-10-bromo-6-isopropyl-2-oxo-2,6,7,11b-tetrahydro-1H-pyrido[2,1-a]isoquinoline-3-carboxylate (2.0 g, 4.0 mmol), chloranil (1.1 g, 4.5 mmol) and dimethoxyethane (20 mL). The reaction mixture was stirred at 80 éC for 2 hours, then cooled to rt, and concentrated in vacuo to remove the solvent. The residue was purified by silica gel column chromatography (DCM/CH$_3$OH (V/V)=10/1) to give the title compound as a gray solid (1.9 g, 98%).

MS (ESI, pos.ion) m/z: 496.1 [M+H]$^+$.

Step 2: 9-(benzyloxy)-6-isopropyl-2-oxo-10-(thiazol-2-yl)-6,7-dihydro-2H-pyrido[2,1-a]isoquinoline-3-carboxylic Acid

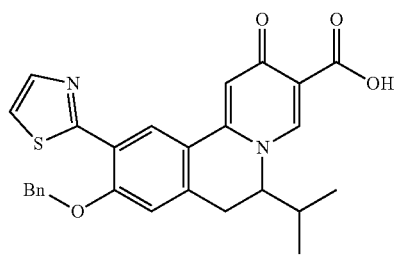 [SMILES: CC(C)C1Cc2cc(OCc3ccccc3)c(-c3nccs3)cc2-c2cc(=O)c(C(=O)O)cn21]

To a single-neck flask were added ethyl 9-(benzyloxy)-10-bromo-6-isopropyl-2-oxo-6,7-dihydro-2H-pyrido[2,1-a]isoquinoline-3-carboxylate (2.0 g, 4.0 mmol), bis(triphenylphosphine)palladium (II) (57 mg, 0.08 mmol), 2-(tributylstannyl)thiazole (2.3 g, 6.1 mmol) and dioxane (20 mL). The reaction mixture was degassed and filled with nitrogen for three times, then heated to 100 ĕC and stirred for 12 h. After the reaction was completed, the mixture was concentrated in vacuo, and the residue was purified by silica gel column chromatography (DCM/MeOH(V/V)=10/1) to give the title compound as a brown solid (1.85 g, 92%).

MS (ESI, pos.ion) m/z: 473.1 [M+H]$^+$.

Step 3: 9-hydroxy-6-isopropyl-2-oxo-10-(thiazol-2-yl)-6,7-dihydro-2H-pyrido[2,1-a]isoquinoline-3-carboxylic Acid

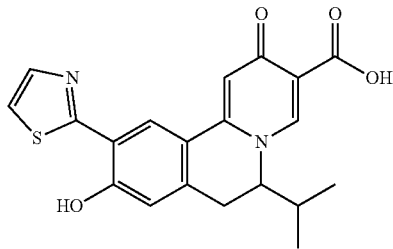 [SMILES: CC(C)C1Cc2cc(O)c(-c3nccs3)cc2-c2cc(=O)c(C(=O)O)cn21]

To a single-neck flask were added 9-(benzyloxy)-6-isopropyl-2-oxo-10-(thiazol-2-yl)-6,7-dihydro-2H-pyrido[2,1-a]isoquinoline-3-carboxylic acid (2.0 g, 4.2 mmol), methanol (20 mL) and Pd/C (0.7 g). The reaction mixture was degassed and filled with nitrogen for three times, then heated to 100 ĕC and stirred for 8 h at rt. The reaction mixture was filtered to remove the Pd/C, then the filtrate was concentrated in vacuo, and the residue was purified by silica gel column chromatography (DCM/MeOH(V/V)=10/1) to give the title compound as a brownish black solid (1.0 g, 62%).

MS (ESI, pos.ion) m/z: 383.2 [M+H]$^+$.

Step 4: 9-(heptan-4-yloxy)-6-isopropyl-2-oxo-10-(thiazol-2-yl)-6,7-dihydro-2H-pyrido[2,1-a]isoquinoline-3-carboxylic Acid

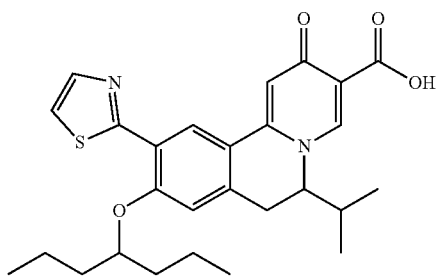 [SMILES: CCCC(CCC)Oc1cc2c(cc1-c1nccs1)-c1cc(=O)c(C(=O)O)cn1C(C(C)C)C2]

To a single-neck flask were added 9-hydroxy-6-isopropyl-2-oxo-10-(thiazol-2-yl)-6,7-dihydro-2H-pyrido[2,1-a]isoquinoline-3-carboxylic acid (0.2 g, 0.52 mmol), potassium carbonate (0.29 g, 2.1 mmol), acetonitrile (4 mL) and 4-bromoheptane (0.24 g, 1.31 mmol). The reaction mixture was heated to 80 ĕC and stirred for 12 h, then adjusted with hydrochloric acid (1 M) to pH 5, and there was a yellow solid precipitated out. The mixture was filtered, and the filter cake was recrystalized from methanol to give the the title compound as a light yellow solid (90 mg, 36%).

MS (ESI, pos.ion) m/z: 481.22 [M+H]$^+$;

$^1$H NMR (400 MHz, DMSO-d$_6$) 8.80 (d, J=14.8 Hz, 2H), 7.99 (s, 1H), 7.82 (s, 1H), 7.45 (s, 1H), 7.19 (s, 1H), 4.88 (s, 1H), 4.51 (s, 1H), 3.41 (s, 1H), 3.30 (s, 1H), 1.90-1.66 (m, 4H), 1.60 (s, 1H), 1.53-1.24 (m, 4H), 0.88 (s, 9H), 0.73 (d, J=6.1 Hz, 3H).

Example 20: 6-isopropyl-2-oxo-9-(pentyloxy)-10-(thiazol-2-yl)-6,7-dihydro-2H-pyrido[2,1-a]isoquinoline-3-carboxylic Acid

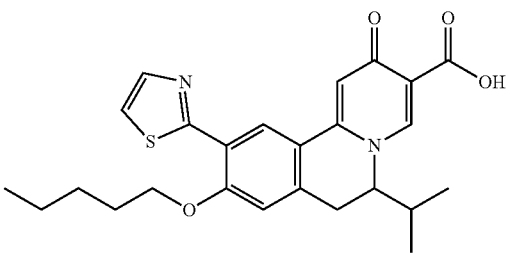 [SMILES: CCCCCOc1cc2c(cc1-c1nccs1)-c1cc(=O)c(C(=O)O)cn1C(C(C)C)C2]

To a single-neck flask were added 9-hydroxy-6-isopropyl-2-oxo-10-(thiazol-2-yl)-6,7-dihydro-2H-pyrido[2,1-a]isoquinoline-3-carboxylic acid (100 mg, 0.26 mmol), potassium carbonate (145 mg, 1.05 mmol), acetonitrile (2 mL) and 1-bromopentane (100 mg, 0.66 mmol). The reaction mixture was stirred at 80 ĕC for 24 hours, then hydrochloric acid (1 M) was added to adjust the pH to 5. The resulting mixture was concentrated in vacuo, and the residue was purified by silica gel column chromatography (DCM/CH$_3$OH (V/V)=10/1) to give the title compound as a light yellow solid (50 mg, 54%).

MS (ESI, pos.ion) m/z: 453.19 [M+H]$^+$;

$^1$H NMR (400 MHz, DMSO-d$_6$) 8.82 (s, 1H), 8.76 (s, 1H), 8.00 (s, 1H), 7.87 (s, 1H), 7.43 (s, 1H), 7.19 (s, 1H), 4.52 (s, 1H), 4.36 (s, 2H), 1.94 (s, 2H), 1.53 (d, J=6.8 Hz, 3H), 1.41 (dd, J=14.5, 7.3 Hz, 2H), 1.20 (d, J=20.7 Hz, 4H), 0.90 (dt, J=23.0, 11.7 Hz, 6H), 0.73 (d, J=6.5 Hz, 3H).

Example 21: 6-isopropyl-2-oxo-9-((tetrahydro-2H-pyran-4-yl)methoxy)-10-(thiazol-2-yl)-6,7-dihydro-2H-pyrido[2,1-a]isoquinoline-3-carboxylic Acid

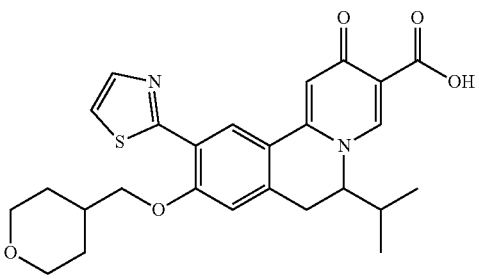 [SMILES: CC(C)C1Cc2cc(OCC3CCOCC3)c(-c3nccs3)cc2-c2cc(=O)c(C(=O)O)cn21]

Step 1: Ethyl 6-isopropyl-2-oxo-9-((tetrahydro-2H-pyran-4-yl)methoxy)-10-(thiazol-2-yl)-6,7-dihydro-2H-pyrido[2,1-a]isoquinoline-3-carboxylate

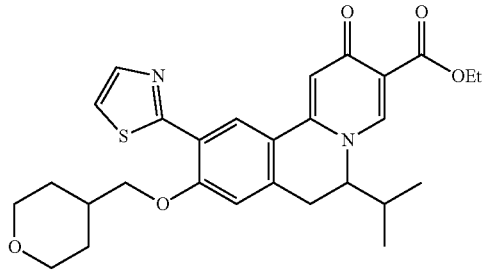 [SMILES: CCOC(=O)c1cn2c(cc1=O)-c1cc(-c3nccs3)c(OCC3CCOCC3)cc1CC2C(C)C]

To a single-neck flask were added ethyl 9-hydroxy-6-isopropyl-2-oxo-10-(thiazol-2-yl)-6,7-dihydro-2H-pyrido[2,1-a]isoquinoline-3-carboxylate (200 mg, 0.49 mmol), potassium carbonate (270 mg, 1.95 mmol), acetone (3 mL) and 4-bromomethyltetrahydropyrane (220 mg, 1.23 mmol). The reaction mixture was stirred at 80 ẽC for 8 hours, then concentrated in vacuo, and the residue was purified by silica gel column chromatography (DCM/CH$_3$OH (V/V)=10/1) to give the title compound as a yellow solid (180 mg, 73%).

MS (ESI, pos.ion) m/z: 509.1 [M+H]$^+$.

Step 2: 6-isopropyl-2-oxo-9-((tetrahydro-2H-pyran-4-yl)methoxy)-10-(thiazol-2-yl)-6,7-dihydro-2H-pyrido[2,1-a]isoquinoline-3-carboxylic Acid

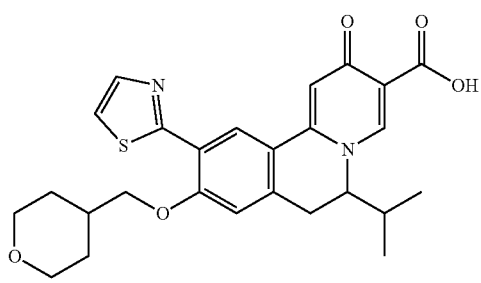 [SMILES: CC(C)C1Cc2cc(OCC3CCOCC3)c(-c3nccs3)cc2-c2cc(=O)c(C(=O)O)cn21]

To a single-neck flask were added ethyl 6-isopropyl-2-oxo-9-((tetrahydro-2H-pyran-4-yl)methoxy)-10-(thiazol-2-yl)-6,7-dihydro-2H-pyrido[2,1-a]isoquinoline-3-carboxylate (160 mg, 0.32 mmol), lithium hydroxide monohydrate (55 mg, 1.3 mmol) and methanol (4 mL). The mixture was stirred at rt for 8 hours, then hydrochloric acid (1 M) was added to adjust pH to 5. The mixture was filtered to give a yellow solid, and the filter cake was recrystalized from methanol to give the title compound as a light yellow solid (60 mg, 39%).

MS (ESI, pos.ion) m/z: 481.18 [M+H]$^+$;

$^1$H NMR (400 MHz, CDCl$_3$) 16.08 (s, 1H), 8.91 (s, 1H), 8.47 (s, 1H), 7.97 (d, J=3.2 Hz, 1H), 7.50 (d, J=3.2 Hz, 1H), 7.31 (s, 1H), 6.95 (s, 1H), 4.15 (d, J=6.2 Hz, 2H), 4.10 (dd, J=11.3, 3.2 Hz, 2H), 3.94 (dd, J=9.3, 4.4 Hz, 1H), 3.54 (dd, J=19.2, 7.5 Hz, 2H), 3.45 (d, J=5.1 Hz, 1H), 3.22 (d, J=16.2 Hz, 1H), 2.36 (s, 1H), 1.95 (s, 2H), 1.83 (qd, J=13.4, 6.7 Hz, 1H), 1.62 (s, 2H), 0.99 (d, J=6.6 Hz, 3H), 0.85 (d, J=6.7 Hz, 3H).

Example 22: 9-(2-cyclopropylethoxy)-6-isopropyl-2-oxo-10-(thiazol-2-yl)-6,7-dihydro-2H-pyrido[2,1-a]isoquinoline-3-carboxylic Acid

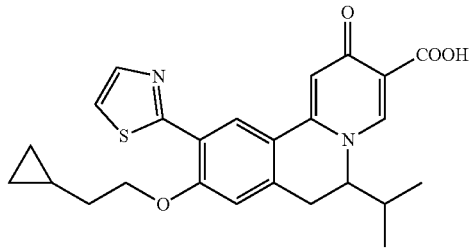 [SMILES: CC(C)C1Cc2cc(OCCC3CC3)c(-c3nccs3)cc2-c2cc(=O)c(C(=O)O)cn21]

Step 1: Ethyl 9-(2-cyclopropylethoxy)-6-isopropyl-2-oxo-10-(thiazol-2-yl)-6,7-dihydro-2H-pyrido[2,1-a]isoquinoline-3-carboxylate

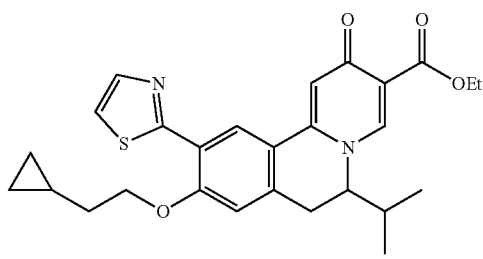 [SMILES: CCOC(=O)c1cn2c(cc1=O)-c1cc(-c3nccs3)c(OCCC3CC3)cc1CC2C(C)C]

To a single-neck flask were added ethyl 9-hydroxy-6-isopropyl-2-oxo-10-(thiazol-2-yl)-6,7-dihydropyrido[2,1-a]isoquinoline-3-carboxylate (250 mg, 0.61 mmol), potassium carbonate (336 mg, 2.4 mmol), acetonitrile (3 mL) and 2-cyclopropylethylbromide (270 mg, 1.5 mmol). The reaction mixture was stirred at 80 ẽC for 8 hours, then concentrated in vacuo, and the residue was purified by silica gel column chromatography (DCM/CH$_3$OH (V/V)=10/1) to give the title compound as a yellow solid (180 mg, 73%).

MS (ESI, pos.ion) m/z: 479.1 [M+H]$^+$.

Step 2: 9-(2-cyclopropylethoxy)-6-isopropyl-2-oxo-10-(thiazol-2-yl)-6,7-dihydro-2H-pyrido[2,1-a]isoquinoline-3-carboxylic Acid

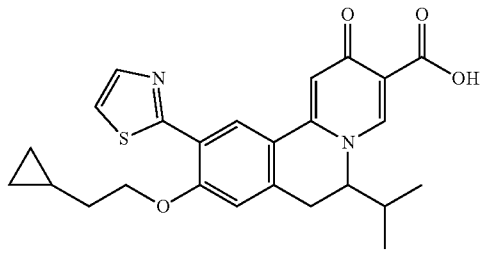 [SMILES: CC(C)C1Cc2cc(OCCC3CC3)c(-c3nccs3)cc2-c2cc(=O)c(C(=O)O)cn21]

To a single-neck flask were added ethyl 9-(2-cyclopropylethoxy)-6-isopropyl-2-oxo-10-(thiazol-2-yl)-6,7-dihydro-2H-pyrido[2,1-a]isoquinoline-3-carboxylate (270 mg, 0.32 mmol), lithium hydroxide monohydrate (95 mg, 2.3 mmol)

and methanol (5 mL). The reaction mixture was stirred at rt for 8 h, then adjusted with hydrochloric acid (1 M) to pH=5, and there was a yellow solid precipitated out. The mixture was filtered, and the filter cake was recrystallized from methanol to give the the title compound as a light yellow solid (120 mg, 47%).

MS (ESI, pos.ion) m/z: 451.17 [M+H]$^+$;
$^1$H NMR (400 MHz, CDCl$_3$) 16.11 (s, 1H), 8.92 (s, 1H), 8.47 (s, 1H), 7.97 (d, J=3.2 Hz, 1H), 7.48 (d, J=3.2 Hz, 1H), 7.32 (s, 1H), 6.98 (s, 1H), 4.37 (dd, J=10.1, 6.5 Hz, 2H), 4.01-3.87 (m, 1H), 3.47 (dd, J=16.4, 4.5 Hz, 1H), 3.22 (d, J=16.1 Hz, 1H), 2.01-1.91 (m, 2H), 1.83 (dt, J=13.5, 6.7 Hz, 1H), 0.99 (d, J=6.6 Hz, 3H), 0.85 (d, J=6.7 Hz, 3H), 0.58 (d, J=7.6 Hz, 2H), 0.22 (d, J=4.9 Hz, 2H).

Example 23: 9-(2-ethyl butoxy)-6-isopropyl-2-oxo-10-(thiazol-2-yl)-6,7-dihydro-2H-pyrido[2,1-a]isoquinoline-3-carboxylic Acid

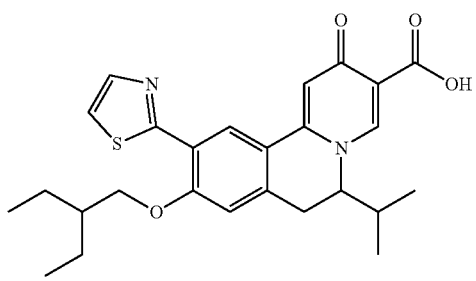 [SMILES: CCC(CC)COc1cc2c(cc1-c1nccs1)-c1cc(=O)c(C(=O)O)cn1C(C(C)C)C2]

To a single-neck flask were added 9-hydroxy-6-isopropyl-2-oxo-10-(thiazol-2-yl)-6,7-dihydro-2H-pyrido[2,1-a]isoquinoline-3-carb oxylic acid (200 mg, 0.52 mmol), potassium carbonate (290 mg, 2.1 mmol), acetonitrile (5 mL) and 2-ethyl-1-bromobutane (200 mg, 1.2 mmol). The reaction mixture was stirred at 80 ěC for 24 hours, then hydrochloric acid (1 M) was add to adjust the pH to 5. The resulting mixture was concentrated in vacuo, and the residue was purified by silica gel column chromatography (DCM/CH$_3$OH (V/V)=10/1) to give the title compound as a light yellow solid (160 mg, 66%).

MS (ESI, pos.ion) m/z: 467.20 [M+H]$^+$;
$^1$H NMR (400 MHz, CDCl$_3$) 16.12 (s, 1H), 8.93 (s, 1H), 8.48 (s, 1H), 7.97 (d, J=3.2 Hz, 1H), 7.49 (d, J=3.2 Hz, 1H), 7.33 (s, 1H), 6.97 (s, 1H), 4.18 (dd, J=11.7, 6.9 Hz, 2H), 3.95 (dd, J=9.6, 4.4 Hz, 1H), 3.46 (dd, J=16.3, 5.1 Hz, 1H), 3.22 (d, J=16.2 Hz, 1H), 1.98-1.88 (m, 1H), 1.85 (dd, J=6.6, 3.1 Hz, 1H), 1.69 (dd, J=14.4, 7.1 Hz, 4H), 1.06-0.96 (m, 9H), 0.85 (d, J=6.7 Hz, 3H).

Example 24: 10-(5-bromothiazol-2-yl)-6-isopropyl-9-(3-methoxypropoxy)-2-oxo-6,7-dihydro-2H-pyrido[2,1-a]isoquinoline-3-carboxylic Acid

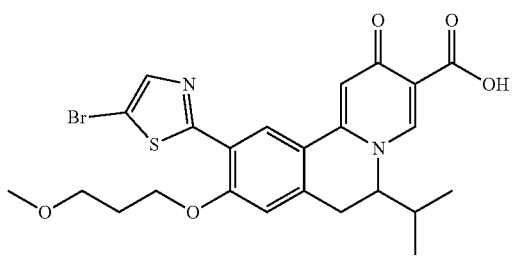 [SMILES: COCCCOc1cc2c(cc1-c1ncc(Br)s1)-c1cc(=O)c(C(=O)O)cn1C(C(C)C)C2]

Step 1: 1-(3-(3-methoxypropoxy)-4-(thiazol-2-yl)phenyl)-3-methylbutan-2-amine

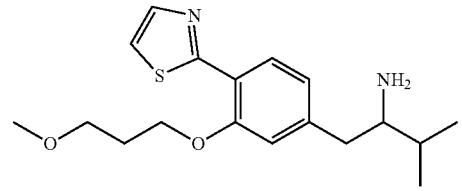 [SMILES: COCCCOc1cc(CC(N)C(C)C)ccc1-c1nccs1]

1-(3-(3-M ethoxypropoxy)-4-(thiazol-2-yl)phenyl)-3-methylbutan-2-one (4.4 g, 13 mmol), MeOH (45 mL) and NH$_4$OAc (12 g, 155.7 mmol, mass percent: 100%) were added into a 100 mL single-neck flask. The reaction mixture was stirred at rt for 1 h, then cooled to 0 ěC, and NaBH$_3$CN (2.5 g, 40 mmol) was added. The mixture was warmed to rt and stirred at rt overnight. After the reaction was completed, the reaction mixture was concentrated in vacuo to remove the solvent. Ammonium hydroxide (5 mL) and water (10 mL) was added in turn to dilute the residue. The mixture was extracted with EA (30 mL B4), and the combined organic layers were concentrated in vacuo to give the title compound as yellow oil (4.41 g, 13.20 mmol, 100%).

MS (ESI, pos.ion) m/z: 335.3 [M+H]$^+$.

Step 2: N-(1-(3-(3-methoxypropoxy)-4-(thiazol-2-yl)phenyl)-3-methylbutan-2-yl)formamide

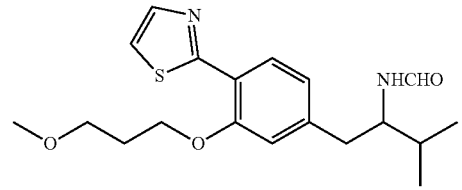

To a 100 mL single-neck flask were added 1-(3-(3-methoxypropoxy)-4-(thiazol-2-yl)phenyl)-3-methylbutan-2-amine (4.415 g, 13.20 mmol), formic acid (9.721 g, 211.2 mmol) and dioxane (20 mL). The mixture was heated to 110 ěC and stirred for 12 h, then concentrated in vacuo to remove the solvent. The residue was diluted with saturated brine (20 mL), then extracted with EA (30 mL B4). The combined organic layers were washed with saturated brine (10 mL B 2), and concentrated in vacuo to give the title compound as yellow oil (4.785 g, 13.20 mmol, 100.0%).

MS (ESI, pos.ion) m/z: 363.2 [M+H]$^+$.

Step 3: N-(1-(4-(5-bromothiazol-2-yl)-3-(3-methoxypropoxy)phenyl)-3-methylbutan-2-yl)formamide

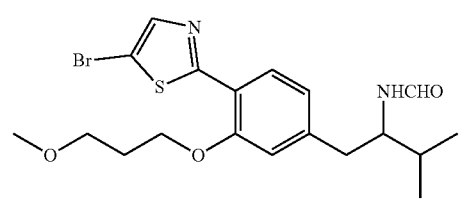

N-(1-(3-(3-methoxypropoxy)-4-(thiazol-2-yl)phenyl)-3-methylbutan-2-yl)formamide (0.700 g, 1.93 mmol), NBS (344 mg, 1.93 mmol) and CHCl₃ (10 mL) was added into a 100 mL single-neck flask. The mixture was stirred at rt overnight. After the reaction was completed, the reaction mixture was diluted with water (10 mL), then partitioned. The aqueous layer was extracted with DCM (15 mL B 3). The combined organic layers were washed with water (10 mL B 2), and the organic layer was concentrated in vacuo. The residue was purified by silica gel column chromatography (EA) to give the title compound as a white solid (0.82 g, 1.9 mmol, 96%).

MS (ESI, pos.ion) m/z: 441.1 [M+H]⁺.

Step 4: 9-(5-bromothiazol-2-yl)-5-isopropyl-8-(3-methoxypropoxy)-5,6-dihydro-2H-oxazolo[2,3-a]isoquinoline-2,3(10bH)-dione

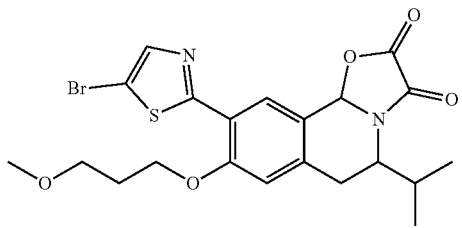 [SMILES: COCCCOc1cc2c(cc1-c1ncc(Br)s1)C1OC(=O)C(=O)N1C(C(C)C)C2]

N-(1-(4-(5-Bromothiazol-2-yl)-3-(3-methoxypropoxy)phenyl)-3-methylbutan-2-yl) formamide (0.2 g, 0.5 mmol) and DCM (50 mL) were added into a 50 mL two-neck flask, then oxalyl chloride (63 mg, 0.50 mmol) was added. The mixture was stirred at −10 ěC under nitrogen protection, then FeCl₃ (87 mg, 0.54 mmol) was added, and the mixture was warmed to rt and stirred overnight. Then to the mixture was added HCl (5 mL, 2 M), and the mixture was stirred for 1 h, and then water (10 mL) was added into the mixture. The mixture was extracted with DCM (30 mL B4), and the combined organic layers were concentrated in vacuo to give the title compound as brownness oil (0.22 g, 0.45 mmol, 100%).

MS (ESI, pos.ion) m/z: 495.3 [M+H]⁺.

Step 5: 5-bromo-2-(3-isopropyl-6-(3-methoxypropoxy)-3,4-dihydroisoquinolin-7-yl)thiazole

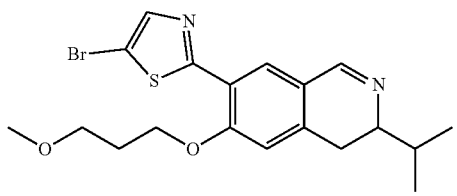 [SMILES: COCCCOc1cc2c(cc1-c1ncc(Br)s1)C=NC(C(C)C)C2]

9-(5-Bromothiazol-2-yl)-5-isopropyl-8-(3-methoxypropoxy)-5,6-dihydro-2H-oxazolo[2, 3-a]isoquinoline-2,3(10bH)-dione (0.2 g, 0.4 mmol) and DCM (10 mL) were added into a 50 mL single-neck flask, then methanol (10 mL) and concentrated sulfuric acid (0.5 mL) were added in turn. The reaction mixture was heated to 70 ěC and stirred overnight, then concentrated in vacuo. The residue was diluted with water (10 mL) and EA (30 mL) in turn, then partitioned. The organic layer was washed with HCl (10 mL B 2, 2 M), The combined organic layers were adjusted with ammonium hydroxide to pH 9-10, then the mixture was extracted with EA (20 mL B3). The combined organic layers were concentrated in vacuo to give the crude product as a black solid (115 mg, 0.27 mmol, 70%).

MS (ESI, pos.ion) m/z: 423.1 [M+H]⁺.

Step 6: Ethyl 10-(5-bromothiazol-2-yl)-6-isopropyl-9-(3-methoxypropoxy)-2-oxo-2,6,7,11b-tetrahydro-1H-pyrido[2,1-a]isoquinoline-3-carboxylate

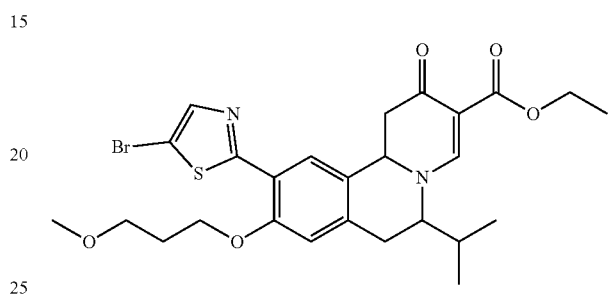

5-Bromo-2-(3-isopropyl-6-(3-methoxypropoxy)-3,4-dihydroisoquinolin-7-yl)thiazole (390 mg, 0.92 mmol), ethyl 2-(ethoxymethylene)-3-oxobutanoate (343 mg, 1.84 mmol) and EtOH (9 mL) were added into a 100 mL single-neck flask. The mixture was stirred at 85 ěC for 6 h. After the reaction was completed, the reaction mixture was cooled to rt and concentrated in vacuo, and the residue was purified by silica gel column chromatography (DCM/MeOH (V/V)=10/1) to give the title compound as a brown solid (300 mg, 0.53 mmol, 57.80%).

MS (ESI, pos.ion) m/z: 563.0 [M+H]⁺.

Step 7: Ethyl 10-(5-bromothiazol-2-yl)-6-isopropyl-9-(3-methoxypropoxy)-2-oxo-6,7-dihydro-2H-pyrido[2,1-a]isoquinoline-3-carboxylate

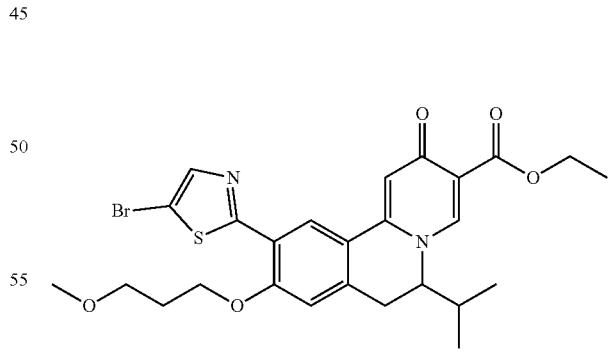

Ethyl 10-(5-bromothiazol-2-yl)-6-isopropyl-9-(3-methoxypropoxy)-2-oxo-2,6,7,11b-tetrahydro-1H-pyrido[2,1-a]isoquinoline-3-carboxylate (330 mg, 0.59 mmol) was dissolved in dimethoxyethane (9 mL), then chloranil (144 mg, 0.58570 mmol) was added. The mixture was heated to 90 ěC and stirred for 1 hour under nitrogen protection, then cooled to rt and concentrated in vacuo. The residue was purified by thin-layer chromatography (DCM/CH₃OH (V/V)=20/1) to give the title compound as a brownness solid (250 mg, 0.45 mmol, 76.03%).

MS (ESI, pos.ion) m/z: 561.1 [M+H]+.

Step 8: 10-(5-bromothiazol-2-yl)-6-isopropyl-9-(3-methoxypropoxy)-2-oxo-6,7-dihydro-2H-pyrido[2,1-a]isoquinoline-3-carboxylic Acid

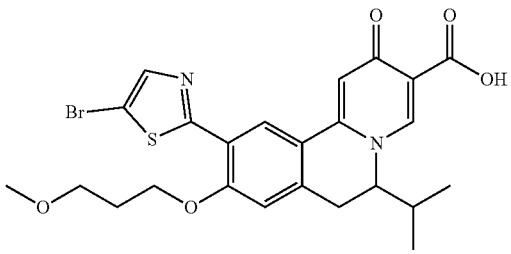 [SMILES: COCCCOc1cc2c(cc1-c1ncc(Br)s1)-c1cc(=O)c(C(=O)O)cn1C(C(C)C)C2]

Ethyl 10-(5-bromothiazol-2-yl)-6-isopropyl-9-(3-methoxypropoxy)-2-oxo-6,7-dihydro-2H-pyrido[2,1-a]isoquinoline-3-carboxylate (240 mg, 0.43 mmol), LiOH.H₂O (17 mg, 0.40 mmol) and EtOH (10 mL) was added into a 50 mL single-neck flask. The mixture was stirred at rt for 3 hours, then adjusted with aqueous HCl solution (1 M) to pH 4-5, then concentrated in vacuo. The residue was purified by thin-layer chromatography (DCM/CH₃OH (V/V)=20/1) to give the title compound as a gray solid (125 mg, 0.23 mmol, 54.83%).

MS (ESI, pos.ion) m/z: 533.1 [M+H]+;

¹H NMR (400 MHz, CDCl₃) 16.025 (br, 1H), 8.841 (s, 1H), 8.480 (s, 1H), 7.852 (s, 1H), 7.297 (s, 1H), 6.977 (s, 1H), 4.465-4.374 (m, 2H), 3.991-3.909 (m, 1H), 3.716-3.647 (m, 2H), 3.475-3.372 (m, 4H), 3.255-3.174 (m, 1H), 2.350-2.290 (m, 2H), 1.861-1.778 (m, 1H), 0.984 (d, J=6.8 Hz, 3H), 0.852 (d, J=6.4 Hz, 3H).

Example 25: 10-acetoxy-6-isopropyl-9-(3-methoxypropoxy)-2-oxo-6,7-dihydro-2H-pyrido[2,1-a]isoquinoline-3-carboxylic Acid

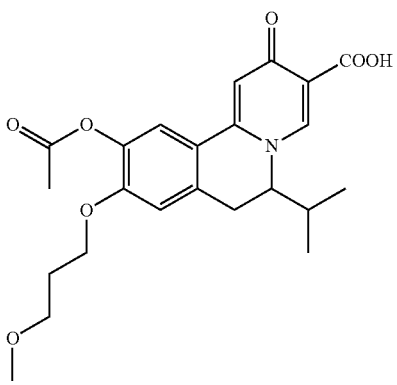 [SMILES: COCCCOc1cc2c(cc1OC(C)=O)-c1cc(=O)c(C(=O)O)cn1C(C(C)C)C2]

Step 1: Ethyl 10-hydroxy-6-isopropyl-9-(3-methoxypropoxy)-2-oxo-6,7-dihydro-2H-pyrido[2,1-a]isoquinoline-3-carboxylic Acid

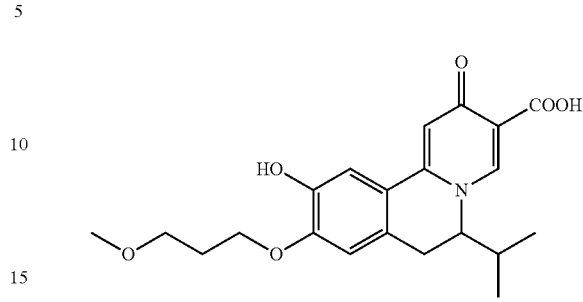

Ethyl 10-hydroxy-6-isopropyl-9-(3-methoxypropoxy)-2-oxo-6,7-dihydro-2H-pyrido[2,1-a]isoquinoline-3-carboxylate (1.90 g, 4.57 mmol), THF (6 mL), EtOH (3 mL), H₂O (1.5 mL) and LiOH.H₂O (0.672 g, 16.0 mmol) were added into a 100 mL single-neck flask, then the mixture was stirred at rt for 4 h. After the reaction was completed, the reaction mixture was concentrated in vacuo, and to the residue was added water (10 mL). The mixture was extracted with DCM (20 mL B 4). The combined organic layers were dried over anydrous sodium sulfate and filtered. The filtrate was concentrated in vacuo, and the residue was purified by silica gel column chromatography (DCM/MeOH (V/V)=10/1) to give the title compound as a gray solid (1.2 g, 3.1 mmol, 68%).

MS (ESI, neg.ion) m/z: 388.2 [M+H]+.

Step 2: 10-acetoxy-6-isopropyl-9-(3-methoxypropoxy)-2-oxo-6,7-dihydro-2H-pyrido[2,1-a]isoquinoline-3-carboxylic Acid

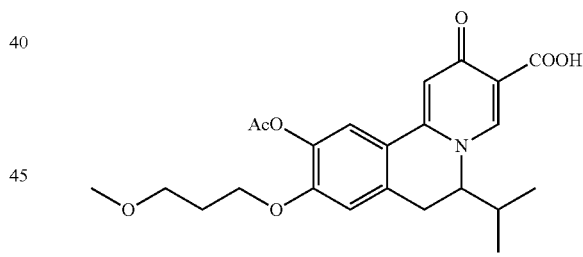

10-Hydroxy-6-isopropyl-9-(3-methoxypropoxy)-2-oxo-6,7-dihydro-2H-pyrido[2,1-a]iso quinoline-3-carboxylic acid (0.7 g, 2 mmol) was added into a 50 mL single-neck flask, then DCM (20 mL) was added. The mixture was cooled to 0 ěC, and then acetyl chloride (0.45 mL, 6.32 mmol) and TEA (0.92 g, 9.04 mmol) were added in turn. The reaction mixture was heated to rt and stirred overnight, then poured into ice-water. The mixture was extracted with DCM (30 mL B 3), and the combined organic layers were washed with saturated brine (20 mL), then concentrated in vacuo. The residue was purified by silica gel column chromatography (DCM/MeOH (V/V)=10/1) to give the crude product, which was purified by recrystallization from methanol (10 mL) to give the title compound as a gray solid (0.3 g, 0.7 mmol, 40%).

MS (ESI, pos.ion) m/z: 430.2 [M+H]+;

¹H NMR (400 MHz, CDCl₃) 16.025 (br, 1H), 8.494 (s, 1H), 7.445 (s, 1H), 7.015 (s, 1H), 6.876 (s, 1H), 4.233-4.109

(m, 2H), 4.026-3.865 (m, 1H), 3.574-3.494 (m, 2H), 3.427-3.302 (m, 4H), 3.214-3.073 (m, 1H), 2.350 (s, 3H), 2.131-2.008 (m, 2H), 1.838-1.831 (m, 1H), 0.968 (d, J=6 Hz, 3H), 0.822 (d, J=6.4 Hz, 3H).

Example 26: 6-isopropyl-9-(3-methoxypropoxy)-2-oxo-10-(pivaloyloxy)-6,7-dihydro-2H-pyrido[2,1-a]isoquinoline-3-carboxylic Acid

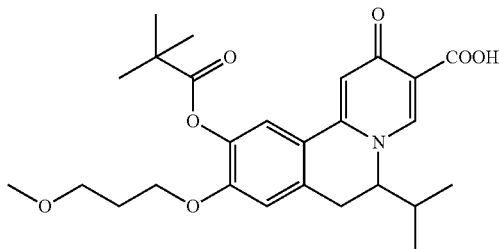 [SMILES: COCCCOc1cc2c(cc1OC(=O)C(C)(C)C)-c1cc(=O)c(C(=O)O)cn1C(C(C)C)C2]

10-Hydroxy-6-isopropyl-9-(3-methoxypropoxy)-2-oxo-6,7-dihydro-2H-pyrido[2,1-a]iso quinoline-3-carboxylic acid (0.26 g, 0.67 mmol) was added into a 50 mL two-neck flask, then DCM (6 mL) was added. The mixture was cooled to 0 ěC, and then pivaloyl chloride (0.41 mL, 3.36 mmol) and TEA (0.47 mL, 3.4 mmol) were added in turn. The reaction mixture was stirred for 30 min then warmed to rt and continue to stir overnight. After the reaction was completed, the reaction mixture was poured into ice-water (20 g). The mixture was extracted with DCM (30 mL B 4), The combined organic layers were concentrated in vacuo. The residue was purified by thin-layer chromatography (DCM/CH₃OH (V/V)=20/1) to give the crude product, which was purified twice by recrystallization from methanol (6 mL) to give the title compound as a gray solid (100 mg, 0.21 mmol, 32%).

MS (ESI, pos.ion) m/z: 472.1 [M+H]⁺;

¹H NMR (400 MHz, CDCl₃) 15.994 (br, 1H), 8.465 (s, 1H), 7.415 (s, 1H), 7.029 (s, 1H), 6.860 (s, 1H), 4.219-4.088 (m, 2H), 3.959-3.859 (m, 1H), 3.595-3.487 (m, 2H), 3.449-3.290 (m, 4H), 3.200-3.099 (m, 1H), 2.127-2.071 (s, 2H), 1.895-1.793 (m, 1H), 1.405 (s, 9H), 0.969 (d, J=2.8 Hz, 3H), 0.834 (d, J=3.2 Hz, 3H).

Example 27: 10-(isobutyryloxy)-6-isopropyl-9-(3-methoxypropoxy)-2-oxo-6,7-dihydro-2H-pyrido[2,1-a]isoquinoline-3-carboxylic Acid

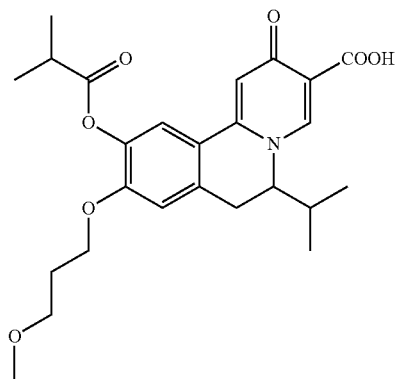 [SMILES: COCCCOc1cc2c(cc1OC(=O)C(C)C)-c1cc(=O)c(C(=O)O)cn1C(C(C)C)C2]

10-Hydroxy-6-isopropyl-9-(3-methoxypropoxy)-2-oxo-6,7-dihydro-2H-pyrido[2,1-a]isoquinoline-3-carboxylic acid (0.21 g, 0.56 mmol) was added into a 50 mL two-neck flask, then DCM (6 mL) was added. The mixture was cooled to 0 ěC, and then 2-methylpropionyl chloride (0.29 mL, 2.8 mmol) and TEA (0.39 mL, 2.8 mmol) were added in turn. The reaction mixture was stirred for 30 min then warmed to rt and stirred overnight. After the reaction was completed, the reaction mixture was poured into ice-water (30 mL). The mixture was extracted with DCM (30 mL B 4). The combined organic layers were dried over anydrous sodium sulfate, and filtered. The filtrate was concentrated in vacuo, and the residue was purified by thin-layer chromatography (DCM/CH₃OH(V/V)=20/1) to give the title compound as a white solid (50 mg, 0.11 mmol, 20%).

MS (ESI, pos.ion) m/z: 458.1 [M+H]⁺;

¹H NMR (400 MHz, CDCl₃) 15.971 (br, 1H), 8.460 (s, 1H), 7.428 (s, 1H), 7.021 (s, 1H), 6.865 (s, 1H), 4.220-4.103 (m, 2H), 3.935-3.853 (m, 1H), 3.538 (t, J=6.4, 2H), 3.403-3.370 (m, 4H), 3.188-3.111 (m, 1H), 2.920-2.839 (m, 1H), 2.101-2.011 (s, 2H), 1.889-1.802 (m, 1H), 1.364 (d, J=6.0, 6H), 0.973 (d, J=6.8 Hz, 3H), 0.839 (d, J=6.8 Hz, 3H).

Example 28: 10-((cyclohexanecarbonyl)oxy)-6-isopropyl-9-(3-methoxypropoxy)-2-oxo-6,7-dihydro-2H-pyrido[2,1-a]isoquinoline-3-carboxylic Acid

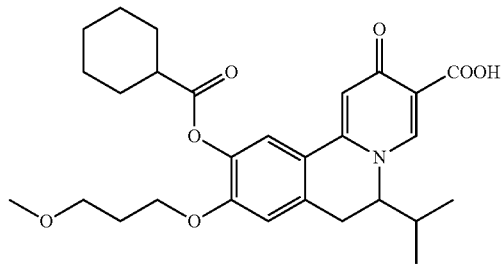 [SMILES: COCCCOc1cc2c(cc1OC(=O)C1CCCCC1)-c1cc(=O)c(C(=O)O)cn1C(C(C)C)C2]

10-Hydroxy-6-isopropyl-9-(3-methoxypropoxy)-2-oxo-6,7-dihydro-2H-pyrido[2,1-a]isoquinoline-3-carboxylic acid (0.26 g, 0.67 mmol) was added into a 50 mL two-neck flask, then DCM (6 mL) was added. The mixture was cooled to 0 ěC, and then cyclohexanecarbonyl chloride (0.45 mL, 3.36 mmol) and TEA (0.47 mL, 3.4 mmol) were added in turn. The mixture was stirred at this temperature for 30 min, then warmed to rt and stirred overnight. After the reaction was completed, the reaction mixture was poured into ice-water (20 g), and the mixture was extracted with DCM (30 mL B 3). The combined organic layers were concentrated in vacuo. The residue was purified by thin-layer chromatography (DCM/CH₃OH (V/V)=20/1) to give the crude product, which was purified by recrystallization from methanol (6 mL) to give the title compound as a gray solid (100 mg, 0.2 mmol, 30%).

MS (ESI, pos.ion) m/z: 498.2 [M+H]⁺;

¹H NMR (400 MHz, CDCl₃) 15.997 (br, 1H), 8.474 (s, 1H), 7.415 (s, 1H), 7.022 (s, 1H), 6.864 (s, 1H), 4.197-4.129 (m, 2H), 3.966-3.862 (m, 1H), 3.589-3.794 (m, 2H), 3.456-3.313 (m, 4H), 3.200-3.096 (m, 1H), 2.691-2.597 (m, 1H), 2.085-2.037 (m, 3H), 1.869-1.848 (m, 3H), 1.767-1.719 (m, 2H), 1.666-1.608 (m, 3H), 1.441-1.380 (m, 2H), 0.973 (d, J=4.4 Hz, 3H), 0.836 (d, J=4.4 Hz, 3H).

Example 29: 6-isopropyl-9-(3-methoxypropoxy)-2-oxo-10-(2-oxopropoxy)-6,7-dihydro-2H-pyrido[2,1-a]isoquinoline-3-carboxylic Acid

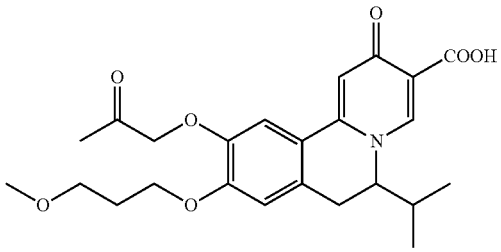 [SMILES: COCCCOc1cc2c(cc1OCC(C)=O)-c1cc(=O)c(C(=O)O)cn1C(C(C)C)C2]

Step 1: Ethyl 6-isopropyl-9-(3-methoxypropoxy)-2-oxo-10-(2-oxopropoxy)-6,7-dihydro-2H-pyrido[2,1-a]isoquinoline-3-carboxylate

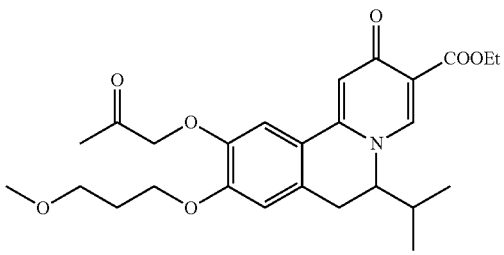 [SMILES: CCOC(=O)c1cn2c(cc1=O)-c1cc(OCC(C)=O)c(OCCCOC)cc1CC2C(C)C]

Ethyl 10-hydroxy-6-isopropyl-9-(3-methoxypropoxy)-2-oxo-6,7-dihydro-2H-pyrido[2,1-a]isoquinoline-3-carboxylate (0.25 g, 0.60 mmol), 1-bromopropan-2-one (0.165 g, 1.20 mmol), DMF (5 mL) and $K_2CO_3$ (0.415 g, 3.01 mmol) were added into a 25 mL single-neck flask, then the mixture was stirred at 50 °C overnight. After the reaction was completed, the reaction mixture was cooled to rt, then diluted with water (20 mL). The mixture was extracted with DCM (30 mL B 4). The combined organic layer was washed with saturated brine (20 mL), dried over anhydrous sodium sulfate, filtered, and concentrated in vacuo. The residue was purified by silica gel column chromatography (DCM/MeOH (V/V)=10/1) to give the title compound as black brown oil (0.28 g, 0.6 mmol, 99%).

MS (ESI, pos.ion) m/z: 472.3 $[M+H]^+$.

Step 2: 6-isopropyl-9-(3-methoxypropoxy)-2-oxo-10-(2-oxopropoxy)-6,7-dihydro-2H-pyrido[2,1-a]isoquinoline-3-carboxylic Acid

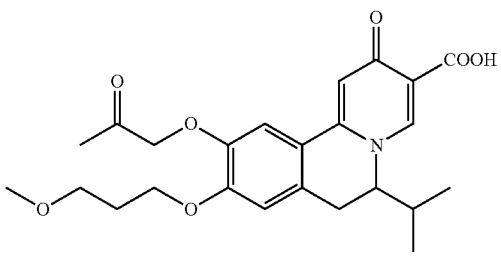 [SMILES: COCCCOc1cc2c(cc1OCC(C)=O)-c1cc(=O)c(C(=O)O)cn1C(C(C)C)C2]

Ethyl 6-isopropyl-9-(3-methoxypropoxy)-2-oxo-10-(2-oxopropoxy)-6,7-dihydro-2H-pyrido[2,1-a]isoquinoline-3-carboxylate (0.284 g, 0.602 mmol) was added into a 25 mL single-neck flask, then THF (4 mL), EtOH (2 mL), $H_2O$ (1 mL) and $LiOH \cdot H_2O$ (0.101 g, 2.40 mmol) were added. The reaction mixture was stirred at rt overnight, then concentrated in vacuo. The residue was diluted with water (10 mL), and the mixture was extracted with DCM (20 mL B 4). The combined organic layers were concentrated in vacuo. The residue was purified by silica gel column chromatography (DCM/$CH_3OH$ (V/V)=20/1) to give the crude product, which was purified by recrystallization from methanol to give the title compound as a gray solid (50 mg, 0.11 mmol, 18.7%).

MS (ESI, pos.ion) m/z: 444.1 $[M+H]^+$;

$^1H$ NMR (400 MHz, $CDCl_3$) 8.533 (s, 1H), 7.196 (s, 1H), 7.134 (s, 1H), 6.830 (s, 1H), 4.707 (s, 2H), 4.275-4.145 (m, 2H), 3.972-3.954 (m, 1H), 3.604 (t, J=5.2, 2H), 3.432-3.303 (m, 4H), 3.157-3.048 (m, 1H), 2.344 (s, 2H), 2.205-2.069 (m, 2H), 1.903-1.736 (m, 1H), 0.963 (d, J=6 Hz, 3H), 0.830 (d, J=6.4 Hz, 3H).

Example 30: 10-acetyl-6-isopropyl-2-oxo-9-(pyrrolidin-1-yl)-6,7-dihydro-2H-pyrido[2,1-a]isoquinoline-3-carboxylic Acid

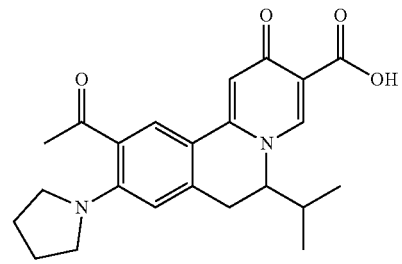 [SMILES: CC(=O)c1cc2c(cc1N1CCCC1)CC(C(C)C)n1cc(C(=O)O)c(=O)cc1-2]

Step 1: 1-(2-(benzyloxy)-4-bromophenyl)ethanone

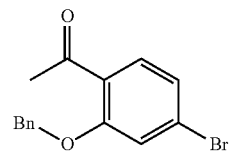

To a single-neck flask were added 1-(4-bromo-2-hydroxyphenyl)ethanone (20 g, 93 mmol), potassium carbonate (25.7 g, 186 mmol), acetonitrile (100 mL) and benzyl bromide (12.2 mL, 103 mmol). The reaction mixture was heated to 70 °C and stirred for 2 h, then cooled to rt, and filtered to remove the solid. The filtrate was concentrated in vacuo to give the title compound as a white solid (28 g, 99%).

Step 2: 2-(2-(benzyloxy)-4-bromophenyl)-2-methyl-1,3-dioxolane

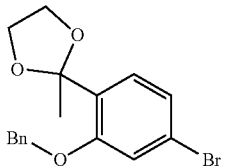

To a reaction flask were added 1-(2-(benzyloxy)-4-bromophenyl)ethanone (28.1 g, 92 mmol), ethanediol (10 mL, 184 mmol), cyclohexane (200 mL), triethyl orthoformate (31 mL, 190 mmol) and p-toluene sulfonic acid (1.8 g, 9.2 mmol). The reaction mixture was heated to 40 ěC and stirred for 24 h, then concentrated in vacuo. The residue was diluted with saturated aqueous sodium bicarbonate solution (100 mL), then extracted with EA (200 mL B2). The combined organic layers were washed with saturated aqueous sodium chloride solution (30 mL), dried over anhydrous sodium sulfate, and concentrated in vacuo to give the title compound as a light yellow oil (32 g, 99%).

MS (ESI, pos.ion) m/z: 371.1 [M+Na]$^+$.

Step 3: 1-(3-(benzyloxy)-4-(2-methyl-1,3-dioxolan-2-yl)phenyl)-3-methylbutan-2-one

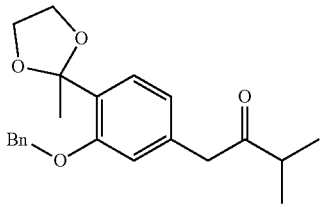 [SMILES: CC(C)C(=O)Cc1ccc(C2(C)OCCO2)c(OCc2ccccc2)c1]

To a single-neck flask were added 2-(2-(benzyloxy)-4-bromophenyl)-2-methyl-1,3-dioxolane (32.0 g, 91.6 mmol), 3-methyl-butan-2-one (19.7 mL, 184 mmol), sodium tert-butoxide (17.6 g, 183 mmol), tetrahydrofuran (400 mL), tris(dibenzylideneacetone)dipalladium (3.76 g, 6.41 mmol) and X antPhos (3.83 g, 6.42 mmol). The reaction mixture was degassed and filled with nitrogen for three times, then heated to 60 ěC and stirred for 4 hours, then concentrated in vacuo, and the residue was purified by silica gel column chromatography (PE/EA (V/V)=10/1) to give the title compound as a light yellow solid (23.34 g, 72%).

MS (ESI, pos.ion) m/z: 355.1 [M+H]$^+$.

Step 4: 1-(3-(benzyloxy)-4-(2-methyl-1,3-dioxolan-2-yl)phenyl)-3-methylbutan-2-amine

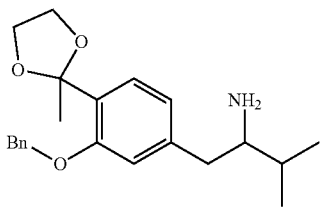 [SMILES: CC(C)C(N)Cc1ccc(C2(C)OCCO2)c(OCc2ccccc2)c1]

To a single-neck flask were added 1-(3-(benzyloxy)-4-(2-methyl-1,3-dioxolan-2-yl) phenyl)-3-methylbutan-2-one (30 g, 84.7 mmol), methanol (150 mL) and ammonium acetate (32.6 g, 423 mmol). The mixture was stirred at rt for 1 h under nitrogen protection, then NaBH$_3$CN (8 g, 130 mmol) was added at 0 ěC. The resulting mixture was stirred at 0 ěC for 24 h. After the reaction was completed, the mixture was concentrated in vacuo, and the residue was diluted with water (100 mL) and aqueous sodium hydroxide solution (30 mL, 10%), then extracted with EA (200 mL B3). The combined organic layers were washed with saturated aqueous sodium chloride solution (50 mL), dried over anhydrous sodium sulfate, and concentrated in vacuo to give the title compound as colorless oil (30.0 g, 99.7%).

MS (ESI, pos.ion) m/z: 356.1 [M+H]$^+$.

Step 5: N-(1-(3-(benzyloxy)-4-(2-methyl-1,3-dioxolan-2-yl)phenyl)-3-methylbutan-2-yl)formamide

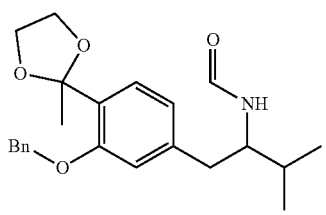 [SMILES: CC(C)C(Cc1ccc(C2(C)OCCO2)c(OCc2ccccc2)c1)NC=O]

To a single-neck flask were added 1-(3-(benzyloxy)-4-(2-methyl-1,3-dioxolan-2-yl)phenyl)-3-methylbutan-2-amine (0.69 g, 1.9 mmol) and ethyl formate (10 mL). The reaction mixture was heated to reflux and stirred for 12 hours, then concentrated in vacuo, and the residue was purified by silica gel column chromatography (PE/EA (V/V)=1/1) to give the title compound as colorless oil (0.3 g, 40%).

MS (ESI, pos.ion) m/z: 384.4 [M+H]$^+$.

Step 6: 1-(6-(benzyloxy)-3-isopropyl-3,4-dihydroisoquinolin-7-yl)ethanone

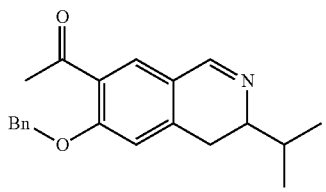 [SMILES: CC(=O)c1cc2c(cc1OCc1ccccc1)CC(C(C)C)N=C2]

To a single-neck flask were added N-(1-(3-(benzyloxy)-4-(2-methyl-1,3-dioxolan-2-yl)phenyl)-3-methylbutan-2-yl) formamide (0.30 g, 0.78 mmol) and dichloromethane (5 mL). The mixture was cooled to 0 ěC under a cold-bath condition, then phosphorus oxychloride (0.36 mL, 3.9 mmol) was added into the mixture. The reaction mixture was stirred at rt for 12 h, then concentrated in vacuo, and the residue was purified by silica gel column chromatography (DCM/MeOH (V/V)=20/1) to give the title compound as brown viscous product (0.20 g, 80%).

MS (ESI, pos.ion) m/z: 322.3 [M+H]$^+$.

Step 7: Ethyl 10-acetyl-9-(benzyloxy)-6-isopropyl-2-oxo-2,6,7,11b-tetrahydro-1H-pyrido[2,1-a]isoquinoline-3-carboxylate

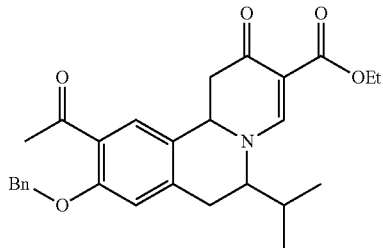 [SMILES: CCOC(=O)C1=CN2C(CC1=O)c1cc(C(C)=O)c(OCc3ccccc3)cc1CC2C(C)C]

To a single-neck flask were added 1-(6-(benzyloxy)-3-isopropyl-3,4-dihydroisoquinolin-7-yl)ethanone (3.1 g, 9.6 mmol), ethyl 2-(ethoxymethylene)-3-oxobutanoate (3.6 g, 19.3 mmol) and ethanol (30 mL). The reaction mixture was heated to 90 ēC and stirred for 12 h. After the reaction was completed, the reaction mixture was concentrated in vacuo, and the residue was purified by silica gel column chromatography (PE/EA (V/V)=1/1) to give the title compound as a brown solid (4.0 g, 90%).

MS (ESI, pos.ion) m/z: 462.4 [M+H]$^+$.

Step 8: Ethyl 10-acetyl-9-(benzyloxy)-6-isopropyl-2-oxo-6,7-dihydro-2H-pyrido[2,1-a]isoquinoline-3-carboxylate

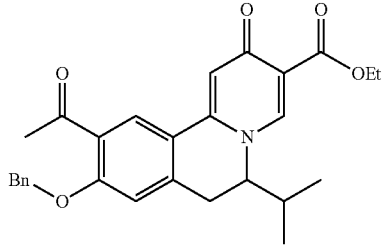 [SMILES: CCOC(=O)c1cn2c(cc1=O)-c1cc(C(C)=O)c(OCc3ccccc3)cc1CC2C(C)C]

To a single-neck flask were added ethyl 10-acetyl-9-(benzyloxy)-6-isopropyl-2-oxo-2,6,7,11b-tetrahydro-1H-pyrido[2,1-a]isoquinoline-3-carboxylate (4.50 g, 9.75 mmol), chloranil (4.53 g, 18.4 mmol) and dimethoxyethane (50 mL). The reaction mixture was stirred at 80 ēC for 2 hours, then concentrated in vacuo to remove the solvent. The residue was purified by silica gel column chromatography (DCM/MeOH(V/V)=10/1) to give the title compound as a gray solid (3.9 g, 87%).

MS (ESI, pos.ion) m/z: 460.1 [M+H]$^+$.

Step 9: Ethyl 10-acetyl-9-hydroxy-6-isopropyl-2-oxo-6,7-dihydro-2H-pyrido[2,1-a]isoquinoline-3-carboxylate

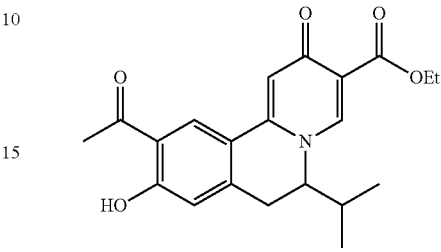

To a single-neck flask were added ethyl 10-acetyl-9-(benzyloxy)-6-isopropyl-2-oxo-6,7-dihydro-2H-pyrido[2,1-a]isoquinoline-3-carboxy late (3.1 g) and methanol (30 mL). The mixture was degassed and filled with hydrogen for three times, then stirred at rt for 8 h equipped with a hydrogen balloon. The mixture was filtered through a celite pad to remove Pd/C, and the filtrate was concentrated in vacuo. The residue was purified by silica gel column chromatography (DCM/MeOH(V/V)=10/1) to give the title compound as a brownish black solid (2.7 g, 86%).

MS (ESI, pos.ion) m/z: 370.1 [M+H]$^+$.

Step 10: Ethyl 10-acetyl-6-isopropyl-2-oxo-9-(((trifluoromethyl)sulfonyl)oxy)-6,7-dihydro-2H-pyrido[2,1-a]isoquinoline-3-carboxylate

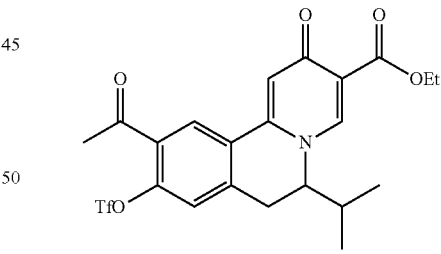

To a two-neck flask were added DCM (10 mL), ethyl 10-acetyl-9-hydroxy-6-isopropyl-2-oxo-6,7-dihydro-2H-pyrido[2,1-a]isoquinoline-3-carboxylate (0.50 g, 1.4 mmol) and TEA (0.38 mL, 2.7 mmol). The reaction mixture was cooled to 0 ēC, then N-phenyl-bis(trifluoromethanesulfonimide) (0.53 g, 1.5 mmol) was added in portions. Then the mixture was stirred at rt for 12 h, and concentrated in vacuo. The residue was purified by silica gel column chromatography (DCM/MeOH(V/V)=10/1) to give the title compound as a yellow solid (0.65 g, 95%).

MS (ESI, pos.ion) m/z: 502.1 [M+H]$^+$.

Step 11: Ethyl 10-acetyl-6-isopropyl-2-oxo-9-(pyrrolidin-1-yl)-6,7-dihydro-2H-pyrido[2,1-a]isoquinoline-3-carboxylate

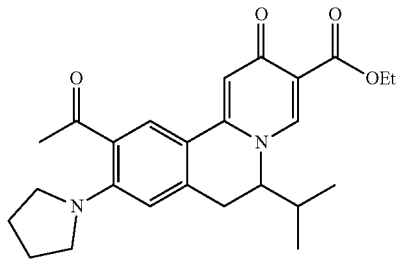 [SMILES: CCOC(=O)c1cn2c(cc1=O)-c1cc(C(C)=O)c(N3CCCC3)cc1CC2C(C)C]

To a single-neck flask were added ethyl 10-acetyl-6-isopropyl-2-oxo-9-(((trifluoromethyl)sulfonyl)oxy)-6,7-dihydro-2H-pyrido[2,1-a]iso quinoline-3-carboxylate (650 mg, 1.3 mmol), cesium carbonate (1.056 g, 3.2 mmol), toluene (10 mL), tertiary butanol (2 mL), tetrahydropyrrole (0.163 mL, 1.94 mmol), X-PHOS (0.16 g, 0.33 mmol) and palladium acetate (30 mg, 0.13 mmol). The reaction mixture was degassed and filled with nitrogen for 4 times, then heated to 90 ěC and stirred for 12 h, and then concentrated in vacuo. The residue was diluted with water (10 mL), then the mixture was extracted with dichloromethane (20 mL B2). The combined organic layers were washed with saturated aqueous sodium chloride solution (20 mL), dried over anydrous sodium sulfate, and filtered. The filtrate was concentrated in vacuo, and the residue was purified by thin-layer chromatography (DCM/MeOH (V/V)=20/1) to give the title compound as a yellow solid (0.320 g, 58.4%).

MS (ESI, pos.ion) m/z: 423.2 [M+H]$^+$.

Step 12: 10-acetyl-6-isopropyl-2-oxo-9-(pyrrolidin-1-yl)-6,7-dihydro-2H-pyrido[2,1-a]isoquinoline-3-carboxylic Acid

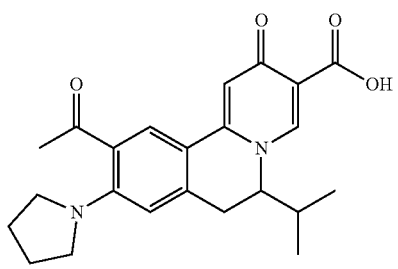 [SMILES: CC(=O)c1cc2c(cc1N1CCCC1)CC(C(C)C)n1cc(C(=O)O)c(=O)cc1-2]

To a single-neck flask were added ethyl 10-acetyl-6-isopropyl-2-oxo-9-(pyrrolidin-1-yl)-6,7-dihydro-2H-pyrido[2,1-a]isoquinoline-3-carboxylate (0.23 g, 0.544 mmol), lithium hydroxide monohydrate (0.069 g, 1.6 mmol), methanol (1 mL) and THF (1 mL). The reaction mixture was stirred at rt for 5 h, then hydrochloric acid (1 M) was added to adjust the pH to 5. The mixture was filtered to give the title compound as a yellow solid (0.16 g 77%).

MS (ESI, pos.ion) m/z: 395.20 [M+H]$^+$;

$^1$H NMR (400 MHz, DMSO-d$_6$) 8.72 (s, 1H), 8.16 (s, 1H), 7.42 (s, 1H), 6.83 (s, 1H), 4.43 (dd, J=9.3, 3.6 Hz, 1H), 3.29 (d, J=4.5 Hz, 2H), 3.11 (d, J=3.3 Hz, 4H), 2.68 (s, 3H), 1.90 (s, 4H), 1.65-1.54 (m, 1H), 0.89 (d, J=6.6 Hz, 3H), 0.69 (d, J=6.7 Hz, 3H).

Example 31: 10-acetyl-9-(furan-2-yl)-6-isopropyl-2-oxo-6,7-dihydro-2H-pyrido[2,1-a]isoquinoline-3-carboxylic Acid

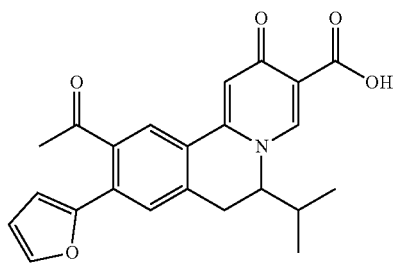 [SMILES: CC(=O)c1cc2c(cc1-c1ccco1)CC(C(C)C)n1cc(C(=O)O)c(=O)cc1-2]

Step 1: Ethyl 10-acetyl-9-(furan-2-yl)-6-isopropyl-2-oxo-6,7-dihydro-2H-pyrido[2,1-a]isoquinoline-3-carboxylate

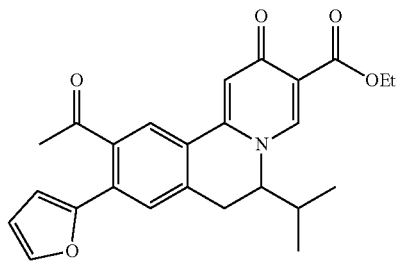 [SMILES: CCOC(=O)c1cn2c(cc1=O)-c1cc(C(C)=O)c(-c3ccco3)cc1CC2C(C)C]

To a single-neck flask were added ethyl 10-acetyl-6-isopropyl-2-oxo-9-(((trifluoromethyl)sulfonyl)oxy)-6,7-dihydro-2H-pyrido[2,1-a]iso quinoline-3-carboxylate (250 mg, 0.50 mmol), potassium carbonate (0.132 g, 1.25 mmol), dioxane (5 mL), ethanol (2 mL), 2-furanboric acid (0.084 g, 0.75 mmol) and tetrakispalladium (58 mg, 0.05 mmol). The reaction mixture was degassed and filled with nitrogen for 4 times, then heated to 90 ěC and stirred for 2 h, and then concentrated in vacuo. The residue was diluted with water (10 mL), then the mixture was extracted with dichloromethane (20 mL B2). The combined organic layers were washed with saturated aqueous sodium chloride solution (20 mL), dried over anydrous sodium sulfate, and filtered. The filtrate was concentrated in vacuo, and the residue was purified by thin-layer chromatography (DCM/MeOH (V/V)=20/1) to give the title compound as a yellow solid (0.20 g, 96%).

MS (ESI, pos.ion) m/z: 423.2 [M+H]$^+$.

Step 2: 10-acetyl-9-(furan-2-yl)-6-isopropyl-2-oxo-6,7-dihydro-2H-pyrido[2,1-a]isoquinoline-3-carboxylic Acid

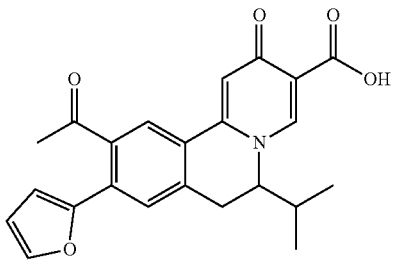 [SMILES: CC(=O)c1cc2c(cc1-c1ccco1)CC(C(C)C)n1cc(C(=O)O)c(=O)cc1-2]

To a single-neck flask were added ethyl 10-acetyl-9-(furan-2-yl)-6-isopropyl-2-oxo-6,7-dihydro-2H-pyrido[2,1-a]isoquinoline-3-carboxy late (0.23 g, 0.55 mmol), lithium hydroxide monohydrate (0.069 g, 1.6 mmol) and methanol (1 mL). The reaction mixture was stirred at rt for 5 h, then hydrochloric acid (1 M) was added to adjust the pH to 5. The mixture was filtered to give the title compound as a yellow solid (0.163 g, 76%).

MS (ESI, pos.ion) m/z: 392.1497 [M+H]$^+$;
$^1$H NMR (400 MHz, CDCl$_3$) 15.73 (s, 1H), 8.50 (s, 1H), 7.78 (s, 1H), 7.59 (d, J=1.2 Hz, 1H), 7.56 (s, 1H), 7.20 (s, 1H), 6.75 (d, J=3.3 Hz, 1H), 6.58 (dd, J=3.4, 1.8 Hz, 1H), 3.96 (dd, J=9.7, 4.2 Hz, 1H), 3.43 (dd, J=16.4, 4.7 Hz, 1H), 3.28 (d, J=16.3 Hz, 1H), 2.37 (s, 3H), 1.77 (qd, J=13.4, 6.7 Hz, 1H), 0.97 (d, J=6.6 Hz, 3H), 0.85 (d, J=6.7 Hz, 3H).

Example 32: 9-(furan-2-yl)-6-isopropyl-10-(methoxycarbonyl)-2-oxo-6,7-dihydro-2H-pyrido[2,1-a]isoquinoline-3-carboxylic Acid

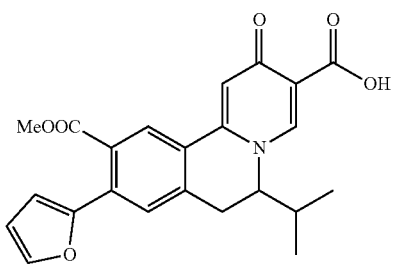 [SMILES: COC(=O)c1cc2c(cc1-c1ccco1)CC(C(C)C)n1cc(C(=O)O)c(=O)cc1-2]

Step 1: Methyl 2-bromo-4-iodobenzoate

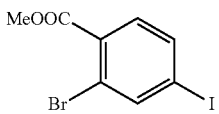

To a 250 mL single-neck flask were added 2-bromo-4-iodobenzoic acid (20.0 g, 61.2 mmol), DMF (100 mL) and K$_2$CO$_3$ (16.89 g, 122.4 mmol), then CH$_3$I (5.71 mL, 91.7 mmol) was added. The reaction mixture was stirred at rt overnight, then diluted with water (100 mL). The mixture was extracted with EA (100 mL B4). The combined organic layers were washed with saturated brine (50 mL B 3), and concentrated in vacuo to give the title compound as black brown oil (20.6 g, 60.4 mmol, 98.8%), which was directly used in the next step.

MS (ESI, pos.ion) m/z: 341.0 [M+H]$^+$.

Step 2: 2-bromo-4-(3-methyl-2-oxobutyl)benzoic Acid

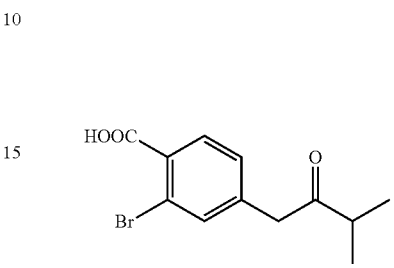

To a 500 mL two-neck flask were added methyl 2-bromo-4-iodobenzoate (20.6 g, 60.4 mmol), 3-methylbutan-2-one (10.4 g, 121 mmol), Pd(dba)$_2$ (869 mg, 1.5113 mmol), X antPHOS (1.4 g, 2.4 mmol), sodium tert-butoxide (19.9 g, 207 mmol) and dixoane (200 mL). The mixture was stirred at 90 ěC overnight under nitrogen protection. After the reaction was completed, the reaction mixture was cooled to rt, and diluted with water (100 mL) and EA (100 mL) in turn, then partitioned. The organic layer was washed with water (50 mL B3). The combined aqueous layers were adjusted with HCl (1 M) to pH 3-4 ⊢ then extracted with EA (100 mL B 4). The combined organic layers were concentrated in vacuo. The residue was purified by silica gel column chromatography (EA) to give the title compound as brown oil (17.23 g, 60.43 mmol, 100%).

MS (ESI, pos.ion) m/z: 285.0 [M+H]$^+$.

Step 3: Methyl 2-bromo-4-(3-methyl-2-oxobutyl)benzoate

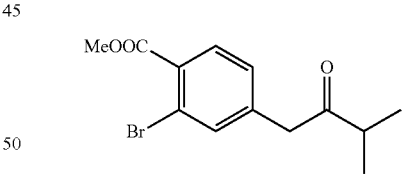

2-Bromo-4-(3-methyl-2-oxobutyl)benzoic acid (17.23 g, 60.43 mmol) was dissolved in MeOH (200 mL), then the solution was stirred and cooled to 0 ěC, and thionyl chloride (43.8 mL, 604 mmol) was added. The mixture was heated to 70 ěC and stirred for 8 h, then cooled naturally to rt and stirred overnight. After the reaction was completed, the mixture was concentrated in vacuo, and to the residue was added EA (100 mL) and water (100 mL). The mixture was partitioned, and the aqueous layer was extracted with ethyl acetate (100 mL B 3). The combined organic layers were concentrated in vacuo, and the residue was purified by silica gel column chromatography (PE/EA (V/V)=20/1) to give the title compound as yellow oil (13.9 g, 46.5 mmol, 76.9%).

MS (ESI, pos.ion) m/z: 299.0 [M+H]$^+$.

Step 4: Methyl 4-(2-amino-3-methylbutyl)-2-bromobenzoate

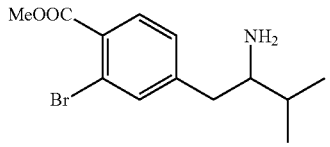 [SMILES: COC(=O)c1ccc(CC(N)C(C)C)cc1Br]

To a 500 mL single-neck flask were added methyl 2-bromo-4-(3-methyl-2-oxobutyl)benzoate (13.9 g, 46.5 mmol), MeOH (150 mL) and NH₄OAc (35.8 g, 464 mmol). The mixture was stirred at rt for 1 h, then cooled to 0 ℃ and NaBH₃CN (8.76 g, 139 mmol) was added. Then the mixture was warmed to rt and stirred overnight. After the reaction was completed, the mixture was concentrated in vacuo, and to the residue was added water (100 mL), EA (100 mL) and ammonium hydroxide (3 mL). The mixture was partitioned, and the aqueous layer was extracted with ethyl acetate (100 mL B 3). The combined organic layers were concentrated in vacuo to give the title compound as brown oil (13.95 g, 46.47 mmol, 100%), which was directly used in the next step.

MS (ESI, pos.ion) m/z: 300.1 [M+H]$^+$.

Step 5: Methyl 2-bromo-4-(2-formamido-3-methylbutyl)benzoate

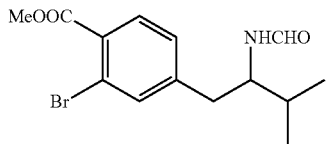

To a 500 mL single-neck flask were added methyl 4-(2-amino-3-methylbutyl)-2-bromobenzoate (13.95 g, 46.47 mmol) and ethyl formate (140 mL). The mixture was stirred at 70 ℃ overnight, then concentrated in vacuo, and the residue was purified by silica gel column chromatography (PE/EA (V/V)=1/1) to give the title compound as a white solid (10.0 g, 30.5 mmol, 65.6%).

MS (ESI, pos.ion) m/z: 351.9 [M+Na]$^+$.

Step 6: Methyl 8-bromo-5-isopropyl-2,3-dioxo-3,5,6,10b-tetrahydro-2H-oxazolo[2,3-a]isoquinoline-9-carboxylate

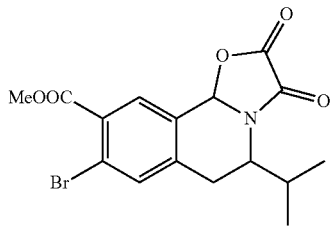 [SMILES: COC(=O)c1cc2c(cc1Br)CC(C(C)C)N1C(=O)C(=O)OC21]

To a 50 mL single-neck flask were added methyl 2-bromo-4-(2-formamido-3-methylbutyl)benzoate (0.256 g, 0.780 mmol) and DCM (10 mL). The mixture was cooled to 0 ℃, then oxalyl chloride (0.149 g, 1.17 mmol) was added. The reaction mixture was stirred at rt for 1 h, then cooled to −10 ℃, and FeCl₃ (201 mg, 1.2497 mmol) was added. The reaction mixture was stirred at rt overnight. Then to the mixture was added HCl (10 mL, 2 M), and the mixture was stirred for 30 min. The mixture was extracted with DCM (15 mL B 3), and the combined organic layers were concentrated in vacuo to give the title compound as brownness oil (0.29 g, 0.76 mmol, 97.5%), which was used directly in the next step.

MS (ESI, pos.ion) m/z: 382.1 [M+Na]$^+$.

Step 7: Methyl 6-bromo-3-isopropyl-3,4-dihydroisoquinoline-7-carboxylate

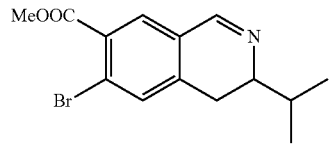 [SMILES: COC(=O)c1cc2c(cc1Br)CC(C(C)C)N=C2]

Methyl 8-bromo-5-isopropyl-2,3-dioxo-3,5,6,10b-tetrahydro-2H-oxazolo[2,3-a]isoquinoline-9-carboxylate (0.29 g, 0.76 mmol) was dissolved in MeOH (10 mL), then concentrated H₂SO₄ (0.5 mL) was added. The mixture was heated to 70 ℃ and stirred for 5 h. After the reaction was completed, the reaction mixture was cooled to rt and concentrated in vacuo. The residue was diluted with EA (20 mL), and the mixture was partitioned. The organic layer was washed with HCl (20 mL B 3, 2 M), and the combined organic layers were cooled to 0 ℃, adjusted with ammonium hydroxide to pH 9-10. The resulting mixture was extracted with EA (30 mL B 4), and the combined organic layers were concentrated in vacuo. The residue was purified by thin-layer chromatography (PE/EA (V/V)=½) to give the title compound as light yellow oil (0.12 g, 0.39 mmol, 51%).

MS (ESI, pos.ion) m/z: 310.0 [M+H]$^+$.

Step 8: Methyl 6-(furan-2-yl)-3-isopropyl-3,4-dihydroisoquinoline-7-carboxylate

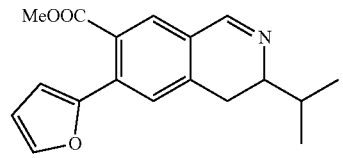 [SMILES: COC(=O)c1cc2c(cc1-c1ccco1)CC(C(C)C)N=C2]

To 50 mL two-neck flask were added methyl 6-bromo-3-isopropyl-3,4-dihydroisoquinoline-7-carboxylate (0.273 g, 0.880 mmol), 2-furanboric acid (0.148 g, 1.32 mmol), tetrakis(triphenylphosphine)palladium (102 mg, 0.0884 mmol), H₂O (2 mL), K₂CO₃ (0.364 g, 2.64 mmol) and dioxane (10 mL). The mixture was heated to 100 ℃ and stirred for 5 h under nitrogen protection. After the reaction was completed, the mixture was cooled to rt, and to the mixture were added saturated brine (20 mL) and EA (30 mL). The mixture was partitioned, and the aqueous layer was extracted with ethyl acetate (30 mL B 3). The combined organic layers were concentrated in vacuo, and the residue was purified by silica gel column chromatography (PE/EA (V/V)=1/1) to give the title compound as light yellow oil (0.260 g, 0.874 mmol, 99.3%).

MS (ESI, pos.ion) m/z: 298.2 [M+H]⁺.

Step 9: 3-tert-butyl 10-methyl 9-(furan-2-yl)-6-isopropyl-2-oxo-2,6,7,11b-tetrahydro-1H-pyrido[2,1-a]isoquinoline-3,10-dicarboxylate

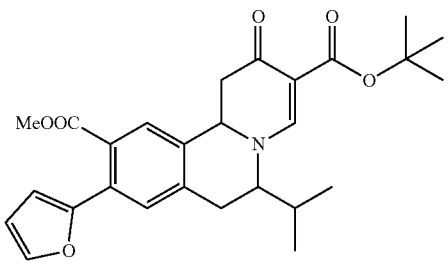 [SMILES: COC(=O)c1cc2c(cc1-c1ccco1)CC(C(C)C)N1C=C(C(=O)OC(C)(C)C)C(=O)CC21]

Tert-butyl 2-((dimethylamino)methylene)-3-oxobutanoate (367 mg, 1.7208 mmol), t-BuOH (15 mL) and methyl 6-(furan-2-yl)-3-isopropyl-3,4-dihydroisoquinoline-7-carboxylate (260 mg, 0.8742 mmol) were added into a 100 mL single-neck flask. The reaction mixture was heated to 100 ěC and stirred for 5 h, then the reaction was stopped. The reaction mixture was cooled to rt and concentrated in vacuo, and the residue was purified by thin-layer chromatography (PE/acetone (V/V)=2/1) to give the title compound as brown oil (0.407 g, 0.874 mmol, 100%).

MS (ESI, pos.ion) m/z: 466.3 [M+H]⁺.

Step 10: 9-(furan-2-yl)-6-isopropyl-10-(methoxycarbonyl)-2-oxo-6,7-dihydro-2H-pyrido[2,1-a]isoquinoline-3-carboxylic Acid

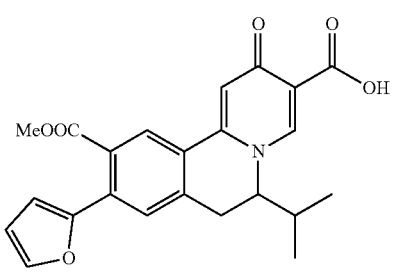 [SMILES: COC(=O)c1cc2c(cc1-c1ccco1)CC(C(C)C)n1cc(C(=O)O)c(=O)cc1-2]

To a 100 mL single-neck flask were added 3-tert-butyl 10-methyl 9-(furan-2-yl)-6-isopropyl-2-oxo-2,6,7,11b-tetrahydro-1H-pyrido[2,1-a]isoquinoline-3,10-dicarboxylate (0.41 g, 0.87 mmol), dimethoxyethane (15 mL) and chloranil (322 mg, 1.31 mmol). The reaction mixture was stirred at 90 ěC for 6 hours, then concentrated in vacuo to remove the solvent. The residue was purified by silica gel column chromatography (DCM/MeOH(V/V)=10/1) to give the title compound as a white solid (108 mg, 30.3%).

MS (ESI, pos.ion) m/z: 408.1 [M+H]⁺;
¹H NMR (400 MHz, DMSO-d₆) 8.86 (s, 1H), 8.29 (s, 1H), 7.87 (s, 2H), 7.52 (s, 1H), 6.95 (s, 1H), 6.68 (s, 1H), 4.61-4.53 (m, 1H), 3.85 (s, 3H), 3.51-3.42 (m, 2H), 1.64-1.56 (m, 1H), 0.93-0.69 (m, 6H).

Example 33: 6-isopropyl-9-(3-methoxypropoxy)-2-oxo-10-(thiazol-5-yl)-6,7-dihydro-2H-pyrido[2,1-a]isoquinoline-3-carboxylic Acid

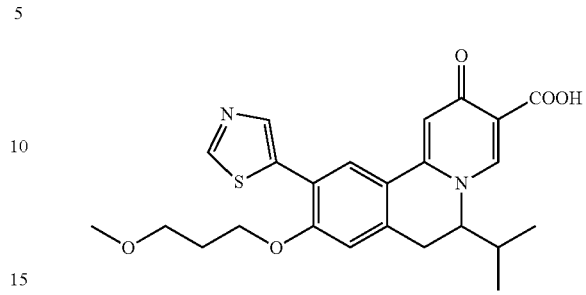

To a 25 mL single-neck flask were added ethyl 6-isopropyl-9-(3-methoxyphenoxy)-2-oxo-10-(((trifluoromethyl)sulfonyl)oxy)-6,7-dihydro-2H-pyrido[2,1-a]isoquinoline-3-carboxylate (0.310 g, 0.570 mmol), 5-(tributylstannyl)thiazole (198 mg, 0.53 mmol), anhydrous dioxane (10 mL) and bis(triphenylphosphine)palladium(II) chloride (99 mg, 0.14 mmol). The reaction mixture was stirred at 110 ěC for 12 hours under a nitrogen protection, then concentrated in vacuo, and the residue was purified by silica gel column chromatography (DCM/MeOH(V/V)=15/1) to give the title compound as a gray solid (40 mg, 0.566 mmol, 16%).

MS (ESI, pos.ion) m/z: 455.3 [M+H]⁺;
¹H NMR (400 MHz, CDCl₃) 15.942ʲ br, 1Hʲ, 8.878 (s, 1H), 8.493 (s, 1H), 8.341 (s, 1H), 8.003 (s, 1H), 7.171 (s, 1H), 6.946 (s, 1H), 4.375-4.265 (m, 2H), 3.959-3.906 (m, 1H), 3.679-3.596 (m, 2H), 3.464-3.410ʲ m, 1Hʲ, 3.387 (s, 3H), 3.246-3.158 (m, 1H), 2.250-2.191 (m, 2H), 1.882-1.8102 (m, 1H), 0.996 (d, J=6.4 Hz, 3H), 0.872 (d, J=6.8 Hz, 3H).

Example 34: 6-isopropyl-10-(methoxycarbonyl)-2-oxo-9-(pyrrolidin-1-yl)-6,7-dihydro-2H-pyrido[2,1-a]isoquinoline-3-carboxylic Acid

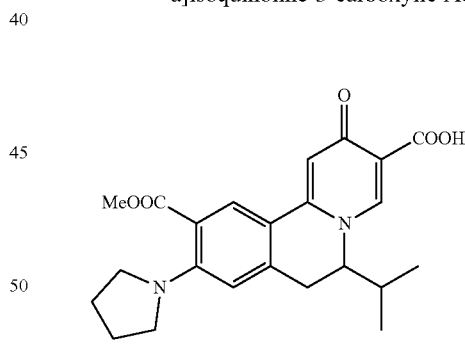

Step 1: Methyl 4-bromo-2-(pyrrolidin-1-yl)benzoate

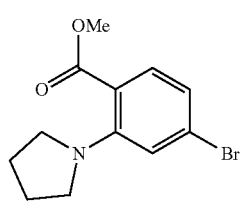 [SMILES: COC(=O)c1ccc(Br)cc1N1CCCC1]

To a 50 mL single-neck flask were added tetrahydropyrrole (2.1 g, 30 mmol), KI (0.14 mg, 0.00084 mmol), K₂CO₃ (5.9 g, 43 mmol), DMSO (30 mL) and methyl 4-bromo-2-fluoro-benzoate (5.0 g, 21 mmol). The mixture was heated to 100 ěC, and stirred overnight. After the reaction was completed, the reaction mixture was cooled to rt and diluted with water (300 mL). The resulting mixture was extracted with EtOAc (100 mL B 4). The combined organic layers were washed with saturated brine (100 mL), dried over anhydrous sodium sulfate and filtered. The filtrate was concentrated in vacuo. The residue was purified by silica gel column chromatography eluted with PE/EtOAc ((v/v)=10/1) to give colorless oil (4.13 g, 14.5 mmol, 48%).

MS (ESI, pos.ion) m/z: 284.3 [M+H]⁺.

Step 2: Methyl 4-(3-methyl-2-oxobutyl)-2-(pyrrolidin-1-yl)benzoate

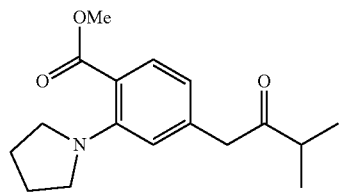 [SMILES: COC(=O)c1ccc(CC(=O)C(C)C)cc1N1CCCC1]

To a two-neck flask were added 3-methylbutan-2-one (2.0 g, 23 mmol), X PHOS (0.294 g, 0.508 mmol), sodium tert-butoxide (4.19 g, 43.6 mmol), THF (60 mL) and methyl 4-bromo-2-(pyrrolidin-1-yl)benzoate (4.13 g, 14.5 mmol). The mixture was degassed and filled with nitrogen for three times, then heated to 100 ěC and stirred overnight. Postprocessing: the reaction mixture was cooled to rt, then concentrated to remove most of the solvent, and poured into ice-water; the mixture was extracted with ethyl acetate (30 mL B 3); the combined organic layer was dried over anhydrous sodium sulfate, and filtered; the filtrate was concentrated in vacuo to give the title compound as colorless oil, which was used directly in the next step.

MS (ESI, pos.ion) m/z: 290.5 [M+H]⁺.

Step 3: Methyl 4-(2-amino-3-methylbutyl)-2-(pyrrolidin-1-yl)benzoate

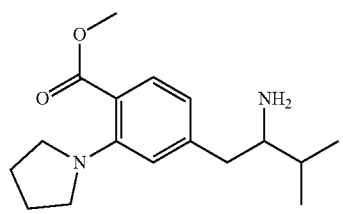 [SMILES: COC(=O)c1ccc(CC(N)C(C)C)cc1N1CCCC1]

To a 100 mL single-neck flask were added methyl 4-(3-methyl-2-oxobutyl)-2-(pyrrolidin-1-yl)benzoate (4.2 g, 15 mmol), NH₄OAc (13 g, 168.7 mmol) and MeOH (42 mL). The mixture was stirred at rt for 1 h, then cooled to 0 ěC and NaBH₃CN (1.8 g, 29 mmol) was added. Then the mixture was warmed to rt and stirred overnight. Postprocessing: the reaction mixture was concentrated to remove the solvent, and the residue was diluted with saturated aqueous ammonium chloride (20 mL); the mixture was extracted with DCM (50 mL B 4), and the combined organic layers were washed with saturated brine (30 mL), dried over anhydrous sodium sulfate, and filtered. The filtrate was concentrated in vacuo to give the title compound as colorless oil, which was directly used in the next step.

MS (ESI, pos.ion) m/z: 291.5 [M+1]⁺.

Step 4: Methyl 4-(2-formamido-3-methylbutyl)-2-(pyrrolidin-1-yl)benzoate

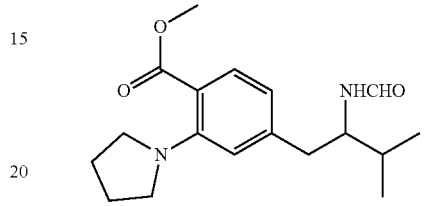

To a 50 mL single-neck flask was added methyl 4-(2-amino-3-methylbutyl)-2-(pyrrolidin-1-yl)benzoate (4.2 g, 14 mmol), then dioxane (21 mL) and formic acid (11 g, 239.00 mmol) were added. The mixture was heated to 110 KC and stirred for 24 h under nitrogen protection. The reaction mixture was worked up by concentrating to remove the solvent, and the residue was diluted with saturated brine (20 mL); the mixture was extracted with ethyl acetate (30 mL B 4); the combined organic layers were washed with saturated brine (20 mL), dried over anhydrous sodium sulfate, and filtered; the filtrate was concentrated in vacuo to give the title compound as a light yellow solid (4.6 g, 14 mmol, 100%).

MS-ESI: (ESI, pos.ion) m/z: 319.5 [M+1]⁺.

Step 5: Methyl 3-isopropyl-6-(pyrrolidin-1-yl)-3,4-dihydroisoquinoline-7-carboxylate

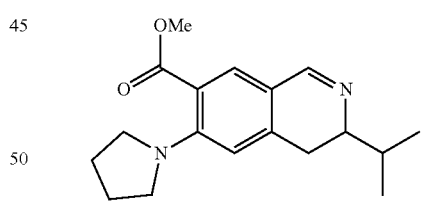

To a 50 mL single-neck flask were added methyl 4-(2-formamido-3-methylbutyl)-2-(pyrrolidin-1-yl)benzoate (4.6 g, 14 mmol), DCM (46 mL) and POCl₃ (2.7 mL, 29 mmol). The reaction mixture was heated to 50 ěC and stirred for 8 h under nitrogen protection. The reaction mixture was worked up by concentrating to remove the solvent, and the residue was diluted with saturated brine (20 mL); the mixture was extracted with ethyl acetate (30 mL B 4); the combined organic layers were washed with saturated brine (20 mL), dried over anhydrous sodium sulfate, and filtered; the filtrate was concentrated in vacuo to give the title compound as light yellow oil (4.2 g, 13.6 mmol, 97%).

MS (ESI, pos.ion) m/z: 301.2 [M+H]⁺.

Step 6: 3-benzyl 10-methyl 6-isopropyl-2-oxo-9-(pyrrolidin-1-yl)-2,6,7,11b-tetrahydro-1H-pyrido[2,1-a]isoquinoline-3,10-dicarboxylate

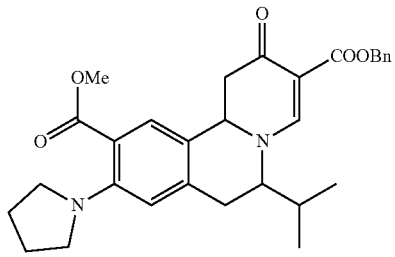

To a 50 mL single-neck flask were added benzyl 2-(ethoxymethylene)-3-oxobutanoate (0.8 g, 3 mmol) and methyl 3-isopropyl-6-(pyrrolidin-1-yl)-3,4-dihydroisoquinoline-7-carboxylate (0.54 g, 1.8 mmol), then DMSO (5 mL) was added. The reaction mixture was heated to 110 ěC and stirred for 5 days under nitrogen protection. The reaction mixture was worked up by concentrating to remove the solvent, and the residue was diluted with saturated brine (20 mL); the mixture was extracted with ethyl acetate (30 mL B 4); the combined organic layers were washed with saturated brine (20 mL), dried over anhydrous sodium sulfate, and filtered; the filtrate was concentrated in vacuo, and the residue was purified by silica gel column chromatography (PE/EA (V/V)=1/1) to give the title compound as brown oil (0.13 g, 14%).

MS (ESI, pos.ion) m/z: [M+1]$^+$: 503.2.

Step 7: 3-benzyl 10-methyl 6-isopropyl-2-oxo-9-(pyrrolidin-1-yl)-6,7-dihydro-2H-pyrido[2,1-a]isoquinoline-3,10-dicarboxylate

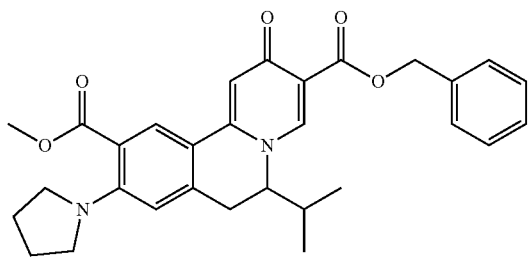 [SMILES: COC(=O)c1cc2c(cc1N1CCCC1)CC(C(C)C)n1cc(C(=O)OCc3ccccc3)c(=O)cc1-2]

To a 50 mL single-neck flask were added 3-benzyl 10-methyl 6-isopropyl-2-oxo-9-(pyrrolidin-1-yl)-2,6,7,11b-tetrahydro-1H-pyrido[2,1-a]isoquinoline-3,10-di carboxylate (64 mg, 0.1273 mmol), DME (13 mL) and chloranil (64 mg, 0.26029 mmol). The mixture was stirred overnight. The reaction mixture was worked up by concentrating, and the residue was purified by silica gel column chromatography (DCM/MeOH (V/V)=10/1) to give the title compound as brown oil (40 mg, 62.75%).

MS (ESI, pos.ion) m/z: 503.2 [M+1]$^+$.

Step 8: 6-isopropyl-10-(methoxycarbonyl)-2-oxo-9-(pyrrolidin-1-yl)-6,7-dihydro-2H-pyrido[2,1-a]isoquinoline-3-carboxylic Acid

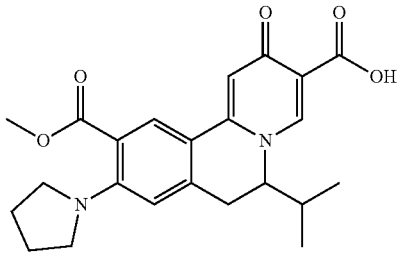 [SMILES: COC(=O)c1cc2c(cc1N1CCCC1)CC(C(C)C)n1cc(C(=O)O)c(=O)cc1-2]

3-Benzyl 10-methyl 6-isopropyl-2-oxo-9-(pyrrolidin-1-yl)-6,7-dihydro-2H-pyrido[2,1-a]isoquinoline-3,10-dicarboxylate (0.13 g, 0.26 mmol) was added into a 50 mL single-neck flask, then THF (5 mL) and Pd/C (50 mg) was added. The mixture was stirred at 50 ěC for 36 h in a hydrogen atmosphere. The reaction mixture was worked up by cooling to rt and filtering through a celite pad, and the filter cake was washed with DCM (30 mL); the filtrate was concentrated in vacuo, and the residue was purified by chromatograph to give the title compound as a yellow solid (30 mg, 0.073 mmol, 28%).

MS (ESI, pos.ion) m/z: 411.6 [M+1]$^+$; and
$^1$H NMR (400 MHz, CDCl$_3$) 16.28 (b, 1H), 8.41 (s, 1H), 8.11 (s, 1H), 7.05 (s, 1H), 6.60 (s, 1H), 3.95 (s, 3H), 3.82-3.88 (m, H), 3.27-3.43 (m, 5H), 3.08-3.16 (m, 1H), 1.96-2.10 (m, 4H), 1.76-1.86 (m, 1H), 0.96 (d, J=8 Hz, 3H), 0.83 (d, J=8 Hz, 3H).

Example 35: 10-((2,2-difluoroethoxy)carbonyl)-6-isopropyl-9-(3-methoxypropoxy)-2-oxo-6,7-dihydro-2H-pyrido[2,1-a]isoquinoline-3-carboxylic Acid

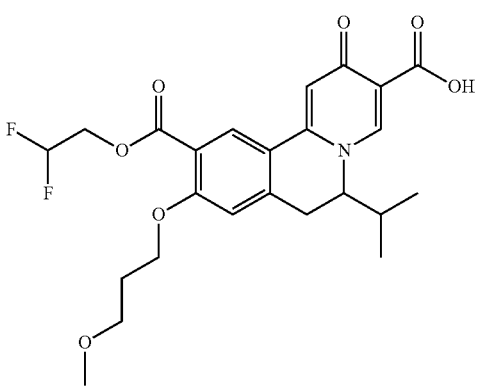 [SMILES: COCCCOc1cc2c(cc1C(=O)OCC(F)F)-c1cc(=O)c(C(=O)O)cn1C(C(C)C)C2]

The title compound was prepared according to the synthetic method of step 1 to step 2 in example 3 by using 3-(tert-butoxycarbonyl)-6-isopropyl-9-(3-methoxypropoxy)-2-oxo-6,7-dihydro-2H-pyrido[2,1-a]isoquinoline-10-carboxylic acid (0.350 g, 0.742 mmol) and 2-bromo-1,1-difluoroethane (0.430 g, 2.97 mmol) as raw materials to give a gray solid (0.10 g, 0.21 mmol).

MS (ESI, pos.ion) m/z: 480.1 [M+H]$^+$;
$^1$H NMR (400 MHz, CDCl$_3$) 15.929 (b, 1H), 8.502 (s, 1H), 8.286 (s, 1H), 7.151 (s, 1H), 6.944 (s, 1H), 6.252-5.958

(m, 1H), 4.581-4.503 (m, 2H), 4.298-4.203 (m, 2H), 4.032-3.943 (m, 1H), 3.670-3.586 (m, 2H), 3.502-3.422 (m, 1H), 3.380 (s, 3H), 3.260-3.177 (m, 1H), 2.181-2.121 (m, 2H), 1.809-1.722 (m, 1H), 0.974 (d, J=6.8 Hz, 3H), 0.849 (d, J=6.8 Hz, 3H).

Example 36: 6-isopropyl-9-(3-methoxypropoxy)-2-oxo-10-((prop-2-yn-1-yloxy)carbonyl)-6,7-dihydro-2H-pyrido[2,1-a]isoquinoline-3-carboxylic Acid

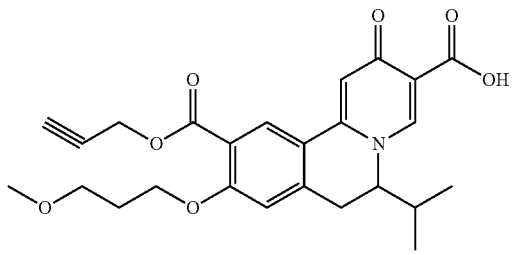 [SMILES: C#CCOC(=O)c1cc2c(cc1OCCCOC)CC(C(C)C)n1cc(C(=O)O)c(=O)cc1-2]

The title compound was prepared according to the synthetic method of step 1 to step 2 in example 3 by using 3-(tert-butoxycarbonyl)-6-isopropyl-9-(3-methoxypropoxy)-2-oxo-6,7-dihydro-2H-pyrido[2,1-a]isoquinoline-10-carboxylic acid (0.31 g, 0.66 mmol) and propargyl bromide (0.31 g, 2.62 mmol) as raw materials to give a gray solid (80 mg, 0.18 mmol).

MS (ESI, pos.ion) m/z: 454.2 [M+H]$^+$;

$^1$H NMR (400 MHz, CDCl$_3$) 15.915 (b, 1H), 8.473 (s, 1H), 8.289 (s, 1H), 7.164 (s, 1H), 6.924 (s, 1H), 4.946 (d, J=2 Hz, 2H), 4.293-4.199 (m, 2H), 3.981-3.902 (m, 1H), 3.696-3.612 (m, 2H), 3.450-3.385 (m, 4H), 3.245-3.168 (m, 1H), 2.562 (s, 1H), 2.188-2.130 (m, 2H), 1.808-1.725 (m, 2H), 0.963 (d, J=6.8 Hz, 3H), 0.848 (d, J=6.8 Hz, 3H).

Example 37: 6-isopropyl-9-(3-methoxypropoxy)-2-oxo-10-((pentan-3-yloxy)carbonyl)-6,7-dihydro-2H-pyrido[2,1-a]isoquinoline-3-carboxylic Acid

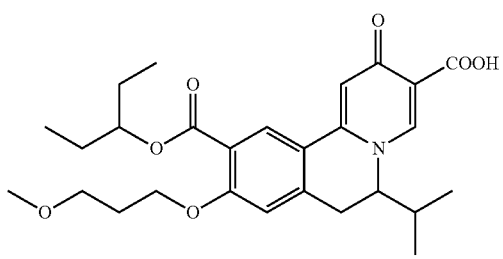 [SMILES: CCC(CC)OC(=O)c1cc2c(cc1OCCCOC)CC(C(C)C)n1cc(C(=O)O)c(=O)cc1-2]

The title compound was prepared according to the synthetic method of step 1 to step 2 in example 3 by using 3-(tert-butoxycarbonyl)-6-isopropyl-9-(3-methoxypropoxy)-2-oxo-6,7-dihydro-2H-pyrido[2,1-a]isoquinoline-10-carboxylic acid (0.40 g, 0.85 mmol) and 3-bromopentane (0.26 g, 1.69 mmol) as raw materials to give a gray solid (0.2 g, 0.4 mmol).

MS (ESI, pos.ion) m/z: 486.3 [M+H]$^+$;

$^1$H NMR (400 MHz, CDCl$_3$) 15.986 (b, 1H), 8.488 (s, 1H), 8.187 (s, 1H), 7.144 (s, 1H), 6.913 (s, 1H), 5.142-5.009 (m, 1H), 4.293-4.190 (m, 2H), 4.107-3.900 (m, 1H), 3.672-3.575 (m, 2H), 3.481-3.326 (m, 4H), 3.227-3.153 (m, 1H), 2.207-2.098 (m, 2H), 1.840-1.589 (m, 5H), 1.062-0.921 (m, 9H), 0.968 (d, J=6 Hz, 3H).

Example 38: 10-((2-cyclopropyl-2-oxoethoxy)carbonyl)-6-isopropyl-9-(3-methoxypropoxy)-2-oxo-6,7-dihydro-2H-pyrido[2,1-a]isoquinoline-3-carboxylic Acid

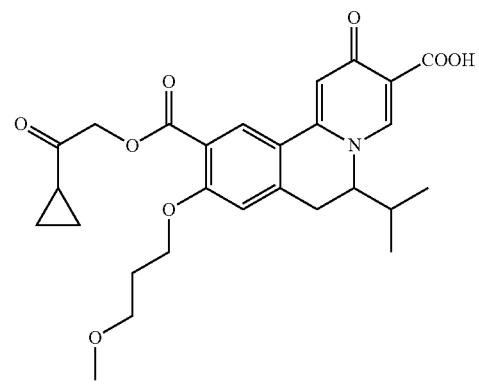 [SMILES: COCCCOc1cc2c(cc1C(=O)OCC(=O)C1CC1)-c1cc(=O)c(C(=O)O)cn1C(C(C)C)C2]

The title compound was prepared according to the synthetic method of step 1 to step 2 in example 3 by using 3-(tert-butoxycarbonyl)-6-isopropyl-9-(3-methoxypropoxy)-2-oxo-6,7-dihydro-2H-pyrido[2,1-a]isoquinoline-10-carboxylic acid (0.40 g, 0.85 mmol) and 1-cyclopropyl-2-bromoethanone (0.55 g, 3.39 mmol) as raw materials to give a gray solid (50 mg, 0.1005 mmol).

MS (ESI, pos.ion) m/z: 498.3 [M+H]$^+$;

$^1$H NMR (400 MHz, CDCl$_3$) 15.925 (b, 1H), 8.460 (s, 1H), 8.384 (s, 1H), 7.169 (s, 1H), 6.927 (s, 1H), 5.168-5.052 (m, 2H), 4.271-4.209 (m, 2H), 3.948-3.896 (m, 1H), 3.645-3.595 (m, 2H), 3.456-3.377 (m, 4H), 3.239-3.183 (m, 1H), 2.177-2.116 (m, 2H), 2.075-2.010 (m, 1H), 1.826-1.762 (m, 1H), 1.224-1.185 (m, 2H), 1.069-1.022 (m, 2H), 0.990-0.964 (m, 3H), 0.885-0.845 (m, 3H).

Example 39: 6-isopropyl-9-(3-methoxypropoxy)-2-oxo-10-(((1,1,1-trifluoro-2-methylpropan-2-yl)oxy)carbonyl)-6,7-dihydro-2H-pyrido[2,1-a]isoquinoline-3-carboxylic Acid

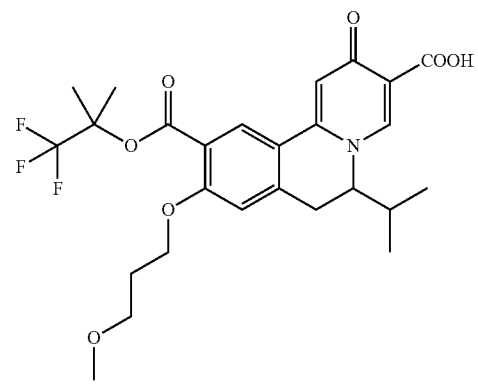 [SMILES: COCCCOc1cc2c(cc1C(=O)OC(C)(C)C(F)(F)F)-c1cc(=O)c(C(=O)O)cn1C(C(C)C)C2]

Step 1: 1,1,1-trifluoro-2-methylpropan-2-yl 2-(3-methoxypropoxy)-4-(3-methyl-2-oxobutyl) benzoate

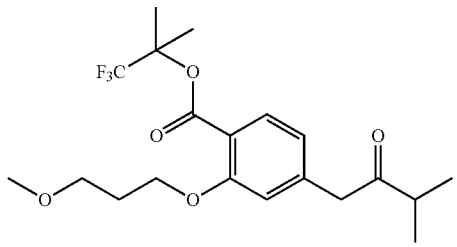 [SMILES: COCCCOc1cc(CC(=O)C(C)C)ccc1C(=O)OC(C)(C)C(F)(F)F]

To a 100 mL single-neck flask were added 2-(3-methoxypropoxy)-4-(3-methyl-2-oxobutyl)benzoic acid (2.00 g, 6.80 mmol), 1,1,1-trifluoro-2-methylpropan-2-ol (1.3 g, 10 mmol), DCM (5 mL) and SOCl$_2$ (0.64 mL, 8.8 mmol). The mixture was heated to 50 °C and stirred overnight. The reaction mixture was cooled to rt, poured into ice-water (20 g), then extracted with DCM (30 mL B 3). The combined organic layers were concentrated in vacuo to give the title compound as colorless oil (2.75 g, 6.80 mmol, 100%).

MS (ESI, pos.ion) m/z: 427.3 [M+Na]$^+$.

Step 2: 1,1,1-trifluoro-2-methylpropan-2-yl 4-(2-amino-3-methylbutyl)-2-(3-methoxypropoxy) benzoate

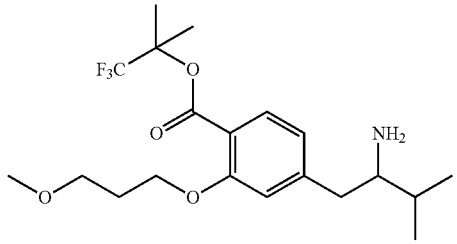 [SMILES: COCCCOc1cc(CC(N)C(C)C)ccc1C(=O)OC(C)(C)C(F)(F)F]

To a 100 mL single-neck flask were added 1,1,1-trifluoro-2-methylpropan-2-yl 2-(3-methoxypropoxy)-4-(3-methyl-2-oxobutyl)benzoate (4.125 g, 10.20 mmol), MeOH (41 mL) and NH$_4$OAc (9.435 g, 122.4 mmol). The mixture was stirred at rt for 1 h. The mixture was cooled to 0 °C, and NaBH$_3$CN (1.923 g, 30.60 mmol) was added in portions, then the mixture was heated to rt and stirred overnight. The reaction mixture was worked up by concentrating in vacuo to remove the solvent, and the residue was diluted with saturated aqueous ammonium chloride (20 mL); the mixture was extracted with EA (50 mL B 4), and the combined organic layers were dried over anhydrous sodium sulfate, and filtered; the filtrate was concentrated in vacuo to give the title compound as colorless oil (4.135 g, 10.20 mmol, 100.0%), which was directly used in the next step.

MS (ESI, pos.ion) m/z: 406.0 [M+1]$^+$.

Step 3: 1,1,1-trifluoro-2-methylpropan-2-yl 4-(2-formamido-3-methylbutyl)-2-(3-methoxypropoxy) benzoate

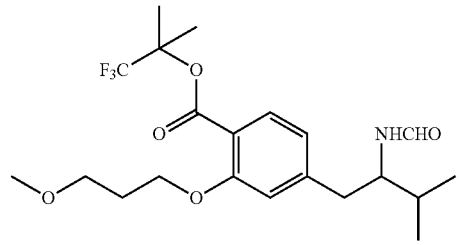

To a 100 mL single-neck flask were added 1,1,1-trifluoro-2-methylpropan-2-yl 4-(2-amino-3-methylbutyl)-2-(3-methoxypropoxy)benzoate (4.13 g, 10.20 mmol), dioxane (28 mL) and formic acid (7.51 g, 163.2 mmol). The mixture was heated to 110 °C and stirred overnight. The mixture was worked up by cooling to rt and concentrating in vacuo; to the residue were added EA (100 mL) and water (50 mL); the mixture was extracted with ethyl acetate (100 mL B 3); the combined organic layers were concentrated in vacuo, and the residue was purified by silica gel column chromatography (PE/EA (V/V)=1/1) to give the title compound as a brown thickness product (2.3 g, 5.3 mmol, 52%).

MS (ESI, pos.ion) m/z: 434.3 [M+1]$^+$.

Step 4: 1,1,1-trifluoro-2-methylpropan-2-yl 3-isopropyl-6-(3-methoxypropoxy)-3,4-dihydroisoquinoline-7-carboxylate

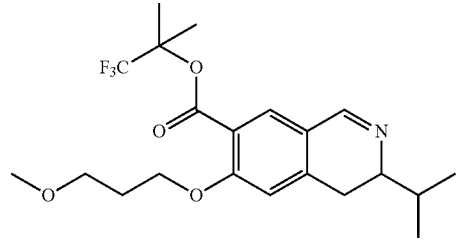 [SMILES: COCCCOc1cc2c(cc1C(=O)OC(C)(C)C(F)(F)F)C=NC(C(C)C)C2]

To a 50 mL single-neck flask were added 1,1,1-trifluoro-2-methylpropan-2-yl 4-(2-amino-3-methylbutyl)-2-(3-methoxypropoxy)benzoate (2.3 g, 5.3 mmol), then DCM (23 mL) was added. The mixture was cooled to 0 °C and POCl$_3$ (0.99 mL, 11 mmol) was added. The mixture was heated to 50 °C and stirred for 4 h. The mixture was worked up by cooling to rt and pouring into ice-water (30 g); the mixture was adjusted with ammonium hydroxide to pH=10, then the resulting mixture was extracted with EA (30 mL B 3); the combined organic layers were washed with saturated brine (10 mL), dried over anhydrous sodium sulfate and filtered; the filtrate was concentrated in vacuo, and the residue was purified by silica gel column chromatography (EA) to give the title compound as brown oil (1.79 g, 4.31 mmol, 81%).

MS (ESI, pos.ion) m/z: 416.3 [M+1]$^+$.

Step 5: 3-tert-butyl 10-(1,1,1-trifluoro-2-methylpropan-2-yl) 6-isopropyl-9-(3-methoxypropoxy)-2-oxo-2,6,7,11b-tetrahydro-1H-pyrido[2,1-a]isoquinoline-3,10-dicarboxylate

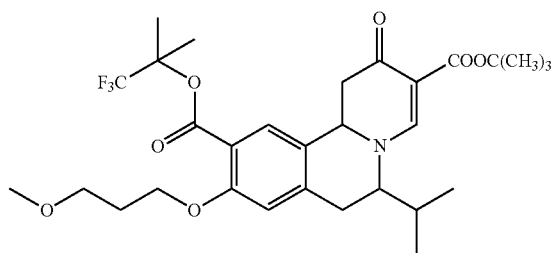

To a 100 mL two-neck flask were added 1,1,1-trifluoro-2-methylpropan-2-yl 3-isopropyl-6-(3-methoxypropoxy)-3,4-dihydroisoquinoline-7-carboxylate (1.79 g, 4.31 mmol) and tert-butyl (2E)-2-((dimethylamino)methyl ene)-3-oxobutanoate (1.84 g, 8.62 mmol). Then to the mixture was added t-BuOH (5 mL), and the mixture was stirred at 90 ěC under nitrogen protection for 48 h. The mixture was worked up by concentrating in vacuo, and the residue was purified by silica gel column chromatography (DCM/MeOH (V/V)=10/1) to give the title compound as black oil (2.2 g, 3.8 mmol, 87%).

MS (ESI, pos.ion) m/z: 584.4 [M+1]$^+$.

Step 6: 6-isopropyl-9-(3-methoxypropoxy)-2-oxo-10-(((1,1,1-trifluoro-2-methylpropan-2-yl)oxy)carbonyl)-6,7-dihydro-2H-pyrido[2,1-a]isoquinoline-3-carboxylic Acid

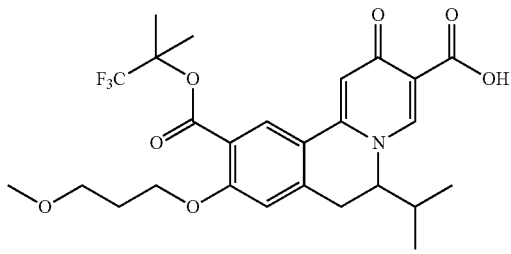 [SMILES: COCCCOc1cc2c(cc1C(=O)OC(C)(C)C(F)(F)F)-c1cc(=O)c(C(=O)O)cn1C(C(C)C)C2]

To a 100 mL single-neck flask were added 3-tert-butyl 10-(1,1,1-trifluoro-2-methylpropan-2-yl) 6-isopropyl-9-(3-methoxypropoxy)-2-oxo-2,6,7,11b-tetrahydro-1H-pyrido[2,1-a]isoquinoline-3,10-dicarboxylate (0.23 g, 0.39 mmol), DME (6 mL) and chloranil (0.85 mg, 0.39 mmol). The mixture was heated to 90 ěC and stirred for 1 h, then cooled to rt, and concentrated in vacuo. The residue was purified by silica gel column chromatography (DCM/MeOH (V/V)=10/1) to give the title compound as a gray solid (150 mg, 0.2854 mmol, 72%).

MS (ESI, pos.ion) m/z: 525.9 [M+1]$^+$;

$^1$H NMR (400 MHz, CDCl$_3$) 15.971 (br, 1H), 8.490 (s, 1H), 8.186 (s, 1H), 7.283 (s, 1H), 6.921 (s, 1H), 4.276-4.180 (m, 2H), 4.025-3.919 (m, 1H), 3.669-3.552 (m, 2H), 3.471-3.332 (m, 4H), 3.256-3.145 (m, 1H), 2.195-2.119 (m, 2H), 1.846 (s, 6H), 1.806-1.739 (m, 1H), 0.969 (d, J=6.4 Hz, 3H), 0.847 (d, J=6.4 Hz, 3H).

Example 40: 6-isopropyl-10-(methoxycarbonyl)-2-oxo-9-phenoxy-6,7-dihydro-2H-pyrido[2,1-a]isoquinoline-3-carboxylic Acid

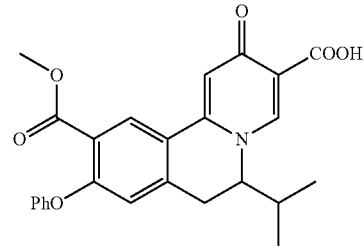 [SMILES: COC(=O)c1cc2c(cc1Oc1ccccc1)CC(C(C)C)n1cc(C(=O)O)c(=O)cc1-2]

Step 1: 2-(4-bromo-2-fluorophenyl)-1,3-dioxolane

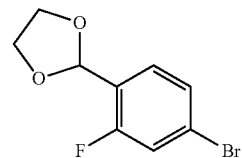 [SMILES: Fc1cc(Br)ccc1C1OCCO1]

To a 100 mL single-neck flask were added 4-bromo-2-fluorobenzaldehyde (4.71 g, 23.21 mmol), triethyl orthoformate (6.88 g, 46.4 mmol), p-toluenesulfonic acid monohydrate (0.88 g, 4.64 mmol), ethanediol (2.88 g, 46.42 mmol) and n-hexane (50 mL). The mixture was heated to 65 ěC and stirred overnight under nitrogen protection. The mixture was worked up by cooling to rt, then water (30 mL) was added; the resulting mixture was extracted with petroleum ether (20 mL B 3), and the combined organic layers were washed with water (10 mL B 2), concentrated in vacuo; the residue was purified by silica gel column chromatography (PE/EA (V/V)=30/1) to give the title compound as colorless oil (2.24 g, 9.07 mmol, 39.1%).

$^1$H NMR (400 Hz, CDCl$_3$) 7.451-7.412 (m, 1H), 7.323 (d, J=8.4 Hz, 1H), 7.277 (d, J=9.6 Hz, 1H), 6.047 (s, 1H), 4.170-4.111 (m, 2H), 4.085-4.007 (m, 2H).

Step 2: 1-(4-(1,3-dioxolan-2-yl)-3-fluorophenyl)-3-methylbutan-2-one

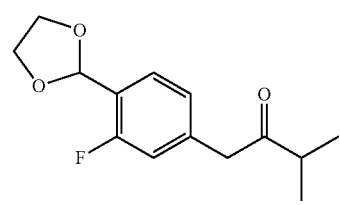 [SMILES: CC(C)C(=O)Cc1ccc(C2OCCO2)c(F)c1]

To a 50 mL two-neck flask were added 3-methylbutan-2-one (1.19 g, 13.79 mmol), 2-(4-bromo-2-fluorophenyl)-1,3-dioxolane (1.12 g, 4.60 mmol), Pd(dba)$_2$ (0.26 g, 0.46 mmol), X antphos (0.40 g, 0.69 mmol), sodium tert-butoxide (1.33 g, 13.80 mmol) and dioxane (12 mL). The mixture was stirred at 90 ěC for 4 h under nitrogen protection. The mixture was cooled to rt, and to the mixture were added EA (50 mL) and water (30 mL). The mixture was partitioned, and the aqueous layer was extracted with ethyl acetate (30 mL B 3). The combined organic layers were concentrated in vacuo, and the residue was purified by silica gel column chromatography (EA) to give the title compound as light yellow oil (1.16 g, 4.60 mmol, 100%).

MS (ESI, pos.ion) m/z: 253.1 [M+H]$^+$.

Step 3: 1-(4-(1,3-dioxolan-2-yl)-3-fluorophenyl)-3-methylbutan-2-amine

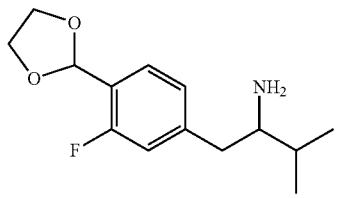 [SMILES: CC(C)C(N)Cc1ccc(C2OCCO2)c(F)c1]

To a 250 mL single-neck flask were added 1-(4-(1,3-dioxolan-2-yl)-3-fluorophenyl)-3-methylbutan-2-one (1.18 g, 4.68 mmol), MeOH (12 mL) and NH$_4$OAc (4.33 g, 56.2 mmol). The mixture was stirred at rt for 60 min, then cooled to 0 ěC and NaBH$_3$CN (0.882 g, 14.0 mmol) was added. Then the mixture was warmed to rt and stirred overnight. The mixture was concentrated, and to the residue was added water (30 mL). The mixture was extracted with EA (50 mL B 4). The combined organic layers were concentrated to give the title compound as light yellow oil (1.185 g, 4.678 mmol, 100%), which was used directly in the next step.

MS (ESI, pos.ion) m/z: 254.3 [M+H]$^+$.

Step 4: N-(1-(4-(1,3-dioxolan-2-yl)-3-fluorophenyl)-3-methylbutan-2-yl)formamide

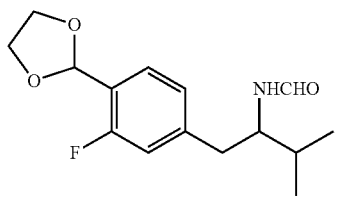

To a 100 mL single-neck flask were added 1-(4-(1,3-dioxolan-2-yl)-3-fluorophenyl)-3-methylbutan-2-amine (1.19 g, 4.68 mmol) and ethyl formate (30 mL). The mixture was heated to 70 ěC and stirred for 48 h. The mixture was cooled to rt and concentrated in vacuo. The residue was purified by silica gel column chromatography (PE/EA (V/V)=1/1) to give the title compound as yellow oil (0.89 g, 3.2 mmol, 68%).

MS (ESI, pos.ion) m/z: 282.2 [M+H]$^+$.

Step 5: N-(1-(3-fluoro-4-formyl phenyl)-3-methylbutan-2-yl)formamide

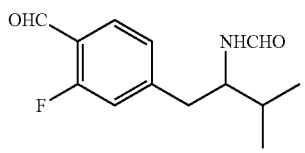

N-(1-(4-(1,3-dioxolan-2-yl)-3-fluorophenyl)-3-methylbutan-2-yl)formamide (0.13 g, 0.46 mmol) was dissolved in dioxane (4 mL), then the mixture was cooled to 0 ěC, and HCl (2 mL, 6 M) was added dropwise into the mixture. The resulting mixture was warmed to rt and stirred for 4 h. The mixture was cooled to 0 ěC, and to the mixture was added water (10 mL). The mixture was extracted with EA (15 mL), and the aqueous layer was extracted with EA (15 mL B 3). The combined organic layers were concentrated in vacuo, and the residue was purified by silica gel column chromatography (EA) to give the title compound as colorless oil (108 mg, 0.45 mmol, 100%).

MS (ESI, pos.ion) m/z: 238.1 [M+H]$^+$.

Step 6: 2-fluoro-4-(2-formamido-3-methylbutyl)benzoic Acid

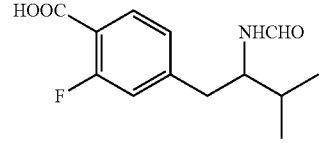

N-(1-(3-fluoro-4-formyl phenyl)-3-methylbutan-2-yl)formamide (843.6 mg, 3.56 mmol) was added into a 50 mL single-neck flask, then acetonitrile (10 mL), t-BuOH (2.6 g), CuBr$_2$ (156 mg) and H$_2$O (520 mg) were added. The mixture was stirred overnight at rt, and then concentrated. To the residue was added aqueous NaOH solution (1 M, 10 mL), and the mixture was washed with EA (10 mL B 2). The organic layer was washed with aqueous NaOH solution (1 M, 10 mL) once. The combined aqueous layers were adjusted with HCl (2 M) to pH=3-4, and there was a white solid precipitated out. The mixture was extracted with EA (20 mL B 4). The combined organic layers were concentrated in vacuo to give the title compound as a white solid (606 mg, 2.392 mmol, 67.30%).

MS (ESI, pos.ion) m/z: 254.3 [M+H]$^+$.

Step 7: Methyl 2-fluoro-4-(2-formamido-3-methylbutyl)benzoate

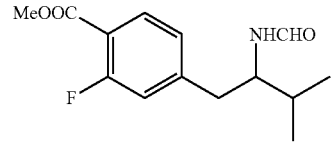

To a 50 mL single-neck flask were added 2-fluoro-4-(2-formamido-3-methylbutyl)benzoic acid (680 mg, 2.69 mmol), K$_2$CO$_3$ (740 mg, 5.36 mmol) and DMF (5 mL). The mixture was stirred to dissolve the solid, then CH$_3$I (571 mg, 4.02 mmol) was added. The mixture was stirred at rt for 2.5 h. To the mixture was added 10 mL of water; the resulting mixture was extracted with ethyl acetate (10 mL B 4); the combined organic layers were concentrated in vacuo, and the residue was purified by silica gel column chromatography (EA) to give the title compound as brown oil (0.52 g, 1.9 mmol, 72%).

MS (ESI, pos.ion) m/z: 268.2 [M+H]+.

Step 8: Methyl 8-fluoro-5-isopropyl-2,3-dioxo-3,5,6,10b-tetrahydro-2H-oxazolo[2,3-a]isoquinoline-9-carboxylate

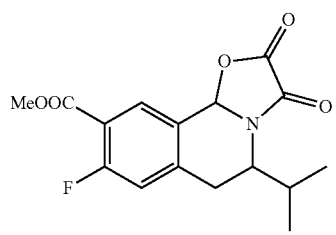 [SMILES: COC(=O)c1cc2c(cc1F)CC(C(C)C)N1C(=O)C(=O)OC21]

To a 100 mL single-neck flask were added methyl 2-fluoro-4-(2-formamido-3-methylbutyl)benzoate (0.27 g, 1.0 mmol), DCM (10 mL) and oxalyl chloride (190 mg, 1.50 mmol). The mixture was stirred at rt for 30 min. The mixture was cooled to −10 ěC, then FeCl₃ (260 mg, 1.62 mmol) was added. The mixture was warmed to rt and stirred overnight. To the mixture was added HCl (5 mL, 2 M), and the mixture was stirred for 30 min. The mixture was extracted with DCM (15 mL B3), and the combined organic layers were concentrated in vacuo to give the title compound as brownness oil (0.29 g, 0.91 mmol, 90%).

MS (ESI, pos.ion) m/z: 322.1 [M+H]+.

Step 9: Methyl 6-fluoro-3-isopropyl-3,4-dihydroisoquinoline-7-carboxylate

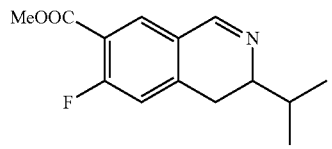 [SMILES: COC(=O)c1cc2c(cc1F)CC(C(C)C)N=C2]

Methyl 8-fluoro-5-isopropyl-2,3-dioxo-3,5,6,10b-tetrahydro-2H-oxazolo[2,3-a]isoquinoline-9-carboxylate (0.2914 g, 0.9069 mmol), MeOH (10 mL) and H₂SO₄ (0.4 mL) were added into a 50 mL single-neck flask. The mixture was heated to 75 ěC and stirred for 1.5 h, then stirred at rt for 10 h. The mixture was concentrated, and the residue was diluted with water (15 mL) and EA (15 mL). The mixture was partitioned, and the organic layer was washed with hydrochloric acid (2 M, 10 mL B 2). The combined aqueous layers were adjusted with ammonium hydroxide to pH=9-10, and the resulting mixture was extracted with EA (20 mL B 3). The combined organic layers were concentrated in vacuo to give the title compound as brown oil (150 mg, 0.60 mmol, 66.34%), which was directly used in the next step.

MS (ESI, pos.ion) m/z: 250.2 [M+1]+.

Step 10: Methyl 3-isopropyl-6-phenoxy-3,4-dihydroisoquinoline-7-carboxylate

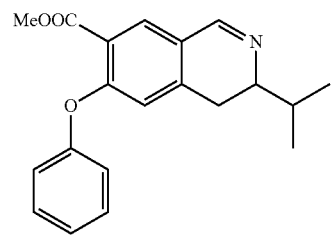 [SMILES: COC(=O)c1cc2c(cc1Oc1ccccc1)CC(C(C)C)N=C2]

Methyl 6-fluoro-3-isopropyl-3,4-dihydroisoquinoline-7-carboxylate (230 mg, 0.92 mmol) was added into a 50 mL two-neck flask, then K₂CO₃ (254 mg, 1.84 mmol), phenol (130 mg, 1.38 mmol), DMF (10 mL) and KI (5 mg) were added. The mixture was heated to 90 ěC and stirred for 5.5 h under nitrogen protection. The mixture was cooled to rt, and to the mixture were added EA (30 mL) and water (15 mL) in turn. The mixture was partitioned, and the aqueous layer was extracted with ethyl acetate (30 mL B 3). The combined organic layers were washed with saturated brine (15 mL B 3), dried over anhydrous sodium sulfate, and concentrated in vacuo. The residue was purified by silica gel column chromatography (EA) to give the title compound as brown oil (240 mg, 0.74 mmol, 80%).

MS (ESI, pos.ion) m/z: 324.1 [M+H]+.

Step 11: 3-tert-butyl 10-methyl 6-isopropyl-2-oxo-9-phenoxy-2,6,7,11b-tetrahydro-1H-pyrido[2,1-a]isoquinoline-3,10-dicarboxylate

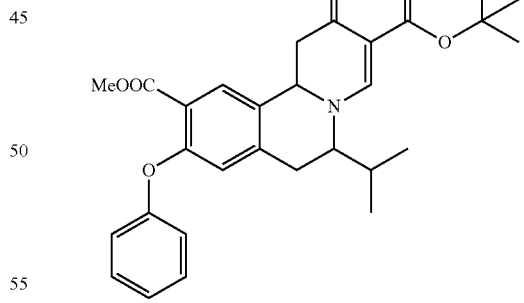

tert-Butyl 2-((dimethyl amino)methyl ene)-3-oxobutanoate (0.46 g, 2.13 mmol), methyl 3-isopropyl-6-phenoxy-3,4-dihydroisoquinoline-7-carboxylate (345 mg, 1.067 mmol) and t-BuOH (10 mL) were added into a 100 mL single-neck flask, then the mixture was heated to 100 ěC under nigrogen protection and stirred for 6 days. The mixture was concentrated in vacuo, and the residue was purified by thin-layer chromatography (PE/acetone (V/V)=2/1) to give the title compound as brown oil (0.5244 g, 1.07 mmol, 99.99%).

MS (ESI, pos.ion) m/z: 492.1 [M+H]+.

Step 12: 6-isopropyl-10-(methoxycarbonyl)-2-oxo-9-phenoxy-6,7-dihydro-2H-pyrido[2,1-a]isoquinoline-3-carboxylic Acid

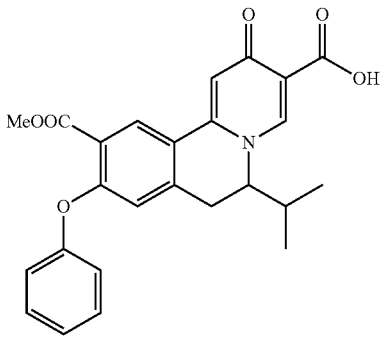 [SMILES: COC(=O)c1cc2c(cc1Oc1ccccc1)CC(C(C)C)n1cc(C(=O)O)c(=O)cc1-2]

3-tert-Butyl 10-methyl 6-isopropyl-2-oxo-9-phenoxy-2,6,7,11b-tetrahydro-1H-pyrido[2,1-a]isoquinoline-3,10-dicarboxylate (524.4 mg, 1.07 mmol) was added into a 100 mL single-neck flask, then dimethoxyethane (20 mL) was added to dissolved the reagent, and chloranil (393 mg, 1.5985 mmol) was added. The mixture was heated to 90 ẽC and stirred for 3.5 hour under nitrogen protection. The reaction mixture was concentrated in vacuo. The residue was purified by thin-layer chromatography (DCM/MeOH (V/V)=10/1) to give the title compound as a light yellow solid (215 mg, 0.50 mmol, 46.50%).

MS (ESI, pos.ion) m/z: 434.1 [M+H]$^+$;
$^1$H NMR (400 MHz, CDCl$_3$) 15.837 (b, 1H), 8.487 (s, 1H), 8.363 (s, 1H), 7.470-7.431 (m, 2H), 7.261-7.221 (m, 2H), 7.099 (d, J=8.0 Hz, 2H), 6.802 (s, 1H), 4.103-3.874 (m, 4H), 3.404-3.295 (m, 1H), 3.154-2.990 (m, 1H), 1.807-1.704 (m, 1H), 0.917 (d, J=6.4 Hz, 3H), 0.849 (d, J=6.4 Hz, 3H).

Example 41: 6-isopropyl-10-(methoxycarbonyl)-9-((R)-3-methoxypyrrolidin-1-yl)-2-oxo-6,7-dihydro-2H-pyrido[2,1-a]isoquinoline-3-carboxylic Acid

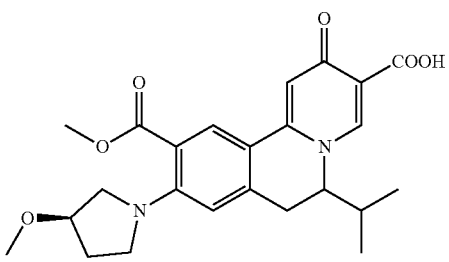 [SMILES: COC(=O)c1cc2c(cc1N1CC[C@@H](OC)C1)CC(C(C)C)n1cc(C(=O)O)c(=O)cc1-2]

Step 1: Methyl 3-isopropyl-6-((R)-3-methoxypyrrolidin-1-yl)-3,4-dihydroisoquinoline-7-carboxylate

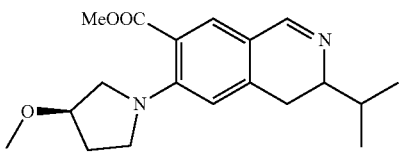 [SMILES: COC(=O)c1cc2c(cc1N1CC[C@@H](OC)C1)CC(C(C)C)N=C2]

Methyl 6-fluoro-3-isopropyl-3,4-dihydroisoquinoline-7-carboxylate (210 mg, 0.84 mmol), (3S)-3-methoxypyrrole (173 mg, 1.26 mmol), K$_2$CO$_3$ (348 mg, 2.52 mmol), KI (5 mg) and DMSO (10 mL) was added into a 50 mL two-neck flask. The mixture was heated to 100 ẽC and stirred for 3.5 h under nitrogen protection. The mixture was cooled to rt, and to the mixture was added water (15 mL); the resulting mixture was extracted with EA (20 mL B 4); the combined organic layers were washed with saturated brine (15 mL B 3), dried over anhydrous sodium sulfate, and concentrated in vacuo; the residue was purified by silica gel column chromatography (EA) to give the title compound as brown oil (0.25 g, 0.75 mmol, 89.5%).

MS (ESI, pos.ion) m/z: 331.2 [M+H]$^+$.

Step 2: 3-tert-butyl 10-methyl 6-isopropyl-9-((R)-3-methoxypyrrolidin-1-yl)-2-oxo-2,6,7,11b-tetrahydro-1H-pyrido[2,1-a]isoquinoline-3,10-dicarboxylate

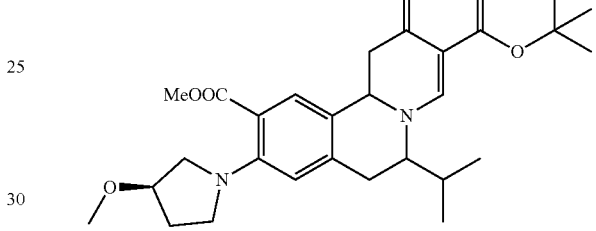

Methyl 3-isopropyl-6-((R)-3-methoxypyrrolidin-1-yl)-3,4-dihydroisoquinoline-7-carboxylate (0.249 g, 0.754 mmol), methyl 3-isopropyl-6-phenoxy-3,4-dihydroisoquinoline-7-carboxylate (0.321 g, 1.51 mmol) and t-BuOH (10 mL) were added into a 50 mL single-neck flask, then the mixture was heated to 95 ẽC under nigrogen protection and stirred for 5 days. The reaction mixture was concentrated; and the residue was purified by thin-layer chromatography (PE/acetone (V/V)=1/1) to give the title compound as brown oil (0.376 g, 0.75 mmol, 100%).

MS (ESI, pos.ion) m/z: 499.5 [M+H]$^+$.

Step 3: 6-isopropyl-10-(methoxycarbonyl)-9-((R)-3-methoxypyrrolidin-1-yl)-2-oxo-6,7-dihydro-2H-pyrido[2,1-a]isoquinoline-3-carboxylic Acid

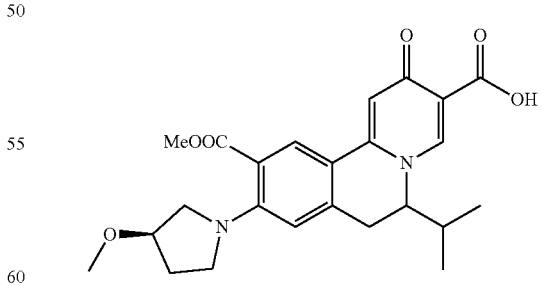

To a 100 mL single-neck flask were added 3-tert-butyl 10-methyl 6-isopropyl-9-((R)-3-methoxypyrrolidin-1-yl)-2-oxo-2,6,7,11b-tetrahydro-1H-pyrido[2,1-a]isoquinoline-3,10-dicarboxylate (0.53 g, 1.07 mmol), dimethoxyethane (15 mL) and chloranil (394 mg, 1.60 mmol). The mixture was stirred at 90 ẽC for 4 h. The reaction mixture was cooled to rt, and concentrated in vacuo. The residue was purified by silica gel column chromatography (DCM/MeOH (V/V)=15/1) to give the title compound as a light yellow solid (175 mg, 0.40 mmol, 37.11%).

MS (ESI, pos.ion) m/z: 441.3 [M+H]⁺;
¹H NMR (400 MHz, CDCl₃) 16.273 (b, 1H), 8.422 (s, 1H), 8.019 (s, 1H), 7.050 (d, J=11.2 Hz, 1H), 6.614 (d, J=2.2 Hz, 1H), 4.124-4.039 (m, 1H), 3.951 (s, 3H), 3.885-3.825 (m, 1H), 3.689-3.626 (m, 1H), 3.589-3.509 (m, 1H), 3.450-3.404 (m, 1H), 3.370-3.270 (m, 4H), 3.152-2.994 (m, 2H), 2.257-2.014 (m, 2H), 1.864-1.756 (m, 1H), 0.982-0.936 (m, 3H), 0.822 (d, J=8 Hz, 3H).

Example 42: 6-isopropyl-10-(methoxycarbonyl)-9-((S)-3-methoxypyrrolidin-1-yl)-2-oxo-6,7-dihydro-2H-pyrido[2,1-a]isoquinoline-3-carboxylic Acid

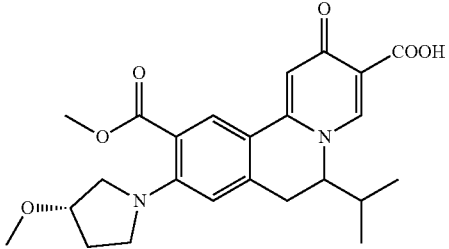 [SMILES: COC(=O)c1cc2c(cc1N1CC[C@H](OC)C1)CC(C(C)C)n1cc(C(=O)O)c(=O)cc1-2]

The title compound was prepared according to the synthetic method of example 41 by using methyl 6-fluoro-3-isopropyl-3,4-dihydroisoquinoline-7-carboxylate (300 mg, 1.2 mmol) and (S))-3-methoxypyrrolidine (173 mg, 1.26 mmol) as raw materials to give an off-white solid (0.20 g, 0.45 mmol).

MS (ESI, pos.ion) m/z: 441.1 [M+H]⁺;
¹H NMR (400 MHz, CDCl₃) 8.450 (s, 1H), 7.285 (s, 1H), 7.269 (d, J=11.6 Hz, 1H), 6.615 (s, 1H), 4.151-4.028 (m, 1H), 4.022-3.831 (m, 4H), 3.665-3.631 (m, 1H), 3.568-3.532 (m, 1H), 3.393-3.263 (m, 4H), 3.202-3.006 (m, 2H), 2.296-1.230 (m, 4H), 0.956-0.936 (d, J=9.2 Hz, 3H), 0.809 (d, J=0.8 Hz, 3H).

Example 43: 9-(3,3-difluoropyrrolidin-1-yl)-6-isopropyl-10-(methoxycarbonyl)-2-oxo-6,7-dihydro-2H-pyrido[2,1-a]isoquinoline-3-carboxylic Acid

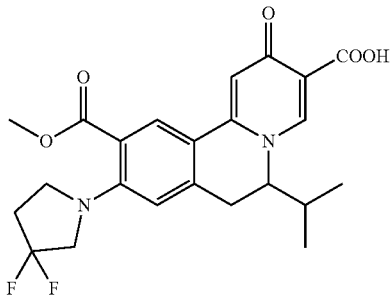 [SMILES: COC(=O)c1cc2c(cc1N1CCC(F)(F)C1)CC(C(C)C)n1cc(C(=O)O)c(=O)cc1-2]

The title compound was prepared according to the synthetic method of example 41 by using methyl 6-fluoro-3-isopropyl-3,4-dihydroisoquinoline-7-carboxylate (300 mg, 1.2 mmol) and 3,3-difluoropyrrolidine hydrochloric acid (259 mg, 1.80 mmol) as raw materials to give an off-white solid (0.25 g, 0.731 mmol).

MS (ESI, pos.ion) m/z: 447.1 [M+H]⁺;
¹H NMR (400 MHz, CDCl₃) 16.066 (b, 1H), 8.440 (d, J=4.4 Hz, 1H), 8.093 (d, J=4.8 Hz, 1H), 7.090 (d, J=14.4 Hz, 1H), 6.640 (s, 1H), 3.979 (s, 3H), 3.935-3.786 (m, 1H), 3.764-3.497 (m, 4H), 3.445-3.320 (m, 1H), 3.229-3.094 (m, 1H), 2.598-2.444 (m, 2H), 1.847-1.729 (m, 1H), 0.971-0.941 (d, J=4.8 Hz, 3H), 0.841 (d, J=5.2 Hz, 3H).

Example 44: 9-((S)-3-hydroxypyrrolidin-1-yl)-6-isopropyl-10-(methoxycarbonyl)-2-oxo-6,7-dihydro-2H-pyrido[2,1-a]isoquinoline-3-carboxylic Acid

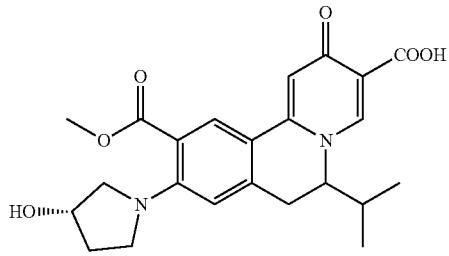 [SMILES: COC(=O)c1cc2c(cc1N1CC[C@H](O)C1)CC(C(C)C)n1cc(C(=O)O)c(=O)cc1-2]

Step 1: 9-((S)-3-(benzyloxy) pyrrolidin-1-yl)-6-isopropropyl-10-(methoxycarbonyl)-2-oxo-6,7-dihydro-2H-pyrido[2,1-a]isoquinoline-3-carboxylic Acid

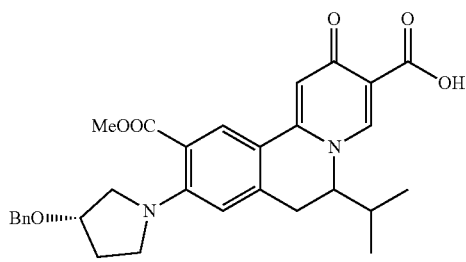 [SMILES: COC(=O)c1cc2c(cc1N1CC[C@H](OCc3ccccc3)C1)CC(C(C)C)n1cc(C(=O)O)c(=O)cc1-2]

The title compound was prepared according to the synthetic method of example 41 by using methyl 6-fluoro-3-isopropyl-3,4-dihydroisoquinoline-7-carboxylate (200 mg, 0.80 mmol) and (S)-3-(benzyloxy)pyrrolidine (213 mg, 1.20 mmol) as raw materials to give brown oil (0.32 g, 0.79 mmol, 98%).

MS (ESI, pos.ion) m/z: 517.2 [M+H]⁺.

Step 2: 9-((S)-3-hydroxypyrrolidin-1-yl)-6-isopropyl-10-(methoxycarbonyl)-2-oxo-6,7-dihydro-2H-pyrido[2,1-a]isoquinoline-3-carboxylic Acid

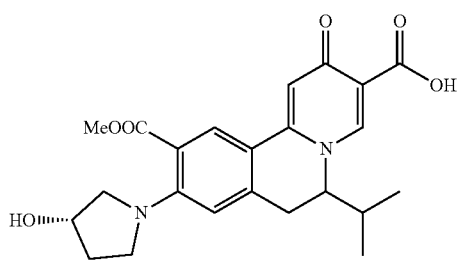 [SMILES: COC(=O)c1cc2c(cc1N1CC[C@H](O)C1)CC(C(C)C)n1cc(C(=O)O)c(=O)cc1-2]

9-((S)-3-(Benzyloxy) pyrrolidin-1-yl)-6-isopropyl-10-(methoxycarbonyl)-2-oxo-6,7-dihydro-2H-pyrido[2,1-a]isoquinoline-3-carboxylic acid (200 mg, 0.39 mmol) was added into a 100 mL single-neck flask, then MeOH (20 mL) and Pd/C (40 mg) was added. The mixture was degassed and filled with nitrogen for three times, then stirred at 65 ẽC for 5 h in a hydrogen atmosphere. The reaction was stopped, and the mixture was filtered. The filter cake was washed with DCM, and the filtrate was concentrated. The residue was purified by silica gel column chromatography (DCM/MeOH (V/V)=8/1) to give the title compound as a yellow solid (100 mg, 0.23 mmol, 60%).

MS (ESI, pos.ion) m/z: 427.1 [M+H]$^+$;

$^1$H NMR (400 MHz, CDCl$_3$) 16.2996 (b, 1H), 8.411 (d, J=4.4 Hz, 1H), 8.017 (d, J=4.8 Hz, 1H), 7.043 (d, J=14.4 Hz, 1H), 6.634 (s, 1H), 4.634 (s, 1H), 3.956 (d, J=4.4 Hz, 3H), 3.904-3.825 (m, 1H), 3.895-3.619 (m, 3H), 3.462-3.400 (m, 1H), 3.371-3.303 (m, 1H), 3.181-2.958 (m, 2H), 2.254-2.068 (m, 2H), 1.859-1.737 (m, 1H), 0.987-0.941 (m, 3H), 0.827 (d, J=6.4 Hz, 3H).

Example 45: 9-((S)-3-(2,2-difluoroethoxy)pyrrolidin-1-yl)-6-isopropyl-10-(methoxycarbonyl)-2-oxo-6,7-dihydro-2H-pyrido[2,1-a]isoquinoline-3-carboxylic Acid

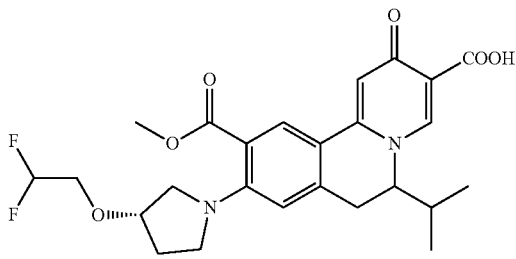 [SMILES: COC(=O)c1cc2c(cc1N1CC[C@H](OCC(F)F)C1)CC(C(C)C)n1cc(C(=O)O)c(=O)cc1-2]

The title compound was prepared according to the synthetic method of example 41 by using methyl 6-fluoro-3-isopropyl-3,4-dihydroisoquinoline-7-carboxylate (300 mg, 1.2 mmol) and (S)-3-(2,2-difluoroethoxy)pyrrolidine trifluoroacetate (0.638 g, 2.41 mmol) as raw materials to give an off-white solid (30 mg, 0.879 mmol).

MS (ESI, pos.ion) m/z: 490.9 [M+H]$^+$;

$^1$H NMR (400 MHz, CDCl$_3$) 8.443 (s, 1H), 8.046 (s, 1H), 7.089 (d, J=12.4 Hz, 1H), 6.622 (d, J=3.2 Hz, 1H), 5.989-5.771 (m, 2H), 4.340-4.264 (m, 1H), 9.962 (d, J=2.4 Hz, 3H), 3.925-3.894 (m, 1H), 3.751-3.686 (m, 2H), 3.636-3.549 (m, 1H), 3.441-3.413 (m, 1H), 3.374-3.315 (m, 1H), 3.199-3.085 (m, 2H), 2.207-2.265 (m, 2H), 2.115-2.026 (m, 1H), 0.989-0.948 (m, 3H), 0.832 (d, J=4.0 Hz, 3H).

Example 46: 9-((S)-3-isobutoxypyrrolidin-1-yl)-6-isopropyl-10-(methoxycarbonyl)-2-oxo-6,7-dihydro-2H-pyrido[2,1-a]isoquinoline-3-carboxylic Acid

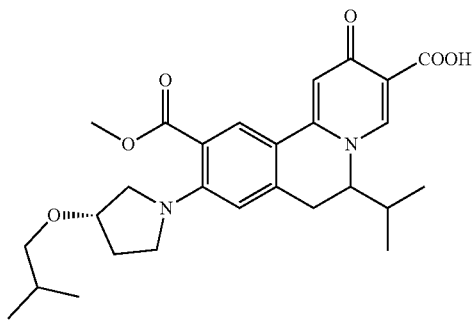 [SMILES: COC(=O)c1cc2c(cc1N1CC[C@H](OCC(C)C)C1)CC(C(C)C)n1cc(C(=O)O)c(=O)cc1-2]

The title compound was prepared according to the synthetic method of example 41 by using methyl 6-fluoro-3-isopropyl-3,4-dihydroisoquinoline-7-carboxylate (300 mg, 1.2 mmol) and (S)-3-isobutoxypyrrolidine trifluoroacetate (0.779 g, 3.20 mmol) as raw materials to give an off-white solid (62 mg, 0.1285 mmol).

MS (ESI, pos.ion) m/z: 483.1 [M+H]$^+$;

$^1$H NMR (400 MHz, CDCl$_3$) 8.428 (s, 1H), 8.021 (s, 1H), 7.077 (d, J=10.0 Hz, 1H), 6.612 (s, 1H), 4.203-4.106 (m, 1H), 4.056-3.787 (m, 4H), 3.714-3.543 (m, 2H), 3.459-3.291 (m, 2H), 3.255-3.050 (m, 3H), 2.301-2.015 (m, 3H), 1.891-1.713 (m, 2H), 1.036-0.823 (m, 12H).

Example 47: 9-((S)-3-acetoxypyrrolidin-1-yl)-6-isopropyl-10-(methoxycarbonyl)-2-oxo-6,7-dihydro-2H-pyrido[2,1-a]isoquinoline-3-carboxylic Acid

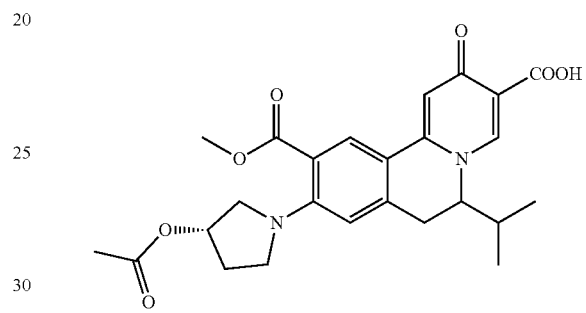

The title compound was prepared according to the synthetic method of example 41 by using methyl 6-fluoro-3-isopropyl-3,4-dihydroisoquinoline-7-carboxylate (300 mg, 1.2 mmol) and (S)-pyrrolidin-3-yl acetate trifluoroacetate (0.93 g, 3.20 mmol) as raw materials to give an off-white solid (150 mg, 0.32 mmol).

MS (ESI, pos.ion) m/z: 469.2 [M+H]$^+$;

$^1$H NMR (400 MHz, CDCl$_3$) 8.438 (s, 1H), 8.042 (s, 1H), 7.072 (d, J=13.2 Hz, 1H), 6.622 (d, J=4.4 Hz, 1H), 5.435-5.402 (m, 1H), 3.962 (d, J=2.8 Hz, 3H), 3.919-3.819 (m, 2H), 3.801-3.759 (m, 1H), 3.717-3.602 (m, 1H), 3.440-3.3375 (m, 2H), 3.271-3.241 (m, 1H), 3.164-3.093 (m, 1H), 2.298-2.204 (m, 2H), 2.068 (d, J=13.2 Hz, 3H), 0.993-0.941 (m, 3H), 0.832 (d, J=6.8 Hz, 3H).

Example 48: 10-acetyl-6-isopropyl-9-((S)-3-methoxypyrrolidin-1-yl)-2-oxo-6,7-dihydro-2H-pyrido[2,1-a]isoquinoline-3-carboxylic Acid

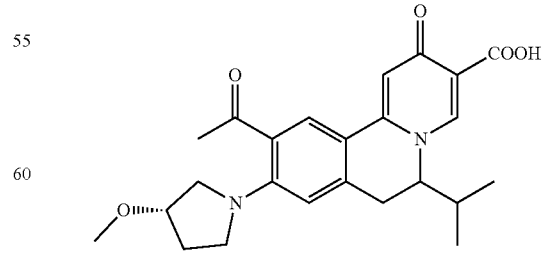

The title compound was prepared according to the synthetic method of step 11 to step 12 in example 30 by using ethyl 10-acetyl-6-isopropyl-2-oxo-9-(((trifluoromethyl)

sulfonyl)oxy)-6,7-dihydro-2H-pyrido[2,1-a]isoquinoline-3-carboxylate (250 mg, 0.5 mmol) and (S)-(+)-3-methoxypyrrolidine hydrochloride (0.137 g, 1.0 mmol) as raw materials to give a yellow solid (0.110 g).

MS (ESI, pos.ion) m/z: 425.2 [M+H]+;

$^1$H NMR (400 MHz, CDCl$_3$) 16.18 (s, 1H), 8.43 (s, 1H), 7.92 (d, J=1.9 Hz, 1H), 7.05 (d, J=12.9 Hz, 1H), 6.64 (d, J=2.3 Hz, 1H), 4.09 (s, 1H), 3.92-3.83 (m, 1H), 3.52 (ddd, J=20.3, 14.0, 5.5 Hz, 2H), 3.35 (d, J=18.5 Hz, 4H), 3.14 (dd, J=16.1, 5.5 Hz, 1H), 2.97-2.74 (m, 1H), 2.68 (d, J=3.7 Hz, 3H), 2.31-1.97 (m, 3H), 1.81 (d, J=6.8 Hz, 1H), 0.97 (dd, J=15.8, 6.6 Hz, 3H), 0.89-0.77 (m, 3H).

Example 49: 10-acetyl-6-isopropyl-9-((R)-3-methoxypyrrolidin-1-yl)-2-oxo-6,7-dihydro-2H-pyrido[2,1-a]isoquinoline-3-carboxylic Acid

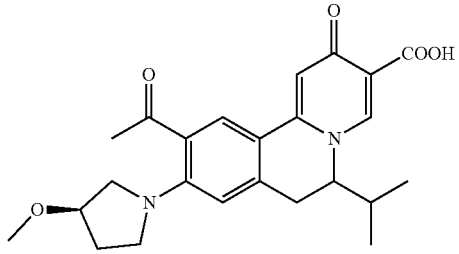 [SMILES: CO[C@@H]1CCN(c2cc3c(cc2C(C)=O)-c2cc(=O)c(C(=O)O)cn2C(C(C)C)C3)C1]

The title compound was prepared according to the synthetic method of step 11 to step 12 in example 30 by using ethyl 10-acetyl-6-isopropyl-2-oxo-9-(((trifluoromethyl)sulfonyl)oxy)-6,7-dihydro-2H-pyrido[2,1-a]isoquinoline-3-carboxylate (250 mg, 0.5 mmol) and (R)-(+)-3-methoxypyrrolidine hydrochloride (0.137 g, 1.0 mmol) as raw materials to give a yellow solid (0.107 g).

MS (ESI, pos.ion) m/z: 425.2[M+H]+;

$^1$H NMR (400 MHz, CDCl$_3$) 16.18 (s, 1H), 8.43 (s, 1H), 7.92 (d, J=1.9 Hz, 1H), 7.05 (d, J=12.9 Hz, 1H), 6.64 (d, J=2.2 Hz, 1H), 4.09 (s, 1H), 3.92-3.82 (m, 1H), 3.37 (s, 3H), 3.32 (s, 2H), 3.14 (dd, J=15.2, 5.8 Hz, 1H), 2.92 (d, J=11.8 Hz, 1H), 2.80 (d, J=11.8 Hz, 1H), 2.68 (d, J=3.7 Hz, 3H), 2.33-1.97 (m, 3H), 1.90-1.72 (m, 1H), 0.99-0.95 (m, 3H), 0.86-0.77 (m, 3H).

Example 50: 10-acetyl-6-isopropyl-9-morpholino-2-oxo-6,7-dihydro-2H-pyrido[2,1-a]isoquinoline-3-carboxylic Acid

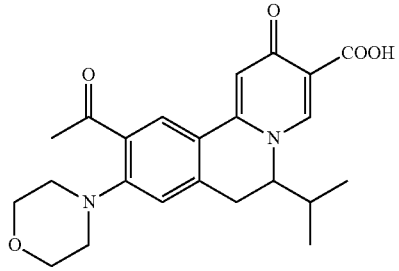 [SMILES: CC(=O)c1cc2c(cc1N1CCOCC1)CC(C(C)C)n1cc(C(=O)O)c(=O)cc1-2]

The title compound was prepared according to the synthetic method of step 11 to step 12 in example 30 by using ethyl 10-acetyl-6-isopropyl-2-oxo-9-(((trifluoromethyl)sulfonyl)oxy)-6,7-dihydro-2H-pyrido[2,1-a]isoquinoline-3-carboxylate (250 mg, 0.5 mmol) and morpholine (0.065 g, 0.74 mmol) as raw materials to give a yellow solid (0.030 g).

MS (ESI, pos.ion) m/z: 411.19 [M+H]+;

$^1$H NMR (400 MHz, CDCl$_3$) 15.90 (s, 1H), 8.44 (s, 1H), 7.82 (s, 1H), 7.10 (s, 1H), 6.88 (s, 1H), 3.97-3.81 (m, 5H), 3.38 (dd, J=16.2, 4.6 Hz, 1H), 3.22-3.14 (m, 1H), 3.14-3.07 (m, 3H), 2.68 (s, 3H), 1.77 (dd, J=16.5, 6.7 Hz, 1H), 0.97 (d, J=6.6 Hz, 3H), 0.83 (d, J=6.7 Hz, 3H).

Example 51: 10-acetyl-6-isopropyl-9-(4-(2-methoxyethyl)piperazin-1-yl)-2-oxo-6,7-dihydro-2H-pyrido[2,1-a]isoquinoline-3-carboxylic Acid

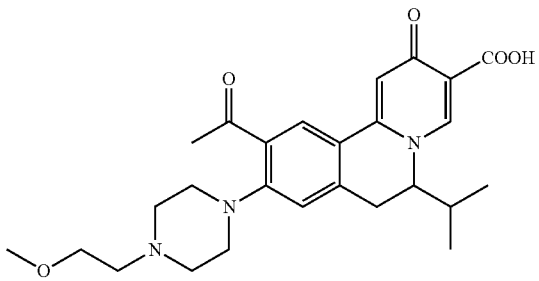 [SMILES: COCCN1CCN(c2cc3c(cc2C(C)=O)-c2cc(=O)c(C(=O)O)cn2C(C(C)C)C3)CC1]

The title compound was prepared according to the synthetic method of step 11 to step 12 in example 30 by using ethyl 10-acetyl-6-isopropyl-2-oxo-9-(((trifluoromethyl)sulfonyl)oxy)-6,7-dihydro-2H-pyrido[2,1-a]isoquinoline-3-carboxylate (250 mg, 0.5 mmol) and 1-(2-methoxyethyl)piperazine (0.165 g, 1.14 mmol) as raw materials to give a yellow solid (65 mg).

MS (ESI, pos.ion) m/z: 468.25 [M+H]+;

$^1$H NMR (400 MHz, CDCl$_3$) 16.02 (s, 1H), 8.47 (s, 1H), 7.82 (s, 1H), 7.10 (s, 1H), 6.88 (s, 1H), 3.94 (dd, J=9.6, 4.4 Hz, 1H), 3.59 (t, J=4.9 Hz, 2H), 3.38 (d, J=6.1 Hz, 4H), 3.21 (d, J=5.1 Hz, 4H), 2.81-2.69 (m, 5H), 2.67 (s, 3H), 1.86-1.69 (m, 2H), 1.27 (d, J=1.5 Hz, 1H), 0.97 (d, J=6.6 Hz, 3H), 0.83 (d, J=6.7 Hz, 3H).

Example 52: 10-acetyl-9-(4-hydroxypiperidin-1-yl)-6-isopropyl-2-oxo-6,7-dihydro-2H-pyrido[2,1-a]isoquinoline-3-carboxylic Acid

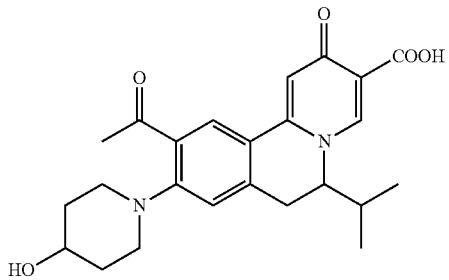 [SMILES: CC(=O)c1cc2c(cc1N1CCC(O)CC1)CC(C(C)C)n1cc(C(=O)O)c(=O)cc1-2]

The title compound was prepared according to the synthetic method of step 11 to step 12 in example 30 by using ethyl 10-acetyl-6-isopropyl-2-oxo-9-(((trifluoromethyl)sulfonyl)oxy)-6,7-dihydro-2H-pyrido[2,1-a]isoquinoline-3- carboxylate (550 mg, 1.1 mmol) and piperidin-4-ol (65 m g, 1.6 mmol) as raw materials to give a yellow solid (133 mg).

MS (ESI, pos.ion) m/z: 425.2066 [M+H]$^+$;

$^1$H NMR (400 MHz, DMSO-d$_6$) 8.77 (s, 1H), 7.94 (s, 1H), 7.30 (s, 1H), 7.15 (s, 1H), 4.78 (d, J=3.9 Hz, 1H), 4.47 (d, J=5.8 Hz, 1H), 3.67 (d, J=3.6 Hz, 1H), 3.34 (s, 1H), 3.26 (d, J=8.1 Hz, 2H), 3.17 (d, J=5.1 Hz, 1H), 2.92 (t, J=10.9 Hz, 2H), 2.60 (s, 3H), 1.84 (d, J=10.6 Hz, 2H), 1.64-1.43 (m, 3H), 0.89 (d, J=6.6 Hz, 3H), 0.70 (d, J=6.6 Hz, 3H).

Example 53: 6-isopropyl-9-(3-methoxypropoxy)-2-oxo-10-(4,4,4-trifluorobutanoyl)-6,7-dihydro-2H-pyrido[2,1-a]isoquinoline-3-carboxylic Acid

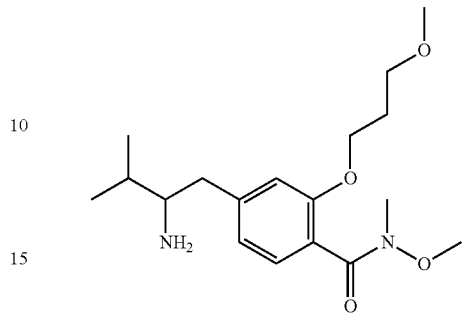

Step 1: N-methoxy-2-(3-methoxypropoxy)-N-methyl-4-(3-methyl-2-oxobutyl)benzamide

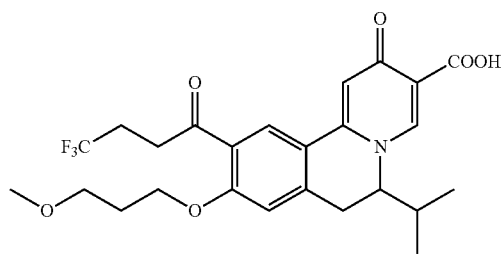 [SMILES: COCCCOc1cc2c(cc1C(=O)CCC(F)(F)F)-c1cc(=O)c(C(=O)O)cn1C(C(C)C)C2]

To a 50 mL single-neck flask were added 2-(3-methoxypropoxy)-4-(3-methyl-2-oxobutyl)benzoic acid (1 g, 3.398 mmol), DMF (6 mL), DIPEA (1.78 mL, 10.2 mmol), N,O-dimethylhydroxylamine hydrochloride (500 mg, 5.126 mmol) and HATU (2 g, 5.2598 mmol). The mixture was stirred at rt for 24 h. The mixture was adjusted with hydrochloric acid (1 M) to pH=5, and the resulting mixture was extracted with ethyl acetate (3 B 20 mL); the combined organic layers were dried over anydrous sodium sulfate and filtered; the filtrate was concentrated in vacuo, and the residue was purified by silica gel column chromatography (PE/EA (V/V)=1/1) to give the title compound as colorless oil (200 mg, 0.60 mmol, 17.45%).

MS (ESI, pos.ion) m/z: 338.3 [M+H]$^+$.

Step 2: 4-(2-amino-3-methylbutyl)-N-methoxy-2-(3-methoxypropoxy)-N-methylbenzamide

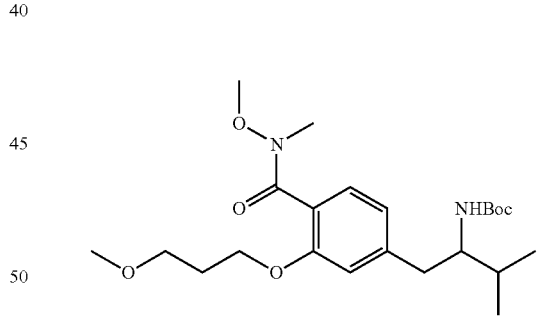

To a 100 mL single-neck flask were added methanol (45 mL), N-methoxy-2-(3-methoxypropoxy)-N-methyl-4-(3-methyl-2-oxobutyl)benzamide (4.5 g, 13 mmol) and ammonium acetate (7.2 g, 93 mmol). The mixture was stirred at rt for 1 h, then cooled to 0 ěC, and sodium cyanoborohydride (1.7 g, 27 mmol) was added slowly. The resulting mixture was warmed to rt and stirred for 24 h. The reaction mixture was concentrated by rotary evaporation to remove the methanol; to the residue was added saturated aqueous sodium bicarbonate solution (50 mL) to quenche the reaction, then the mixture was extracted with ethyl acetate (3B 50 mL); the combined organic layers were dried over anydrous sodium sulfate and filtered; the filtrate was concentrated in vacuo to give the title compound as colorless oil (4 g, 11.82 mmol, 89%).

MS (ESI, pos.ion) m/z: 339.1 [M+H]$^+$.

Step 3: Tert-butyl (1-(4-(methoxy(methyl)carbamoyl)-3-(3-methoxypropoxy)phenyl)-3-methylbutan-2-yl)carbamate

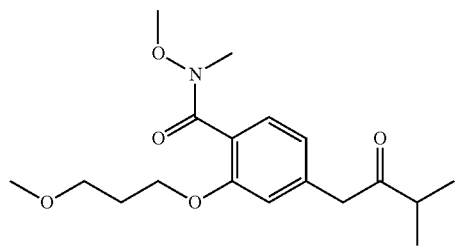 [SMILES: COCCCOc1cc(CC(=O)C(C)C)ccc1C(=O)N(C)OC]

To a 250 mL single-neck flask were added 4-(2-amino-3-methylbutyl)-N-methoxy-2-(3-methoxypropoxy)-N-methylbenzamide (4 g, 11.82 mmol), TEA (3.7 mL, 27 mmol) and DCM (50 mL) in turn, then Boc$_2$O (5.8 g, 27 mmol) was added dropwise. The mixture was stirred at rt for 2 h. The reaction mixture was concentrated by rotary evaporation to remove the solvent, and to the residue was added hydrochloric acid (1 M) to pH=5; the resulting mixture was extracted with ethyl acetate (3 B 20 mL), and the combined organic layers were dried over anydrous sodium sulfate and filtered. The filtrate was concentrated in vacuo, and the residue was purified by silica gel column chromatography (PE/EA (V/V)=1/1) to give the title compound as colorless oil (3.2 g, 7.3 mmol, 62%).

¹H NMR (600 MHz, CDCl₃) 7.20 (d, J=7.3 Hz, 1H), 6.83-6.77 (m, 2H), 4.37 (d, J=9.3 Hz, 1H), 4.10 (t, J=6.2 Hz, 2H), 3.76 (s, 1H), 3.67-3.44 (m, 5H), 3.39-3.20 (m, 6H), 2.93 (q, J=7.3 Hz, 1H), 2.83-2.76 (m, 1H), 2.72-2.65 (m, 1H), 2.06-2.01 (m, 1H), 1.79-1.71 (m, 1H), 1.40 (s, 9H), 0.98 (d, J=6.8 Hz, 3H), 0.93 (d, J=6.8 Hz, 3H).

Step 4: Tert-butyl (1-(3-(3-methoxypropoxy)-4-(4,4,4-trifluorobutanoyl)phenyl)-3-methylbutan-2-yl)carbamate

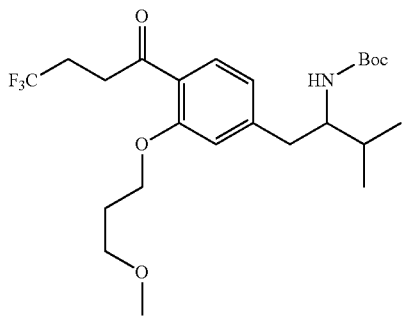 [SMILES: COCCCOc1cc(CC(NC(=O)OC(C)(C)C)C(C)C)ccc1C(=O)CCC(F)(F)F]

To a dried 50 mL three-neck flask equipped with thermometer and reflux condenser were added magnesium powder (0.3 g, 10 mmol) and THF (8 mL), then a grain of iodine was added, and 3-bromo-1,1,1-trifluoropropane (2 mL) was added. After addition, the mixture was heated to 70 ěC and stirred for 2 h, then cooled to rt. To another 50 mL two-neck flask were added tert-butyl (1-(4-(methoxy(methyl)carbamoyl)-3-(3-methoxypropoxy)phenyl)-3-methylbutan-2-yl)carbamate (2 g, 4.560 mmol) and THF (10 mL), and the mixture was degassed and filled with nitrogen for three times, then cooled to 0 ěC; to the mixture was added dropwised the Grignard reagent prepared above. The resulting mixture was stirred at 0 ěC for 1 h, then warmed to rt and stirred for 4 h. The reaction was quenched with saturated aqueous ammonium chloride solution (20 mL), and the mixture was extracted with ethyl acetate (3 B 20 mL); the combined organic layers were dried over anydrous sodium sulfate and filtered; the filtrate was concentrated in vacuo, and the residue was purified by silica gel column chromatography (PE/EA (V/V)=10/1) to give the title compound as colorless oil (200 mg, 0.4206 mmol, 9.224%).
MS (ESI, pos.ion) m/z: 499.15 [M+Na]⁺.

Step 5: 1-(4-(2-amino-3-methylbutyl)-2-(3-methoxypropoxy)phenyl)-4,4,4-trifluorobutan-1-one

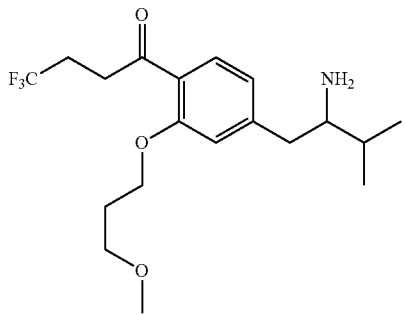 [SMILES: COCCCOc1cc(CC(N)C(C)C)ccc1C(=O)CCC(F)(F)F]

To a 100 mL single-neck flask were added tert-butyl (1-(3-(3-methoxypropoxy)-4-(4,4,4-trifluorobutanoyl)phenyl)-3-methylbutan-2-yl)carbamate (400 mg, 0.8412 mmol), DCM (2 mL) and TFA (2 mL). The mixture was stirred at rt for 4 h. The reaction mixture was concentrated by rotary evaporation; to the residue was added saturated aqueous sodium bicarbonate solution to adjust the pH=8, then the mixture was extracted with ethyl acetate (3 mL B 20). The combined organic layers were dried over anydrous sodium sulfate and filtered. The filtrate was concentrated in vacuo to give the title compound as colorless oil (320 mg, 0.84 mmol, 99%), which was used directly in the next step.
MS (ESI, pos.ion) m/z: 376.3 [M+H]⁺.

Step 6: N-(1-(3-(3-methoxypropoxy)-4-(4,4,4-trifluorobutanoyl)phenyl)-3-methylbutan-2-yl)formamide

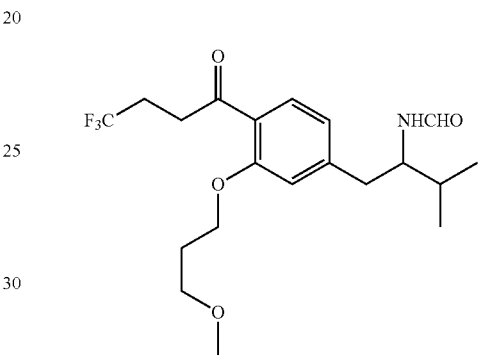

To a 50 mL single-flask were added 1,4-dioxane (6 mL), 1-(4-(2-amino-3-methylbutyl)-2-(3-methoxypropoxy)phenyl)-4,4,4-trifluorobutan-1-one (330 mg, 0.8791 mmol) and formic acid (0.5 mL, 10 mmol). The mixture was heated to reflux and stirred for 12 h under nitrogen protection. The mixture was concentrated in vacuo, and the residue was purified by silica gel column chromatography (DCM/MeOH (V/V)=20/1) to give the title compound as colorless oil (260 mg, 0.6445 mmol, 73.32%).
MS (ESI, pos.ion) m/z: 404.4 [M+H]⁺.

Step 7: 4,4,4-trifluoro-1-(3-isopropyl-6-(3-methoxypropoxy)-3,4-dihydroisoquinolin-7-yl)butan-1-one

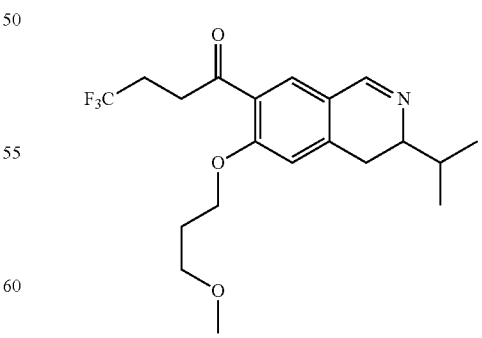

To a 50 mL single-neck flask were added N-(1-(3-(3-methoxypropoxy)-4-(4,4,4-trifluorobutanoyl)phenyl)-3-methylbutan-2-yl)formamide (260 mg, 0.6445 mmol) and DCM (5 mL), then the mixture was cooled to 0 ěC, and POCl₃ (0.1 mL, 1 mmol) was added. After addition, the mixture was heated to reflux and stirred for 6 h. The reaction mixture was concentrated by rotary evaporation, and to the residue was added saturated aqueous sodium bicarbonate to adjust pH=8; the resulting mixture was extracted with ethyl acetate (3 B 20 mL), and the combined organic layers were dried over anhydrous sodium sulfate, filtered; the filtrate was concentrated in vacuo, and the residue was purified by silica gel column chromatography (PE/EA(V/V)=2/1) to give the title compound as brown oil (138 mg, 0.3581 mmol, 55.56%).

MS (ESI, pos.ion) m/z: 386.3 [M+H]⁺.

Step 8: Ethyl 6-isopropyl-9-(3-methoxypropoxy)-2-oxo-10-(4,4,4-trifluorobutanoyl)-2,6,7,11b-tetrahydro-1H-pyrido[2,1-a]isoquinoline-3-carboxylate

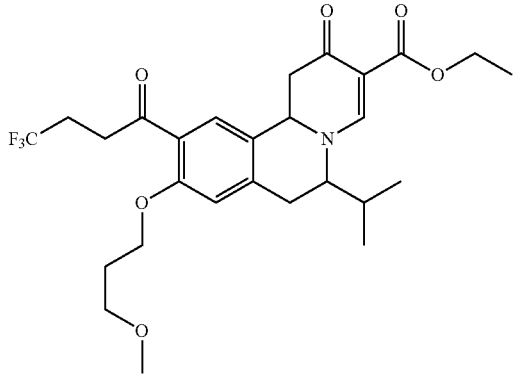 [SMILES: CCOC(=O)C1=CN2C(CC1=O)c1cc(C(=O)CCC(F)(F)F)c(OCCCOC)cc1CC2C(C)C]

To a 50 mL single-neck flask were added 4,4,4-trifluoro-1-(3-isopropyl-6-(3-methoxypropoxy)-3,4-dihydroisoquinolin-7-yl)butan-1-one (138 mg, 0.361 mmol), ethanol (5 mL) and ethyl 2-(ethoxymethylene)-3-oxo-butyrate (330 mg, 1.77 mmol). The mixture was degassed and filled with nitrogen for three times, then heated and refluxed for 20 h. The mixture was concentrated in vacuo, and the residue was purified by silica gel column chromatography (PE/EA (V/V)=2/1) to give the title compound as brown oil (140 mg, 0.2664 mmol, 74.39%).

MS (ESI, pos.ion) m/z: 526.4 [M+H]⁺.

Step 9: Ethyl 6-isopropyl-9-(3-methoxypropoxy)-2-oxo-10-(4,4,4-trifluorobutanoyl)-6,7-dihydro-2H-pyrido[2,1-a]isoquinoline-3-carboxylate

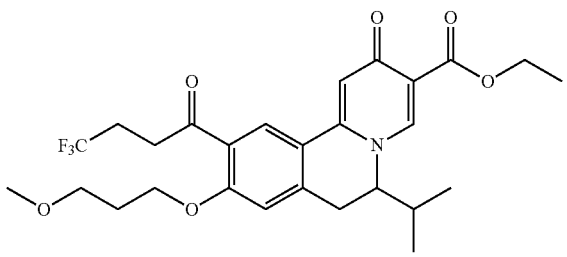 [SMILES: CCOC(=O)c1cn2c(cc1=O)-c1cc(C(=O)CCC(F)(F)F)c(OCCCOC)cc1CC2C(C)C]

To a 50 mL single-neck flask were added ethyl 6-isopropyl-9-(3-methoxypropoxy)-2-oxo-10-(4,4,4-trifluorobutanoyl)-2,6,7,11b-tetrahydro-1H-pyrido[2,1-a]isoquinoline-3-carboxylate (188 mg, 0.3577 mmol), DME (6 mL) and chloranil (87 mg, 0.35383 mmol). The mixture was heated to reflux and stirred for 1 h. The mixture was concentrated in vacuo, and the residue was purified by silica gel column chromatography (PE/EA (V/V)=2/1) to give the title compound as a white solid (140 mg, 0.2674 mmol, 74.77%).

Step 10: 6-isopropyl-9-(3-methoxypropoxy)-2-oxo-10-(4,4,4-trifluorobutanoyl)-6,7-dihydro-2H-pyrido[2,1-a]isoquinoline-3-carboxylic Acid

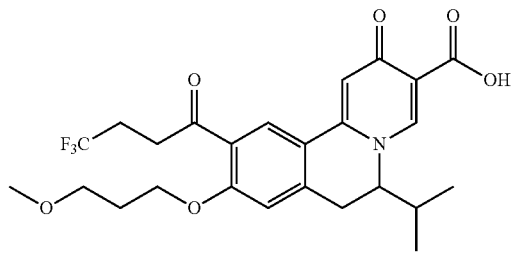 [SMILES: COCCCOc1cc2c(cc1C(=O)CCC(F)(F)F)-c1cc(=O)c(C(=O)O)cn1C(C(C)C)C2]

To a 50 mL single-neck flask were added ethyl 6-isopropyl-9-(3-methoxypropoxy)-2-oxo-10-(4,4,4-trifluorobutanoyl)-6,7-dihydro-2H-pyrido[2, 1-a]isoquinoline-3-carboxylate (140 mg, 0.2674 mmol), methanol (5 mL) and lithium hydroxide monohydrate (56 mg, 1.33 mmol). The mixture was stirred at rt for 12 h. The combined organic layers concentrated by rotary evaporation to remove the solvent, and to the residue was added hydrochloric acid (1 M) to pH=5; the resulting mixture was extracted with ethyl acetate (3 B 20 mL), and the combined organic layers were dried over anydrous sodium sulfate and filtered. The filtrate was concentrated in vacuo, and the residue was purified by silica gel column chromatography (DCM/CH₃OH (V/V)=10/1) to give the title compound as a white solid (50 mg, 0.10 mmol, 37.73%).

MS (ESI, pos.ion) m/z: 496.3 [M+H]⁺;

1H NMR (600 MHz, CDCl₃) 16.03 (s, 1H), 8.53 (s, 1H), 8.21 (s, 1H), 7.14 (s, 1H), 6.97 (s, 1H), 4.33 (s, 2H), 4.06 (s, 1H), 3.61 (s, 2H), 3.51-3.18 (m, 7H), 2.58 (d, J=6.4 Hz, 2H), 2.19 (s, 2H), 1.74 (s, 1H), 0.97 (s, 3H), 0.82 (s, 3H).

Example 54: 6-isopropyl-9-(3-methoxypropoxy)-10-(3-methylbutanoyl)-2-oxo-6,7-dihydro-2H-pyrido[2,1-a]isoquinoline-3-carboxylic Acid

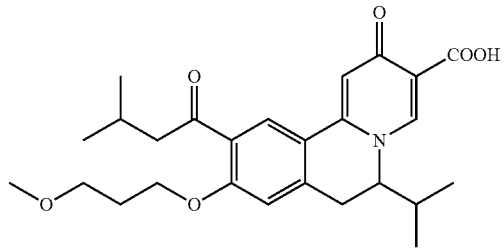

The title compound was prepared according to the synthetic method of example 6 by using 1-(4-bromo-2-hydroxyphenyl)-3-methylbutan-1-one (3.7 g, 14 mmol) as a raw material to give a white solid (200 mg, 0.4391 mmol).

MS (ESI, pos.ion) m/z: 456.1 [M+H]+;
1H NMR (400 MHz, CDCl3) 15.96 (s, 1H), 8.45 (s, 1H), 8.02 (s, 1H), 7.13 (s, 1H), 6.87 (s, 1H), 4.24 (d, J=5.2 Hz, 2H), 3.92 (s, 1H), 3.59 (t, J=5.2 Hz, 2H), 3.37 (s, 3H), 3.18 (d, J=14.6 Hz, 1H), 2.95-2.80 (m, 2H), 2.32-2.10 (m, 3H), 1.75 (s, 1H), 1.26 (s, 1H), 1.08-0.88 (m, 9H), 0.82 (d, J=6.1 Hz, 3H).

Example 55: 6-isopropyl-9-(3-methoxypropoxy)-2-oxo-10-(3-phenyl propanoyl)-6,7-dihydro-2H-pyrido[2,1-a]isoquinoline-3-carboxylic Acid

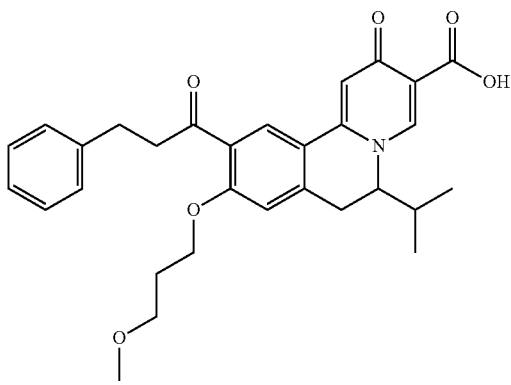 [SMILES: COCCCOc1cc2c(cc1C(=O)CCc1ccccc1)-c1cc(=O)c(C(=O)O)cn1C(C(C)C)C2]

The title compound was prepared according to the synthetic method of example 6 by using 1-(4-bromo-2-hydroxyphenyl)-3-phenylpropan-1-one (1.8 g, 9.83 mmol) as a raw material to give a white solid (190 mg, 0.40 mmol).
MS (ESI, pos.ion) m/z: 504.2[M+H]+;
1H NMR (400 MHz, CDCl3) 16.01 (s, 1H), 8.48 (s, 1H), 8.08 (s, 1H), 7.40-7.09 (m, 6H), 6.90 (s, 1H), 4.40-4.19 (m, 2H), 3.60-2.92 (m, 9H), 2.12 (s, 2H), 1.76 (s, 2H), 1.28 (s, 2H), 1.15-0.60 (m, 6H).

Example 56: 6-isopropyl-10-(methoxycarbamoyl)-9-(3-methoxypropoxy)-2-oxo-6,7-dihydro-2H-pyrido[2,1-a]isoquinoline-3-carboxylic Acid

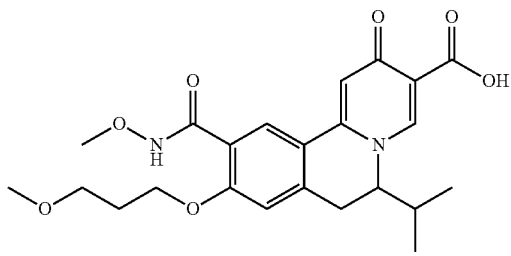 [SMILES: COCCCOc1cc2c(cc1C(=O)NOC)-c1cc(=O)c(C(=O)O)cn1C(C(C)C)C2]

The title compound was prepared according to the synthetic method of example 5 by using 3-(ethoxycarbonyl)-6-isopropyl-9-(3-methoxypropoxy)-2-oxo-6,7-dihydro-2H-pyrido[2,1-a]isoquinoline-10-carboxylic acid (0.1 g, 0.2 mmol) and O-methylhydroxylamine hydrochloride (60 mg, 0.72 mmol) as raw materials to give a yellow solid (50 mg).
MS (ESI, pos.ion) m/z: 445.6 [M+1]+;
1H NMR (400 MHz, CDCl3) 11.20 (s, 1H), 8.60 (s, 1H), 8.53 (s, 1H), 7.19 (s, 1H), 6.90 (s, 1H), 4.26-4.40 (m, 2H), 3.99-4.12 (m, 1H), 3.90 (s, 3H), 3.64-3.76 (m, 3H), 3.40-3.57 (s, 4H), 3.17-3.28 (m, 1H), 2.13-2.31 (m, 2H), 0.96 (d, J=8 Hz, 3H), 0.80 (d, J=8 Hz, 3H).

Example 57: 6-isopropyl-10-(methoxy(methyl)carbamoyl)-9-(3-methoxypropoxy)-2-oxo-6,7-dihydro-2H-pyrido[2,1-a]isoquinoline-3-carboxylic Acid

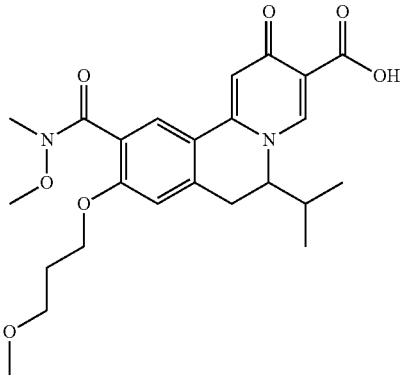 [SMILES: COCCCOc1cc2c(cc1C(=O)N(C)OC)-c1cc(=O)c(C(=O)O)cn1C(C(C)C)C2]

The title compound was prepared according to the synthetic method of example 5 by using 3-(ethoxycarbonyl)-6-isopropyl-9-(3-methoxypropoxy)-2-oxo-6,7-dihydro-2H-pyrido[2,1-a]isoquinoline-10-carboxylic acid (90 mg, 0.2 mmol) and N,O-dimethylhydroxylamine hydrochloride (30 mg, 0.31 mmol) as raw materials to give a gray solid (25 mg, 0.054 mmol).
MS (ESI, pos.ion) m/z: 459.20 [M+1]+;
1H NMR (400 MHz, CDCl3) 16.03 (s, 1H), 8.50 (s, 2H), 7.69 (s, 2H), 7.28 (s, 1H), 6.86 (s, 2H), 4.20 (t, J=5.7 Hz, 2H), 4.02-3.93 (s, 1H), 3.55 (t, J=5.9 Hz, 3H), 3.48-3.25 (m, 8H), 3.22-3.14 (m, 1H), 2.15-2.10 (m, 2H), 1.85-1.73 (m, 1H), 0.96 (d, J=6.5 Hz, 3H), 0.83 (d, J=6.6 Hz, 3H).

Example 58: 10-(cyclopropylcarbamoyl)-6-isopropyl-9-(3-methoxypropoxy)-2-oxo-6,7-dihydro-2H-pyrido[2,1-a]isoquinoline-3-carboxylic Acid

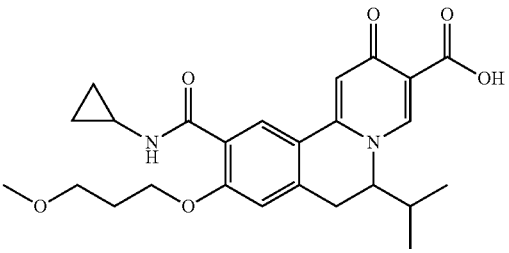 [SMILES: COCCCOc1cc2c(cc1C(=O)NC1CC1)-c1cc(=O)c(C(=O)O)cn1C(C(C)C)C2]

The title compound was prepared according to the synthetic method of example 5 by using 3-(ethoxycarbonyl)-6-isopropyl-9-(3-methoxypropoxy)-2-oxo-6,7-dihydro-2H-pyrido[2,1-a]isoquinoline-10-carboxylic acid (100 mg, 0.26 mmol) and cyclopropylamine (15 mg, 0.26 mmol) as raw materials to give a gray solid (53 mg, 0.12 mmol).
MS (ESI, pos.ion) m/z: 455.20 [M+1]+;
1H NMR (400 MHz, CDCl3) 16.16 (s, 1H), 8.54 (s, 1H), 8.46 (s, 1H), 8.07 (s, 1H), 7.07 (s, 1H), 6.89 (s, 1H), 4.30 (s, 2H), 4.02 (s, 1H), 3.65-3.45 (m, 3H), 3.37 (s, 3H), 3.19 (s, 1H), 2.91 (dd, J=6.8, 3.4 Hz, 1H), 2.16 (s, 2H), 1.69 (s, 1H), 0.92 (d, J=4.9 Hz, 2H), 0.85 (d, J=7.0 Hz, 3H), 0.77 (d, J=6.1 Hz, 3H), 0.60 (s, 2H).

Example 59: 6-isopropyl-10-(5-isopropylthiazol-2-yl)-9-(3-methoxypropoxy)-2-oxo-6,7-dihydro-2H-pyrido[2,1-a]isoquinoline-3-carboxylic Acid

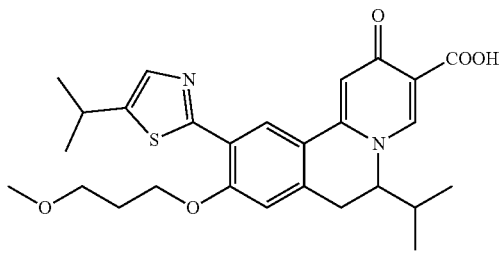 [SMILES: COCCCOc1cc2c(cc1-c1ncc(C(C)C)s1)-c1cc(=O)c(C(=O)O)cn1C(C(C)C)C2]

To a 25 mL single-neck flask were added ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (0.15 g, 0.27 mmol), 5-isopropyl-2-(tributylstannyl)thiazole (285 mg, 0.69 mmol), anhydrous dioxane (10 mL) and bis(triphenylphosphine)palladium(II) chloride (57 mg, 0.082 mmol). The mixture was heated to 110 ěC and stirred overnight in nitrogen atmosphere. The reaction mixture was concentrated by rotary evaporation, and the residue was purified by silica gel column chromatography (DCM/MeOH (V/V)=15/1) to give the title compound as a gray solid (15 mg, 0.274 mmol).

MS (ESI, pos.ion) m/z: 497.2 [M+H]$^+$;

$^1$H NMR (400 MHz, CDCl$_3$) 16.13 (s, 1H), 8.84 (s, 1H), 8.47 (s, 1H), 7.65 (s, 1H), 7.32 (s, 1H), 6.94 (s, 1H), 4.46-4.33 (m, 2H), 3.99-3.85 (m, 1H), 3.78-3.64 (m, 2H), 3.48-3.38 (m, 4H), 3.35-3.26 (m, 1H), 3.24-3.15 (m, 1H), 2.33-2.20 (m, 2H), 2.10-1.95 (m, 1H), 1.5-1.40 (m, 6H), 0.98 (d, J=6.5 Hz, 3H), 0.85 (d, J=6.7 Hz, 3H).

Example 60: 6-isopropyl-10-(4-isopropylthiazol-2-yl)-9-(3-methoxypropoxy)-2-oxo-6,7-dihydro-2H-pyrido[2,1-a]isoquinoline-3-carboxylic Acid

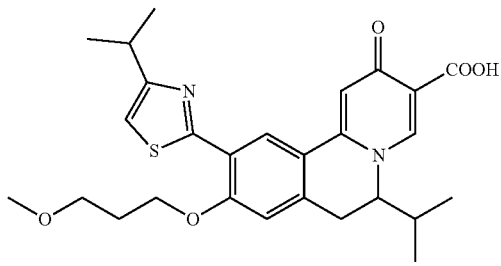 [SMILES: COCCCOc1cc2c(cc1-c1nc(C(C)C)cs1)-c1cc(=O)c(C(=O)O)cn1C(C(C)C)C2]

The title compound was prepared according to the synthetic method of example 59 by using ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (0.15 g, 0.27 mmol) and 4-isopropyl-2-(tributylstannyl)thiazole (285 mg, 0.69 mmol) as raw materials to give a gray solid (20 mg, 0.27 mmol).

MS (ESI, pos.ion) m/z: 497.1 [M+H]$^+$;

1H NMR (400 MHz, CDCl$_3$) 16.129 (br, 1H), 8.907 (s, 1H), 8.408 (s, 1H), 7.328 (d, J=7.6 Hz, 1H), 7.012 (s, 1H), 6.945 (s, 1H), 4.425-4.340 (m, 2H), 3.989-3.900 (m, 1H), 3.748-3.665 (m, 2H), 3.495-3.422 (m, 1H), 3.3952 (s, 3H), 3.257-3.154 (m, 2H), 2.320-2.264 (m, 2H), 1.873-1.775 (m, 1H), 1.411 (d, J=2.4 Hz, 3H), 1.396 (d, J=2.4 Hz, 3H), 0.976 (d, J=6.4 Hz, 3H), 0.836 (d, J=6.8 Hz, 3H).

Example 61: 6-isopropyl-9-(3-methoxypropoxy)-2-oxo-10-(5-phenylthiazol-2-yl)-6,7-dihydro-2H-pyrido[2,1-a]isoquinoline-3-carboxylic Acid

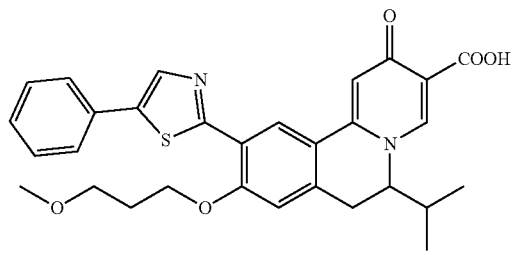 [SMILES: COCCCOc1cc2c(cc1-c1ncc(-c3ccccc3)s1)-c1cc(=O)c(C(=O)O)cn1C(C(C)C)C2]

Step 1: N-(1-(3-(3-methoxypropoxy)-4-(5-phenyl thiazol-2-yl)phenyl)-3-methylbutan-2-yl)formamide

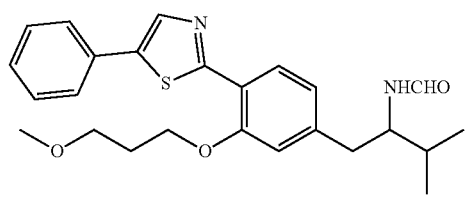

To a 50 mL two-neck flask were added N-(1-(4-(5-bromothiazol-2-yl)-3-(3-methoxypropoxy)phenyl)-3-methylbutan-2-yl)formamide (1.0 g, 2.26 mmol), phenylboronic acid (414 mg, 3.40 mmol), tetrakis(triphenylphosphine)palladium (261 mg, 0.23 mmol), H$_2$O (2 mL), K$_2$CO$_3$ (937 mg, 6.79 mmol) and dioxane (20 mL), then the mixture was heated to 100 ěC and stirred overnight in nitrogen atmosphere. The mixture was cooled to rt and concentrated in vacuo, and to the mixture was added EA (30 mL) and water (20 mL). The mixture was partitioned, and the aqueous layer was extracted with EA (30 mL B 3). The combined organic layers were concentrated in vacuo, and the residue was purified by silica gel column chromatography (EA) to give the title compound as a white solid (990 mg, 2.26 mmol, 99.63%).

Step 2: 6-isopropyl-9-(3-methoxypropoxy)-2-oxo-10-(5-phenylthiazol-2-yl)-6,7-dihydro-2H-pyrido[2,1-a]isoquinoline-3-carboxylic Acid

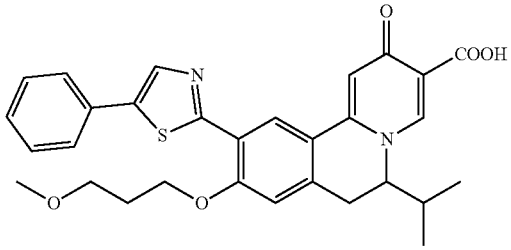 [SMILES: COCCCOc1cc2c(cc1-c1ncc(-c3ccccc3)s1)-c1cc(=O)c(C(=O)O)cn1C(C(C)C)C2]

The title compound was prepared according to synthetic method of step 4 to step 8 in example 24 by using N-(1-(3-(3-methoxypropoxy)-4-(5-phenylthiazol-2-yl)phenyl)-3-methylbutan-2-yl)formamide (990 mg, 2.26 mmol) as a raw material to give a white solid (430 mg, 0.81 mmol).

MS (ESI, pos.ion) m/z: 531.3 [M+H]$^+$;

$^1$H NMR (400 MHz, CDCl$_3$) 8.903 (s, 1H), 8.479 (s, 1H), 8.123 (s, 1H), 7.652 (d, J=4.8 Hz, 2H), 7.462 (t, J=5.2 Hz, 5.2 Hz, 1H), 7.393-7.369 (m, 1H), 7.335 (d, J=4.0 Hz, 1H), 6.984 (s, 1H), 4.485-4.369 (m, 2H), 3.991-3.906 (m, 1H), 3.767-3.707 (m, 2H), 3.448-3.384 (m, 4H), 3.265-3.179 (m, 1H), 2.365-2.312 (m, 2H), 1.866-1.807 (m, 1H), 0.988 (d, J=4.4 Hz, 3H), 0.858 (d, J=6.0 Hz, 3H).

Example 62: 6-isopropyl-9-(3-methoxypropoxy)-2-oxo-10-(2-phenylthiazol-4-yl)-6,7-dihydro-2H-pyrido[2,1-a]isoquinoline-3-carboxylic Acid

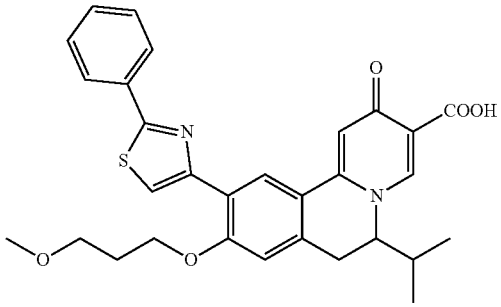 [SMILES: COCCCOc1cc2c(cc1-c1csc(-c3ccccc3)n1)-c1cc(=O)c(C(=O)O)cn1C(C(C)C)C2]

The title compound was prepared according to synthetic method of step 10 to step 14 in example 14 by using thiobenzamide (288 mg, 2.10 mmol) and N-(1-(4-(2-bromoacetyl)-3-(3-methoxypropoxy)phenyl)-3-methylbutan-2-yl)formamide (0.8 g, 2 mmol) as raw materials to give a white solid (200 mg, 0.57 mmol).

MS (ESI, pos.ion) m/z: 531.1 [M+H]$^+$;

$^1$H NMR (400 MHz, CDCl$_3$) 16.192 (br, 1H), 8.929 (s, 1H), 8.467 (s, 1H), 8.096 (d, J=6.4 Hz, 2H), 8.109 (s, 1H), 7.542-7.490 (m, 3H), 7.314 (s, 1H), 6.930 (s, 1H), 4.390-4.303 (m, 2H), 3.933-3.899 (m, 1H), 3.666-3.638 (m, 2H), 3.501-3.429 (m, 1H), 3.397 (s, 3H), 3.25117-3.138 (m, 1H), 2.291-2.215 (m, 2H), 1.894-1.790 (m, 1H), 0.973 (d, J=6.4 Hz, 3H), 0.837 (d, J=6.8 Hz, 3H).

Example 63: 6-isopropyl-10-(2-(4-methoxyphenyl)thiazol-4-yl)-9-(3-methoxypropoxy)-2-oxo-6,7-dihydro-2H-pyrido[2,1-a]isoquinoline-3-carboxylic Acid

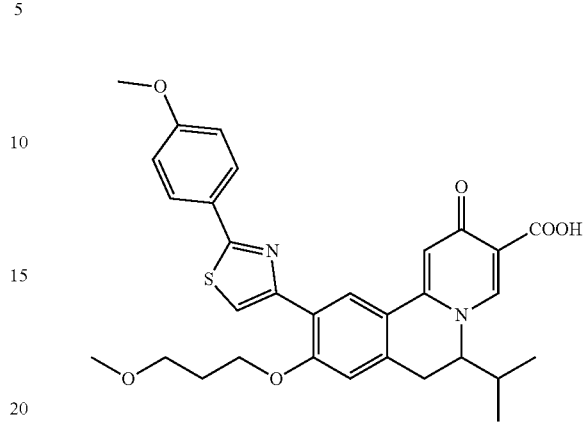

The title compound was prepared according to synthetic method of step 10 to step 14 in example 14 by using 4-methoxythiobenzamide (0.63 g, 4.1 mmol) and N-(1-(4-(2-bromoacetyl)-3-(3-methoxypropoxy)phenyl)-3-methylbutan-2-yl)formamide (1.5 g, 3.7 mmol) as raw materials to give a white solid (150 mg, 0.2675 mmol).

MS (ESI, pos.ion) m/z: 561.4 [M+H]$^+$;

$^1$H NMR (400 MHz, CDCl$_3$) 16.177 (br, 1H), 8.947 (s, 1H), 8.480 (s, 1H), 8.046 (d, J=8.4 Hz, 2H), 7.956 (s, 1H), 7.348 (s, 1H), 7.043 (d, J=8.8 Hz, 2H), 6.932 (s, 1H), 4.396-4.308 (m, 2H), 3.955-3.900 (m, 4H), 3.696-3.618 (m, 2H), 3.480-3.427 (m, 1H), 3.402 (s, 3H), 3.239-3.154 (m, 1H), 2.294-2.223 (m, 2H), 1.912-1.818 (m, 1H), 0.987 (d, J=6.4 Hz, 3H), 0.857 (d, J=6.8 Hz, 3H).

Example 64: 10-(2-(4-cyanophenyl)thiazol-4-yl)-6-isopropyl-9-(3-methoxypropoxy)-2-oxo-6,7-dihydro-2H-pyrido[2,1-a]isoquinoline-3-carboxylic Acid

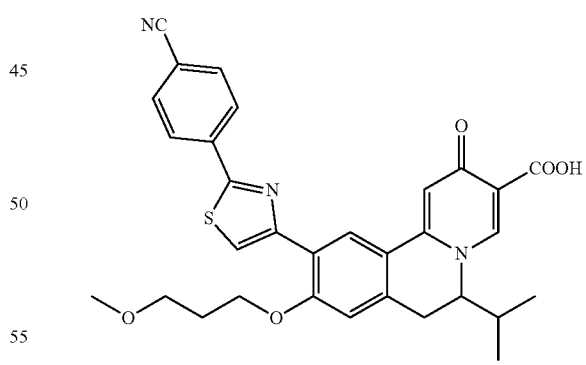

The title compound was prepared according to synthetic method of step 10 to step 14 in example 14 by using 4-cyanolthiobenzamide (0.438 g, 2.70 mmol) and N-(1-(4-(2-bromoacetyl)-3-(3-methoxypropoxy)phenyl)-3-methylbutan-2-yl)formamide (0.9 g, 2 mmol) as raw materials to give a white solid (183 mg, 0.2675 mmol).

MS (ESI, pos.ion) m/z: 556.4 [M+H]$^+$;

1H NMR (400 MHz, CDCl$_3$) 16.086 (br, 1H), 8.900 (s, 1H), 8.497 (s, 1H), 8.211 (d, J=7.6 Hz, 2H), 8.158 (s, 1H), 7.817 (d, J=7.6 Hz, 2H), 7.327 (s, 1H), 6.961 (d, J=8.8 Hz,

1H), 4.456-4.282 (m, 2H), 3.965-3.936 (m, 1H), 3.703-3.609 (m, 2H), 3.511-3.442 (m, 1H), 3.402 (s, 3H), 3.255-3.165 (m, 1H), 2.318-2.222 (m, 2H), 1.919-1.790 (m, 1H), 0.990 (d, J=6.4 Hz, 3H), 0.857 (d, J=6.8 Hz, 3H).

Example 65: 10-(benzofuran-2-yl)-6-isopropyl-9-(3-methoxypropoxy)-2-oxo-6,7-dihydro-2H-pyrido[2,1-a]isoquinoline-3-carboxylic Acid

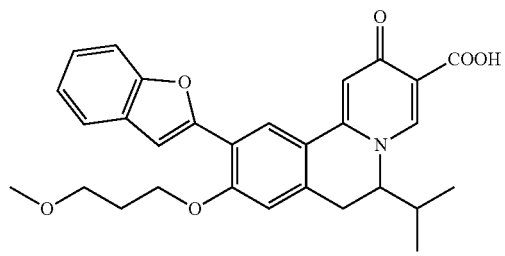 [SMILES: COCCCOc1cc2c(cc1-c1cc3ccccc3o1)-c1cc(=O)c(C(=O)O)cn1C(C(C)C)C2]

Step 1:
4-bromo-1-iodo-2-(3-methoxypropoxy)benzene

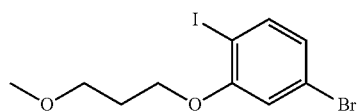

5-Bromo-2-iodophenol (10.0 g, 33.5 mmol), K$_2$CO$_3$ (9.23 g, 66.9 mmol), DMF (50 mL) and 1-bromo-3-methoxypropane (6.14 g, 40.1 mmol) were added into a 100 mL single-neck flask. To the mixture was added water (50 mL), and the mixture was extracted with EA (40 mL B 5). The combined organic layers were washed with saturated brine (30 mL B 3) and then concentrated in vacuo to give the title compound as brownness oil (12.4 g, 33.4 mmol, 99.9%).
MS (ESI, pos.ion) m/z: 370.9 [M+H]$^+$.

Step 2:
2-(4-bromo-2-(3-methoxypropoxy)phenyl)benzofuran

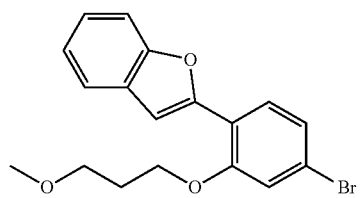 [SMILES: COCCCOc1cc(Br)ccc1-c1cc2ccccc2o1]

To a 50 mL two-neck flask were added benzofuran2-ylboronic acid (1.309 g, 8.083 mmol), 4-bromo-1-iodo-2-(3-methoxypropoxy)benzene (3 g, 8.09 mmol), THF (15 mL), K$_2$CO$_3$ (4.46 g, 32.34 mmol) and H$_2$O (15 mL). Then to the mixture was added tetrakis(triphenylphosphine)palladium (0.47 g, 0.40 mmol). The mixture was heated to 60 ěC and stirred overnight in nitrogen atmosphere. The mixture was cooled to rt and extracted with ethyl acetate (20 mL B 4); the combined organic layers were concentrated in vacuo, and the residue was purified by silica gel column chromatography (PE/EA (V/V)=20/1) to give the title compound as yellow oil (2.9 g, 8.0 mmol).
MS (ESI, pos.ion) m/z: 361.2 [M+H]$^+$.

Step 3: 1-(4-(benzofuran-2-yl)-3-(3-methoxypropoxy)phenyl)-3-methylbutan-2-one

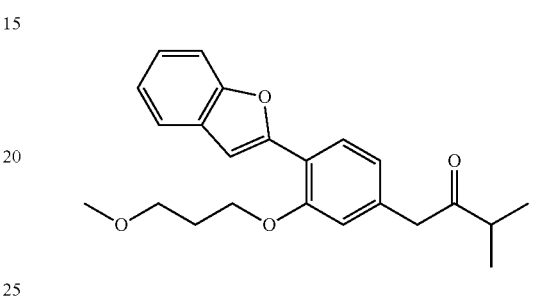

To a 50 mL two-neck flask were added 3-methylbutan-2-one (2.1 g, 24 mmol), 2-(4-bromo-2-(3-methoxypropoxy)phenyl)benzofuran (2.9 g, 8.0 mmol), dixoane (30 mL), X antphos (0.19 g, 0.33 mmol), sodium tert-butoxide (2.6 g, 27 mmol) and Pd(dba)$_2$ (0.12 g, 0.21 mmol). The mixture was stirred at 90 ěC for 5 h under nitrogen protection. The mixture was cooled to rt and extracted with ethyl acetate (30 mL B 4). The combined organic layers were concentrated in vacuo, and the residue was purified by silica gel column chromatography (PE/EA (V/V)=6/1) to give the title compound as a brown thickness product (1.76 g, 4.80 mmol, 60%).
MS (ESI, pos.ion) m/z: 367.1 [M+H]$^+$.

Step 4: 1-(4-(benzofuran-2-yl)-3-(3-methoxypropoxy)phenyl)-3-methylbutan-2-amine

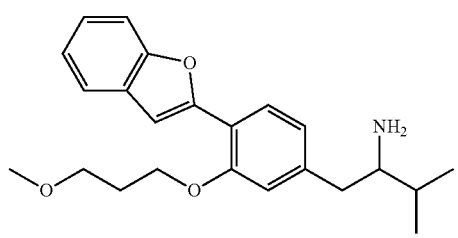 [SMILES: COCCCOc1cc(CC(N)C(C)C)ccc1-c1cc2ccccc2o1]

To a 100 mL single-neck flask were added 1-(4-(benzofuran-2-yl)-3-(3-methoxypropoxy)phenyl)-3-methylbutan-2-one (0.5606 g, 1.530 mmol), MeOH (6 mL) and NH$_4$OAc (1.415 g, 18.36 mmol). The mixture was stirred at rt for 60 min, then cooled to 0 ěC and NaBH$_3$CN (0.288 g, 4.58 mmol) was added. Then the mixture was warmed to rt and stirred overnight. The mixture was concentrated to remove the solvent, and to the residue was added saturated brine (15 mL) and ammonium hydroxide (2 mL). The mixture was extracted with EA (50 mL B 3), and the combined organic layers were concentrated in vacuo to give the title compound as brown oil (0.56 g, 1.53 mmol, 100.0%).
MS (ESI, pos.ion) m/z: 368.4 [M+H]$^+$.

Step 5: N-(1-(4-(benzofuran-2-yl)-3-(3-methoxypropoxy)phenyl)-3-methylbutan-2-yl)formamide

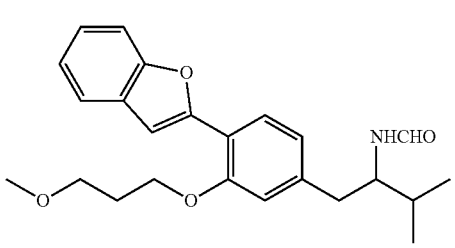

To a 100 mL single-neck flask were added 1-(4-(benzofuran-2-yl)-3-(3-methoxypropoxy)phenyl)-3-methylbutan-2-amine (0.56 g, 1.53 mmol), formic acid (1.13 g, 24.48 mmol) and dioxane (9 mL), then the mixture was heated to 110 ēC and stirred overnight in nitrogen atmosphere. The residue was purified by silica gel column chromatography (EA) to give the title compound as a white solid (0.60 g, 1.5 mmol, 99%).

MS (ESI, pos.ion) m/z: 396.4 [M+H]$^+$.

Step 6: 7-(benzofuran-2-yl)-3-isopropyl-6-(3-methoxypropoxy)-3,4-dihydroisoquinoline

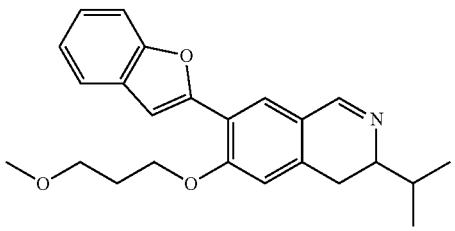 [SMILES: COCCCOc1cc2c(cc1-c1cc3ccccc3o1)C=NC(C(C)C)C2]

To a 100 mL single-neck flask was added N-(1-(4-(benzofuran-2-yl)-3-(3-methoxypropoxy)phenyl)-3-methylbutan-2-yl)formamide (0.60 g, 1.5 mmol), then DCM (12 mL) was added to dissolve the reagent. The mixture was cooled to 0 ēC and POCl$_3$ (0.28 mL, 3.0 mmol) was added. The mixture was heated to 50 ēC and stirred for 3 h. The mixture was cooled to rt and poured into ice-water; the mixture was adjusted with ammonium hydroxide to pH=9-10, then the resulting mixture was extracted with EA (30 mL B 3); the combined organic layers were dried over anhydrous sodium sulfate and filtered; the filtrate was concentrated, and the residue was purified by silica gel column chromatography (EA) to give the title compound as brown oil (0.52 g, 1.4 mmol, 91%).

MS (ESI, pos.ion) m/z: 378.1 [M+H]$^+$.

Step 7: Ethyl 10-(benzofuran-2-yl)-6-isopropyl-9-(3-methoxypropoxy)-2-oxo-2,6,7,11b-tetrahydro-1H-pyrido[2,1-a]isoquinoline-3-carboxylate

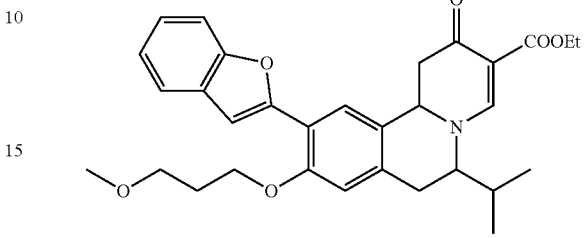

7-(Benzofuran-2-yl)-3-isopropyl-6-(3-methoxypropoxy)-3,4-dihydroisoquinoline (0.52 g, 1.4 mmol), ethyl 2-(ethoxymethylene)-3-oxobutanoate (0.51 g, 2.7 mmol) and EtOH (10 mL) were added into a 50 mL single-neck flask. The mixture was stirred at 90 ēC overnight under nitrogen protection. The residue was purified by silica gel column chromatography (EA) to give the title compound as brown oil (0.48 g, 0.93 mmol, 68%).

MS (ESI, pos.ion) m/z: 518.4 [M+H]$^+$.

Step 8: Ethyl 10-(benzofuran-2-yl)-6-isopropyl-9-(3-methoxypropoxy)-2-oxo-6,7-dihydro-2H-pyrido[2,1-a]isoquinoline-3-carboxylate

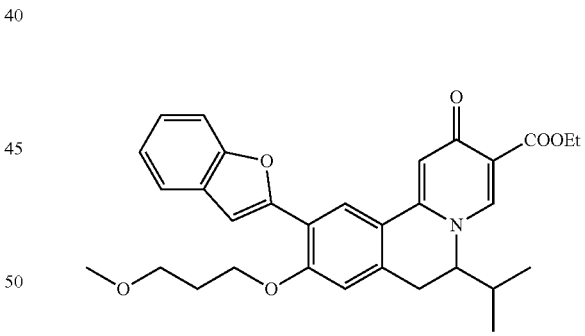

Ethyl 10-(benzofuran-2-yl)-6-isopropyl-9-(3-methoxypropoxy)-2-oxo-2,6,7,11b-tetrahydro-1H-pyrido[2,1-a]isoquinoline-3-carboxylate (0.48 g, 0.93 mmol) was added into a 50 mL single-neck flask, then dimethoxyethane (9 mL) was added to dissolve the reagent, and then chloranil (0.29 g, 1.2 mmol) was added. The mixture was heated to 90 ēC and stirred for 1 hour under nitrogen protection, then cooled to rt. The residue was purified by silica gel column chromatography (DCM/MeOH (V/V)=10/1) to give the title compound as black brown oil (430 mg, 0.8340 mmol, 89.4%).

MS (ESI, pos.ion) m/z: 516.4 [M+H]$^+$.

Step 9: 10-(benzofuran-2-yl)-6-isopropyl-9-(3-methoxypropoxy)-2-oxo-6,7-dihydro-2H-pyrido[2,1-a]isoquinoline-3-carboxylic Acid

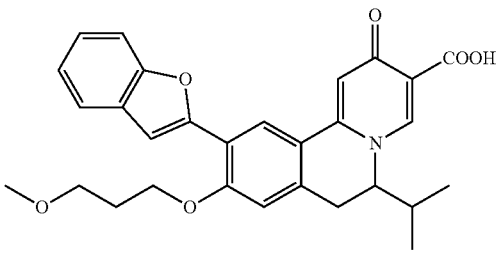 [SMILES: COCCCOc1cc2c(cc1-c1cc3ccccc3o1)-c1cc(=O)c(C(=O)O)cn1C(C(C)C)C2]

Ethyl 10-(benzofuran-2-yl)-6-isopropyl-9-(3-methoxypropoxy)-2-oxo-6,7-dihydro-2H-pyrido[2,1-a]isoquinoline-3-carboxylate (430 mg, 0.83 mmol), THF (4 mL), EtOH (2 mL) and H$_2$O (1 mL) were added into a 50 mL single-neck flask, then LiOH.H$_2$O (70 mg, 1.67 mmol) was added into the mixture. The resulting mixture was stirred at rt for 3 h. Postprocessing: the mixture was adjusted with HCl (1 M) to pH=6, then concentrated to remove the solvent; the residue was dissolved in DCM, and to the mixture was added saturated brine (5 mL); the mixture was partitioned, and the aqueous layer was extracted with DCM (15 mL B 4); the combined organic layers were concentrated in vacuo and the residue was purified by silica gel column chromatography (DCM/MeOH (V/V)=20/1) to give the title compound as a white solid (210 mg, 0.43 mmol, 51.65%).

MS (ESI, pos.ion) m/z: 488.1 [M+H]$^+$.

$^1$H NMR (400 MHz, CDCl$_3$) 16.093 (br, 1H), 8.502 (d, J=8 Hz, 2H), 7.647-7.80 (m, 2H), 7.380-7.330 (m, 3H), 7.299-7.262 (m, 1H), 6.942 (s, 1H), 4.424-4.327 (m, 2H), 3.965-3.930 (m, 1H), 3.735-3.673 (m, 2H), 3.479-3.438 (m, 1H), 3.419 (s, 3H), 3.240-3.161 (m, 1H), 2.343-2.268 (m, 2H), 1.905-1.814 (m, 1H), 0.993 (d, J=6.8 Hz, 3H), 0.862 (d, J=6.8 Hz, 3H).

Example 66: 10-(2-aminopyrimidin-5-yl)-6-isopropyl-9-(3-methoxypropoxy)-2-oxo-6,7-dihydro-2H-pyrido[2,1-a]isoquinoline-3-carboxylic Acid

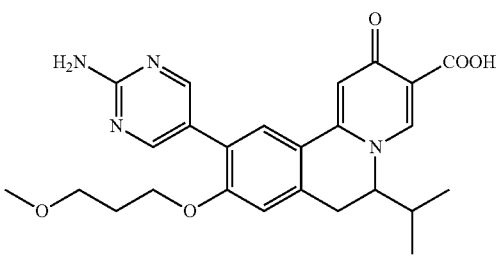 [SMILES: COCCCOc1cc2c(cc1-c1cnc(N)nc1)-c1cc(=O)c(C(=O)O)cn1C(C(C)C)C2]

The title compound was prepared according to the synthetic method of example 12 by using (2-aminopyrimidin-5-yl)boronic acid (60 mg, 0.43190 mmol) and ethyl 6-isopropyl-9-(3-methoxypropoxy)-2-oxo-10-(((trifluoromethyl)sulfonyl)oxy)-6,7-dihydro-2H-pyrido[2,1-a]isoquinoline-3-carboxylate (200 mg, 0.3653 mmol) as raw materials to give a gray solid (70 mg, 0.1507 mmol).

MS (ESI, pos.ion) m/z: 465.4 [M+H]$^+$;

$^1$H NMR (400 MHz, CDCl$_3$) 16.02 (s, 1H), 8.51 (s, 3H), 7.65 (s, 1H), 7.12 (s, 1H), 6.91 (s, 1H), 5.31 (s, 2H), 4.21 (s, 2H), 3.97 (s, 1H), 3.51 (s, 3H), 3.36 (s, 5H), 3.21 (s, 1H), 2.07 (s, 1H), 1.01 (s, 3H), 0.87 (d, J=5.4 Hz, 3H).

Example 67: 6-isopropyl-9-(3-methoxypropoxy)-2-oxo-10-(pyridin-2-yl)-6,7-dihydro-2H-pyrido[2,1-a]isoquinoline-3-carboxylic Acid

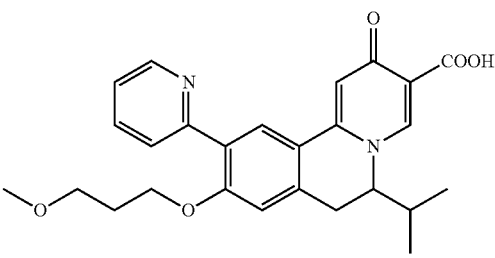 [SMILES: COCCCOc1cc2c(cc1-c1ccccn1)-c1cc(=O)c(C(=O)O)cn1C(C(C)C)C2]

The title compound was prepared according to the synthetic method of example 9 by using 2-(tributylstannyl)pyridine (60 mg, 0.43190 mmol) and ethyl 10-iodo-6-isopropyl-9-(3-methoxypropoxy)-2-oxo-2,6,7,11b-tetrahydro-1H-pyrido[2,1-a]isoquinoline-3-carboxylate (200 mg, 0.3653 mmol) as raw materials to give a gray solid (70 mg, 0.15 mmol).

MS (ESI, pos.ion) m/z: 449.3 [M+H]$^+$;

$^1$H NMR (600 MHz, CDCl$_3$) 8.74 (s, 1H), 8.49 (s, 1H), 8.29 (s, 1H), 7.88 (d, J=7.6 Hz, 1H), 7.76 (t, J=7.0 Hz, 1H), 7.28 (s, 2H), 6.93 (s, 1H), 4.24 (s, 1H), 3.96 (s, 1H), 3.52 (s, 2H), 3.34 (s, 3H), 3.21 (s, 1H), 2.10 (s, 2H), 1.86 (s, 2H), 1.36-1.26 (m, 1H), 0.98 (s, 3H), 0.83 (d, J=5.1 Hz, 3H).

Example 68: 6-isopropyl-9-((3-methoxycyclobutyl)methoxy)-2-oxo-10-(thiazol-2-yl)-6,7-dihydro-2H-pyrido[2,1-a]isoquinoline-3-carboxylic Acid

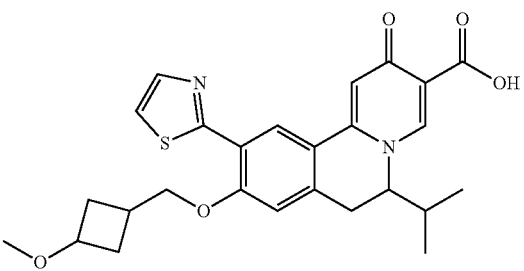 [SMILES: COC1CC(COc2cc3c(cc2-c2nccs2)-c2cc(=O)c(C(=O)O)cn2C(C(C)C)C3)C1]

The title compound was prepared according to the synthetic method of example 19 by using 9-hydroxy-6-isopropyl-2-oxo-10-(thiazol-2-yl)-6,7-dihydro-2H-pyrido[2,1-a]isoquinoline-3-carboxylic acid (200 mg, 0.49 mmol) and (3-methoxycyclobutyl)methyl methanesulfonate (200 mg, 0.3653 mmol) as raw materials to give a gray solid (60 mg, 0.49 mmol).

MS (ESI, pos.ion) m/z: 481.30 [M+H]$^+$;

$^1$H NMR (400 MHz, CDCl$_3$) 8.72 (s, 1H), 8.39 (s, 1H), 7.80 (s, 1H), 7.38 (s, 1H), 7.22 (s, 1H), 6.86 (s, 1H), 4.19-4.10 (m, 2H), 3.84-3.75 (m, 1H), 3.37-3.24 (m, 2H), 3.16-3.08 (m, 4H), 2.53-2.41 (m, 2H), 1.84-1.62 (m, 3H), 1.25-1.20 (m, 1H), 0.84 (d, J=6.5 Hz, 3H), 0.70 (d, J=6.7 Hz, 3H).

Example 69: 6-isopropyl-2-oxo-9-(pyrrolidin-1-yl)-10-(thiazol-2-yl)-6,7-dihydro-2H-pyrido[2,1-a]isoquinoline-3-carboxylic Acid

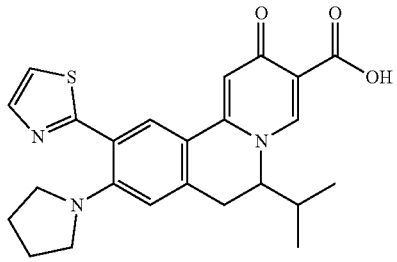 [SMILES: CC(C)C1Cc2cc(N3CCCC3)c(-c3nccs3)cc2-c2cc(=O)c(C(=O)O)cn21]

Step 1: 4-bromo-2-(pyrrolidin-1-yl)benzonitrile

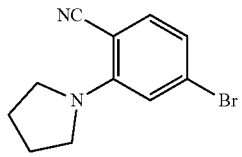 [SMILES: N#Cc1ccc(Br)cc1N1CCCC1]

4-Bromo-2-fluorobenzonitrile (1.0 g, 5.0 mmol), DMSO (20 mL), KI (0.14 mg, 0.00084 mmol), K₂CO₃ (1.4 g, 10 mmol) and pyrrolidine (0.5 g, 7 mmol) was added into a 50 mL two-neck flask. The mixture was heated to 100 ĕC and stirred overnight under nitrogen protection. The mixture was cooled to rt, and to the mixture was added water (20 mL); the resulting mixture was extracted with EA (30 mL B 3); the combined organic layers were washed with water (30 mL), and the organic layers were concentrated in vacuo to give the title compound as a light yellow solid (1.26 g, 5.02 mmol, 100%).

MS (ESI, pos.ion) m/z: 251.0 [M+H]⁺.

Step 2: 4-bromo-2-(pyrrolidin-1-yl)benzothioamide

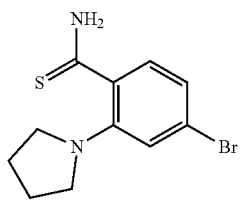 [SMILES: NC(=S)c1ccc(Br)cc1N1CCCC1]

To a 100 mL single-neck flask were added 4-bromo-2-(pyrrolidin-1-yl)benzonitrile (7.04 g, 28.0 mmol), pyridine (10 mL), triethylamine (5.8 mL, 42 mmol) and an aqueous solution of ammonium sulfide (13.9 g, 42.1 mmol, mass percent: 40%). The mixture was heated to 65 ĕC and stirred overnight. The mixture was cooled to rt, and to the mixture was added water (20 mL). The resulting mixture was extracted with EA (50 mL B 3). The combined organic layers were washed with saturated brine (20 mL B 3), and concentrated in vacuo. The residue was purified by silica gel column chromatography (PE/EA (V/V)=4/1) to give the title compound as a red brown solid (2.0 g, 7.0 mmol, 25%).

MS (ESI, pos.ion) m/z: 285.0 [M+H]⁺.

Step 3: 2-(4-bromo-2-(pyrrolidin-1-yl)phenyl)thiazole

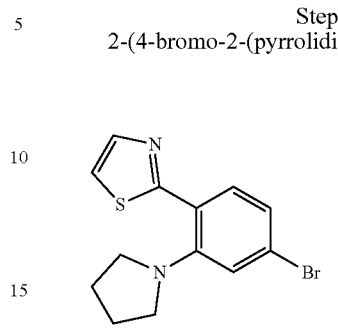

4-Bromo-2-(pyrrolidin-1-yl)benzothioamide (0.57 g, 2.0 mmol), 2-bromo-1,1-diethoxyethane (0.394 g, 2.00 mmol), EtOH (12 mL), water (1 mL) and PTSA ӘH₂O (0.190 g, 1.00 mmol) were added into a 100 mL single-neck flask. The mixture was heated to 100 ĕC and stirred overnight in nitrogen atmosphere. The mixture was cooled to rt and concentrated in vacuo; and the residue was purified by silica gel column chromatography (PE/EA (V/V)=30/1) to give the title compound as brown oil (0.60 g, 1.9 mmol, 97%).

MS (ESI, pos.ion) m/z: 309.0 [M+H]⁺.

Step 4: 3-methyl-1-(3-(pyrrolidin-1-yl)-4-(thiazol-2-yl)phenyl)butan-2-one

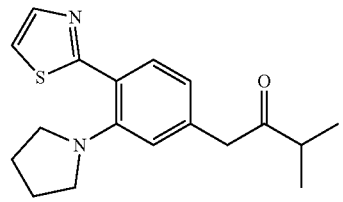 [SMILES: CC(C)C(=O)Cc1ccc(-c2nccs2)c(N2CCCC2)c1]

To a 100 mL two-neck flask were added 3-methylbutan-2-one (1.813 g, 21.05 mmol), 2-(4-bromo-2-(pyrrolidin-1-yl)phenyl)thiazole (2.170 g, 7.018 mmol), Pd(dba)₂ (100 mg, 0.17 mmol), X antphos (162 mg, 0.28 mmol), sodium tert-butoxide (2.31 g, 24.07 mmol) and dixoane (20 mL). The mixture was stirred at 90 ĕC for 24 h under nitrogen protection. The mixture was cooled to rt and concentrated in vacuo; and the residue was purified by silica gel column chromatography (PE/EA (V/V)=30/1) to give the title compound as brown oil (2.21 g, 7.02 mmol, 99.98%).

MS (ESI, pos.ion) m/z: 315.2 [M+H]⁺.

Step 5: 3-methyl-1-(3-(pyrrolidin-1-yl)-4-(thiazol-2-yl)phenyl)butan-2-amine

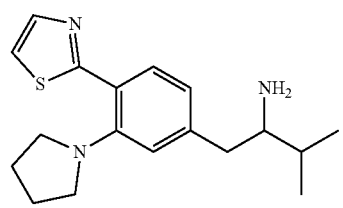 [SMILES: CC(C)C(N)Cc1ccc(-c2nccs2)c(N2CCCC2)c1]

To a 250 mL single-neck flask were added 3-methyl-1-(3-(pyrrolidin-1-yl)-4-(thiazol-2-yl)phenyl)butan-2-one (2.7 g, 8.6 mmol), MeOH (30 mL) and NH₄OAc (7.9 g, 100 mmol). The mixture was stirred at rt for 1 h. The mixture was cooled to 0 ěC, then NaBH₃CN (1.6 g, 25 mmol) was added. The mixture was warmed to rt and stirred overnight. To the mixture was added water (20 mL); the resulting mixture was extracted with EA (30 mL B 3); the combined organic layers were washed with saturated aqueous sodium bicarbonate (20 mL), dried over anhydrous sodium sulfate and concentrated in vacuo to give the title compound as brown oil (2.7 g, 8.6 mmol, 100%).

MS (ESI, pos.ion) m/z: 316.1 [M+H]⁺.

Step 6: N-(3-methyl-1-(3-(pyrrolidin-1-yl)-4-(thiazol-2-yl)phenyl)butan-2-yl)formamide

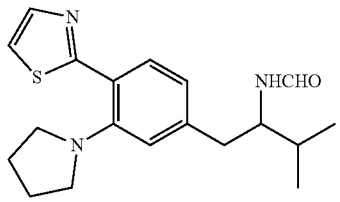

3-Methyl-1-(3-(pyrrolidin-1-yl)-4-(thiazol-2-yl)phenyl) butan-2-amine (2.7 g, 8.6 mmol) was added into a 100 mL single-neck flask, then ethyl formate (27 mL) was added. The mixture was heated to 60 ěC and stirred overnight. The mixture was cooled to rt and concentrated in vacuo; and the residue was purified by silica gel column chromatography (PE/EA (V/V)=30/1) to give the title compound as brown oil (1.0 g, 2.9 mmol, 34%).

MS (ESI, pos.ion) m/z: 344.2 [M+H]⁺.

Step 7: 5-isopropyl-8-(pyrrolidin-1-yl)-9-(thiazol-2-yl)-5,6-dihydro-2H-oxazolo[2,3-a]isoquinoline-2,3(10bH)-dione

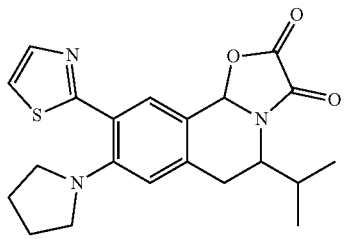 [SMILES: CC(C)C1Cc2cc(N3CCCC3)c(-c3nccs3)cc2C2OC(=O)C(=O)N21]

N-(3-Methyl-1-(3-(pyrrolidin-1-yl)-4-(thiazol-2-yl)phenyl)butan-2-yl)formamide (730 mg, 2.125 mmol) and DCM (30 mL) were added into a 50 mL single-neck flask, then the mixture was cooled to 0 ěC. To the mixture was added oxalyl chloride (0.36 mL, 4.3 mmol), and the resulting mixture was stirred for 30 min. The mixture was cooled to −10 ěC, and FeCl₃ (546 mg, 3.39 mmol) was added. The mixture was heated to rt and stirred overnight. The mixture was cooled to 0 ěC, and quenched with water (10 mL). The mixture was extracted with DCM (30 mL B 4). The combined organic layers were dried over anhydrous sodium sulfate, filtered, and concentrated in vacuo to give the title compound as brown oil (760 mg, 1.912 mmol, 90%), which was used directly in the next step.

MS (ESI, pos.ion) m/z: 398.1 [M+H]⁺.

Step 8: 2-(3-isopropyl-6-(pyrrolidin-1-yl)-3,4-dihydroisoquinolin-7-yl)thiazole

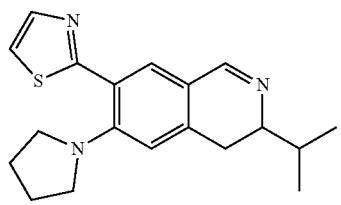 [SMILES: CC(C)C1Cc2cc(N3CCCC3)c(-c3nccs3)cc2C=N1]

5-Isopropyl-8-(pyrrolidin-1-yl)-9-(thiazol-2-yl)-5,6-dihydro-2H-oxazolo[2,3-a]isoquinoline-2,3(10bH)-dione (760 mg, 1.91 mmol), MeOH (40 mL) and H₂SO₄ (0.9 mL) was added in to a 100 mL single-neck flask. The mixture was heated to 70 ěC and stirred for 3 h under nitrogen protection. The mixture was cooled to rt, and concentrated in vacuo. To the residue were added water (15 mL) and EA (20 mL), and the mixture was partitioned. The organic layers were washed with HCl (20 mL B 4, 1 M), and the combined aqueous layers were adjusted with ammonium hydroxide to pH=9-10. The mixture was extracted with EA (30 mL B 4), and the combined organic layers were concentrated in vacuo to give the title compound as brown oil (600 mg, 1.843 mmol, 96%).

MS (ESI, pos.ion) m/z: 326.4 [M+H]⁺.

Step 9: Ethyl 6-isopropyl-2-oxo-9-(pyrrolidin-1-yl)-10-(thiazol-2-yl)-2,6,7,11b-tetrahydro-1H-pyrido[2,1-a]isoquinoline-3-carboxylate

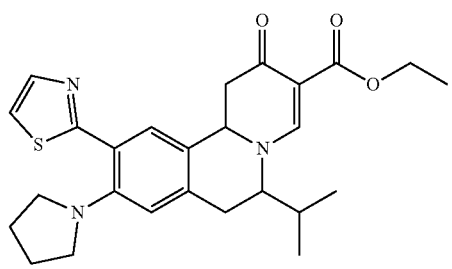 [SMILES: CCOC(=O)C1=CN2C(CC1=O)c1cc(-c3nccs3)c(N3CCCC3)cc1CC2C(C)C]

To a 100 mL single-neck flask were added ethyl 2-(ethoxymethylene)-3-oxobutanoate (543 mg, 2.919 mmol) and 2-(3-isopropyl-6-(pyrrolidin-1-yl)-3,4-dihydroisoquinolin-7-yl)thiazole (500 mg, 1.54 mmol) and EtOH (10 mL). The mixture was heated to 85 ěC and stirred overnight under nitrogen protection. The reaction mixture was concentrated in vacuo. The residue was purified by thin-layer chromatography (PE/EA (V/V)=1/1) to give the title compound as brown oil (80 mg, 0.17 mmol, 11%).

MS (ESI, pos.ion) m/z: 466.4 [M+H]⁺.

Step 10: Ethyl 6-isopropyl-2-oxo-9-(pyrrolidin-1-yl)-10-(thiazol-2-yl)-6,7-dihydro-2H-pyrido[2,1-a]isoquinoline-3-carboxylate

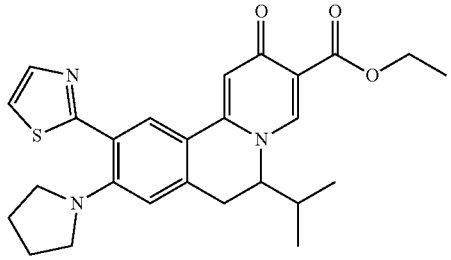 [SMILES: CCOC(=O)c1cn2c(cc1=O)-c1cc(-c3nccs3)c(N3CCCC3)cc1CC2C(C)C]

To a 50 mL single-neck flask were added ethyl 6-isopropyl-2-oxo-9-(pyrrolidin-1-yl)-10-(thiazol-2-yl)-2,6,7,11b-tetrahydro-1H-pyrido[2,1-a]isoquinoline-3-carboxylate (86 mg, 0.185 mmol), dimethoxyethane (9 mL) and chloranil (45 mg, 0.18 mmol). The mixture was stirred at 90 ĕC for 1 h under nitrogen protection, then cooled to rt. The reaction mixture was concentrated in vacuo, and the residue was purified by thin-layer chromatography (DCM/MeOH (V/V)=10/1) to give the title compound as brown oil (53 mg, 0.11 mmol, 62%).

MS (ESI, pos.ion) m/z: 464.4 [M+H]$^+$.

Step 11: 6-isopropyl-2-oxo-9-(pyrrolidin-1-yl)-10-(thiazol-2-yl)-6,7-dihydro-2H-pyrido[2,1-a]isoquinoline-3-carboxylic Acid

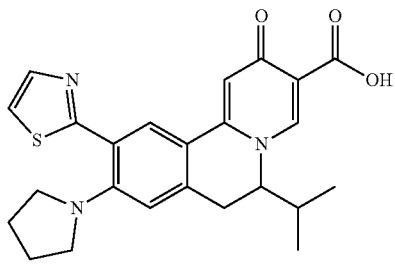 [SMILES: CC(C)C1Cc2cc(N3CCCC3)c(-c3nccs3)cc2-c2cc(=O)c(C(=O)O)cn21]

Ethyl 6-isopropyl-2-oxo-9-(pyrrolidin-1-yl)-10-(thiazol-2-yl)-6,7-dihydro-2H-pyrido[2,1-a]isoquinoline-3-carboxylate (53 mg, 0.1143 mmol) was dissolved in the mixed solvent of EtOH (2 mL), THF (4 mL) and H$_2$O (1 mL). To the mixture was added LiOH H$_2$O (14 mg, 0.3333 mmol), then the mixture was stirred at rt for 1.5 h. The mixture was adjusted to pH 3-4, then concentrated; to the mixture was added water (5 mL). The mixture was extracted with DCM (10 mL B 3); the combined organic layers were concentrated, and the residue was purified by preparative chromatography to give the title compound as a yellow solid (10 mg, 0.023 mmol, 20%).

MS (ESI, pos.ion) m/z: 436.2 [M+H]$^+$;

$^1$H NMR (400 MHz, CDCl$_3$) 8.427 (s, 1H), 7.887 (d, J=3.2 Hz, 1H), 7.75 (s, 1H), 7.460 (d, J=3.2 Hz, 1H), 7.036 (s, 1H), 6.656 (s, 1H), 3.894-3.8519 (m, 1H), 3.776-3.664 (m, 1H), 3.405-3.327 (m, 1H), 3.215-3.103 (m, 4H), 2.064-2.000 (m, 1H), 1.976-1.846 (m, 4H), 0.989 (d, J=6.4 Hz, 3H), 0.840 (d, J=6.8 Hz, 3H).

Example 70: 6-isopropyl-10-(methoxycarbonyl)-2-oxo-9-phenyl-6,7-dihydro-2H-pyrido[2,1-a]isoquinoline-3-carboxylic Acid

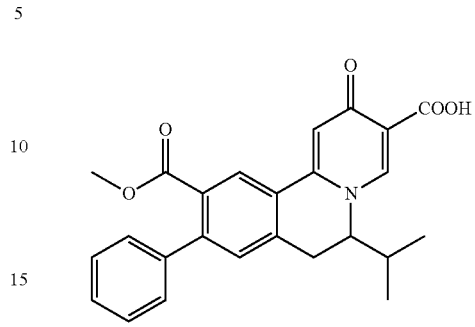

The title compound was prepared according to the synthetic method of step 8 to step 10 in example 32 by using methyl 6-bromo-3-isopropyl-3,4-dihydroisoquinoline-7-carboxylate (0.230 g, 0.741 mmol) and phenylboronic acid (149 mg, 1.2220 mmol) as raw materials to give a white solid (150 mg, 0.631 mmol).

MS (ESI, pos.ion) m/z: 418.3 [M+H]$^+$;

$^1$H NMR (400 MHz, CDCl$_3$) 15.825 (b, 1H), 8.557 (s, 1H), 8.281 (s, 1H), 7.533-7.373 (m, 5H), 7.304 (s, 1H), 7.287 (s, 1H), 4.077-3.960 (m, 1H), 3.740 (s, 3H), 3.513-3.426 (m, 1H), 3.320-3.255 (m, 1H), 1.880-1.756 (m, 1H), 0.989 (d, J=5.2 Hz, 3H), 0.880 (d, J=6.4 Hz, 3H).

Example 71: 6-isopropyl-10-(methoxycarbonyl)-9-(4-methoxyphenyl)-2-oxo-6,7-dihydro-2H-pyrido[2,1-a]isoquinoline-3-carboxylic Acid

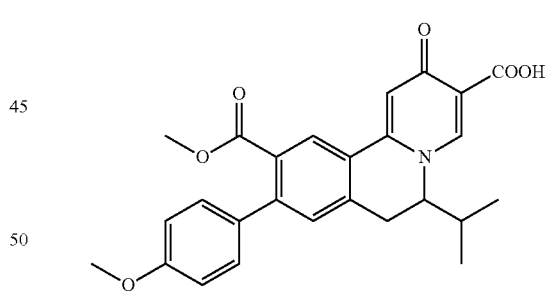

The title compound was prepared according to the synthetic method of step 8 to step 10 in example 32 by using methyl 6-bromo-3-isopropyl-3,4-dihydroisoquinoline-7-carboxylate (0.400 g, 1.29 mmol) and 4-methoxyphenylboronic acid (0.294 g, 1.93 mmol) as raw materials to give a white solid (0.30 g, 0.67 mmol).

MS (ESI, pos.ion) m/z: 448.2 [M+H]$^+$;

$^1$H NMR (400 MHz, CDCl$_3$) 15.909 (b, 1H), 8.562 (s, 1H), 8.234 (s, 1H), 7.354-7.290 (m, 4H), 6.997 (d, J=6.8 Hz, 2H), 4.128-3.969 (m, 1H), 3.888-3.845 (m, 3H), 3.774 (s, 3H), 3.581-3.20 (m, 2H), 1.896-1.804 (m, 1H), 0.984 (d, J=3.2, 3H), 0.869 (d, J=3.2, 3H).

Example 72: 6-isopropyl-10-(methoxycarbonyl)-9-(1-(3-methoxypropyl)-1H-pyrazol-4-yl)-2-oxo-6,7-dihydro-2H-pyrido[2,1-a]isoquinoline-3-carboxylic Acid

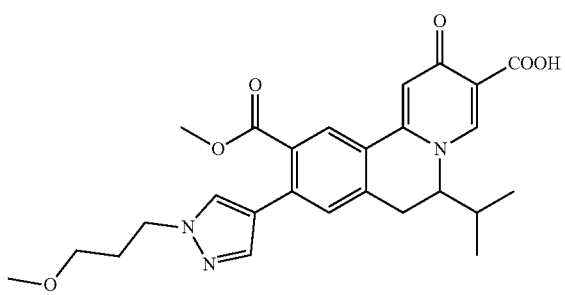 [SMILES: COCCCn1cc(-c2cc3c(cc2C(=O)OC)-c2cc(=O)c(C(=O)O)cn2C(C(C)C)C3)cn1]

Step 1: 4-bromo-1-(3-methoxypropyl)-1H-pyrazole

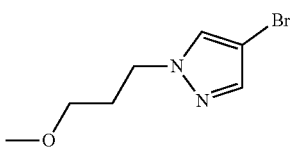

To a 100 mL single-neck flask were added 4-bromo-1H-pyrazole (3.0 g, 20 mmol), 1-bromo-3-methoxypropane (3.7 g, 24 mmol), cesium carbonate (13 g, 39.90 mmol) and DMF (30 mL). The mixture was heated to 50 ĕC and stirred overnight. The mixture was cooled to rt and to the mixture was added water (50 mL). The mixture was extracted with DCM (50 mL B 4). The combined organic layers were concentrated in vacuo, and the residue was purified by silica gel column chromatography (PE/EA (V/V)=1/1) to give the title compound as colorless oil (4.3 g, 20 mmol, 96%).

MS (ESI, pos.ion) m/z: 219.0 [M+H]$^+$.

Step 2: 1-(3-methoxypropyl)-4-(4,4,5,5-tetramethyl-1,3,2-dioxaborolan-2-yl)-1H-pyrazole

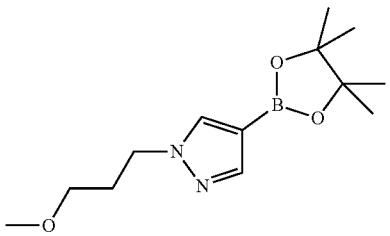

Bis(pinacolato)diboron (1.39 g, 5.47 mmol), 4-bromo-1-(3-methoxypropyl)-1H-pyrazole (1.00 g, 4.56 mmol), Pd(dppf)Cl$_2$ (334 mg, 0.46 mmol), AcOK (1.34 g, 13.7 mmol) and 1,4-dioxane (20 mL) were added into a 50 mL two-neck flask. The mixture was heated to 85 ĕC and stirred for 3 h under nitrogen protection. The mixture was cooled to rt, and to the mixture was added 30 mL of water. The resulting mixture was extracted with ethyl acetate (50 mL B 3), and the combined organic layers were dried over anhydrous sodium sulfate and concentrated in vacuo. The residue was purified by silica gel column chromatography (PE/EA (V/V)=4/1) to give the title compound as colorless oil (1.39 g, 5.47 mmol).

MS (ESI, pos.ion) m/z: 267.3 [M+H]$^+$.

Step 3: 6-isopropyl-10-(methoxycarbonyl)-9-(1-(3-methoxypropyl)-1H-pyrazol-4-yl)-2-oxo-6,7-dihydro-2H-pyrido[2,1-a]isoquinoline-3-carboxylic Acid

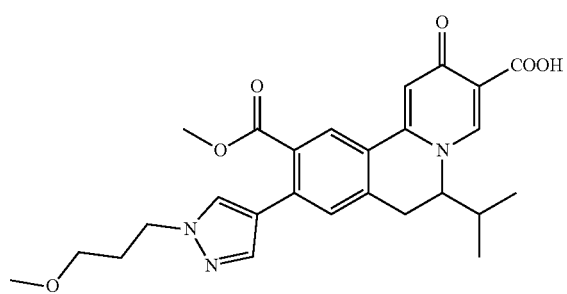 [SMILES: COCCCn1cc(-c2cc3c(cc2C(=O)OC)-c2cc(=O)c(C(=O)O)cn2C(C(C)C)C3)cn1]

The title compound was prepared according to the synthetic method of step 8 to step 10 in example 32 by using 1-(3-methoxypropyl)-4-(4,4,5,5-tetramethyl-1,3,2-dioxaborolan-2-yl)-1H-pyrazole (272 mg, 1.022 mmol) and methyl 6-bromo-3-isopropyl-3,4-dihydroisoquinoline-7-carboxylate (212 mg, 0.6834 mmol) as raw materials to give a white solid (126 mg, 0.26 mmol).

MS (ESI, pos.ion) m/z: 480.2 [M+H]$^+$;
$^1$H NMR (400 MHz, CDCl$_3$) 15.797 (b, 1H), 8.517 (s, 1H), 8.166 (s, 1H), 7.695 (d, J=4.2 Hz, 2H), 7.391 (s, 1H), 7.244 (s, 1H), 4.298 (t, J=6.8, 6.8 Hz, 2H), 4.030-3.960 (m, 1H), 3.907 (s, 3H), 3.495-3.350 (m, 6H), 3.308-3.231 (m, 1H), 2.238-2.127 (m, 2H), 1.840-1.733 (m, 1H), 0.984 (d, J=6.4 Hz, 3H), 0.864 (d, J=6.4 Hz, 3H).

Example 73: 9-(5-chlorothiophen-2-yl)-6-isopropyl-10-(methoxycarbonyl)-2-oxo-6,7-dihydro-2H-pyrido[2,1-a]isoquinoline-3-carboxylic Acid

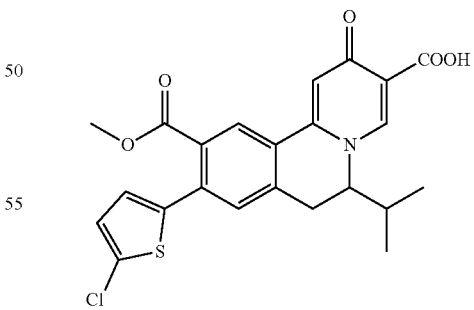

The title compound was prepared according to the synthetic method of step 8 to step 10 in example 32 by using 2-(5-chlorothiophen-2-yl)-4,4,5,5-tetramethyl-1,3,2-dioxaborolane (236 mg, 0.97 mmol) and methyl 6-bromo-3-isopropyl-3,4-dihydroisoquinoline-7-carboxylate (200 mg, 0.64 mmol) as raw materials to give a light yellow solid (92 mg, 0.20 mmol).

MS (ESI, pos.ion) m/z: 458.0 [M+H]⁺;
¹H NMR (400 MHz, CDCl₃) 15.682 (b, 1H), 8.529 (s, 1H), 8.177 (s, 1H), 7.407 (s, 1H), 7.262 (s, 1H), 6.958-6.935 (m, 2H), 4.035-3.963 (m, 1H), 3.882 (s, 3H), 3.495-3.414 (m, 1H), 3.322-3.236 (m, 1H), 1.827-1.748 (m, 1H), 0.989 (d, J=4.4 Hz, 3H), 0.873 (d, J=4.4 Hz, 3H).

Example 74: 9-(5-chlorofuran-2-yl)-6-isopropyl-10-(methoxycarbonyl)-2-oxo-6,7-dihydro-2H-pyrido[2,1-a]isoquinoline-3-carboxylic Acid

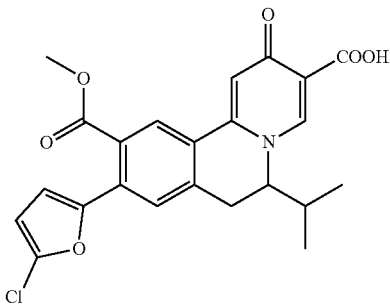 [SMILES: COC(=O)c1cc2c(cc1-c1ccc(Cl)o1)CC(C(C)C)n1cc(C(=O)O)c(=O)cc1-2]

The title compound was prepared according to the synthetic method of example 32 by using methyl 6-bromo-3-isopropyl-3,4-dihydroisoquinoline-7-carboxylate (200 mg, 0.64 mmol) as a raw material to give a light yellow solid (30 mg, 0.20 mmol).

MS (ESI, pos.ion) m/z: 442.0 [M+H]⁺;
¹H NMR (600 MHz, CDCl₃) 15.71 (s, 1H), 8.51 (s, 1H), 8.08 (s, 1H), 7.63 (s, 1H), 7.24 (s, 1H), 6.82 (d, J=3.5 Hz, 1H), 6.35 (d, J=3.5 Hz, 1H), 4.00-3.93 (m, 4H), 3.45 (dd, J=16.3, 5.1 Hz, 1H), 3.31 (d, J=15.9 Hz, 1H), 1.83-1.72 (m, 1H), 0.99 (d, J=6.6 Hz, 3H), 0.87 (d, J=6.7 Hz, 3H).

Example 75: 6-isopropyl-10-methoxy-2-oxo-9-(thiazol-2-yl)-6,7-dihydro-2H-pyrido[2,1-a]isoquinoline-3-carboxylic Acid

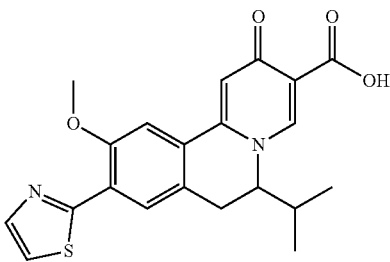 [SMILES: COc1cc2c(cc1-c1nccs1)CC(C(C)C)n1cc(C(=O)O)c(=O)cc1-2]

Step 1: 1-(4-methoxyphenyl)-3-methylbutan-2-one

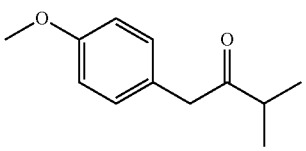

To a reaction flask were added 1-iodo-4-methoxybenzene (53 g, 226.47 mmol), 3-methylbutan-2-one (59 g, 685.0 mmol), X antphos (13 g, 22.47 mmol), Pd₂(dba)₃ (10 g, 10.92 mmoll), t-BuONa (43 g, 447.43 mmol) and tetrahydrofuran (500 mL). The mixture was degassed and filled with nitrogen for three times, then heated to 60 ĕC and stirred for 12 h. The mixture was cooled to rt, filtered, and the filtrate was concentrated in vacuo. The residue was purified by silica gel column chromatography (PE/EA (V/V)=30/1) to give the title compound as yellow oil (36 g, 187.26 mmol, 83%).

MS (ESI, pos.ion) m/z: 193.1[M+H]⁺.

Step 2: 1-(4-methoxyphenyl)-3-methylbutan-2-amine

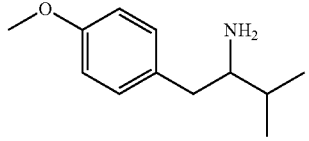

To a reaction flask were added 1-(4-methoxyphenyl)-3-methylbutan-2-one (36 g, 187.26 mmol), methanol (360 mL) and ammonium acetate (101 g, 1310.29 mmol). The mixture was stirred at rt for 1 h, then cooled to 0 ĕC, and sodium cyanoborohydride (24 g, 381.91 mmol) was added in portions, and the resulting mixture was stirred at rt for 24 h. The reaction mixture was concentrated in vacuo to remove methanol, and to the residue was added saturated aqueous sodium bicarbonate (300 mL) to quench the reaction. The resulting mixture was extracted with EA (300 mL B 2). The combined organic layers were washed with saturated aqueous sodium chloride (200 mL), dried over anhydrous sodium sulfate and concentrated in vacuo to give the title compound as yellow oil (31.4 g, 162 mmol, 87%).

MS (ESI, pos.ion) m/z: 194.3[M+H]⁺.

Step 3: Tert-butyl (1-(4-methoxyphenyl)-3-methylbutan-2-yl)carbamate

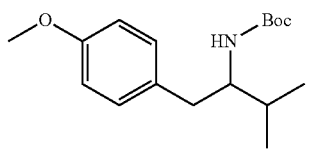 [SMILES: COc1ccc(CC(NC(=O)OC(C)(C)C)C(C)C)cc1]

To a reaction flask were added 1-(4-methoxyphenyl)-3-methylbutan-2-amine (31 g, 163 mmol) and dichloromethane (300 mL). The mixture was cooled to 0 ĕC, then Boc₂O (43 g, 195 mmol) and triethylamine (33 g, 330 mmol) were added. After addition, the mixture was warmed to rt and stirred for 12 h, and saturated aqueous ammonium chloride (200 mL) was added. The mixture was partitioned, and the organic layers were concentrated in vacuo. The residue was purified by silica gel column chromatography (PE/EA (V/V)=20/1) to give the title compound as a white solid (43 g, 146.6 mmol, 90%).

MS (ESI, pos.ion) m/z: 317.3[M+Na]⁺.

Step 4: Tert-butyl (1-(3-iodo-4-methoxyphenyl)-3-methylbutan-2-yl)carbamate

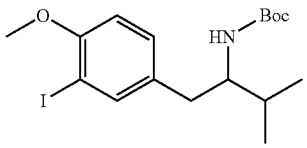 [SMILES: COc1ccc(CC(NC(=O)OC(C)(C)C)C(C)C)cc1I]

To a reaction flask were added tert-butyl (1-(4-methoxyphenyl)-3-methylbutan-2-yl)carbamate (30 g, 102.2 mmol) and methanol (400 mL). The mixture was stirred to dissolve the reagent, then silver sulfate (35 g, 113 mmol) and iodine (28.6 g, 113 mmol) were added. The mixture was stirred at rt for 1 h. The mixture was filtered and concentrated in vacuo. The residue was dissolved in ethyl acetate (400 mL), and the mixture was washed with 20% $Na_2S_2O_3$ solution (200 mL B 2) and saturated sodium chloride (200 mL) in turn. The organic layer was concentrated in vacuo, and the residue was purified by silica gel column chromatography (PE/EA (V/V)=15/1) to give the title compound as a white solid (25 g, 59.62 mmol, 58%).

MS (ESI, pos.ion) m/z: 342.0[M+Na]$^+$; 354.0 [M-tBu]$^+$.

Step 5: 1-(3-iodo-4-methoxyphenyl)-3-methylbutan-2-amine

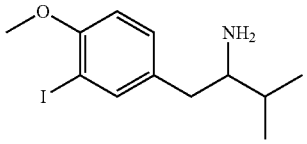

To a reaction flask were added tert-butyl (1-(3-iodo-4-methoxyphenyl)-3-methylbutan-2-yl)carbamate (10 g, 23.85 mmol) and dichloromethane (50 mL). The mixture was stirred to dissolve the reagent, then trifluoroacetic acid (50 mL) was added. The mixture was stirred at rt for 4 h. The mixture was concentrated in vacuo, and the residue was dissolved in ethyl acetate (100 mL). The mixture was adjusted with 20% aqueous potassium carbonate till the pH value of the aqueous layer was 8, and the resulting mixture was partitioned. The aqueous layer was extracted with ethyl acetate (100 mL), and the organic layer was washed with saturated aqueous sodium chloride (100 mL), dried over anhydrous sodium sulfate, then concentrated in vacuo to remove the solvent and give the title compound as a yellow oil (7.6 g, 24 mmol, 100%), which was used directly in the next step.

Step 6: N-(1-(3-iodo-4-methoxyphenyl)-3-methylbutan-2-yl)formamide

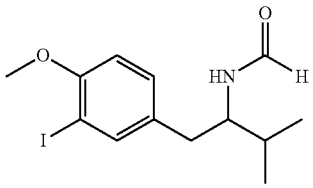 [SMILES: COc1ccc(CC(NC=O)C(C)C)cc1I]

To a reaction flask were added 1-(3-iodo-4-methoxyphenyl)-3-methylbutan-2-amine (7.5 g, 23 mmol) and ethyl acetate (200 mL). The mixture was heated to reflux and stirred for 12 h. The reaction mixture was washed with saturated aqueous sodium bicarbonate (100 mL) and sodium chloride (100 mL) in turn, dried over anydrous sodium sulfate and concentrated in vacuo to remove the solvent and give the title compound as a light yellow solid (6.3 g, 18 mmol, 77%).

MS (ESI, pos.ion) m/z: 348.1 [M+1]$^+$.

Step 7: 6-iodo-3-isopropyl-7-methoxy-3,4-dihydroisoquinoline

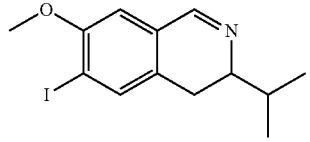 [SMILES: COc1cc2c(cc1I)CC(C(C)C)N=C2]

To a reaction flask were added N-(1-(3-iodo-4-methoxyphenyl)-3-methylbutan-2-yl)formamide (6.0 g, 17.2 mmol) and dichloromethane (150 mL). The mixture was degassed and filled with nitrogen for three times, then the mixture was stirred to dissolve the reagent. Oxalyl chloride (2.8 g, 24 mol) was added. The mixture was stirred at rt for 1 h. The reaction mixture was cooled to −10 ěC, and ferric trichloride (1.7 g, 20 mol) was added. The mixture was warmed to rt and stirred for 12 h. The reaction was quenched with HCl (2 M, 100 mL), and the mixture was partitioned. The aqueous layer was extracted with dichloromethane (50 mL), then the organic layer was washed with saturated aqueous sodium chloride (50 mL), dried over anhydrous sodium sulfate and concentrated in vacuo to remove the solvent. Methanol (150 mL) was added to dissolve the residue, and concentrated sulfuric acid (7.5 mL) was added. The resulting mixture was refluxed for 12 h. The mixture was cooled to rt, and concentrated in vacuo. The residue was adjusted with saturated aqueous sodium bicarbonate to pH=8, then the mixture was extracted with ethyl acetate (60 mL B 2). The combined organic layers were concentrated in vacuo, and the residue was purified by silica gel column chromatography (PE/EA (V/V)=3/1) to give the title compound as red oil (3.0 g, 8.6 mmol, 50%).

MS (ESI, pos.ion) m/z: 330.1[M+1]$^+$; Step 8: ethyl 9-iodo-6-isopropyl-10-methoxy-2-oxo-2,6,7,11b-tetrahydro-1H-pyrido[2,1-a]isoquinoline-3-carboxylate

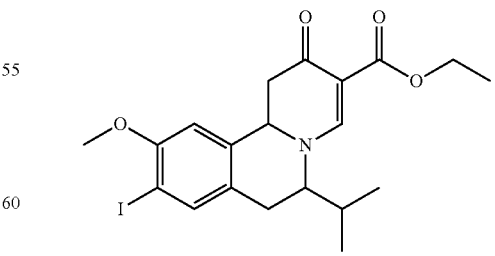

To a reaction flask were added 6-iodo-3-isopropyl-7-methoxy-3,4-dihydroisoquinoline (3 g, 9.1 mmol), ethyl 2-(ethoxymethylene)-3-oxobutanoate (8.5 g, 45.5 mol) and ethanol (30 mL). The reaction mixture was refluxed for 12 h. The reaction mixture was concentrated in vacuo to remove the solvent, and the residue was used directly in the next step.

MS (ESI, pos.ion) m/z: 470.1[M+1]+.

Step 9: Ethyl 9-iodo-6-isopropyl-10-methoxy-2-oxo-6,7-dihydro-2H-pyrido[2,1-a]isoquinoline-3-carboxylate

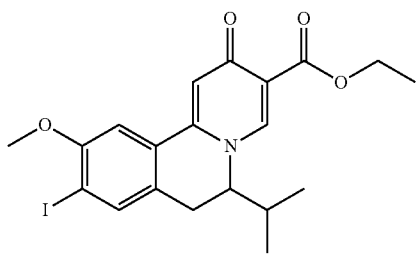 [SMILES: CCOC(=O)c1cn2c(cc1=O)-c1cc(OC)c(I)cc1CC2C(C)C]

To a reaction flask were added ethyl 9-iodo-6-isopropyl-10-methoxy-2-oxo-2,6,7,11b-tetrahydro-1H-pyrido[2,1-a]isoquinoline-3-carboxylate (4.3 g, 9.2 mmol), chloranil (2.3 g, 9.4 mmol) and dimethoxyethane (80 mL). The mixture was refluxed for 8 h. The mixture was concentrated in vacuo, and the residue was purified by silica gel column chromatography (DCM/MeOH (V/V)=15/1) to give the title compound as a brown solid (3.6 g, 7.7 mmol, 84%).

MS (ESI, pos.ion) m/z: 468.1 [M+1]+.

Step 10: 6-isopropyl-10-methoxy-2-oxo-9-(thiazol-2-yl)-6,7-dihydro-2H-pyrido[2,1-a]isoquinoline-3-carboxylic Acid

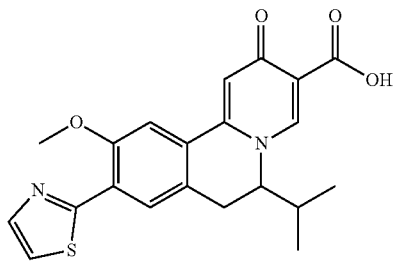 [SMILES: COc1cc2c(cc1-c1nccs1)CC(C(C)C)n1cc(C(=O)O)c(=O)cc1-2]

To a dried reaction flask were added ethyl 9-iodo-6-isopropyl-10-methoxy-2-oxo-6,7-dihydro-2H-pyrido[2,1-a]isoquinoline-3-carboxylate (300 mg, 0.64 mmol), 2-(tributylstannyl)thiazole (0.48 g, 1.28 mmol), bis(triphenylphosphine)palladium(II) chloride (0.1 g, 0.1 mmol) and 1,4-dioxane (10 mL). After addition, the mixture was degassed and filled with nitrogen for three times, then heated to 110 ěC and stirred for 12 h. The reaction mixture was concentrated in vacuo, and the residue was purified by silica gel column chromatography (DCM/MeOH (V/V)=15/1) to give the title compound as a light yellow solid (170 mg, 0.43 mmol, 67%).

MS (ESI, pos.ion) m/z: 397.0[M+1]+;

$^1$H NMR (600 MHz, DMSO-$d_6$) 8.86 (s, 1H), 8.35 (s, 1H), 8.02 (d, J=3.0 Hz, 1H), 7.89 (d, J=3.0 Hz, 1H), 7.83 (s, 1H), 7.71 (s, 1H), 4.53 (d, J=9.8 Hz, 1H), 4.16 (s, 3H), 3.35-3.15 (m, 2H), 1.75-1.44 (m, 1H), 0.88 (d, J=6.6 Hz, 3H), 0.71 (d, J=6.6 Hz, 3H).

Example 76: 9-(4-bromothiazol-2-yl)-6-isopropyl-10-methoxy-2-oxo-6,7-dihydro-2H-pyrido[2,1-a]isoquinoline-3-carboxylic Acid

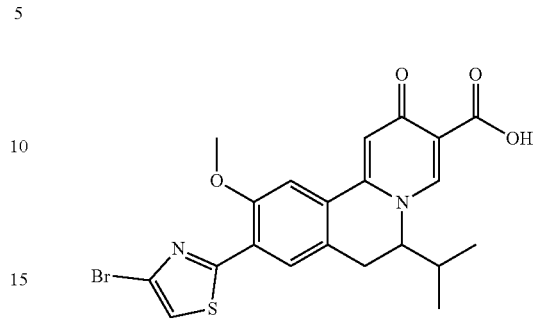

The title compound was prepared according to the synthetic method of step 10 in example 76 by using ethyl 9-iodo-6-isopropyl-10-methoxy-2-oxo-6,7-dihydro-2H-pyrido[2,1-a]isoquinoline-3-carboxylate (300 mg, 0.64 mmol) and 4-bromo-2-(tributylstannyl)thiazole (0.44 g, 0.96 mmol) as raw materials to give a white solid (80 mg, 0.17 mmol).

MS (ESI, pos.ion) m/z: 475.1[M+1]+;

$^1$H NMR (400 MHz, DMSO-$d_6$) 9.26 (s, 1H), 8.85 (s, 1H), 7.92-7.43 (m, 3H), 4.51 (s, 1H), 3.95 (s, 3H), 3.32-3.24 (m, 2H), 1.75-1.50 (m, 1H), 0.80 (dd, J=59.0, 5.3 Hz, 6H).

Example 77: 6-isopropyl-9-(5-isopropylthiazol-2-yl)-10-methoxy-2-oxo-6,7-dihydro-2H-pyrido[2,1-a]isoquinoline-3-carboxylic Acid

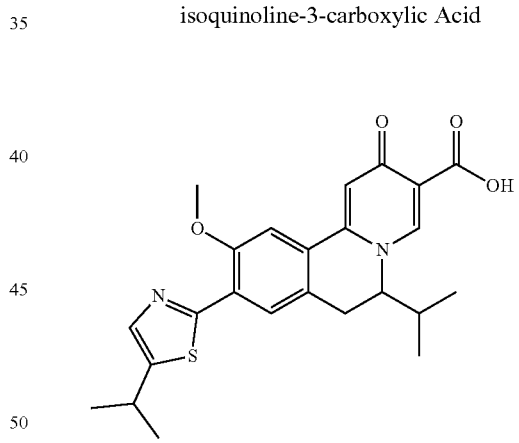

The title compound was prepared according to the synthetic method of step 10 in example 76 by using ethyl 9-iodo-6-isopropyl-10-methoxy-2-oxo-6,7-dihydro-2H-pyrido[2,1-a]isoquinoline-3-carboxylate (300 mg, 0.64 mmol) and 4-bromo-2-(tributylstannyl)thiazole (0.44 g, 0.96 mmol) as raw materials to give a white solid (80 mg, 0.17 mmol).

MS (ESI, pos.ion) m/z: 439.1[M+1]+;

$^1$H NMR (600 MHz, DMSO-$d_6$) 8.86 (s, 1H), 8.28 (s, 1H), 7.80 (s, 1H), 7.74 (s, 1H), 7.69 (s, 1H), 4.52 (d, J=9.8 Hz, 1H), 4.14 (s, 3H), 3.33-3.23 (m, 2H), 3.18 (d, J=5.1 Hz, 1H), 1.65-1.51 (m, 1H), 1.34 (d, J=6.9 Hz, 6H), 0.87 (d, J=7.4 Hz, 3H), 0.71 (d, J=6.7 Hz, 3H).

Example 78: 6-isopropyl-10-methoxy-9-(4-(methoxymethyl)thiazol-2-yl)-2-oxo-6,7-dihydro-2H-pyrido[2,1-a]isoquinoline-3-carboxylic Acid

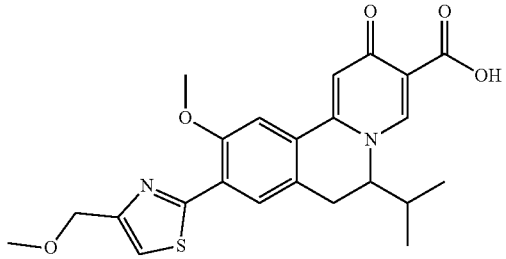 [SMILES: COCc1csc(-c2cc3c(cc2OC)-c2cc(=O)c(C(=O)O)cn2C(C(C)C)C3)n1]

The title compound was prepared according to the synthetic method of step 10 in example 76 by using ethyl 9-iodo-6-isopropyl-10-methoxy-2-oxo-6,7-dihydro-2H-pyrido[2,1-a]isoquinoline-3-carboxylate (300 mg, 0.64 mmol) and 4-(methoxymethyl)-2-(tributylstannyl)thiazole (0.67 g, 1.605 mmol) as raw materials to give a white solid (100 mg, 0.2270 mmol).

MS (ESI, pos.ion) m/z: 441.3[M+1]$^+$;

$^1$H NMR (400 MHz, CDCl$_3$) 15.78 (s, 1H), 8.54 (s, 1H), 8.42 (s, 1H), 7.43 (s, 1H), 7.39 (s, 1H), 7.28 (s, 1H), 4.69 (s, 2H), 4.14 (s, 3H), 4.01-3.92 (m, 1H), 3.53 (s, 3H), 3.39 (dd, J=16.3, 4.1 Hz, 1H), 3.30 (d, J=16.1 Hz, 1H), 1.84-1.78 (m, 1H), 0.92 (dd, J=52.3, 6.6 Hz, 6H).

Example 79: 9-(5-chlorothiophen-2-yl)-6-isopropyl-10-methoxy-2-oxo-6,7-dihydro-2H-pyrido[2,1-a]isoquinoline-3-carboxylic Acid

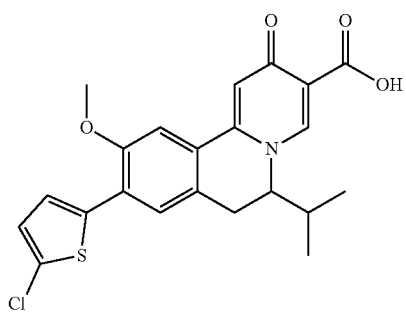

The title compound was prepared according to the synthetic method of example 16 by using ethyl 9-iodo-6-isopropyl-10-methoxy-2-oxo-6,7-dihydro-2H-pyrido[2,1-a]isoquinoline-3-carboxylate (300 mg, 0.64 mmol) and 2-(5-chlorothiophen-2-yl)-4,4,5,5-tetramethyl-1,3,2-dioxaborolane (235 mg, 0.96 mmol) as raw materials to give a gray solid (210 mg, 0.49 mmol).

MS (ESI, pos.ion) m/z: 430.0[M+1]*;

$^1$H NMR (400 MHz, DMSO-d$_6$) 8.83 (s, 1H), 7.94 (s, 1H), 7.76-7.59 (m, 3H), 7.21 (d, J=3.2 Hz, 1H), 4.57-4.45 (m, 1H), 4.07 (s, 3H), 3.29-3.21 (m, 2H), 1.61-1.50 (m, 1H), 0.80 (dd, J=69.3, 6.0 Hz, 6H).

Example 80: 9-(5-bromothiazol-2-yl)-6-isopropyl-10-methoxy-2-oxo-6,7-dihydro-2H-pyrido[2,1-a]isoquioline-3-carboxlic Acid

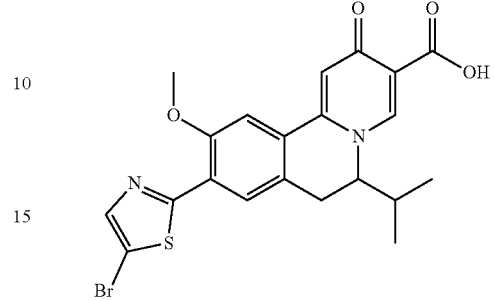

Step 1: Tert-butyl (1-(4-methoxy-3-(thiazol-2-yl)phenyl)-3-methylbutan-2-yl)carbamate

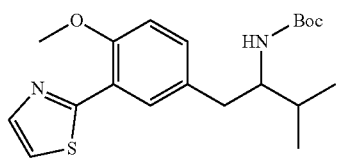 [SMILES: COc1ccc(CC(NC(=O)OC(C)(C)C)C(C)C)cc1-c1nccs1]

To a dried reaction flask were added 1-(3-iodo-4-methoxyphenyl)-3-methylbutan-2-amine (1.30 g, 3.10 mmol), 2-(tributylstannyl)thiazole (1.74 g, 4.65 mmol), bis(triphenylphosphine)palladium(II) chloride (0.54 g, 0.78 mmol) and 1,4-dioxane (30 mL). After addition, the mixture was degassed and filled with nitrogen for three times, then heated to 110 ěC and stirred for 12 h. The reaction mixture was concentrated in vacuo, and the residue was purified by silica gel column chromatography (PE/EA (V/V)=6/1) to give the title compound as a yellow solid (1.0 g, 2.66 mmol, 86%).

MS (ESI, pos.ion) m/z: 377.4 [M+1]$^+$.

Step 2: Tert-butyl (1-(3-(5-bromothiazol-2-yl)-4-methoxyphenyl)-3-methylbutan-2-yl)carbamate

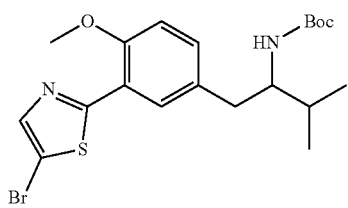 [SMILES: COc1ccc(CC(NC(=O)OC(C)(C)C)C(C)C)cc1-c1ncc(Br)s1]

To a reaction flask were added tert-butyl (1-(4-methoxy-3-(thiazol-2-yl)phenyl)-3-methylbutan-2-yl)carbamate (0.90 g, 2.39 mmol), dichloromethane (20 mL) and NBS (0.425 g, 2.39 mmol). The mixture was stirred at rt for 30 min. The reaction mixture was concentrated in vacuo, and

Step 3: 1-(3-(5-bromothiazol-2-yl)-4-methoxyphenyl)-3-methylbutan-2-amine

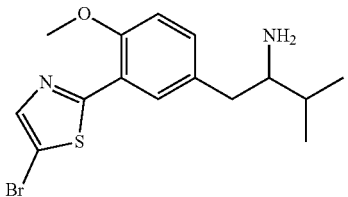 [SMILES: COc1ccc(CC(N)C(C)C)cc1-c1ncc(Br)s1]

To a reaction flask were added tert-butyl (1-(3-(5-bromothiazol-2-yl)-4-methoxyphenyl)-3-methylbutan-2-yl)carbamate (0.9 g, 2 mmol) and dichloromethane (5 mL). The mixture was stirred to dissolve the reagent, then trifluoroacetic acid (5 mL) was added. The mixture was stirred at rt for 4 h. The mixture was concentrated in vacuo, and the residue was dissolved in ethyl acetate (30 mL). The mixture was adjusted with 20% aqueous potassium carbonate till the pH value of the aqueous layer was 8, and the resulting mixture was partitioned. The aqueous layer was extracted with ethyl acetate (20 mL), then the combined organic layers were washed with saturated aqueous sodium chloride (30 mL), dried over anhydrous sodium sulfate and concentrated in vacuo to remove the solvent and give the title compound as yellow oil (0.7 g, 2 mmol, 100%), which was used directly in the next step.

MS (ESI, pos.ion) m/z: 355.1[M+1]$^+$.

Step 4: N-(1-(3-(5-bromothiazol-2-yl)-4-methoxyphenyl)-3-methylbutan-2-yl)formamide

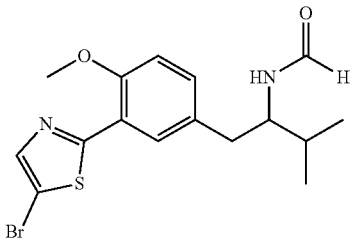 [SMILES: COc1ccc(CC(NC=O)C(C)C)cc1-c1ncc(Br)s1]

To a reaction flask were added 1-(3-(5-bromothiazol-2-yl)-4-methoxyphenyl)-3-methylbutan-2-amine (0.7 g, 2 mmol) and ethyl formate (200 mL). The mixture was heated to reflux and stirred for 12 h. The reaction mixture was washed with saturated aqueous sodium bicarbonate (200 mL) and sodium chloride (200 mL) in turn, dried over anydrous sodium sulfate and concentrated in vacuo to remove the solvent and give the title compound as a light yellow solid (0.8 g, 2 mmol, 100%).

MS (ESI, pos.ion) m/z: 383.1 [M+1]$^+$.

Step 5: 5-bromo-2-(3-isopropyl-7-methoxy-3,4-dihydroisoquinolin-6-yl)thiazole

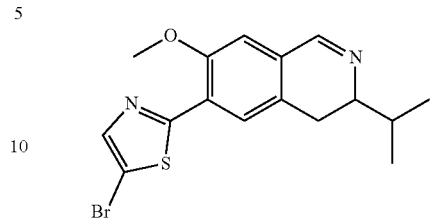

To a reaction flask were added N-(1-(3-(5-bromothiazol-2-yl)-4-methoxyphenyl)-3-methylbutan-2-yl)formamide (0.9 g, 2 mmol) and dichloromethane (20 mL). The mixture was degassed and filled with nitrogen for three times, then the mixture was stirred to dissolve the reagent and oxalyl chloride (0.3 g, 2.2 mmol) was added. The mixture was stirred at rt for 1 h. The reaction mixture was cooled to −10 ẽC, and ferric trichloride (0.4 g, 2.4 mmol) was added. The mixture was warmed to rt and stirred for 12 h. The reaction was quenched with HCl (2 M, 20 mL), and the mixture was partitioned. The aqueous layer was extracted with dichloromethane (20 mL), then the organic layer was washed with saturated aqueous sodium chloride (30 mL), dried over anhydrous sodium sulfate and concentrated in vacuo. The residue was dissolved in methanol (30 mL), and to the mixture was added concentrated sulfuric acid (1.5 mL). The mixture was refluxed for 12 h, then concentrated in vacuo, and to the residue was added saturated aqueous sodium bicarbonate to adjust pH=8. The mixture was extracted with ethyl acetate (20 mL B 2). The combined organic layers were concentrated in vacuo, and the residue was purified by silica gel column chromatography (PE/EA (V/V)=3/1) to give the title compound as red oil (90 mg, 0.2464 mmol, 10%).

MS (ESI, pos.ion) m/z: 365.0[M+1]$^+$.

Step 6: Ethyl 9-(5-bromothiazol-2-yl)-6-isopropyl-10-methoxy-2-oxo-2,6,7,11b-tetrahydro-1H-pyrido[2,1-a]isoquinoline-3-carboxylate

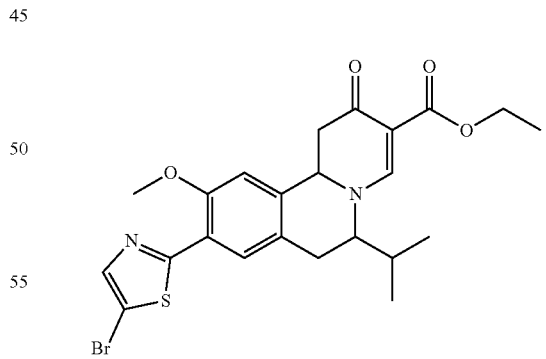

To a reaction flask were added 5-bromo-2-(3-isopropyl-7-methoxy-3,4-dihydroisoquinolin-6-yl)thiazole (90 mg, 0.2464 mmol), ethyl 2-(ethoxymethylene)-3-oxobutanoate (0.25 g, 1.3 mmol) and ethanol (2 mL). The reaction mixture was refluxed for 12 h. The reaction mixture was concentrated in vacuo to remove the solvent, and the residue was used directly in the next step.

MS (ESI, pos.ion) m/z: 505.1[M+1]$^+$.

223

Step 7: Ethyl 9-(5-bromothiazol-2-yl)-6-isopropyl-10-methoxy-2-oxo-6,7-dihydro-2H-pyrido[2,1-a]isoquinoline-3-carboxylate

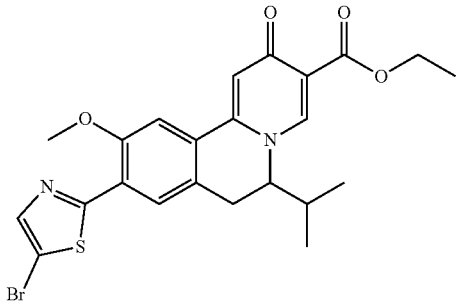 [SMILES: CCOC(=O)c1cn2c(cc1=O)-c1cc(OC)c(-c3ncc(Br)s3)cc1CC2C(C)C]

To a reaction flask were added ethyl 9-(5-bromothiazol-2-yl)-6-isopropyl-10-methoxy-2-oxo-2,6,7,11b-tetrahydro-1H-pyrido[2,1-a]isoquinoline-3-carboxylate (0.13 g, 0.26 mmol), chloranil (0.063 g, 0.26 mmol) and dimethoxyethane (80 mL). The mixture was refluxed for 8 h. The reaction mixture was concentrated in vacuo, and the residue was purified by silica gel column chromatography (DCM/MeOH (V/V)=15/1) to give the title compound as a brown solid (76 mg, 0.15 mmol, 59%).

MS (ESI, pos.ion) m/z: 503.0 [M+1]+.

Step 8: 9-(5-bromothiazol-2-yl)-6-isopropyl-10-methoxy-2-oxo-6,7-dihydro-2H-pyrido[2,1-a]isoquinoline-3-carboxylic Acid

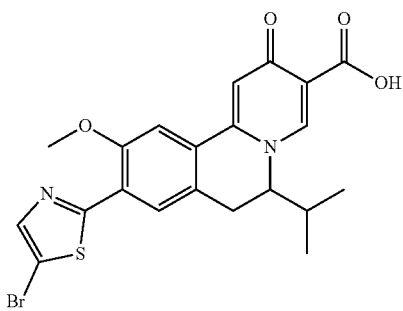 [SMILES: COc1cc2c(cc1-c1ncc(Br)s1)CC(C(C)C)n1cc(C(=O)O)c(=O)cc1-2]

Ethyl 9-(5-bromothiazol-2-yl)-6-isopropyl-10-methoxy-2-oxo-6,7-dihydro-2H-pyrido[2,1-a]isoquinoline-3-carboxylate (76 mg, 0.1510 mmol) was dissolved in methanol (3 mL, 74.2 mmol), and lithium hydroxide (32 mg, 0.7619 mmol) was added. The mixture was stirred at rt for 12 h. The reaction mixture was adjusted with hydrochloric acid (1 M) to pH=2, and there was a solid precipitated out. The mixture was filtered, and the filter cake was recrystallized from methanol (5 mL) to give the title compound as a gray solid (42 mg, 0.088 mmol, 58.52%).

MS (ESI, pos.ion) m/z: 475.0[M+1]+;

$^1$H NMR (400 MHz, DMSO-$d_6$) 8.86 (s, 1H), 8.28 (s, 1H), 8.09 (s, 1H), 7.85 (s, 1H), 7.71 (s, 1H), 4.53 (d, J=9.8 Hz, 1H), 4.17 (s, 3H), 3.39-3.35 (m, 2H), 1.65-1.53 (m, 1H), 0.88 (d, J=6.6 Hz, 3H), 0.71 (d, J=6.6 Hz, 3H).

224

Example 81: 6-isopropyl-10-(2-(4-methoxyphenyl)-2-oxoethoxy)-9-(3-methoxypropoxy)-2-oxo-6,7-dihydro-2H-pyrido[2,1-a]isoquinoline-3-carboxylic Acid

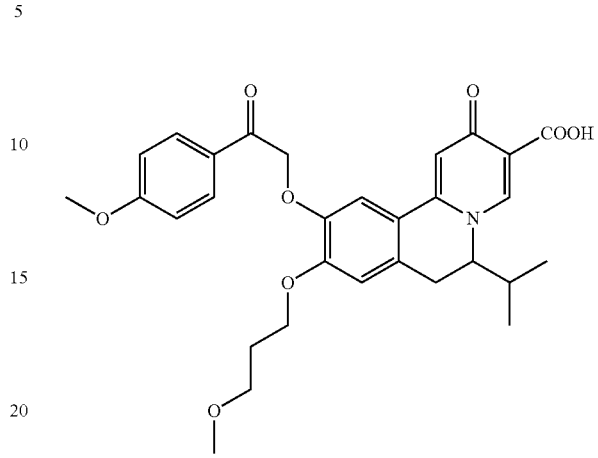

The title compound was prepared according to the synthetic method of example 29 by using ethyl 10-hydroxy-6-isopropyl-9-(3-methoxypropoxy)-2-oxo-6,7-dihydro-2H-pyrido[2,1-a]isoquinoline-3-carboxylate (0.400 g, 1.03 mmol) and 2-bromo-1-(4-methoxyphenyl)ethanone (130 mg, 0.57 mmol) as raw materials to give a white solid (0.28 g, 0.6 mmol).

MS (ESI, pos.ion) m/z: 536.3 [M+H]+;

$^1$H NMR (400 MHz, CDCl$_3$) 16.005 (br, 1H), 8.436 (s, 1H), 8.029 (d, J=8.8 Hz, 1H), 8.341 (s, 2H), 7.181 (s, 1H), 7.019 (d, J=8.8 Hz, 1H), 6.942 (s, 1H), 6.823 (s, 1H), 5.373 (s, 2H), 4.252-4.186 (m, 2H), 3.928 (s, 3H), 3.873-3.830 (m, 1H), 3.614-3.574 (m, 2H), 3.376 (s, 3H), 3.329-3.294 (m, 1H), 3.108-3.056 (m, 1H), 2.183-2.114 (m, 2H), 1.879-1.793 (m, 1H), 0.959 (d, J=6.4 Hz, 3H), 0.834 (d, J=6.8 Hz, 3H).

Biological Assays

HBV Cell Line

The chromosomes of HepG2.2.15 cells (SELLS, PNAS, 1987 and SELLS, JV, 1988) integrate the complete HBV genome and stably express viral RNA and viral proteins. HepG2.2.15 cells are able to secrete mature HBV particles and HBsAg into the culture medium. Viral particle DNA and HBsAg secreted by HepG 2.2.15 cells can be quantified by qPCR and ELISA methods, and the effects of the compound on virus replication and HBsAg secretion are thus examined.

Assay 1: Inhibition of HBV Virus Replication by Compounds of the Invention

Test Method

HepG 2.2.15 Cells (8,000 per well) were seeded into 96-well cell culture plates in duplicate and cultured for 3 days until the cells grew to fill in pores. Cells were treated with 4-fold serial diluted compound solution for 10 days, and the compound solution was exchanged once every other day, the final concentration of DMSO in all wells was 0.5% and DMSO was used as a drug-free control. On the eleventh day, the supernatant was collected for quantitative detection of HBV DNA.

qPCR method was used for detection of viral genomic DNA, HBV primers were as follows: HBV-For-202, CAGGCGGGGTTTTTCTTGTTGA; HBV-Rev-315, GTGATTGGAGGTTGGGGACTGC.

Using the SY BR Premix Ex Taq II—Takara DRR081S kit, 1 ≈L of the cell culture supernatant was used as a template, a plasmid containing the HBV genome was used for plotting a standard curve, and virus copy number was calculated using the standard curve. Concentration-virus copy number was treated with Graphpad Prism 5 software and the $IC_{50}$ of inhibition of virus replication by compounds was calculated by a four-parameter nonlinear regression model.

Conclusion: The inhibition experiment of HB virus replication by the compound of the present invention shows that the $IC_{50}$ of the inhibitory activity of the compound of the present invention against HBV DNA is less than 0.5 μM, and the $IC_{50}$ of the inhibitory activity of most compounds against HBV DNA replication is less than 0.1 μM. The inhibitory activities against HBV DNA replication of part of the compounds were as shown in table 2.

TABLE 2 inhibitory activities against HBV DNA replication of part of the compounds in the invention

| Example | DNA $IC_{50}$ (nM) | Example | DNA $IC_{50}$ (nM) |
|---|---|---|---|
| Example 1 | 6.30 | Example 5 | 10.60 |
| Example 6 | 3.02 | Example 7 | 8.16 |
| Example 8 | 4.46 | Example 9 | 0.18 |
| Example 10 | 7.29 | Example 11 | 1.90 |
| Example 13 | 0.64 | Example 14 | 3.36 |
| Example 15 | 0.39 | Example 16 | 1.99 |
| Example 17 | 3.60 | Example 18 | 8.09 |
| Example 20 | 8.79 | Example 21 | 0.30 |
| Example 22 | 0.84 | Example 24 | 8.63 |
| Example 30 | 7.68 | Example 31 | 6.26 |
| Example 32 | 7.57 | Example 33 | 1.93 |
| Example 34 | 4.74 | Example 35 | 7.59 |
| Example 36 | 2.55 | Example 47 | 6.35 |
| Example 53 | 7.99 | Example 67 | 4.36 |
| Example 69 | 10.18 | Example 73 | 3.88 |
| Example 74 | 2.97 | Example 75 | 2.10 |
| Example 77 | 2.79 | Example 78 | 2.84 |
| Example 79 | 2.01 | Example 80 | 2.57 |

Assay 2: Inhibition of HBsAg Secretion by Compounds of the Invention

Test Method

HepG 2.2.15 Cells (8,000 per well) were seeded into 96-well cell culture plates in duplicate and cultured for 3 days until the cells grew to fill in pores. Cells were treated with 4-fold serial diluted compound solution for 10 days, and the compound solution was exchanged once every other day, the final concentration of DMSO in all wells was 0.5% and DMSO was used as a drug-free control. On the eleventh day, the supernatant was collected for quantitative detection of HBsAg.

The level of HBsAg secreted by the cells after treatment with the compound was detected by ELISA. The method used a hepatitis B surface antigen diagnostic kit (Shanghai K ehua Biotechnology Co., Ltd. 510910113). 25 ≈L of the supernatant to be examined (diluted to 75 ≈L in PBS) was added to each well of the ELISA plate, and a kit-positive control and a negative control were set. The ELISA plates were blocked with mounting paper and incubated at 37 ěC for 60 minutes. The ELISA plate was took out, and the mounting paper was removed, then 50 ≈L of enzyme conjugate was added into each well. After shaking for 10 seconds, the ELISA plates were blocked with mounting paper and incubated at 37 ěC for 30 minutes. The ELISA plate was took out, and the mounting paper was removed, and the ELISA plate was repeated washing five times: liquid in the wells was discard each time; the wells was filled with washing solution, then stood for 60 seconds and spined dry; and liquid residue on blotting paper was patted dry. After the washing was completed, to all wells was immediately added a mixture of freshly prepared developer A and developer B: 100 ≈L per well. After shaking for 10 seconds on oscillator, the ELISA plates were blocked with mounting paper and incubated at 37 ěC for 30 minutes. To all wells were added 50 ≈L of stop solution. Data were read at a wavelength of 450 nm on an Envision plate reader. Concentration-HBsAg OD450 value was treated with Graphpad Prism 5 software and the $IC_{50}$ of inhibition of HBsAg secretion by compounds was calculated by a four-parameter nonlinear regression model.

Conclusion: Inhibitory test of compounds in the invention against HBV Virus replication shows that the $IC_{50}$ value of the inhibitory activity of the compound in the present invention against HBsAg secretion is less than 0.5 μM, and the $IC_{50}$ value of the inhibitory activity of most compounds against HBsAg secretion is less than 0.1 μM. The inhibitory activities against HBsAg secretion of part of the compounds were as shown in table 3.

TABLE 3 inhibitory activities against HBsAg secretion of part of the compounds

| Example | HbsAg $IC_{50}$ (nM) | Example | HbsAg $IC_{50}$ (nM) |
|---|---|---|---|
| Example 1 | 2.25 | Example 5 | 9.88 |
| Example 6 | 3.63 | Example 7 | 13.46 |
| Example 8 | 6.28 | Example 9 | 0.25 |
| Example 10 | 10.50 | Example 11 | 1.60 |
| Example 13 | 1.48 | Example 14 | 7.20 |
| Example 15 | 0.77 | Example 16 | 3.20 |
| Example 17 | 2.14 | Example 18 | 5.53 |
| Example 20 | 8.12 | Example 21 | 0.35 |
| Example 22 | 0.65 | Example 24 | 9.99 |
| Example 30 | 7.83 | Example 31 | 8.20 |
| Example 32 | 9.62 | Example 33 | 3.08 |
| Example 34 | 9.85 | Example 35 | 9.25 |
| Example 36 | 4.22 | Example 67 | 7.77 |
| Example 69 | 15.22 | Example 73 | 12.68 |
| Example 74 | 3.68 | Example 75 | 2.41 |
| Example 77 | 2.87 | Example 78 | 3.26 |
| Example 79 | 2.95 | Example 80 | 2.16 |

Assay 3: Pharmacokinetic Test of Compounds of the Invention in Beagle Dogs, Mice and Rats (1) Pharmacokinetic Test of Compounds of the Invention in Beagle Dogs Pharmacokinetic test of compounds of the invention in beagle dogs (weigh: 10-12 kg, male, age: 10-12 months, three mumbers in each oral group and intravenous group) was shown as follows.

Test Method

Beagle dogs received test compound of the invention at a dose of 2.5 mg/kg or 5 mg/kg by oral gavage or at a dose of 1 mg/kg or 2 mg/kg by intravenous injection.

Blood samples of vein were taken at 0.083, 0.25, 0.5, 1, 2, 4, 6, 8 and 24 hours after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonL in 6.3 software.

Conclusion: the pharmacokinetic data show that the compounds of the invention have good pharmacokinetic properties in vivo of beagle dogs, and have a good application prospect in anti-HBV virus.

(2) Pharmacokinetic Test in Mice

Pharmacokinetic test of compounds of the invention in mice (weigh: 20-25 g, male, age: 45-60 days, three mumbers in each oral group and intravenous group) was shown as follows.

Test Method

ICR mice received test compound of the invention at a dose of 10 mg/kg by oral gavage or at a dose of 2 mg/kg or 10 mg/kg by tail intravenous injection. Blood samples of orbital vein were taken at 0.083, 0.25, 0.5, 1, 2, 4, 6, 8 and 24 hours after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonL in 6.1 software.

Conclusion: the pharmacokinetic data show that the compounds of the invention have good pharmacokinetic properties in vivo of mice, and have a good application prospect in anti-HBV virus.

(3) Pharmacokinetic Test in SD Rat

Pharmacokinetic test of compounds of the invention in SD rats (weigh: 200-250 kg, male, age: 2-3 months, three mumbers in each oral group and intravenous group) was shown as follows.

Test Method

Rats received test compound at a dose of 2.5 mg/kg or 5 mg/kg by oral gavage or at a dose of 1 mg/kg by intravenous injection.

Blood samples of vein were taken at 0.083, 0.25, 0.5, 1, 2, 5, 7 and 24 hours after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonL in 6.3 software.

Conclusion: the pharmacokinetic data show that the compounds of the invention have good pharmacokinetic properties in vivo of SD rats, and have a good application prospect in anti-HBV virus.

Assay 4: The Stability Test of the Compounds of the Invention in Different Species of Liver Microsomes The stability test of the compounds in different species of liver microsomes was shown as follows.

Test Method

To a 96-well plate was added 30 ≈L of a mixed solution of a blank solution and liver microsomes, and to each well was added 15 ≈L of a buffer containing the test compound. Two samples were taken in parallel. After pre-incubating at 37 ěC for 10 min, 15 ≈L of NADPH solution (8 mM) was added according to the time point. The final concentration of the test compound was 1 ≈M, the concentration of liver microsomes was 0.1 mg/mL, and the final concentration of NADPH was 2 mM. After incubation for 0, 15, 30 and 60 min, respectively, 150 L acetonitrile (with internal standard) was added to the mixed system. The acetonitrile diluted sample was centrifuged at 4000 rpm for 5 min and 150 ≈L of the supernatant was analyzed by LC-MS/MS.

Conclusion: The data of stability test in liver microsomes show that the compounds of the present invention have better stability in different species of liver microsomes.

What is claimed is:

1. A compound having Formula (I) or a stereoisomer, a tautomer, an N-oxide, a solvate, a pharmaceutically acceptable salt or a prodrug thereof, wherein,

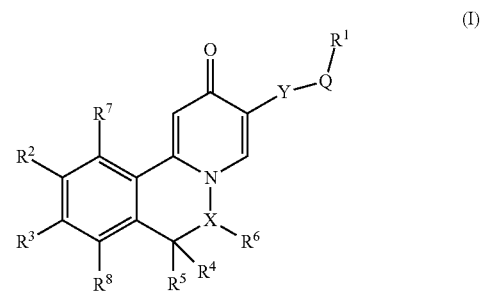

(I)

X is N or —$CR^{6a}$—;
Y is a single bond, —$CH_2$— or —C(=O)—;
Q is a single bond, —O— or —N($R^9$)—;
$R^1$ is H, deuterium, F, Cl, Br, I, OH, —COOH, 5- to 6-membered heterocyclyl, 5- to 6-membered heteroaryl, $C_{1-6}$ alkyl, $C_{2-6}$ alkenyl, $C_{2-6}$ alkynyl, $C_{3-7}$ cycloalkyl, $R^2$—S(=O)$_2$—, $R^{12}$—(C$R^eR^f$)$_n$— or $R^aR^bN$—, wherein each of the 5- to 6-membered heterocyclyl, 5- to 6-membered heteroaryl, $C_{1-6}$ alkyl, $C_{2-6}$ alkenyl, $C_{2-6}$ alkynyl and $C_{3-7}$ cycloalkyl is independently unsubstituted or substituted with 1, 2, 3 or 4 $R^v$;
$R^9$ is H, deuterium, $C_{1-6}$ alkyl or $C_{1-6}$ haloalkyl; or, $R^9$ and $R^1$, together with the nitrogen atom to which they are attached, form a 3- to 12-membered heterocyclyl, wherein each of the $C_{1-6}$ alkyl, $C_{1-6}$ haloalkyl and 3- to 12-membered heterocyclyl is independently unsubstituted or substituted with 1, 2, 3 or 4 substituents selected from —COOH, =O, tetrazolyl or $C_{1-6}$ alkyl-O—C(=O)—;
each of $R^4$ and $R^5$ is independently H, deuterium, $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl or 3- to 12-membered heterocyclyl, wherein each of the $C_{1-6}$ alkyl, $C_{1-6}$ alkylamino, $C_{1-6}$ alkoxy, $C_{2-6}$ alkynyl, $C_{2-6}$ alkenyl, $C_{3-7}$ cycloalkyl and 3- to 12-membered heterocyclyl is independently unsubstituted or substituted with 1, 2, 3 or 4 $R^1$;
$R^6$ is H, deuterium, $C_{1-6}$ alkyl, $C_{2-6}$ alkenyl, $C_{3-7}$ cycloalkyl, 3- to 12-membered heterocyclyl, $C_{6-10}$ aryl, 5- to 10-membered heteroaryl or Ret-C(=O)—O—(C$R^eR^f$)$_q$—, wherein each of the $C_{1-6}$ alkyl, $C_{2-6}$ alkenyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^z$;
$R^{6a}$ is H, deuterium, F, Cl, Br, CN, OH, $C_{1-6}$ alkyl, $C_{2-6}$ alkenyl, $C_{3-7}$ cycloalkyl, 3- to 12-membered heterocyclyl, $C_{6-10}$ aryl, 5- to 10-membered heteroaryl or $R^{17}$—C(=O)—O—(C$R^eR^f$)$_q$—, wherein each of the $C_{1-6}$ alkyl, $C_{2-6}$ alkenyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^z$;
$R^2$ is pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, or naphthyl, wherein each of the pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^w$;

each of $R^3$, $R^7$ and $R^8$ is independently H, deuterium, F, Cl, Br, hydroxy, cyano, $C_{1-12}$ alkyl, $C_{3-7}$ cycloalkyl, 3- to 12-membered heterocyclyl, $C_{6-10}$ aryl, 5- to 10-membered heteroaryl, $R^{13}$—$(CR^eR^f)_m$—, $R^{13}$—$(CR^eR^f)_m$—O—, $R^{13}$—C(=O)—$(CR^eR^f)_m$—, $R^{13}$—C(=O)—N($R^g$)—$(CR^eR^f)_m$—, $R^{13}$—O—C(=O)—$(CR^eR^f)_m$—, $R^{13}$—O—C(=O)—N($R^g$)—$(CR^eR^f)_m$—, $R^e$—C(=O)—$(CR^eR^f)_m$—O—C(=O)—,

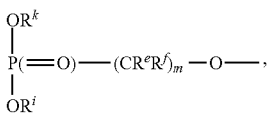

$R^{14}$—S(=O)$_2$—$(CR^eR^f)_m$—, $R^{14}$—S(=O)$_2$—N($R^g$)—$(CR^eR^f)_m$—, $R^{14}$—S(=O)$_2$—N($R^g$)—C(=O)—$R^aR^bN$—, $R^cC(=O)$—, $R^aR^bNC(=O)$—, $R^dOC(=O)$— or $R^{10}O$—, wherein each of the $C_{1-12}$ alkyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^w$;

$R^{10}$ is H, deuterium, $C_{1-12}$ alkyl, $C_{2-12}$ alkynyl, $C_{3-7}$ cycloalkyl, 3- to 12-membered heterocyclyl, $C_{6-10}$ aryl, 5- to 10-membered heteroaryl, $R^{15}$—$(CR^eR^f)_g$—, $R^{15}$—O—$(CR^eR^f)_g$—, $R^{15}$—C(=O)—$(CR^eR^f)_g$—, $R^{15}$O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the $C_{1-12}$ alkyl, $C_{2-12}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 $R^x$;

each $R^{12}$ and $R^{17}$ is independently $C_{3-7}$ cycloalkyl, $C_{6-10}$ aryl, $C_{1-6}$ alkoxy, amino or $C_{1-6}$ alkylamino, wherein each of the $C_{3-7}$ cycloalkyl, $C_{6-10}$ aryl, $C_{1-6}$ alkoxy, amino and $C_{1-6}$ alkylamino is independently unsubstituted or substituted with 1, 2, 3 or 4 $R^j$;

each $R^{13}$, $R^{14}$, $R^{15}$ and $R^{16}$ is independently $C_{1-12}$ alkyl, $C_{1-12}$ alkoxy, $C_{3-7}$ cycloalkyl, 5- to 10-membered heteroaryl, 3- to 12-membered heterocyclyl or $C_{6-10}$ aryl, wherein each of the $C_{1-12}$ alkyl, $C_{1-12}$ alkoxy, $C_{3-7}$ cycloalkyl, 5- to 10-membered heteroaryl, 3- to 12-membered heterocyclyl and $C_{6-10}$ aryl is independently unsubstituted or substituted with 1, 2, 3 or 4 $R^h$;

$R^{13a}$ is methyl, $C_{2-12}$ alkyl, $C_{1-12}$ alkoxy, $C_{3-7}$ cycloalkyl, 5- to 10-membered heteroaryl, 3- to 12-membered heterocyclyl or $C_{6-10}$ aryl, wherein each of the methyl and $C_{6-10}$ aryl is independently substituted with 1, 2, 3 or 4 $R^h$, and wherein $C_{2-12}$ alkyl, $C_{1-12}$ alkoxy, $C_{3-7}$ cycloalkyl, 5- to 10-membered heteroaryl and 3- to 12-membered heterocyclyl is independently unsubstituted or substituted with 1, 2, 3 or 4 $R^h$;

each of $R^a$, $R^b$, $R^c$, $R^d$, $R^e$, $R^f$, $R^g$, $R^k$, $R^i$, and $R^m$ is independently H, deuterium, OH, $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, 3- to 12-membered heterocyclyl or 5- to 10-membered heteroaryl, wherein each of the $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{6-10}$ aryl, 3- to 12-membered heterocyclyl and 5- to 10-membered heteroaryl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

or, $R^a$ and $R^b$, together with the nitrogen atom to which they are attached, form a 3- to 8-membered heterocyclyl or 5- to 8-membered heteroaryl, wherein each of the 3- to 8-membered heterocyclyl and 5- to 8-membered heteroaryl is independently unsubstituted or substituted with 1, 2, 3 or 4 substituents independently selected from F, Cl, Br, CN, OH, amino, $C_{1-6}$ alkyl, $C_{1-6}$ haloalkyl, $C_{1-6}$ alkoxy or $C_{1-6}$ alkylamino;

each $R^v$, $R^w$, $R^x$, $R^y$, $R^z$, $R^j$ and $R^h$ is independently F, Cl, Br, CN, OH, —COOH, amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl or 5- to 10-membered heteroaryl, wherein each of the amino, $C_{1-12}$ alkyl, $C_{1-12}$ haloalkyl, $C_{1-12}$ alkoxy, $C_{1-12}$ haloalkoxy, $C_{1-12}$ alkylthio, $C_{1-12}$ alkylamino, $C_{2-6}$ alkenyl, $C_{2-6}$ alkynyl, $C_{3-7}$ cycloalkyl, 3- to 12-membered heterocyclyl, $C_{6-10}$ aryl and 5- to 10-membered heteroaryl is independently unsubstituted or substituted with 1, 2, 3 or 4 substituents independently selected from F, Cl, Br, CN, OH, =O, —COOH, amino, $C_{1-6}$ alkyl, $C_{1-6}$ haloalkyl, $C_{1-6}$ alkoxy, $C_{1-6}$ alkylthio, $C_{1-6}$ haloalkoxy, $C_{1-12}$ alkylamino, $C_{2-6}$ alkenyl, $C_{2-6}$ alkynyl, $C_{6-10}$ aryl, $C_{3-6}$ cycloalkyl, 5- to 6-membered heteroaryl, 5- to 6-membered heterocyclyl, $C_{1-6}$ alkoxy-$C_{1-6}$-alkyl or $C_{1-6}$ alkylamino-$C_{1-6}$-alkyl;

each n and q is independently 0, 1, 2, 3, 4, 5 or 6;
each t and f is independently 1, 2, 3, 4, 5 or 6; and
each m and g is independently 0, 1, 2, 3, 4, 5, 6, 7, 8, 9 or 10.

2. The compound according to claim 1, wherein $R^1$ is H, deuterium, F, Cl, Br, I, OH, —COOH, 5-membered heterocyclyl, 5-membered heteroaryl, $C_{1-4}$ alkyl, $C_{2-4}$ alkenyl, $C_{2-4}$ alkynyl, $C_{3-6}$ cycloalkyl, $R^{12}$—S(=O)$_2$—, $R^2$—$(CR^eR^f)_n$— or $R^aR^bN$—, wherein each of the 5-membered heterocyclyl, 5-membered heteroaryl, $C_{1-4}$ alkyl, $C_{2-4}$ alkenyl, $C_{2-4}$ alkynyl and $C_{3-6}$ cycloalkyl is independently unsubstituted or substituted with 1, 2, 3 or 4 $R^v$; $R^9$ is H, deuterium, $C_{1-4}$ alkyl or $C_{1-4}$ haloalkyl; or, $R^9$ and $R^1$, together with the nitrogen atom to which they are attached, form a 5- to 6-membered heterocyclyl, wherein each of the $C_{1-4}$ alkyl, $C_{1-4}$ haloalkyl and 5- to 6-membered heterocyclyl is independently unsubstituted or substituted with 1, 2, 3 or 4 substituents selected from —COOH, =O, tetrazolyl or $C_{1-6}$ alkyl-O—C(=O)—.

3. The compound according to claim 1, wherein $R^1$ is H, deuterium, F, Cl, Br, I, OH, —COOH, thiazolyl, tetrazolyl, methyl, ethyl, n-propyl, isopropyl, vinyl, propenyl, ethynyl, propynyl, cyclopropyl, cyclobutyl, cyclopentyl, $R^{12}$—S(=O)$_2$—, $R^{12}$—$(CR^eR^f)_n$— or $R^aR^bN$—, wherein each of the thiazolyl, methyl, ethyl, n-propyl, isopropyl, vinyl, propenyl, ethynyl, propynyl, cyclopropyl, cyclobutyl and cyclopentyl is independently unsubstituted or substituted with 1, 2, 3 or 4 $R^v$;

$R^9$ is H, deuterium, methyl, ethyl, n-propyl, isopropyl or $C_{1-3}$ haloalkyl; or, $R^9$ and $R^1$, together with the nitrogen atom to which they are attached, form pyrrolidinyl, piperazinyl, piperidyl or morpholinyl, wherein each of the methyl, ethyl, n-propyl, isopropyl, $C_{1-3}$ haloalkyl, pyrrolidinyl, piperazinyl, piperidyl and morpholinyl is independently unsubstituted or substituted with 1, 2, 3 or 4 substituents selected from —COOH, =O, tetrazolyl or $C_{1-6}$ alkyl-O—C(=O)—.

4. The compound according to claim 1, wherein $R^2$ is thiazolyl wherein the thiazolyl is unsubstituted or substituted with 1, 2, 3 or 4 $R^w$.

5. The compound according to claim 1, wherein $R^2$ is pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, pyridyl, pyrazolyl, triazolyl, tetrazolyl, oxazolyl, isoxazolyl, oxadiazolyl, 1,3,5-triazinyl, thiazolyl, thienyl, pyrazinyl, pyridazinyl, or pyrimidinyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, pyridyl, pyrazolyl, triazolyl, tetrazolyl, oxazolyl, isoxazolyl, oxadiazolyl, 1,3,5-triazinyl, thiazolyl, thienyl, pyrazinyl, pyridazinyl, and pyrimidinyl is independently unsubstituted or substituted with 1, 2, 3 or 4 $R^w$.

6. The compound according to claim 1, wherein each of $R^3$, $R^7$ and $R^8$ is independently H, deuterium, F, Cl, Br, hydroxy, cyano, $C_{1-6}$ alkyl, $C_{3-6}$ cycloalkyl, 5- to 6-membered heterocyclyl, phenyl, naphthyl, 5- to 6-membered heteroaryl, $R^{13}$—$(CR^eR^f)_m$—, $R^{13}$—$(CR^eR^f)_m$—O—, $R^{13}$—C(=O)—$(CR^eR^f)_m$—, $R^{13}$—C(=O)—N($R^g$)—$(CR^eR^f)_m$—, $R^{13}$—O—C(=O)—$(CR^eR^f)_m$—, $R^{13}$—O—C(=O)—N($R^g$)—$(CR^eR^f)_m$—, $R^c$—C(=O)—$(CR^eR^f)_m$—C(=O)—,

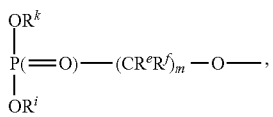

$R^{14}$—S(=O)$_2$—$(CR^eR^f)_m$—, $R^{14}$—S(=O)$_2$—N($R^g$)—$(CR^eR^f)_m$—, $R^{14}$—S(=O)$_2$—N(R)—C(=O)—, $R^aR^bN$—, $R^cC(=O)$—, $R^aR^bNC(=O)$—, $R^dOC(=O)$— or $R^{10}O$—, and wherein each of the $C_{1-6}$ alkyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^w$;

$R^{10}$ is H, deuterium, $C_{1-6}$ alkyl, $C_{2-6}$ alkynyl, $C_{3-6}$ cycloalkyl, 5- to 6-membered heterocyclyl, phenyl, naphthyl, 5- to 6-membered heteroaryl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the $C_{1-6}$ alkyl, $C_{2-6}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 $R^x$.

7. The compound according to claim 1, wherein each of $R^3$, $R^7$ and $R^8$ is independently H, deuterium, F, Cl, Br, hydroxy, cyano, methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{13}$—$(CR^eR^f)_m$—, $R^{13}$—$(CR^eR^f)_m$—O—, $R^{13}$—C(=O)—$(CR^eR^f)_m$—, $R^{13}$—C(=O)—N($R^g$)—$(CR^eR^f)_m$—, $R^{13}$—O—C(=O)—$(CR^eR^f)_m$—, $R^{13}$—O—C(=O)—N($R^g$)—$(CR^eR^f)_m$—, $R^e$—C(=O)—$(CR^eR^f)_m$—O—C(=O)—,

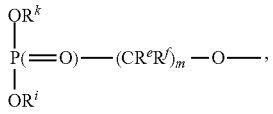

$R^{14}$—S(=O)$_2$—$(CR^eR^f)_m$—, $R^{14}$—S(=O)$_2$—N($R^g$)—$(CR^eR^f)_m$—, $R^{14}$—S(=O)$_2$—N($R^g$)—C(=O)—, $R^aR^bN$—, $R^cC(=O)$—, $R^aR^bNC(=O)$—, $R^dOC(=O)$— or $R^{10}O$—, and wherein each of the methyl, ethyl, n-propyl, isopropyl, n-butyl, isobutyl, n-pentyl, n-hexyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiapyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^w$;

$R^{10}$ is H, deuterium, methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $R^{15}$—$(CR^eR^f)_g$—, $R^{15}$—O—$(CR^eR^f)_g$—, $R^{15}$—C(=O)—$(CR^eR^f)_g$—, $R^{15}$—O—C(=O)—$(CR^eR^f)_g$—, $R^{15}$—O—C(=O)—N($R^g$)—$(CR^eR^f)_g$—, $R^{16}$—S(=O)$_2$—$(CR^eR^f)_g$— or $R^{16}$—S(=O)$_2$—N($R^g$)—$(CR^eR^f)_g$—, wherein each of the methyl, ethyl, n-propyl, isopropyl, n-butyl, isobutyl, n-pentyl, n-hexyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thioxomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 $R^x$.

8. The compound according to claim 1, wherein each of $R^4$ and $R^5$ is independently H, deuterium, $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl or 5- to 6-membered heterocyclyl, and wherein each of the $C_{1-4}$ alkyl, $C_{1-4}$ alkylamino, $C_{1-4}$ alkoxy, $C_{2-4}$ alkynyl, $C_{2-4}$ alkenyl, $C_{3-6}$ cycloalkyl and 5- to 6-membered heterocyclyl is independently unsubstituted or substituted with 1, 2, 3 or 4 $R^y$;

$R^6$ is H, deuterium, $C_{1-4}$ alkyl, $C_{2-4}$ alkenyl, $C_{3-6}$ cycloalkyl, 5- to 6-membered heterocyclyl, phenyl, naphthyl, 5- to 10-membered heteroaryl or Rt-C(=O)—O—$(CR^eR^f)_q$—, wherein each of the $C_{1-4}$ alkyl, $C_{2-4}$ alkenyl, $C_{3-6}$ cycloalkyl, 5- to 6-membered heterocyclyl, phenyl, naphthyl and 5- to 10-membered heteroaryl is independently unsubstituted or substituted with 1, 2, 3 or 4 $R^z$;

$R^{6a}$ is H, deuterium, F, Cl, Br, CN, OH, $C_{1-4}$ alkyl, $C_{2-4}$ alkenyl, $C_{3-6}$ cycloalkyl, 5- to 6-membered heterocyclyl, phenyl, naphthyl, 5- to 10-membered heteroaryl or $R^{17}$—C(=O)—O—$(CR^eR^f)_q$—, wherein each of the $C_{1-4}$ alkyl, $C_{2-4}$ alkenyl, $C_{3-6}$ cycloalkyl, 5- to 6-membered heterocyclyl, phenyl, naphthyl and 5- to 10-membered heteroaryl is independently unsubstituted or substituted with 1, 2, 3 or 4 $R^z$.

9. The compound according to claim 1, wherein each of $R^4$ and $R^5$ is independently H, deuterium, $C_{1-3}$ alkyl, $C_{1-3}$ alkylamino, $C_{1-3}$ alkoxy, $C_{2-4}$ alkynyl, $C_{2-4}$ alkenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl or piperazinyl, wherein each of the $C_{1-3}$ alkyl, $C_{1-3}$ alkylamino, $C_{1-3}$ alkoxy, $C_{2-4}$ alkynyl, $C_{2-4}$ alkenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl and piperazinyl is independently unsubstituted or substituted with 1, 2, 3, or 4 $R^y$;

$R^6$ is H, deuterium, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl, naphthyl, or $R^{17}$—C(=O)—O—$(CR^eR^f)_q$—, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl and naphthyl is independently unsubstituted or substituted with 1, 2, 3, or 4 $R^z$;

$R^{6a}$ is H, deuterium, F, Cl, Br, CN, OH, methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl, naphthyl, or $R^{17}$—C(=O)—O—$(CR^eR^f)_q$—, wherein each of the methyl, ethyl, n-propyl, isopropyl, n-butyl, isobutyl, tert-butyl, vinyl, propenyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, indolyl, purinyl, phenyl and naphthyl is independently unsubstituted or substituted with 1, 2, 3, or 4 $R^z$.

10. The compound according to claim 1, wherein each $R^{12}$ and $R^{17}$ is independently $C_{3-6}$ cycloalkyl, phenyl, naphthyl, $C_{1-4}$ alkoxy, amino or $C_{1-4}$ alkylamino, wherein each of the $C_{3-6}$ cycloalkyl, phenyl, naphthyl, $C_{1-4}$ alkoxy, amino and $C_{1-4}$ alkylamino is independently unsubstituted or substituted with 1, 2, 3 or 4 $R^j$;

each $R^{13}$, $R^{14}$, $R^{15}$ and $R^{16}$ is independently $C_{1-6}$ alkyl, $C_{1-6}$ alkoxy, $C_{3-6}$ cycloalkyl, 5- to 6-membered heteroaryl, 5- to 6-membered heterocyclyl, phenyl or naphthyl, wherein each of the $C_{1-6}$ alkyl, $C_{1-6}$ alkoxy, $C_{3-6}$ cycloalkyl, 5- to 6-membered heteroaryl, 5- to 6-membered heterocyclyl, phenyl and naphthyl is independently unsubstituted or substituted with 1, 2, 3 or 4 $R^h$;

$R^{13a}$ is methyl, $C_{2-6}$ alkyl, $C_{1-6}$ alkoxy, $C_{3-6}$ cycloalkyl, 5- to 6-membered heteroaryl, 5- to 6-membered heterocyclyl, phenyl or naphthyl, wherein each of the methyl, phenyl and naphthyl is independently substituted with 1, 2, 3 or 4 $R^h$, and wherein each of the $C_{2-6}$ alkyl, $C_{1-6}$ alkoxy, $C_{3-6}$ cycloalkyl, 5- to 6-membered heteroaryl and 5- to 6-membered heterocyclyl is independently unsubstituted or substituted with 1, 2, 3 or 4 $R^h$.

11. The compound according to claim 1, wherein each $R^{12}$ and $R^{17}$ is independently cyclopropyl, cyclobutyl, cyclopentyl, cyclohexyl, phenyl, naphthyl, methoxy, ethoxy, propoxy, isopropoxy, n-butoxy, amino, N-methylamino, N-ethylamino, N,N-dimethylamino or N,N-diethylamino, wherein each of the cyclopropyl, cyclobutyl, cyclopentyl, cyclohexyl, phenyl, naphthyl, methoxy, ethoxy, propoxy, isopropoxy, n-butoxy, amino, N-methylamino, N-ethylamino, N,N-dimethylamino and N,N-diethylamino is independently unsubstituted or substituted with 1, 2, 3, or 4 $R^j$;

each $R^{13}$, $R^{14}$, $R^{15}$ and $R^{16}$ is independently methyl, ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the methyl, ethyl, n-propyl, isopropyl, n-butyl, isobutyl, tert-butyl, methoxy, ethoxy, propoxy, isopropyl, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3, or 4 $R^h$;

$R^{13a}$ is methyl, ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the methyl, phenyl and naphthyl is independently substituted with 1, 2, 3 or 4 $R^h$, and wherein each of the ethyl, n-propyl, isopropyl, n-butyl, isobutyl, tert-butyl, methoxy, ethoxy, propoxy, isopropoxy, n-butoxy, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl and pyrimidinyl is independently unsubstituted or substituted with 1, 2, 3, or 4 $R^h$.

12. The compound according to claim 1, wherein each $R^a$, $R^b$, $R^c$, $R^d$, $R^e$, $R^f$, $R^g$, $R^k$, $R^i$ and $R^m$ is independently H, deuterium, OH, $C_{1-4}$ haloalkyl, $C_{1-6}$ alkyl, $C_{1-4}$ alkoxy, $C_{2-4}$ alkenyl, $C_{2-4}$ alkynyl, $C_{3-6}$ cycloalkyl, phenyl, naphthyl, 5- to 6-membered heterocyclyl or 5- to 6-membered heteroaryl, wherein each of the $C_{1-4}$ haloalkyl, $C_{1-6}$ alkyl, $C_{1-4}$ alkoxy, $C_{2-4}$ alkenyl, $C_{2-4}$ alkynyl, $C_{3-6}$ cycloalkyl, phenyl, naphthyl, 5- to 6-membered heterocyclyl and 5- to 6-membered heteroaryl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;
or, $R^a$ and $R^b$, together with the nitrogen atom to which they are attached, form a 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino.

13. The compound according to claim 1, wherein each $R^a$, $R^b$, $R^c$, $R^d$, $R^e$, $R^f$, $R^g$, $R^k$, $R^i$ and $R^m$ is independently H, deuterium, OH, $C_{1-3}$ haloalkyl, methyl, ethyl, n-propyl, isopropyl, n-butyl, isobutyl, tert-butyl, n-pentyl, 3-pentyl, methoxy, ethoxy, propoxy, isopropoxy, n-butoxy, ethenyl, propenyl, ethynyl, propynyl, propargyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl or naphthyl, wherein each of the $C_{1-3}$ haloalkyl, methyl, ethyl, n-propyl, isopropyl, n-butyl, isobutyl, tert-butyl, methoxy, ethoxy, propoxy, isopropoxy, n-butoxy, ethenyl, propenyl, ethynyl, propynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl and naphthyl is independently unsubstituted or substituted with 1, 2, 3, or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino;
or, $R^a$ and $R^b$, together with the nitrogen atom to which they are attached, form pyrrolidinyl, pyrazolidinyl, imidazolidinyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, pyrazinyl, pyridazinyl or pyrimidinyl, wherein each of the pyrrolidinyl, pyrazolidinyl, imidazolidinyl, piperidyl, morpholinyl, thiomorpholinyl, piperazinyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, pyrazinyl, pyridazinyl and pyrimidinyl is independently unsubstituted or substituted with 1, 2, 3, or 4 substituents independently selected from F, Cl, Br, CN, OH, amino, $C_{1-4}$ alkyl, $C_{1-4}$ haloalkyl, $C_{1-4}$ alkoxy or $C_{1-4}$ alkylamino.

14. The compound according to claim 1, wherein each $R^v$, $R^w$, $R^x$, $R^y$, $R^z$, $R^j$ and $R^h$ is independently F, Cl, Br, CN, OH, —COOH, amino, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylamino, $C_{2-4}$ alkenyl, $C_{2-4}$ alkynyl, $C_{3-6}$ cycloalkyl, 5- to 6-membered heterocyclyl, phenyl, naphthyl or 5- to 6-membered heteroaryl, wherein each of the amino, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylamino, $C_{2-4}$ alkenyl, $C_{2-4}$ alkynyl, $C_{3-6}$ cycloalkyl, 5- to 6-membered heterocyclyl, phenyl, naphthyl and 5- to 6-membered heteroaryl is independently unsubstituted or substituted with 1, 2, 3 or 4 substituents independently selected from F, Cl, Br, CN, OH, =O, —COOH, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, phenyl, naphthyl, $C_{3-6}$ cycloalkyl, 5- to 6-membered heteroaryl, 5- to 6-membered heterocyclyl, $C_{1-4}$ alkoxy-$C_{1-4}$-alkyl or $C_{1-4}$ alkylamino-$C_{1-4}$-alkyl.

15. The compound according to claim 1, wherein each $R^v$, $R^w$, $R^x$, $R^y$, $R^z$, $R^j$ and $R^h$ is independently F, Cl, Br, CN, OH, —COOH, amino, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl or naphthyl, wherein each of the cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, dioxazolyl, 1,3,5-triazinyl, thiazolyl, thienyl, pyrazinyl, pyridazinyl, pyrimidinyl, phenyl and naphthyl is independently unsubstituted or substituted with 1, 2, 3 or 4 substituents independently selected from F, Cl, Br, CN, OH, =O, —COOH, amino, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ alkylamino, $C_{2-4}$ alkenyl, $C_{2-4}$ alkynyl, cyclopropyl, cyclobutyl, cyclopentyl, cyclohexyl, pyrrolidinyl, pyrazolidinyl, imidazolidinyl, tetrahydrofuranyl, tetrahydrothiophenyl, tetrahydropyranyl, tetrahydrothiopyranyl, piperidyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, phenyl, naphthyl, $C_{1-3}$ alkoxy-$C_{1-3}$-alkyl and $C_{1-3}$ alkylamino-$C_{1-3}$-alkyl.

16. A compound having one of the following structures:
(1)
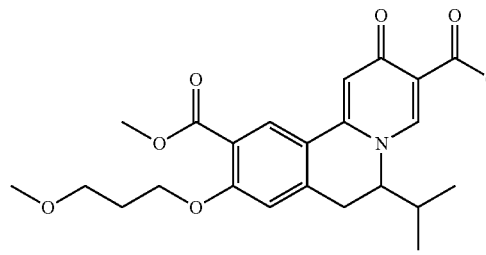
(2)
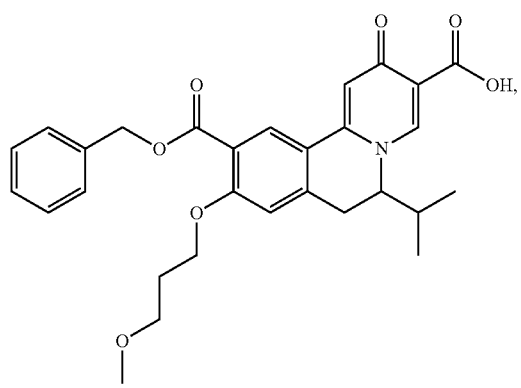
(3)
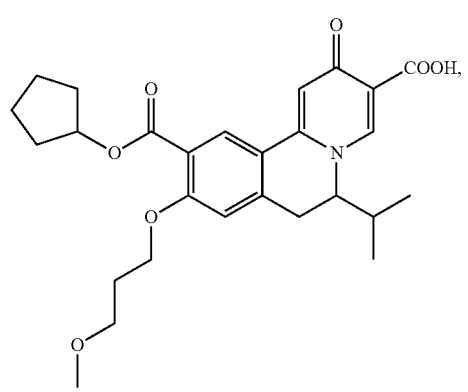
(4)
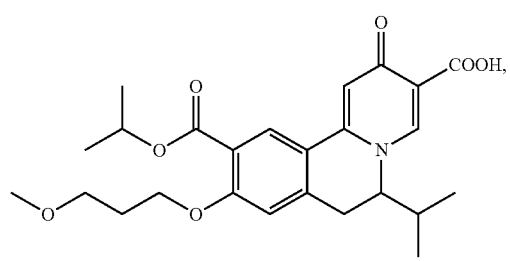
-continued
(5)
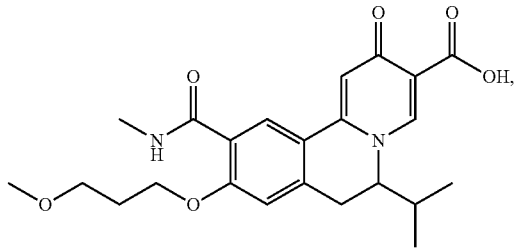
(6)
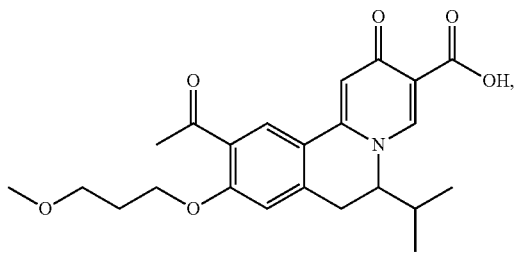
(7)
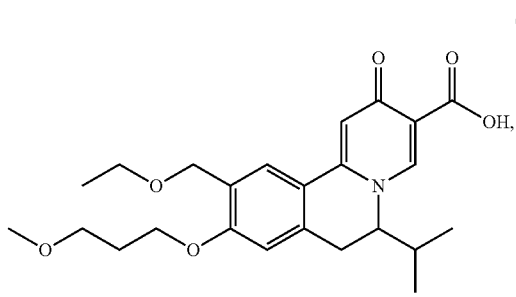
(8)
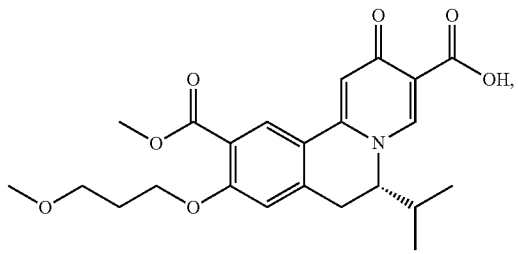
(9)
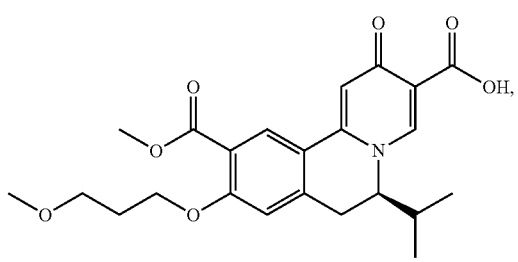

-continued
(10)
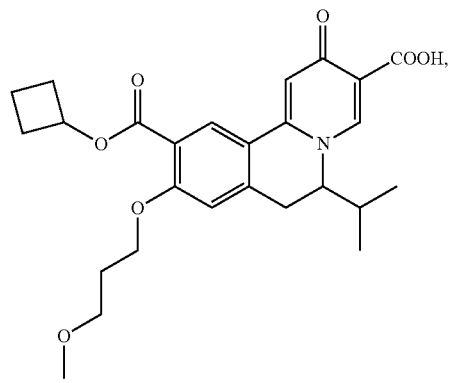
(11)
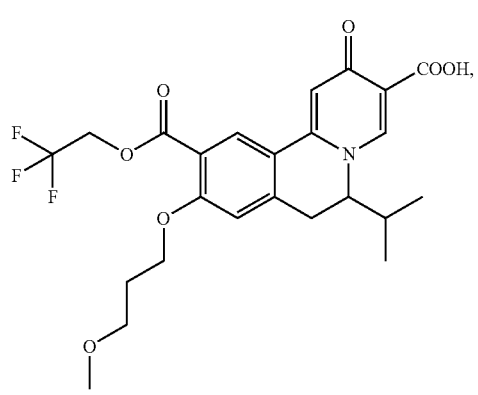
(12)
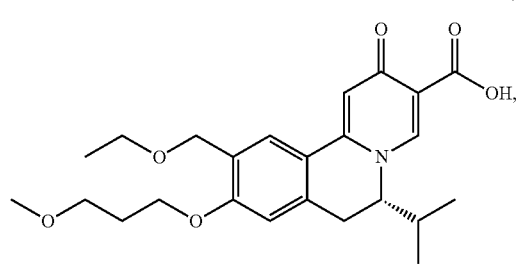
(13)
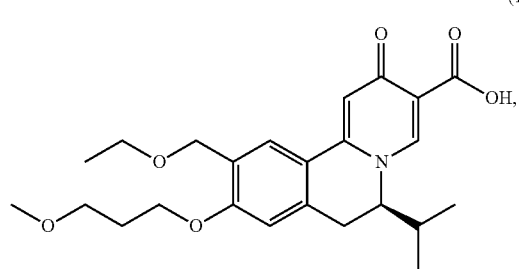
(14)
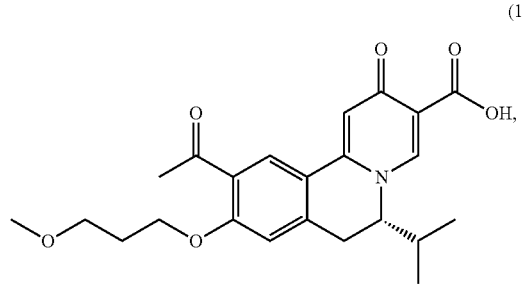
-continued
(15)
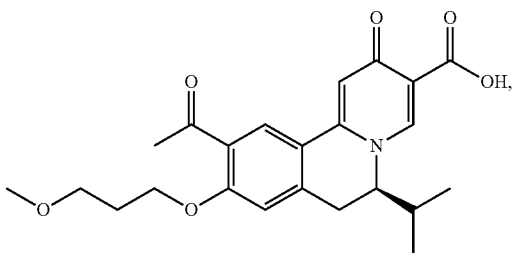
(16)
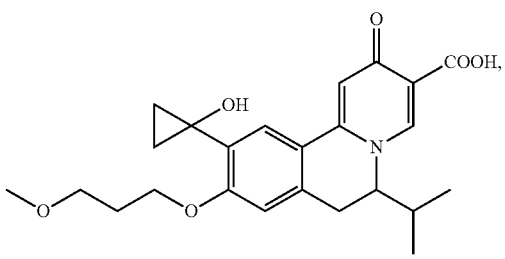
(17)
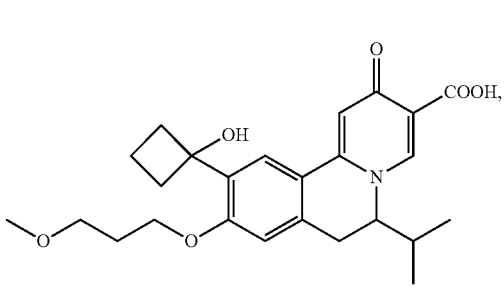
(18)
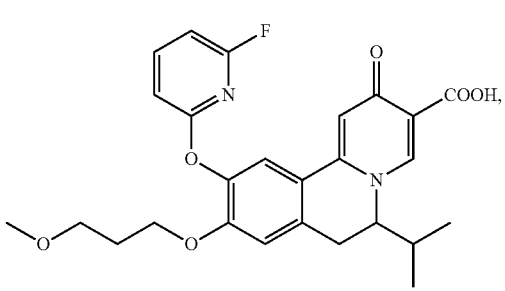
(19)
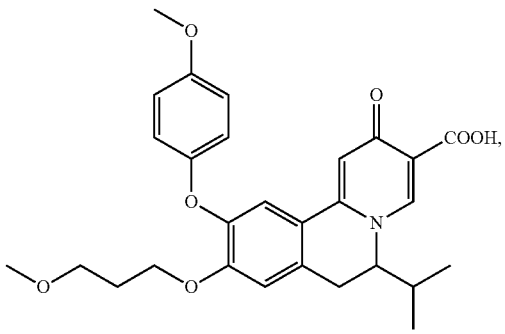

(20) 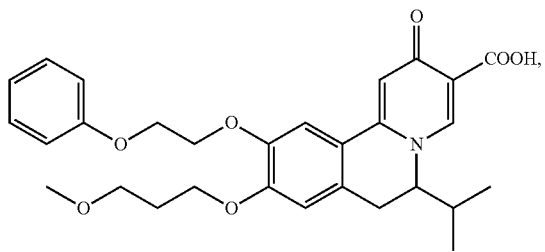
(21) 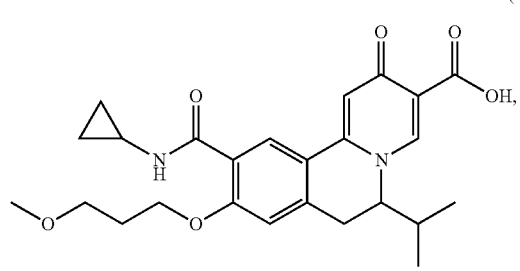
(22) 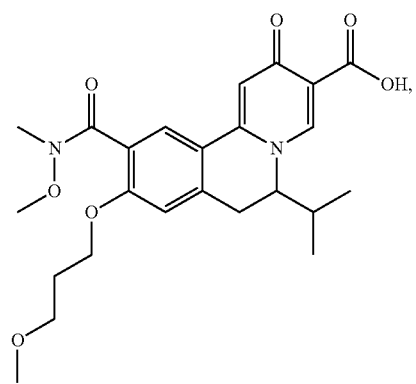
(23) 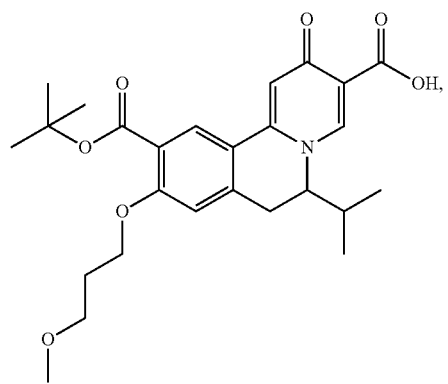
(24) 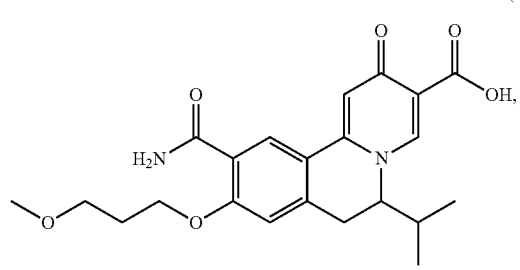
(25) 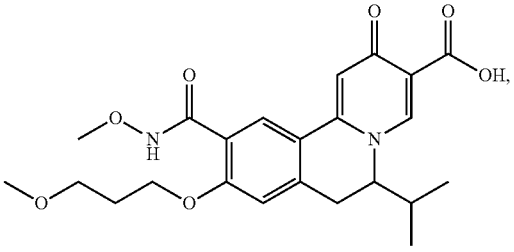
(26) 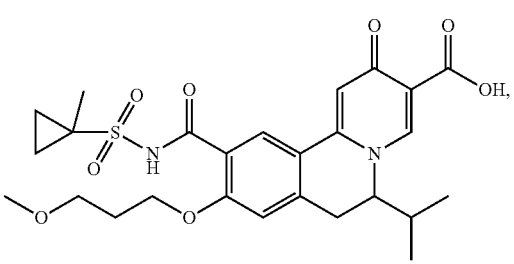
(27) 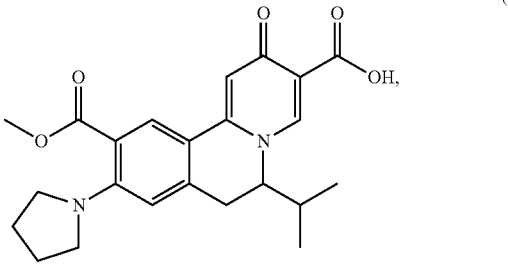
(28) 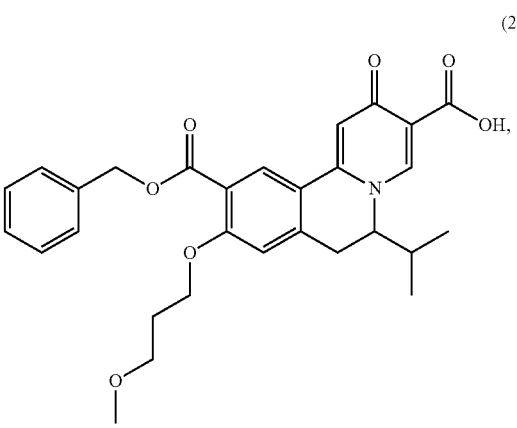
(29) 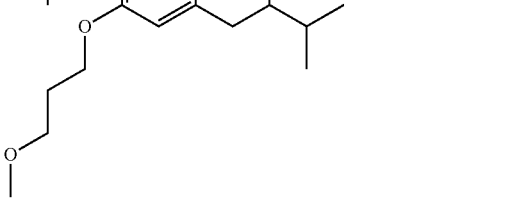

(30)
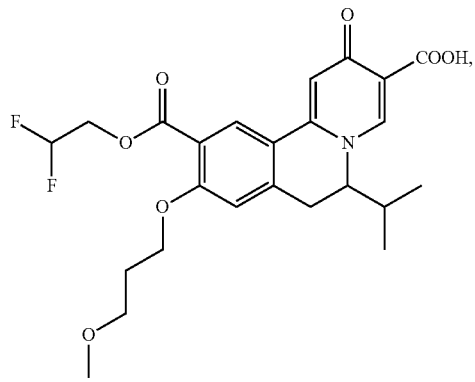
(31)
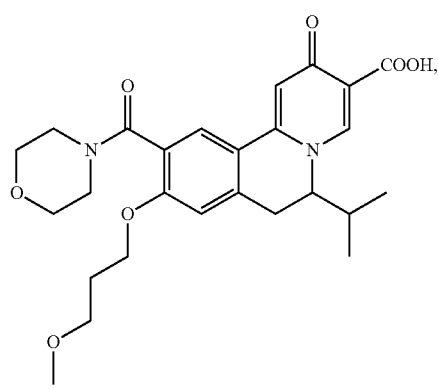
(32)
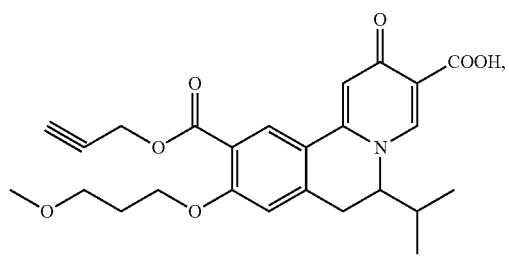
(33)
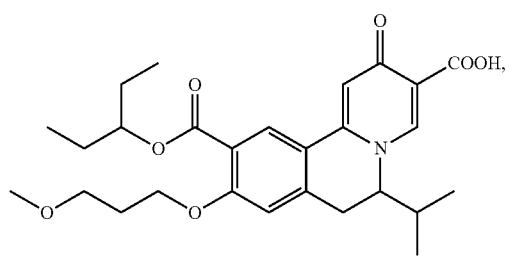
(34)
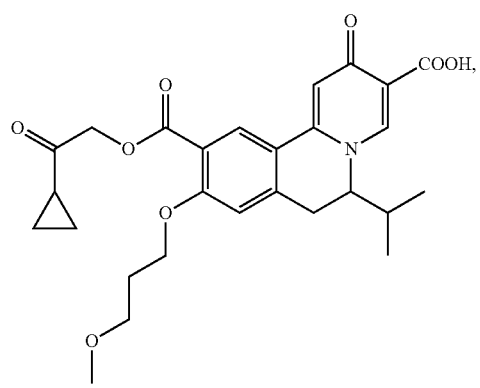
(35)
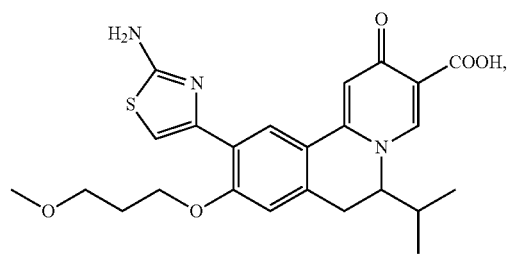
(36)
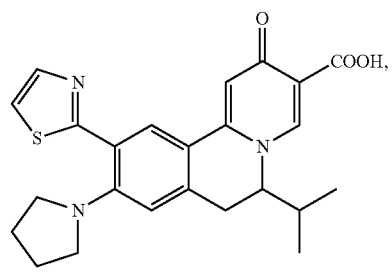
(37)
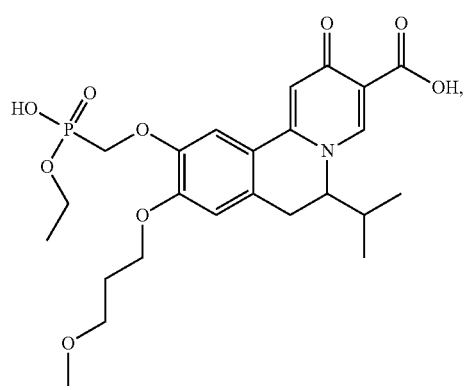
(38)
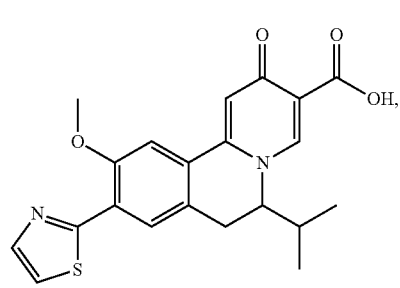

-continued
(39)
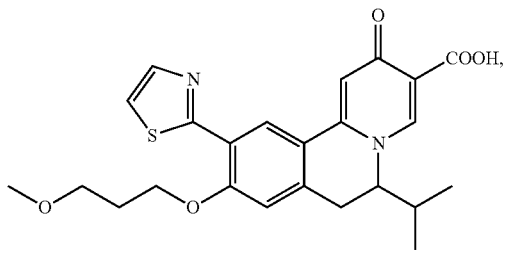
(44)
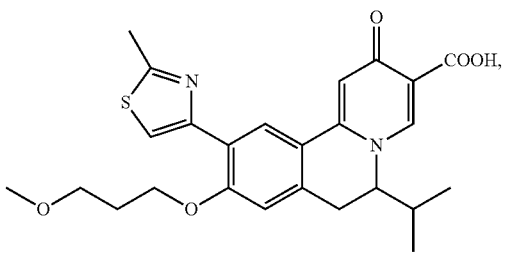
(40)
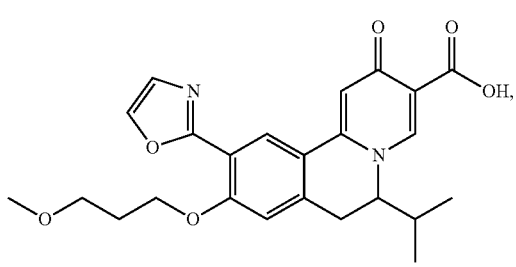
(45)
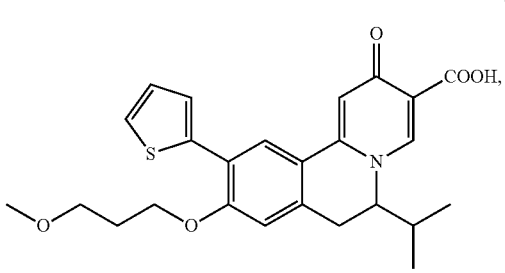
(41)
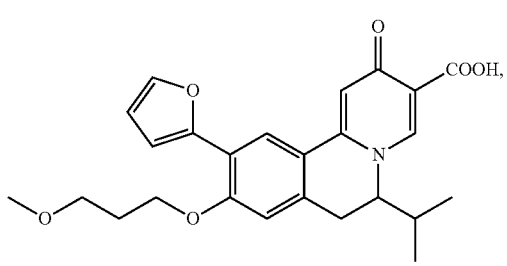
(46)
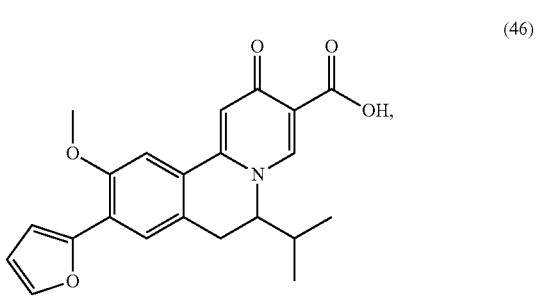
(42)
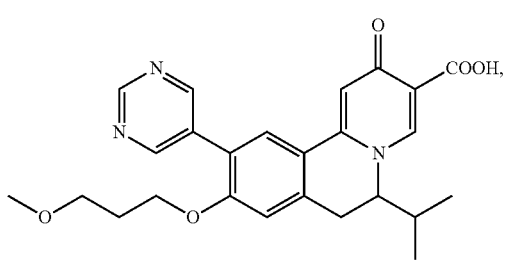
(47)
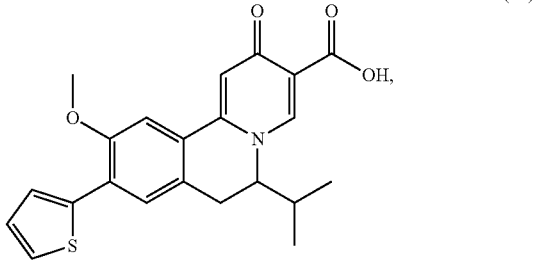
(43)
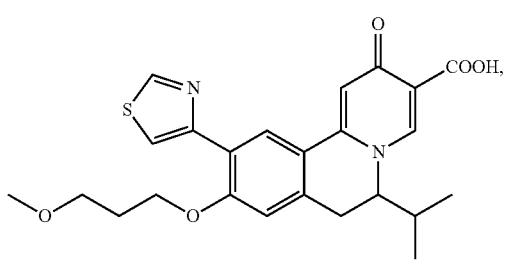
(48)
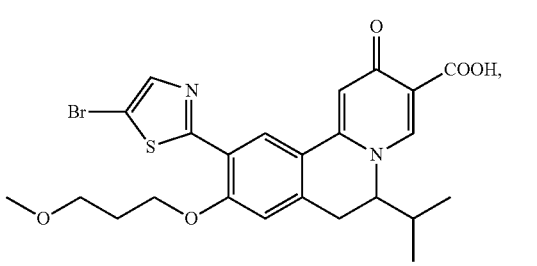

(49)
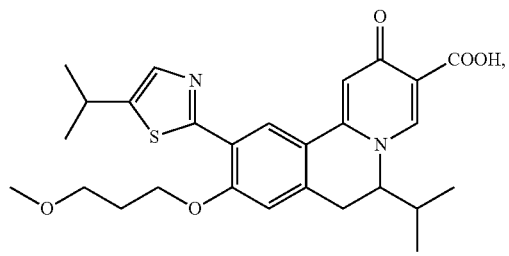
(50)
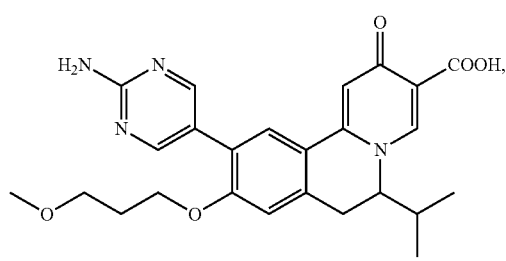
(51)
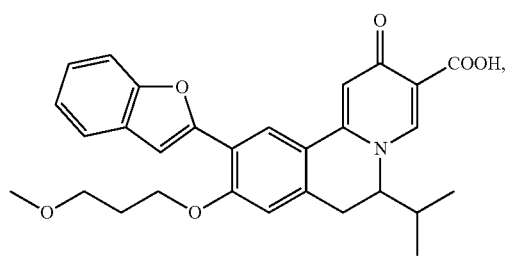
(52)
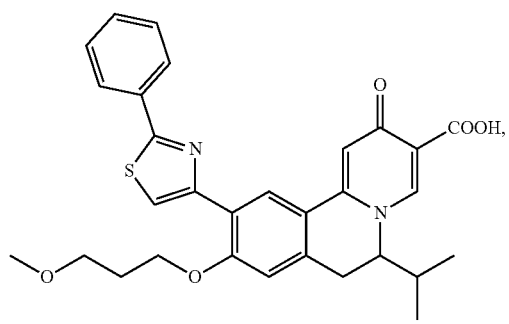
(53)
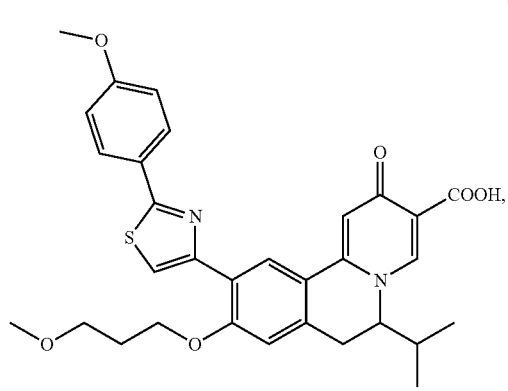
(54)
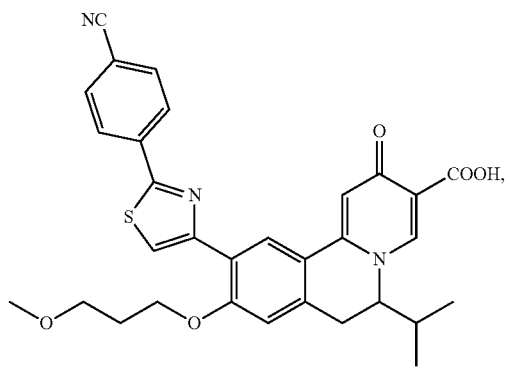
(55)
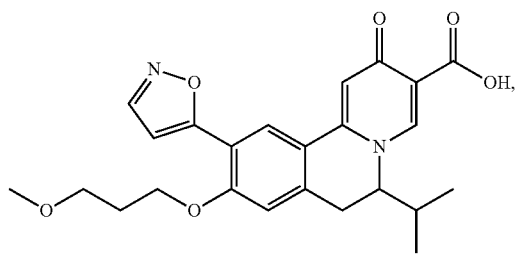
(56)
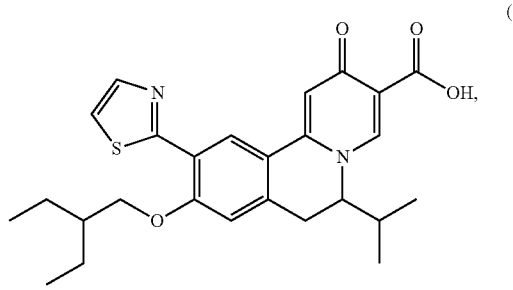
(57)
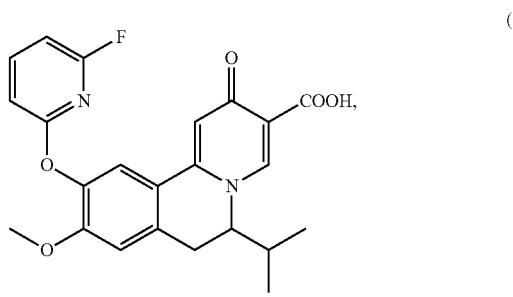
(58)
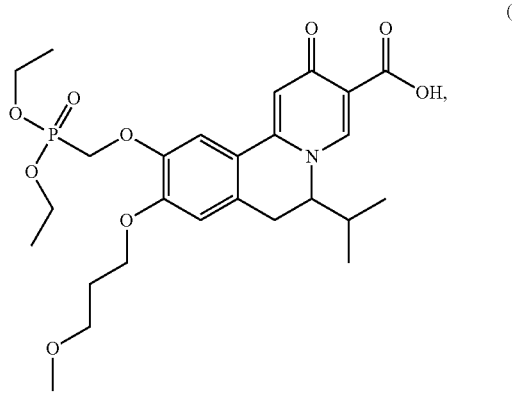

(59) 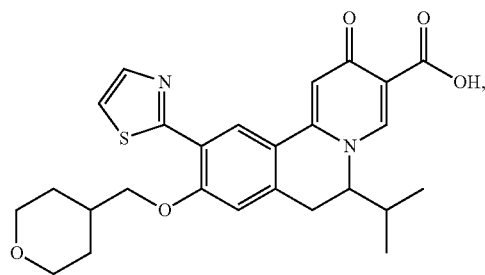
(60) 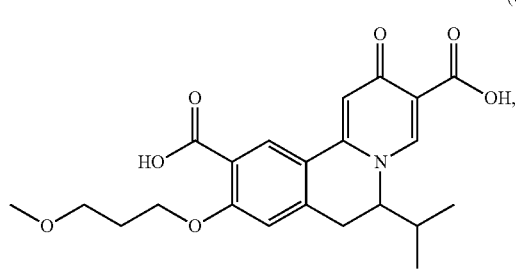
(61) 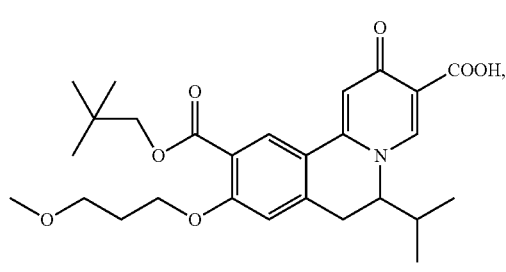
(62) 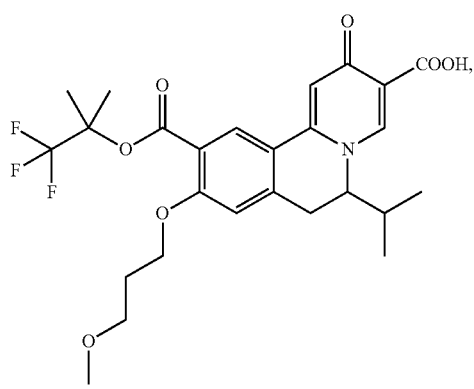
(63) 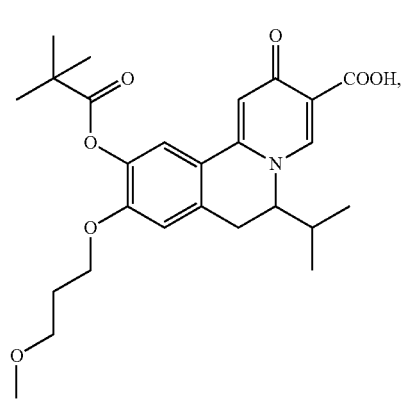
(64) 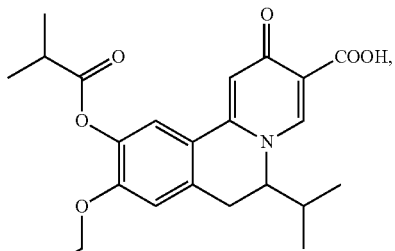
(65) 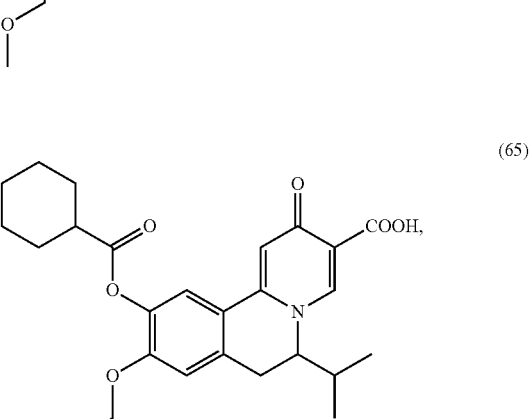
(66) 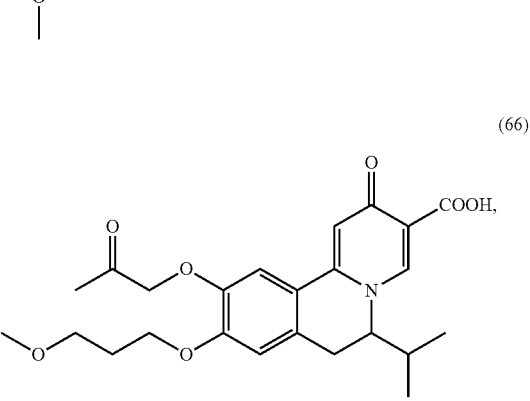
(67) 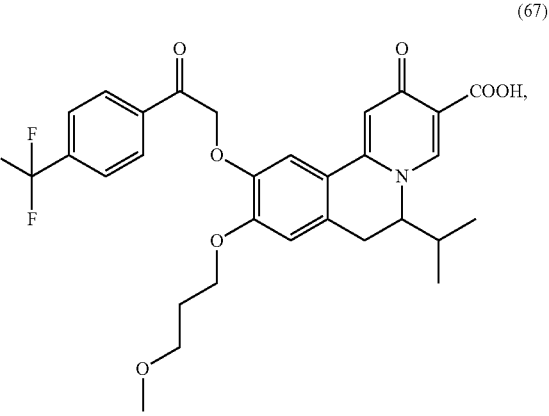

(68)
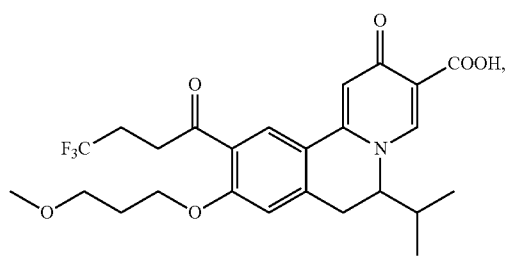
(69)
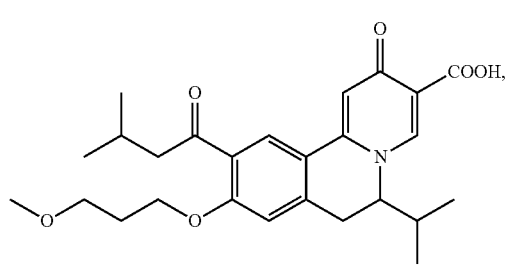
(70)
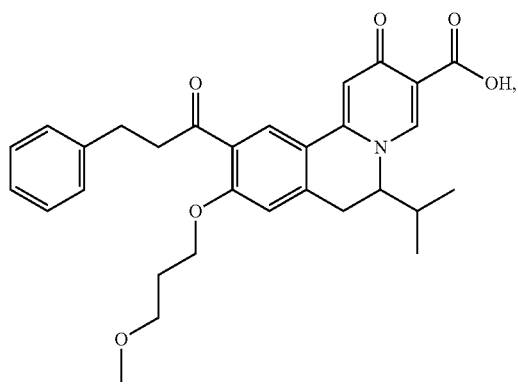
(71)
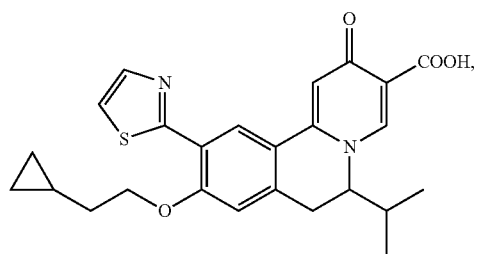
(72)
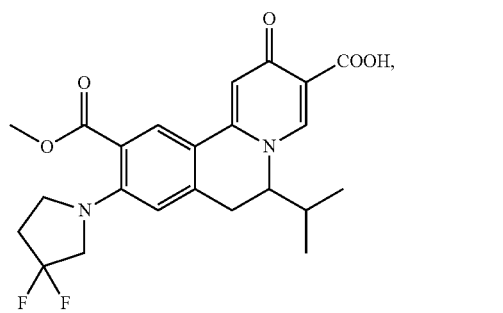
(73)
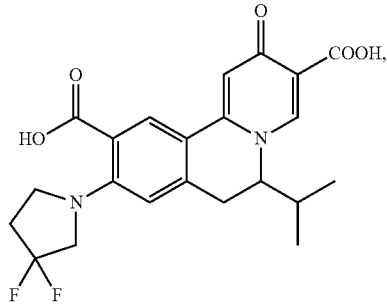
(74)
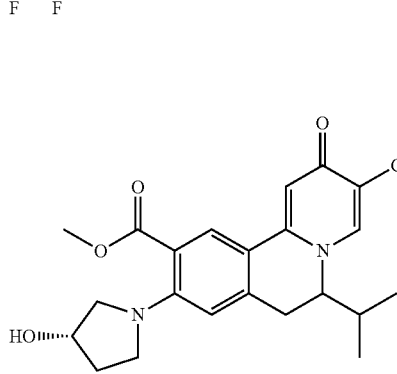
(75)
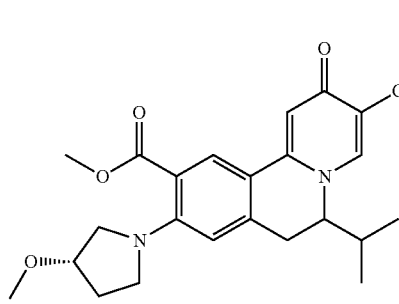
(76)
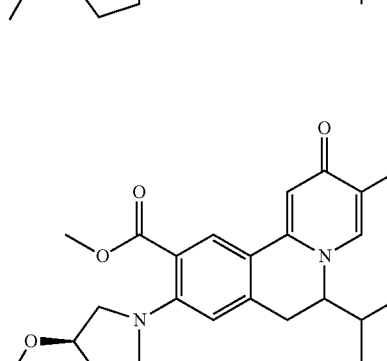
(77)
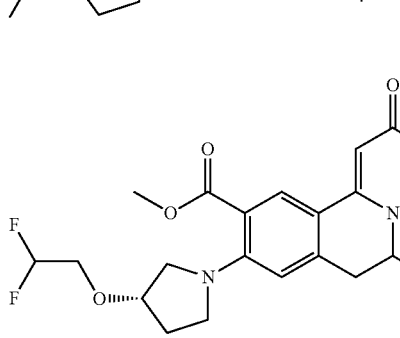

(78)
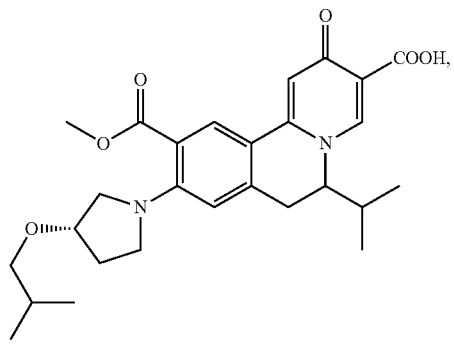
(79)
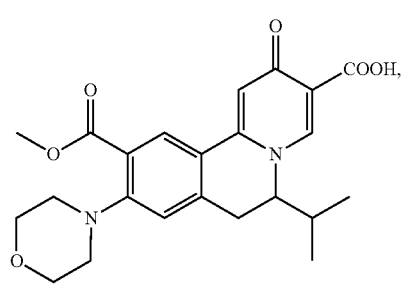
(80)
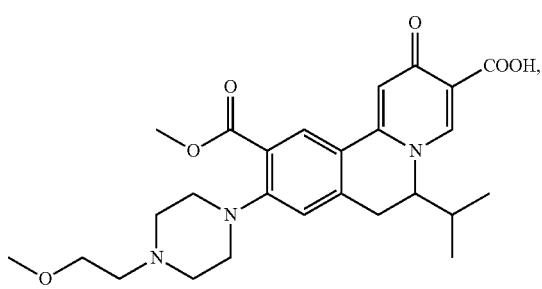
(81)
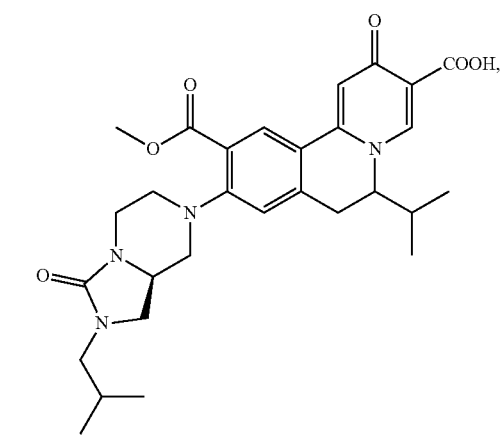
(82)
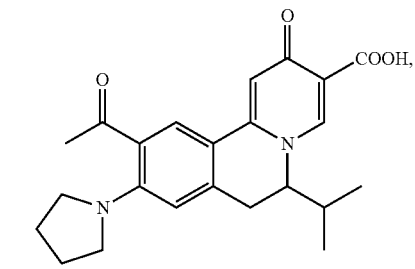
(83)
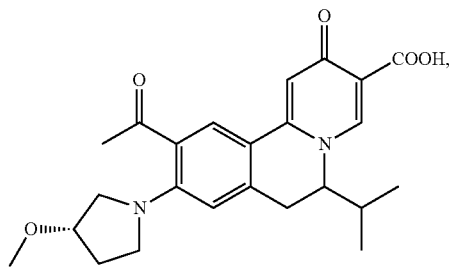
(84)
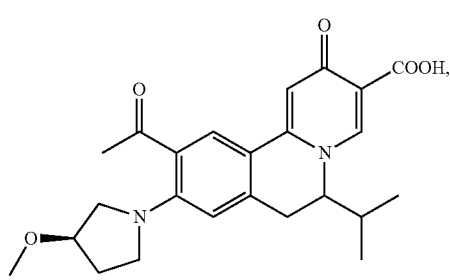
(85)
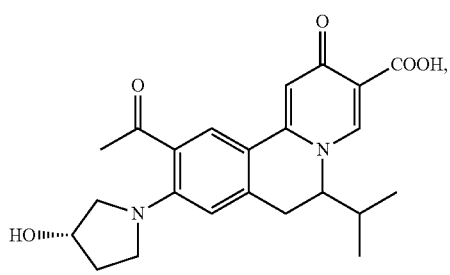
(86)
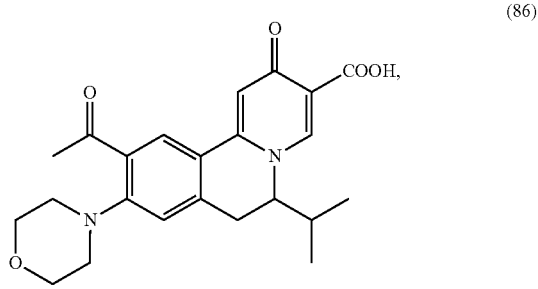
(87)
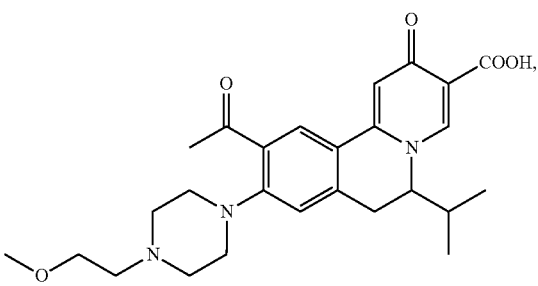

(88)
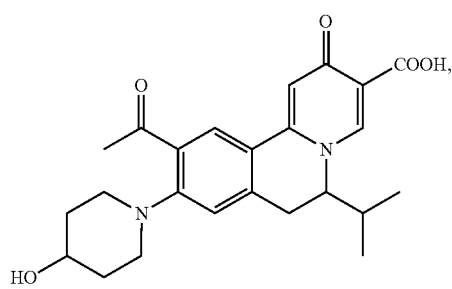
(89)
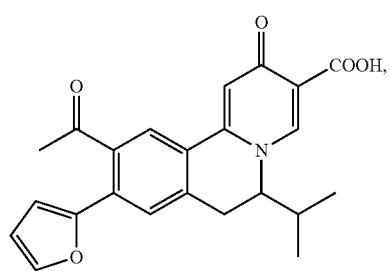
(90)
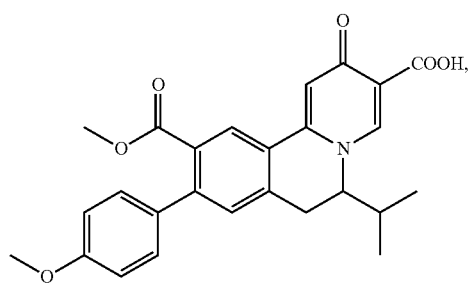
(91)
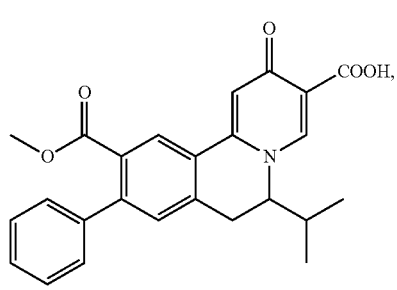
(92)
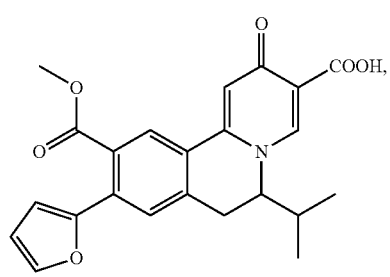
(93)
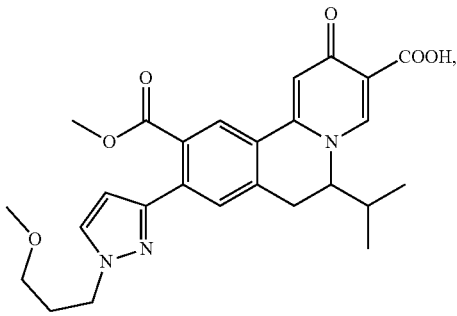
(94)
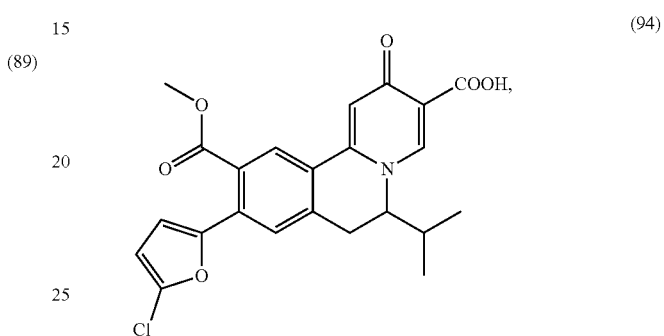
(95)
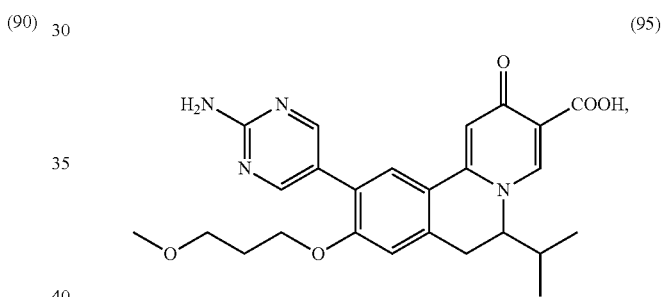
(96)
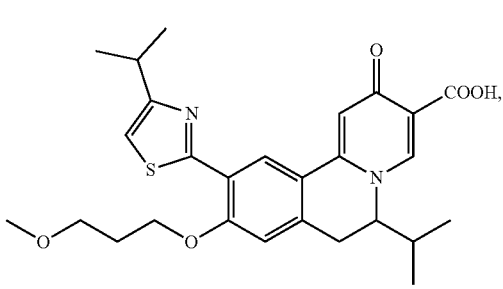
(97)
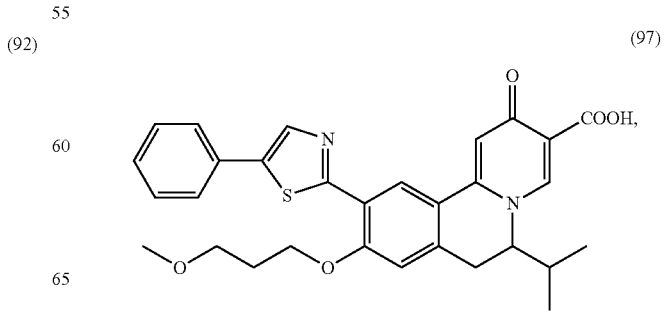

(98) 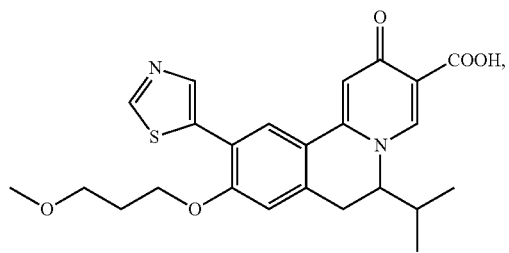
(99) 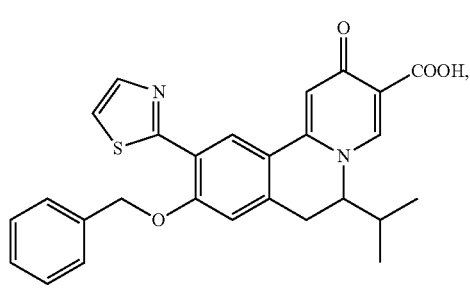
(100) 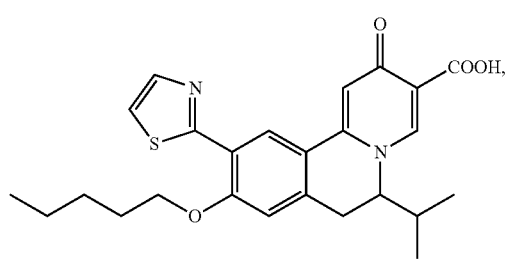
(101) 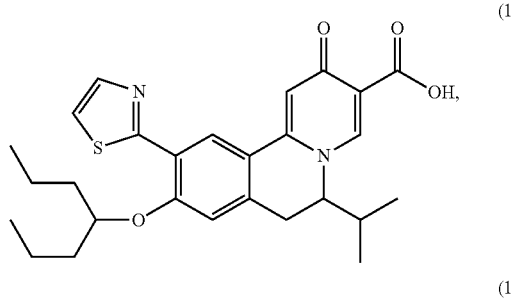
(102) 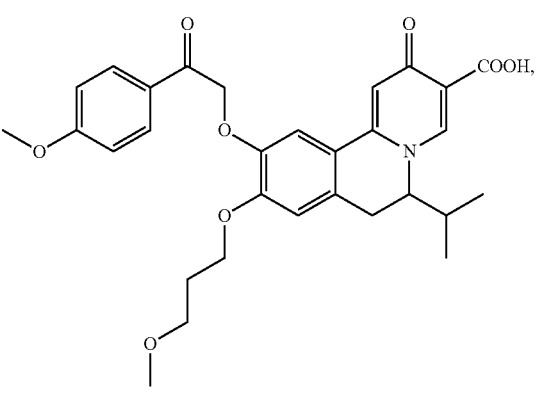
(103) 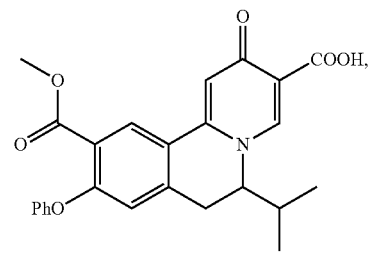
(104) 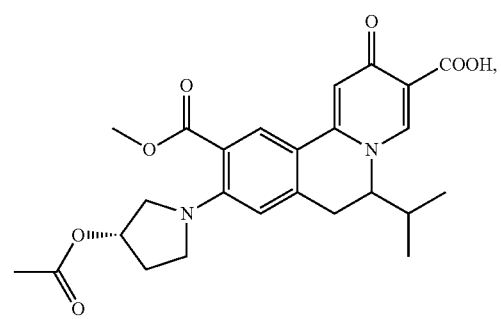
(105) 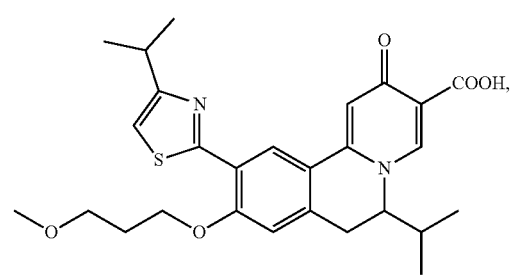
(106) 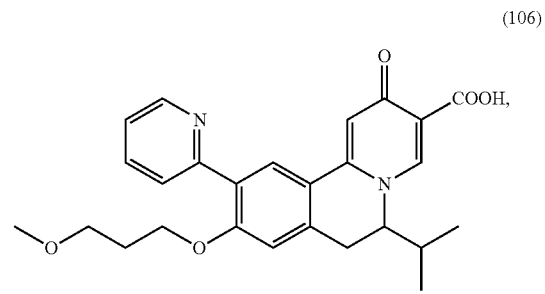
(107) 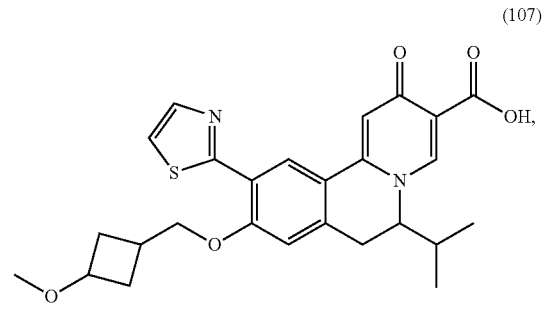

(108) 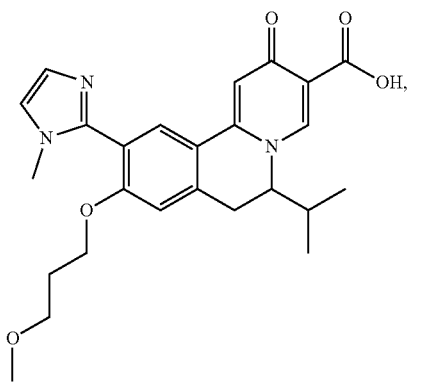

(109) 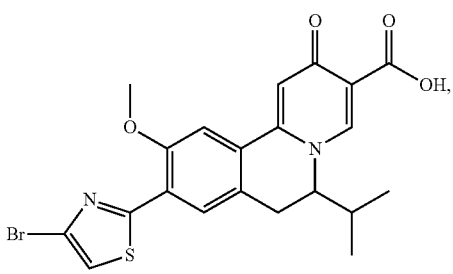

(110) 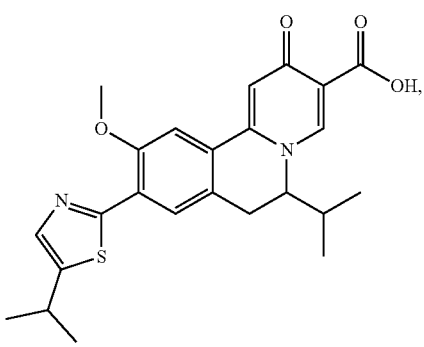

(111) 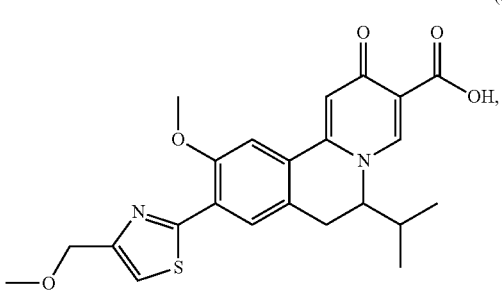

(112) 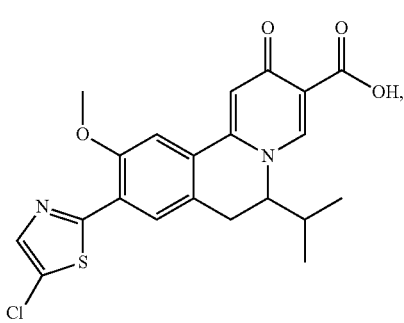

(113) 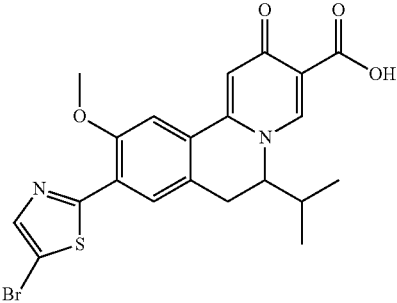

or (114)

or a stereoisomer, a tautomer, an N-oxide, a solvate, a pharmaceutically acceptable salt or a prodrug thereof.

17. A pharmaceutical composition comprising the compound according to claim 1, optionally, wherein the pharmaceutical composition further comprises a pharmaceutically acceptable excipient, or a combination of the excipients.

18. The pharmaceutical composition according to claim 17 further comprising other anti-HBV drug wherein the other anti-HBV drug is a HBV polymerase inhibitor, an immunomodulator or an interferon.

19. The pharmaceutical composition according to claim 18, wherein the other anti-HBV agent is lamivudine, telbivudine, tenofovir, entecavir, adefovir dipivoxil, alfaferone, alloferon, celmoleukin, clevudine, emtricitabine, famciclovir, interferon, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, rintatolimod, phosphazid, interferon α-2b, levamisole or propagermanium.

20. A method of preventing or treating a hepatitis B infection or a disease caused by hepatitis B infection in a patient comprising administering to the patient a therapeutically effective amount of the compound according to claim 1.

21. The method according to claim 20, wherein the disease caused by hepatitis B infection is cirrhosis or hepatocellular carcinogenesis.

22. A method of preventing or treating a hepatitis B infection or a disease caused by hepatitis B infection in a patient comprising administering to the patient a therapeutically effective amount of the pharmaceutical composition according to claim 17.

23. The method according to claim 22, wherein the disease caused by hepatitis B infection is cirrhosis or hepatocellular carcinogenesis.

24. A method of inhibiting the production or secretion of HBsAg, and/or inhibiting the production of HBV DNA in a patient, comprising administering to the patient a therapeutically effective amount of the compound according to claim 1.

25. A method of inhibiting the production or secretion of HBsAg, and/or inhibiting the production of HBV DNA in a patient, comprising administering to the patient a therapeutically effective amount of the compound according to the pharmaceutical composition according to claim 17.

* * * * *